US012590083B2

(12) United States Patent
Lynch et al.

(10) Patent No.: US 12,590,083 B2
(45) Date of Patent: Mar. 31, 2026

(54) INHIBITORS OF SPINSTER HOMOLOG 2 (SPNS2) FOR USE IN THERAPY

(71) Applicants: University of Virginia Patent Foundation, Charlottesville, VA (US); Virginia Tech Intellectual Properties, Inc., Blacksburg, VA (US)

(72) Inventors: Kevin R. Lynch, Charlottesville, VA (US); Yugesh Kharel, Charlottesville, VA (US); Webster L. Santos, Blacksburg, VA (US); Ashley Peralta, Blacksburg, VA (US); Russell G. Fritzemeier, Christiansburg, VA (US); Daniel Foster, Blacksburg, VA (US)

(73) Assignees: University of Virginia Patent Foundation, Charlottesville, VA (US); Virginia Tech Intellectual Properties, Inc., Blacksburg, VA (US)

( * ) Notice: Subject to any disclaimer, the term of this patent is extended or adjusted under 35 U.S.C. 154(b) by 857 days.

(21) Appl. No.: 17/310,179

(22) PCT Filed: Jan. 22, 2020

(86) PCT No.: PCT/US2020/014651
§ 371 (c)(1),
(2) Date: Jul. 23, 2021

(87) PCT Pub. No.: WO2020/154431
PCT Pub. Date: Jul. 30, 2020

(65) Prior Publication Data

US 2022/0089581 A1 Mar. 24, 2022

Related U.S. Application Data

(60) Provisional application No. 62/797,054, filed on Jan. 25, 2019.

(51) Int. Cl.

| | |
|---|---|
| ***C07D 413/04*** | (2006.01) |
| ***C07D 413/14*** | (2006.01) |
| *A61P 1/00* | (2006.01) |
| *A61P 3/10* | (2006.01) |
| *A61P 11/06* | (2006.01) |
| *A61P 17/06* | (2006.01) |
| *A61P 35/00* | (2006.01) |
| *A61P 37/08* | (2006.01) |

(52) U.S. Cl.
CPC ......... *C07D 413/04* (2013.01); *C07D 413/14* (2013.01)

(58) Field of Classification Search
CPC ....... C07D 413/04; C07D 413/14; A61P 1/00; A61P 3/10; A61P 11/06; A61P 17/06; A61P 35/00; A61P 37/08
See application file for complete search history.

(56) References Cited

U.S. PATENT DOCUMENTS

| | | | | |
|---|---|---|---|---|
| 9,688,668 B2 * | 6/2017 | Santos | C07D 413/04 |
| 2009/0197897 A1 | 8/2009 | Bugada et al. | |
| 2012/0022108 A1 | 1/2012 | Bessis et al. | |
| 2014/0057895 A1 * | 2/2014 | Mizuno | A61P 13/02 546/187 |
| 2023/0331683 A1 | 10/2023 | Lynch et al. | |
| 2023/0373937 A1 | 11/2023 | Lynch et al. | |

FOREIGN PATENT DOCUMENTS

| | | | |
|---|---|---|---|
| EP | 3275440 | 1/2018 | |
| WO | 03062252 | 7/2003 | |
| WO | WO-2005044797 A1 * | 5/2005 | A61P 25/00 |
| WO | WO-2006123257 A2 * | 11/2006 | A61P 25/00 |
| WO | WO-2007039781 A2 | 4/2007 | |
| WO | 2008064320 | 5/2008 | |
| WO | WO-2013119946 A1 * | 8/2013 | A61P 35/00 |
| WO | 2016054261 | 4/2016 | |
| WO | 2019018795 | 1/2019 | |
| WO | WO-2020154431 A1 | 7/2020 | |
| WO | 2020219792 | 10/2020 | |
| WO | 2020227101 | 11/2020 | |
| WO | 2022056042 | 3/2022 | |
| WO | 2022056045 | 3/2022 | |

OTHER PUBLICATIONS

Patwardhan et al. Structure-activity relationship studies and in vivo activity of guanidine-based sphingosine kinase inhibitors: discovery of SphK1- and SphK2-selective inhibitors. J Med Chem. Feb. 26, 2015;58(4):1879-1899. doi: 10.1021/jm501760d. Epub Feb. 13, 2015. (Year: 2013).*

Tsai HC, Han MH. Sphingosine-1-Phosphate (S1P) and S1P Signaling Pathway: Therapeutic Targets in Autoimmunity and Inflammation. Drugs. Jul. 2016;76(11):1067-79. doi: 10.1007/s40265-016-0603-2. PMID: 27318702. (Year: 2016).*

"International Application Serial No. PCT/US2020/014651, International Search Report mailed Jun. 29, 2020", 6 pgs.

"International Application Serial No. PCT/US2020/014651, Invitation to Pay Additional Fees and Partial Search Report mailed Apr. 28, 2020", 19 pgs.

"International Application Serial No. PCT/US2020/014651, Written Opinion mailed Jun. 29, 2020", 12 pgs.

Packiarajan, Mathivanan, et al., "Azetidinyl oxadiazoles as potent mGluR5 positive allosteric modulators", Bioorganic & Medicinal Chemistry Letters, vol. 22, No. 20, (Aug. 25, 2012), 6469-6474.

"International Application Serial No. PCT/US2020/014651, International Preliminary Report on Patentability mailed Aug. 5, 2021", 15 pgs.

(Continued)

*Primary Examiner* — Bruck Kifle
*Assistant Examiner* — Kevin S Martin
(74) *Attorney, Agent, or Firm* — Schwegman Lundberg & Woessner, P.A.

(57) ABSTRACT

The present disclosure provides SPNS2 inhibitor compounds according to Formula I and their pharmaceutically acceptable salts, and/or tautomers as described in the disclosure, and the disclosure provides their pharmaceutical compositions and methods of use in therapy.

2 Claims, 1 Drawing Sheet

(56) References Cited

OTHER PUBLICATIONS

"International Application Serial No. PCT/US2021/049531, International Search Report mailed Jan. 4, 2022", 9 pgs.
"International Application Serial No. PCT/US2021/049531, Written Opinion mailed Jan. 4, 2022", 10 pgs.
"International Application Serial No. PCT/US2021/049534, International Search Report mailed Jan. 28, 2022", 8 pgs.
"International Application Serial No. PCT/US2021/049534, Written Opinion mailed Jan. 28, 2022", 9 pgs.
"European Application Serial No. 20709362.6, Response to Communication Pursuant to Rules 161 and 162 EPC filed Feb. 15, 2022", 47 pgs.
Congdon, Molly D, "Structure-Activity Relationship Studies and Molecular Modeling of Naphthalene-Based Sphingosine Kinase 2 Inhibitors", ACS Medicinal Chemistry Letters, vol. 7, No. 3, XP055285993, (Mar. 10, 2016), 229-234.
Kharel, Yugesh, "Sphingosine kinase type 2 inhibition elevates circulating sphingosine 1-phosphate", Biochemical Journal, 447, (Oct. 1, 2012), 149-157.
"U.S. Appl. No. 18/044,686, Preliminary Amendment filed Mar. 9, 2023", 19 pgs.
"U.S. Appl. No. 18/044,688, Preliminary Amendment filed Mar. 9, 2023", 14 pgs.
"European Application Serial No. 21786692.0, Response filed Oct. 26, 2023 to Communication pursuant to Rules 161(1) and 162 EPC mailed Apr. 18, 2023", 10 pgs.
"International Application Serial No. PCT/US2021/049531, International Preliminary Report on Patentability mailed Mar. 23, 2023", 12 pgs.
"International Application Serial No. PCT/US2021/049534, International Preliminary Report on Patentability mailed Mar. 23, 2023", 11 pgs.
"U.S. Appl. No. 18/044,686, Restriction Requirement mailed Jul. 17, 2025", 6 pgs.
"U.S. Appl. No. 18/044,688, Restriction Requirement mailed Jul. 23, 2025", 10 pgs.
"U.S. Appl. No. 18/044,686, Response filed Sep. 17, 2025 to Restriction Requirement mailed Jul. 17, 2025", 19 pgs.
"U.S. Appl. No. 18/044,688, Response filed Sep. 23, 2025 to Restriction Requirement mailed Jul. 23, 2025", 15 pgs.
"U.S. Appl. No. 18/044,688, Non Final Office Action mailed Oct. 17, 2025", 18 pgs.
"Chemical Abstract Registry No. 1906742-77-5, indexed in the Registry File on STN CAS", (May 9, 2016), 4 pgs.

* cited by examiner

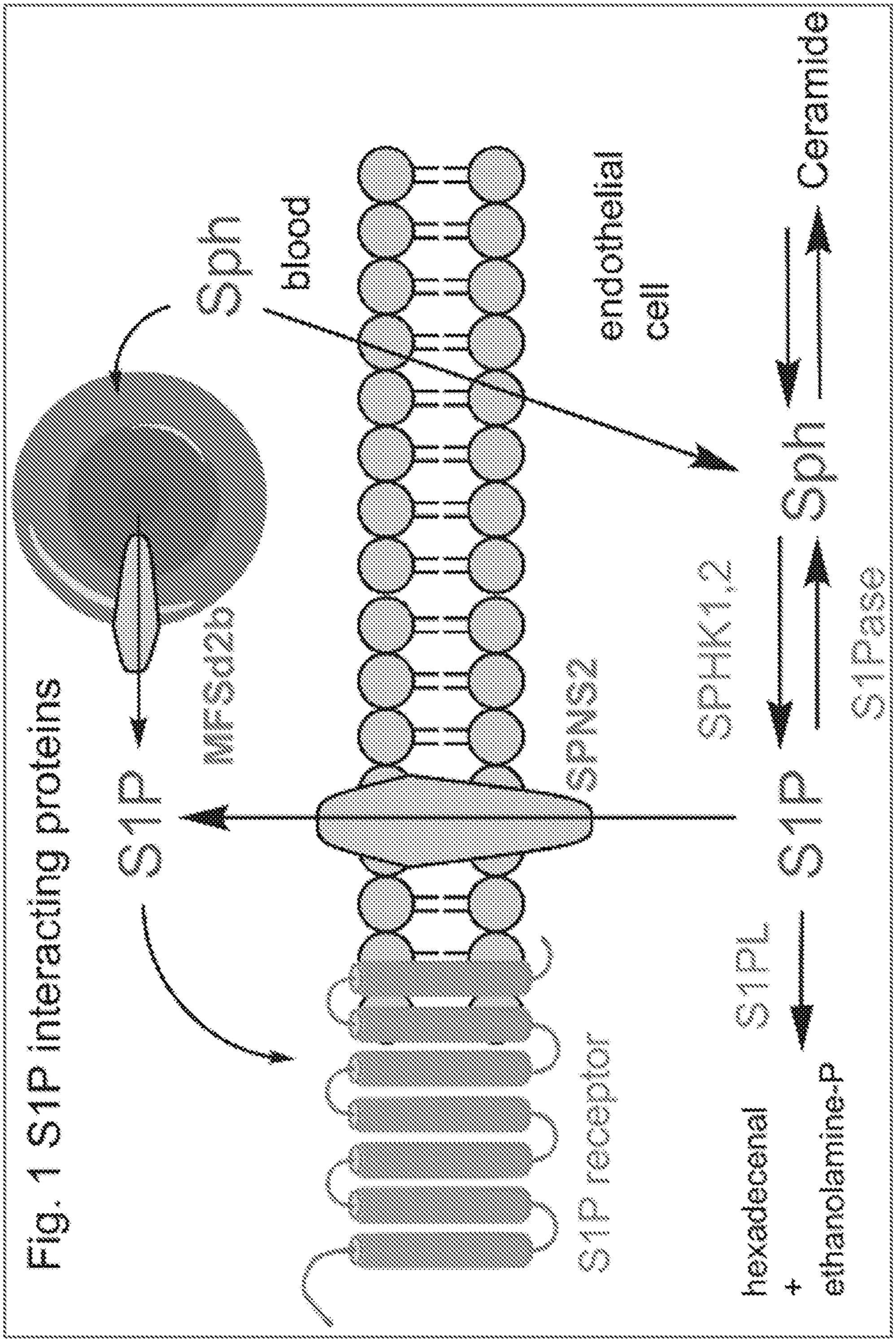
Fig. 1 S1P interacting proteins

INHIBITORS OF SPINSTER HOMOLOG 2 (SPNS2) FOR USE IN THERAPY

This application is a U.S. National Stage of 35 U.S.C. § 371 of PCT Patent Application No. PCT/US2020/014651, filed on Jan. 22, 2020, which claims the benefit of priority to U.S. Provisional Patent Application No. 62/797,054, filed on Jan. 25, 2019, the contents of which applications are incorporated by reference in their entireties as if fully set forth herein.

GOVERNMENT LICENSE RIGHTS

This invention was made with government support under R01AI144026 and R01GM121075 awarded by the National Institutes of Health. The government has certain rights in the invention.

BACKGROUND

Sphingosine 1-phosphate (S1P) is a simple lipid that is chemotactic when present extracellularly, but which is also a second messenger when intracellular. These roles require compartmentalization, which is provided in part by extrusion of S1P from cells. The S1P transporters, SPNS2 (endothelium) and MFSD2B (erythrocytes), release S1P from cells. When this release is coupled with S1P degradation in tissue parenchyma, a differential is generated between the extracellular (high) and intracellular (low) S1P concentrations. Mouse genetic studies indicate that endothelial cells use SPNS2 to provide most of the S1P in lymph as well as about one-third of plasma S1P, whereas erythrocytes provide the remainder of plasma S1P via MFSD2B. The S1P gradient in blood functions both to maintain endothelial barrier integrity and promote migration of lymphocytes from the thymus to the blood.

The lymph S1P gradient is particularly important for egress of lymphocytes from secondary lymphoid tissue into efferent lymph for correct temporal and spatial positioning of immune cells. However, on-target agonist activity at endothelial and cardiac S1P receptors drives adverse events such as first dose bradycardia.

SUMMARY

The present disclosure provides, in various embodiments, compounds and their pharmaceutically acceptable salts conforming to Formula I that are SPNS2 inhibitors and that avoid on-target adverse activity:

(I)

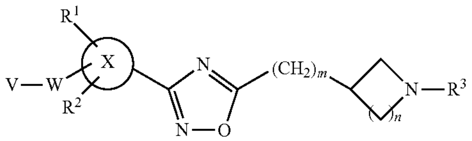

In Formula I, X is a $C_6$-$C_{10}$-aryl or 5- to 10-membered heteroaryl (wherein 1-4 heteroaryl members are independently selected from N, O, and S).

$R^1$ and $R^2$ are independently selected from the group consisting of H, $C_1$-$C_6$-alkyl, $C_1$-$C_6$-alkoxy, $C_3$-$C_8$-cycloalkyl, $C_1$-$C_6$-haloalkyl, CN, and halo.

$R^3$ is H or —C(NH)$NH_2$.

W is a bond, $CH_2$, O, NH, —O—N═C(R)—, or —N(R)—C(O)— (wherein R is H or $C_1$-$C_6$-alkyl).

V is selected from the group consisting of H, $C_1$-$C_{14}$-alkyl, $C_2$-$C_{12}$-alkenyl, ($C_6$-$C_{10}$)aryl, —$C_1$-$C_{10}$-alkyl-($C_6$-$C_{10}$)aryl, —$C_2$-$C_{12}$-alkenyl-($C_6$-$C_{10}$)aryl, —$C_1$-$C_{10}$-alkyl-($C_3$-$C_8$)cycloalkyl, -(3- to 14-membered heterocycloalkyl) (wherein 1-4 heterocycloalkyl members are independently selected from N, O, and S), —($C_1$-$C_{10}$)alkyl-(3- to 14-membered heterocycloalkyl) (wherein 1-4 heterocycloalkyl members are independently selected from N, O, and S).

Subscript m is 0 or 1, and n is 1, 2, 3, or 4.

Each alkyl, alkoxy, alkenyl, alkynyl, aryl, cycloalkyl, heterocycloalkyl, and heteroaryl is optionally substituted with 1-5 substituents independently selected from the group consisting of hydroxy, halo, —NR'$_2$ [wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S], —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl). Further, each alkyl, alkenyl, aryl, and heterocycloalkyl substituent as defined immediately above is optionally substituted with one or more substituents selected from the group consisting of hydroxy, —O$C_1$-$C_6$-alkyl, halo, —$NH_2$, —($C_1$-$C_6$-alkyl)$NH_2$, —C(O)OH, CN, and oxo.

It should be understood that, notwithstanding the definitions described above, the Formula I compound is not:

3-(3-(4-octylphenyl)-1,2,4-oxadiazol-5-yl)pyrrolidine-1-carboximidamide, 3-(3-(4-octylphenyl)-1,2,4-oxadiazol-5-yl)azetidine-1-carboximidamide, or 3-(3-(4-decylphenyl)-1,2,4-oxadiazol-5-yl)azetidine-1-carboximidamide.

Another embodiment of the disclosure is a pharmaceutical composition comprising a compound of Formula I or a pharmaceutically acceptable salt thereof.

The disclosure also provides, in an embodiment, a method of inhibiting spinster homolog 2 (SPNS2), comprising contacting SPNS2 with an effective amount of a compound of Formula I or a pharmaceutically acceptable salt thereof.

Still another embodiment is a method of treating a patient afflicted by a neoplastic disease, comprising administering to the patient a therapeutically effective amount of a compound of Formula I or a pharmaceutically acceptable salt thereof.

In an embodiment, the disclosure provides a method of treating a patient afflicted with an allergic disease, comprising administering to the patient a therapeutically effective amount of a compound of Formula I or a pharmaceutically acceptable salt thereof.

In another embodiment, the disclosure provides a method of treating a patient afflicted with an autoimmune disease, comprising administering to the patient a therapeutically effective amount of a compound of Formula I or a pharmaceutically acceptable salt thereof.

BRIEF DESCRIPTION OF THE DRAWINGS

FIG. 1: Sphingosine 1-phosphate (S1P) interacting proteins.

DETAILED DESCRIPTION

In a properly functioning immune system, the proper cells get to the proper places at the proper times. Gradients of the chemotactic lipid, sphingosine 1-phosphate (S1P), enable correct positioning of immune cells; lymphocyte egress from secondary lymphoid tissues is particularly dependent on S1P signaling. S1P's role in lymphocyte trafficking was discovered when the mechanism of action of the immunosuppressive drug fingolimod (FTY720) was investigated. Fingolimod's active metabolite, phospho-FTY720, desensitizes lymphocyte S1P1 receptors; thereby, rendering these cells unable to detect the S1P-rich environment of efferent lymph[1]. The resulting lymphopenia is now recognized as a general property of S1P1 receptor agonists. Although fingolimod eventually became a medicine for treating relapsing remitting multiple sclerosis[2], S1P1 receptor agonists have several on target liabilities including initial dose bradycardia and compromised endothelial barrier function[2]. Therefore, alternative strategies to achieve immunosuppression by modulating S1P signaling without undesirable on-target activity are needed.

S1P is synthesized ubiquitously, but its intracellular accumulation is limited by degradation and export. In lymph nodes (LN), brisk catabolic activity by S1P lyase keeps S1P[3] low while lymph endothelial cells extrude S1P into lymph via a transporter, SPNS2[4], resulting in a lymph—LN S1P gradient. Vascular (blood) S1P gradients are likewise maintained by prominent S1P catabolic activity in tissue parenchyma coupled with the extrusion of S1P into plasma (FIG. 1). About ⅓ of plasma S1P is provided by vascular endothelial cells via SPNS2[4], with the remainder being released from red blood cells (RBCs) by a different S1P transporter. The transporter was subsequently discovered to be MFSD2B, which is an erythroid lineage-specific major facilitator superfamily member that is distantly related to SPNS2[5,6]. Germ line deletion of Mfsd2b results in a 50% decrease in plasma S1P but an astonishing 60-fold increase in RBC S1P; however, these animals are not lymphopenics. RBCs lack S1P catabolic enzymes but express sphingosine kinase type 1 (SphK1), which accounts for the high levels of S1P in whole blood. Blood S1P gradients are necessary to maintain endothelial barrier integrity[7]. Indeed, Ma has proposed that vascular S1P gradients are a fundamental property of the closed circulatory systems of vertebrates[9].

The role of the catabolic enzyme S1P lyase in maintaining low LN S1P predicts that S1P lyase inhibitors will eliminate the gradient, which will modulate the immune system by disrupting lymphocyte trafficking analogous to S1P1 agonists. Indeed, S1P lyase deficiency, whether accomplished through genetic manipulation of mice or S1P lyase inhibitor administration, raises S1P levels in tissues, including lymph nodes, with a resulting lymphopenia[3,10]. However, administering a selective S1P lyase inhibitor to rats and inducing global deletion of the gene (Sgpl1) in mice were both found to be nephrotoxic[10]. Furthermore, humans deficient in S1P lyase activity because of SGPL1 variant alleles exhibit multiple pathologies including steroid resistant nephrosis, adrenal insufficiency, and ichthyosis[11,12]. Such observations appear to eliminate S1P lyase as a therapeutic target.

Mice rendered deficient in Spns2 either through germ line or endothelium-specific deletion of Spns2, have a 10-fold decrease in S1P levels in thoracic duct lymph and are lymphopenic but the vascular S1P gradient is less affected (30% reduction in plasma S1P)[4]. These results validate the data disclosed herein that SPNS2 inhibitors of this disclosure, by preventing the formation of the lymph S1P gradient, recapitulate the therapeutic efficacy of S1P1 receptor agonists without their adverse events.

Application of an SPNS2 inhibitor in immuno-oncology comes from another mouse genetics study. In a screen of 810 mouse strains with different germ line gene deletions, $Spns2^{-/-}$ mice were found to have remarkably low metastatic colonization of the lungs when injected with B16-F10 melanoma cells[13]. This effect was observed with other lung metastatic colonization models and in similar models in liver. As expected, the total number of immune cells in the lung was reduced in the lymphopenic $Spns2^{-/-}$ mice, but the lung resident population was proportionally enriched in natural killer and $CD8^+$ effector cells[13].

Thus, results from the study of mice rendered deficient in Spns2 indicate that SPNS2 inhibitors are immunomodulatory. The SPNS2 inhibitors of the disclosure recapitulate the SPNS2 null phenotype, and they and enable S1P transport inhibition as a viable therapeutic strategy as well as providing heretofore unavailable chemical biology tools to explore S1P physiology in vivo.

Definitions

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, $—CH(CH_3)_2$, $—CH(CH_3)(CH_2CH_3)$, $—CH(CH_2CH_3)_2$, $—C(CH_3)_3$, $—C(CH_2CH_3)_3$, $—CH_2CH(CH_3)_2$, $—CH_2CH(CH_3)(CH_2CH_3)$, $—CH_2CH(CH_2CH_3)_2$, $—CH_2C(CH_3)_3$, $—CH_2C(CH_2CH_3)_3$, $—CH(CH_3)CH(CH_3)(CH_2CH_3)$, $—CH_2CH_2CH(CH_3)_2$, $—CH_2CH_2CH(CH_3)(CH_2CH_3)$, $—CH_2CH_2CH(CH_2CH_3)_2$, $—CH_2CH_2C(CH_3)_3$, $—CH_2CH_2C(CH_2CH_3)_3$, $—CH(CH_3)CH_2CH(CH_3)_2$, $—CH(CH_3)CH(CH_3)CH(CH_3)_2$, and the like. Thus, alkyl groups include primary alkyl groups, secondary alkyl groups, and tertiary alkyl groups. An alkyl group can be unsubstituted or optionally substituted with one or more substituents as described herein below.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The term "alkenyl" refers to straight or branched chain hydrocarbyl groups including from 2 to about 20 carbon atoms having 1-3, 1-2, or at least one carbon to carbon double bond. An alkenyl group can be unsubstituted or optionally substituted with one or more substituents as described herein below.

"Substituted alkenyl" refers to alkenyl substituted at 1 or more, e.g., 1, 2, 3, 4, 5, or even 6 positions, which substituents are attached at any available atom to produce a stable compound, with substitution as described herein. "Optionally substituted alkenyl" refers to alkenyl or substituted alkenyl.

"Alkyne or "alkynyl" refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

"Substituted alkynyl" refers to an alkynyl substituted at 1 or more, e.g., 1, 2, 3, 4, 5, or even 6 positions, which substituents are attached at any available atom to produce a stable compound, with substitution as described herein. "Optionally substituted alkynyl" refers to alkynyl or substituted alkynyl.

The term "alkoxy" refers to an —O-alkyl group having the indicated number of carbon atoms. For example, a $(C_1-C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "cycloalkyl" refers to a monocyclic, bicyclic, tricyclic, or polycyclic, 3- to 14-membered ring system, which is either saturated, such as "cycloalkyl," or unsaturated, such as "cycloalkenyl." The term "cycloalkenyl" refers specifically to cyclic alkenyl, such as $C_3-C_6$-cycloalkenyl. The cycloalkyl may be attached via any atom. Cycloalkyl, for instance, also contemplates fused rings wherein, for instance, a cycloalkyl is fused to an aryl or heteroaryl ring as defined herein. Representative examples of cycloalkyl include, but are not limited to cyclopropyl, cyclobutyl, cyclopentyl, cyclohexyl, cyclopropenyl, cyclobutenyl, cyclopentenyl, and cyclohexenyl. A cycloalkyl group can be unsubstituted or optionally substituted with one or more substituents as described herein.

"Substituted cycloalkyl" refers to cycloalkyl substituted at 1 or more, e.g., 1, 2, 3, 4, 5, or even 6 positions, which substituents are attached at any available atom to produce a stable compound, with substitution as described herein. "Optionally substituted cycloalkyl" refers to cycloalkyl or substituted cycloalkyl.

"Aryl" when used alone or as part of another term means a carbocyclic aromatic group whether or not fused having the number of carbon atoms designated or if no number is designated, up to 14 carbon atoms, such as a $C_6-C_{14}$-aryl. Particular aryl groups are phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). A particular aryl is phenyl. "Aryl" also includes aromatic ring systems that are optionally fused with a cycloalkyl ring, as herein defined. An aryl group can be unsubstituted or optionally substituted with one or more substituents as described herein below.

A "substituted aryl" is an aryl that is independently substituted with one or more substituents attached at any available atom to produce a stable compound, wherein the substituents are as described herein. "Optionally substituted aryl" refers to aryl or substituted aryl.

The term "heteroatom" refers to N, O, and S. Disclosed compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein below.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" means a saturated or unsaturated non-aromatic monocyclic, bicyclic, tricyclic or polycyclic ring system that has from 3 to 14, such as 3 to 6, atoms in which from 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A hetercycloalkyl group can be unsubstituted or optionally substituted with one or more substituents as described herein below.

"Optionally substituted heterocycloalkyl" denotes a heterocycloalkyl that is substituted with 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

The term "oxo" refers to a ═O atom attached to a saturated or unsaturated moiety. The ═O atom can be attached to a carbon, sulfur, or nitrogen atom that is part of a cyclic or acyclic moiety.

A "hydroxyl" or "hydroxy" refers to an —OH group.

The substituent —$CO_2H$ may be replaced with bioisosteric replacements such as:

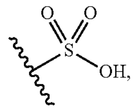
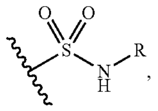
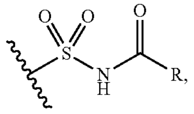
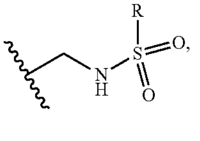
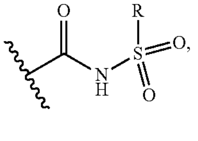
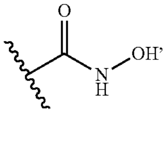

-continued

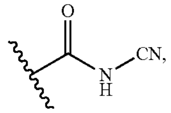, 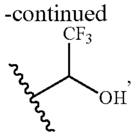, 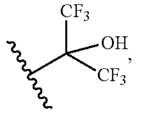,

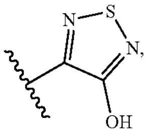, 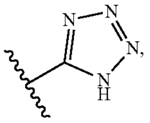, 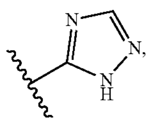,

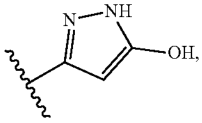, 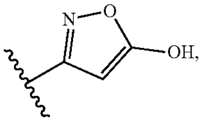,

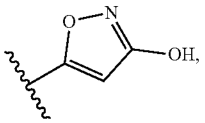, 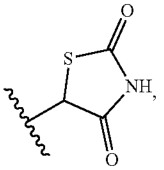, 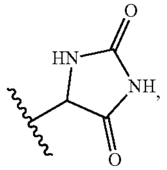,

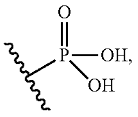, and the like, wherein R has the same definition as RA as defined herein. See, e.g., The Practice of Medicinal Chemistry (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified to the contrary, the term "compound" is inclusive in that it encompasses a compound or a pharmaceutically acceptable salt, stereoisomer, and/or tautomer thereof. Thus, for instance, a compound of Formula I includes a pharmaceutically acceptable salt of the compound.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or synergies with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult.

"Inhibitor" means a compound that induces dose dependent lymphopenia and a modest decrease in plasma S1P. In an embodiment, an inhibitor binds to SPNS2.

Compounds

As described generally above, the present disclosure provides compounds, pharmaceutically acceptable salts, and/or tautomers thereof, wherein the compounds conform to Formula I:

(I)

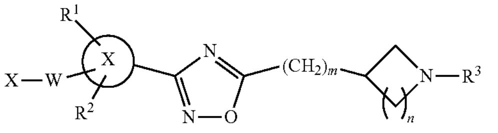

In Formula I, X is a $C_6$-$C_{10}$-aryl or 5- to 10-membered heteroaryl (wherein 1-4 heteroaryl members are independently selected from N, O, and S).

$R^1$ and $R^2$ are independently selected from the group consisting of H, $C_1$-$C_6$-alkyl, $C_1$-$C_6$-alkoxy, $C_3$-$C_8$-cycloalkyl, $C_1$-$C_6$-haloalkyl, CN, and halo.

$R^3$ is H or —C(NH)$NH_2$.

W is a bond, $CH_2$, O, NH, —O—N═C(R)—, or —N(R)—C(O)— (wherein R is H or $C_1$-$C_6$-alkyl).

V is selected from the group consisting of H, $C_1$-$C_{14}$-alkyl, $C_2$-$C_{12}$-alkenyl, ($C_6$-$C_{10}$)aryl, —$C_1$-$C_{10}$-alkyl-($C_6$-$C_{10}$)aryl, —$C_2$-$C_{12}$-alkenyl-($C_6$-$C_{10}$)aryl, —$C_1$-$C_{10}$-alkyl-($C_3$-$C_8$)cycloalkyl, -(3- to 14-membered heterocycloalkyl) (wherein 1-4 heterocycloalkyl members are independently selected from N, O, and S), —($C_1$-$C_{10}$)alkyl-(3- to 14-membered heterocycloalkyl) (wherein 1-4 heterocycloalkyl members are independently selected from N, O, and S).

Subscript m is 0 or 1, and n is 1, 2, 3, or 4.

Each alkyl, alkoxy, alkenyl, alkynyl, aryl, cycloalkyl, heterocycloalkyl, and heteroaryl is optionally substituted with 1-5 substituents independently selected from the group consisting of hydroxy, halo, —NR'$_2$ [wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S], —NHC(O)($OC_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —$OC_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl). Further, each alkyl, alkenyl, aryl, and heterocycloalkyl substituent as defined immediately above is optionally substituted with one or more substituents selected from the group consisting of hydroxy, —$OC_1$-$C_6$-alkyl, halo, —$NH_2$, —($C_1$-$C_6$-alkyl)$NH_2$, —C(O)OH, CN, and oxo.

Excluded from Formula I are the compounds:

3-(3-(4-octylphenyl)-1,2,4-oxadiazol-5-yl)pyrrolidine-1-carboximidamide, 3-(3-(4-octylphenyl)-1,2,4-oxadiazol-5-yl)azetidine-1-carboximidamide, and 3-(3-(4-decylphenyl)-1,2,4-oxadiazol-5-yl)azetidine-1-carboximidamide.

In various embodiments, n is 1 (azetidinyl), n is 2 (pyrrolidinyl), n is 3 (piperidinyl), or n is 4 (azepanyl).

Additional embodiments, optionally in combination with any other embodiment described herein, provide for Formula I compounds wherein m is 0.

Ring X in Formula I is $C_6$-$C_{10}$-aryl or 5- to 10-membered heteroaryl. In some embodiments, X is $C_6$-$C_{10}$-aryl as defined herein. An exemplary Ring X is phenyl. Thus, in accordance with some embodiments, the Formula I compound has the following structure of Formula IA:

(IA)

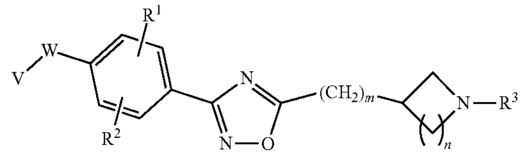

Alternatively, in various embodiments, X is a 5- to 10-membered heteroaryl, such as a 6-membered heteroaryl. Examples of heteroaryl are defined hereinabove. Illustrative of X is pyridyl.

In various embodiments, the Formula I compound has the following structure of Formula IB:

(IB)

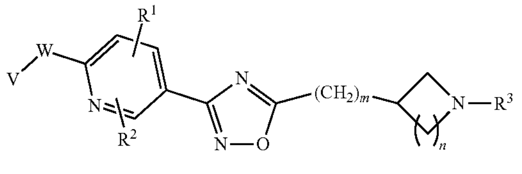

In some embodiments, $R^3$ is H. In other embodiments, $R^3$ is C(NH)$NH_2$.

In additional embodiments, optionally in combination with any other embodiment described herein, the disclosure provides Formula I compounds that conform to Formula IC or Formula ID:

(IC)

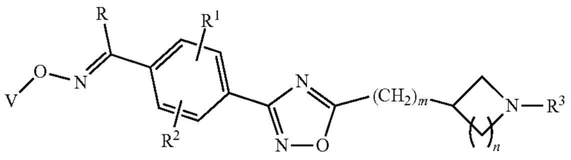

(ID)

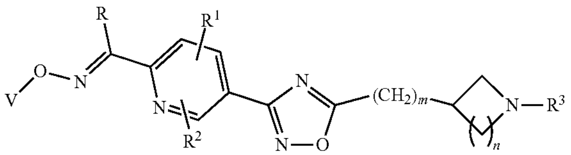

Various embodiments, optionally in combination with others described herein, provide for substitution on Ring X wherein $R^1$ is H and $R^2$ is selected from the group consisting of H, $C_1$-$C_6$-alkyl, $C_1$-$C_6$-alkoxy, $C_1$-$C_6$-alkoxy substituted by 1-3 halo, and $C_1$-$C_6$-haloalkyl. For example, $R^1$ is H and $R^2$ is $C_1$-$C_6$-haloalkyl, such as $CF_3$. Alternatively, an embodiment optionally in combination with any other embodiment described herein provides for a Formula I compound wherein $R^2$ is $C_1$-$C_6$-alkoxy substituted by 1-3 halo, such as —$OCF_3$. In other embodiments, Ring X is unsubstituted, i.e., each of $R^1$ and $R^2$ is H.

Embodiments provide for various combinations of W and V, as described herein. Examples include compounds in which W is a bond or O, and V is $C_1$-$C_{14}$-alkyl or —$C_1$-$C_{10}$-alkyl-($C_6$-$C_{10}$)aryl.

In one embodiment, X is phenyl; $R^1$ and $R^2$ are independently selected from H and $C_1$-$C_6$-haloalkyl; $R^3$ is H or —C(NH)$NH_2$; W is a bond or O; V is $C_1$-$C_{14}$-alkyl; m is 0; and n is 1, 2, 3, or 4.

In various embodiments, the disclosure provides specific examples of Formula I compounds, and their pharmaceutically acceptable salts, and/or tautomers thereof as set forth in Table 1 below.

TABLE 1

Examples of Formula I Compounds

| Compound | Structure |
|---|---|
| 5a | 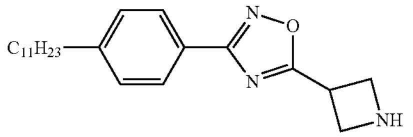 |
| 5e | 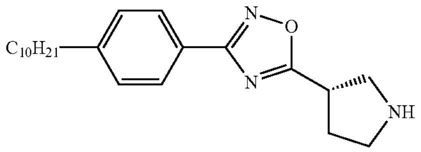 |
| 5f | 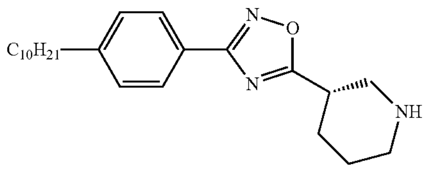 |
| 5g | 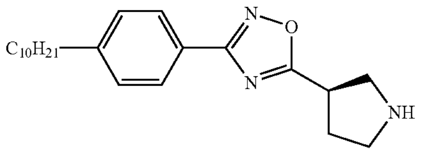 |
| 5h | 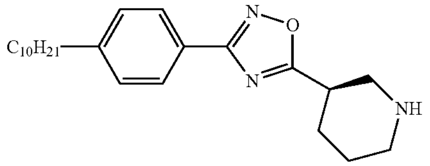 |

TABLE 1-continued
| Examples of Formula I Compounds | |
| --- | --- |
| Compound | Structure |
| 5j | 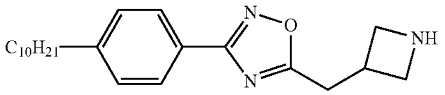 |
| 5l | 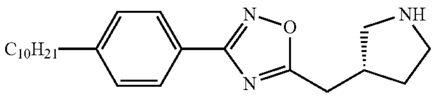 |
| 5p | 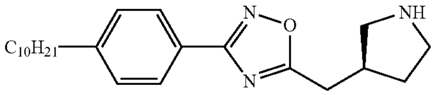 |
| 5q | 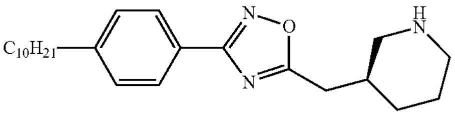 |
| 5aa | 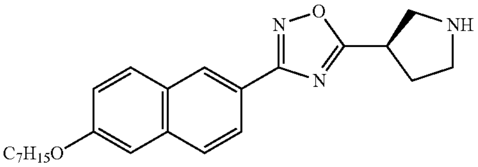 |
| 7a | 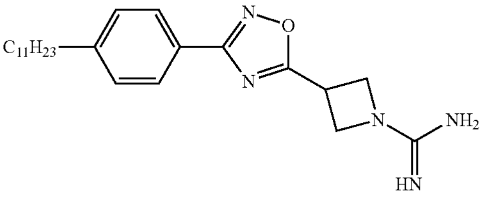 |
| 7b | 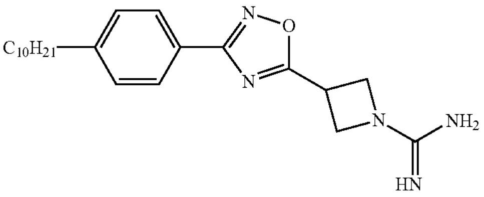 |
| 7c | 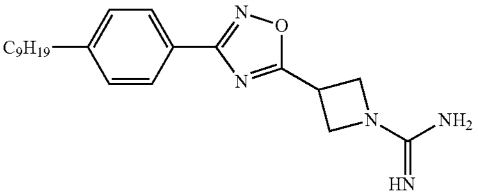 |
| 7d | 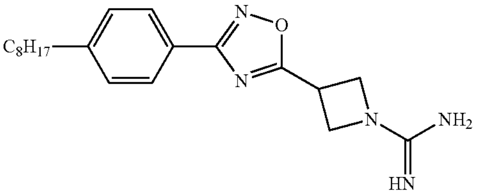 |

TABLE 1-continued
| Examples of Formula I Compounds | |
|---|---|
| Compound | Structure |
| 7e | 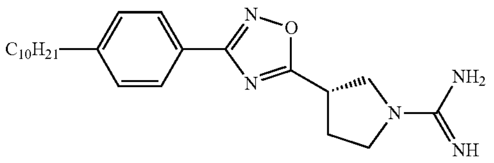 |
| 7f | 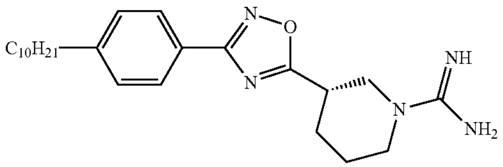 |
| 7g | 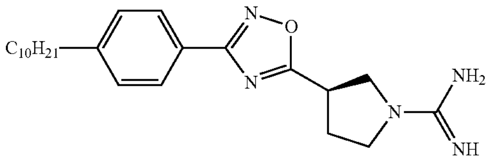 |
| 7h | 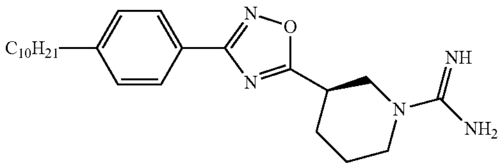 |
| 7i | 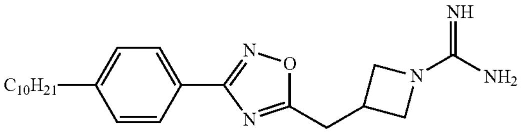 |
| 7j | 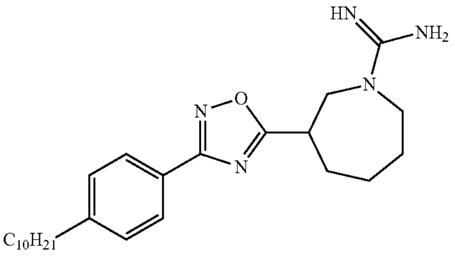 |
| 7k | 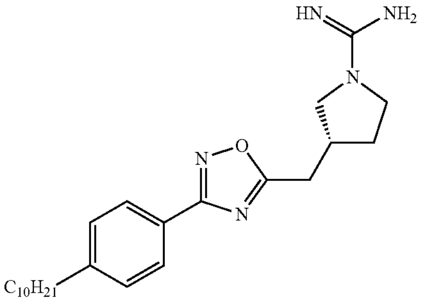 |

TABLE 1-continued
| Compound | Structure |
| --- | --- |
| | Examples of Formula I Compounds |
| 7kk | 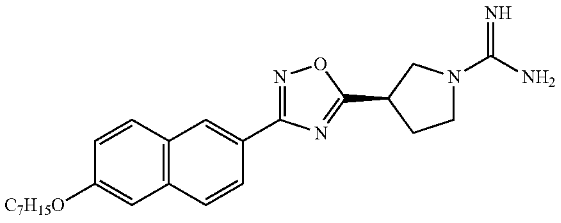 |
| 7p | 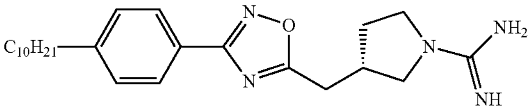 |
| 7q | 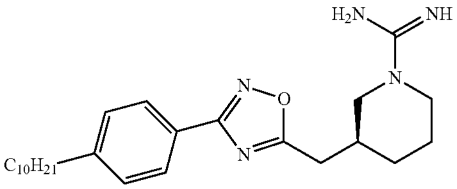 |
| 7t | 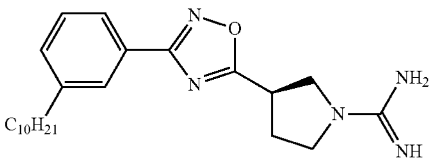 |
| 7xa | 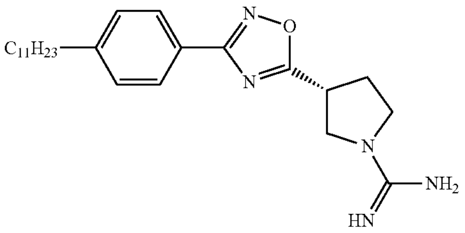 |
| 7xb | 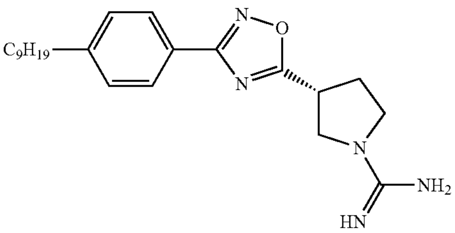 |
| 7ya | 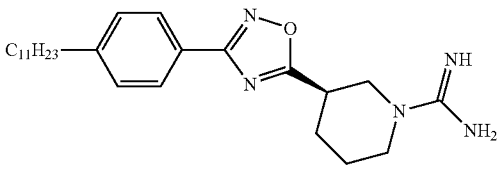 |
| 7yb | 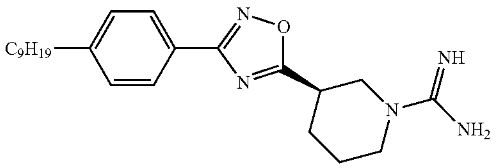 |

TABLE 1-continued
| Examples of Formula I Compounds | |
|---|---|
| Compound | Structure |
| 13a | 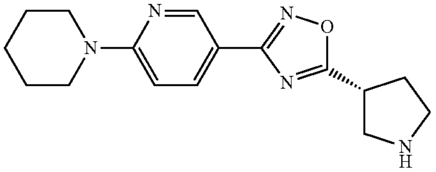 [SMILES: c1cc(N2CCCCC2)ncc1-c1noc([C@@H]2CCNC2)n1] |
| 13b | 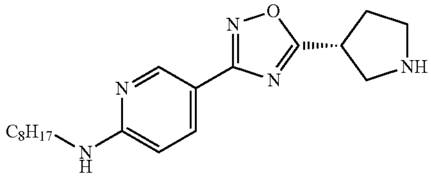 |
| 13c | 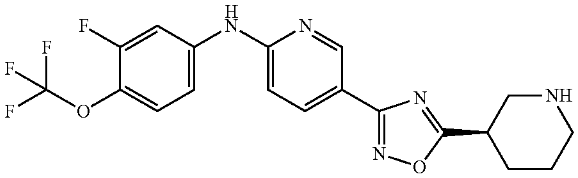 [SMILES: Fc1cc(Nc2ccc(-c3noc([C@@H]4CCCNC4)n3)cn2)ccc1OC(F)(F)F] |
| 13d | 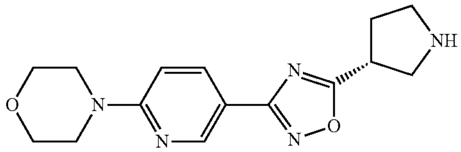 [SMILES: c1cc(N2CCOCC2)ncc1-c1noc([C@@H]2CCNC2)n1] |
| 13e | 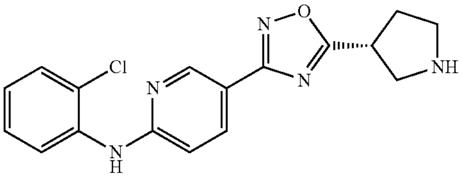 [SMILES: Clc1ccccc1Nc1ccc(-c2noc([C@@H]3CCNC3)n2)cn1] |
| 13f | 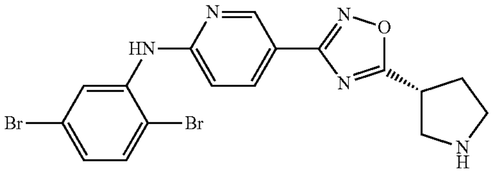 [SMILES: Brc1ccc(Br)c(Nc2ccc(-c3noc([C@@H]4CCNC4)n3)cn2)c1] |
| 13g | 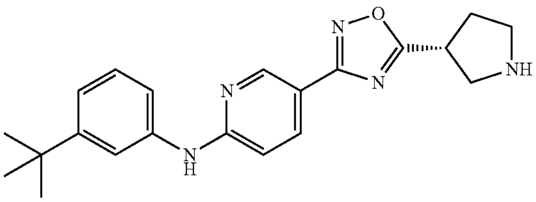 [SMILES: CC(C)(C)c1cccc(Nc2ccc(-c3noc([C@@H]4CCNC4)n3)cn2)c1] |
| 13h | 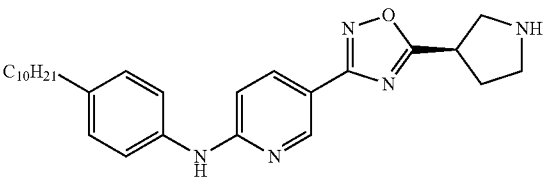 |

TABLE 1-continued
| Examples of Formula I Compounds | |
|---|---|
| Compound | Structure |
| 13i | 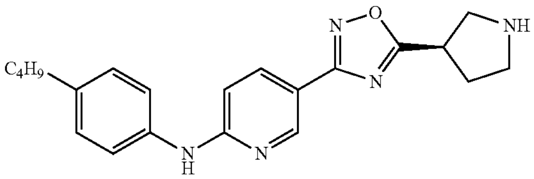 |
| 13j | 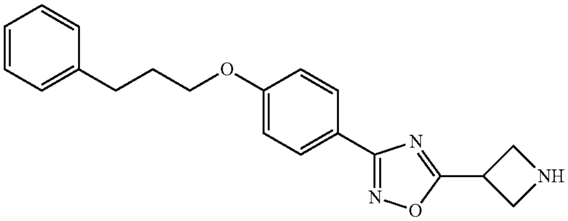 [SMILES: c1ccc(CCCOc2ccc(-c3noc(C4CNC4)n3)cc2)cc1] |
| 15a | 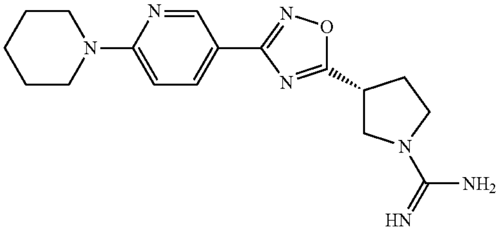 [SMILES: N=C(N)N1CC[C@@H](c2nc(-c3ccc(N4CCCCC4)nc3)no2)C1] |
| 15b | 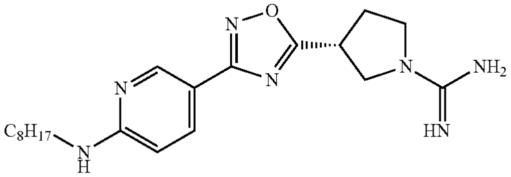 |
| 15c | 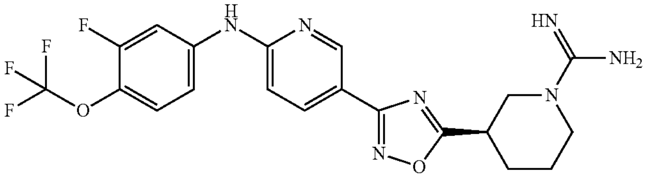 [SMILES: N=C(N)N1CCC[C@@H](c2nc(-c3ccc(Nc4ccc(OC(F)(F)F)c(F)c4)nc3)no2)C1] |
| 15d | 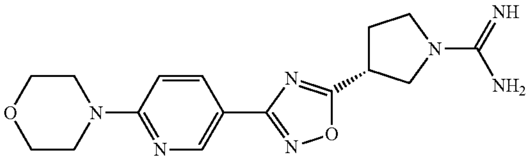 [SMILES: N=C(N)N1CC[C@@H](c2nc(-c3ccc(N4CCOCC4)nc3)no2)C1] |
| 15e | 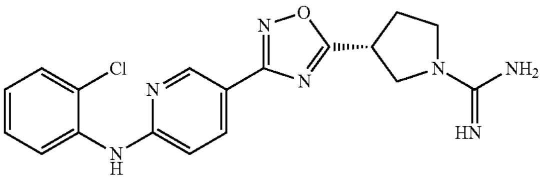 [SMILES: N=C(N)N1CC[C@@H](c2nc(-c3ccc(Nc4ccccc4Cl)nc3)no2)C1] |

TABLE 1-continued
| Examples of Formula I Compounds | |
|---|---|
| Compound | Structure |
| 15f | 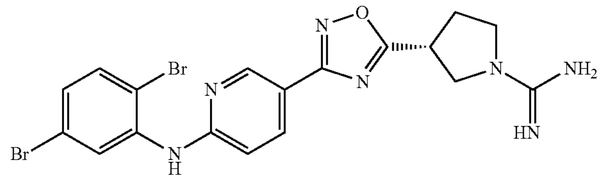 [SMILES: N=C(N)N1CC[C@@H](c2nc(-c3ccc(Nc4cc(Br)ccc4Br)nc3)no2)C1] |
| 15g | 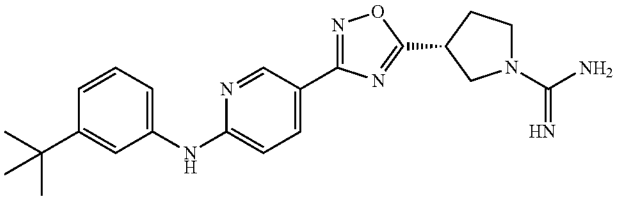 [SMILES: CC(C)(C)c1cccc(Nc2ccc(-c3noc([C@@H]4CCN(C(=N)N)C4)n3)cn2)c1] |
| 15h | 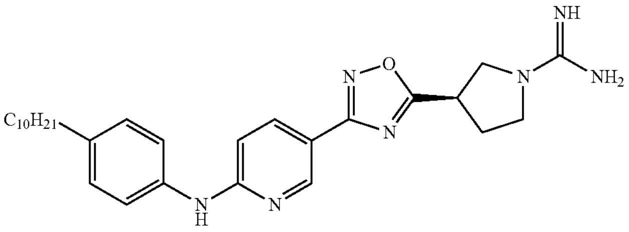 |
| 15i | 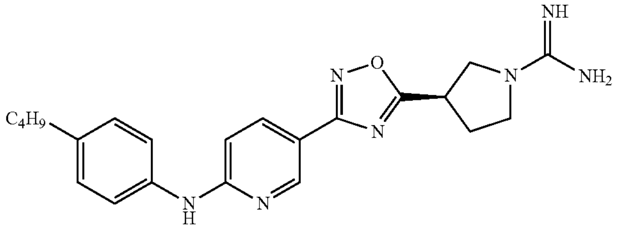 |
| 15j | 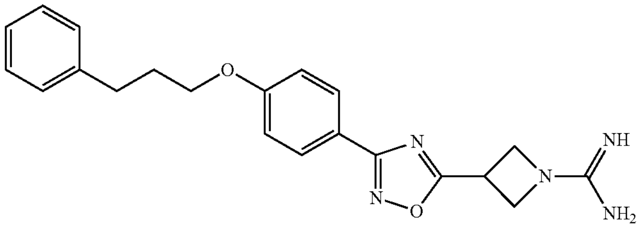 [SMILES: N=C(N)N1CC(c2nc(-c3ccc(OCCCc4ccccc4)cc3)no2)C1] |
| 21c | 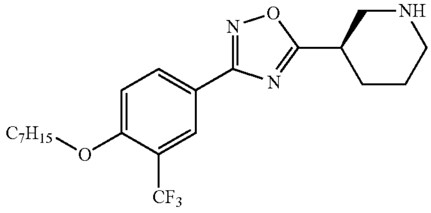 |
| 21d | 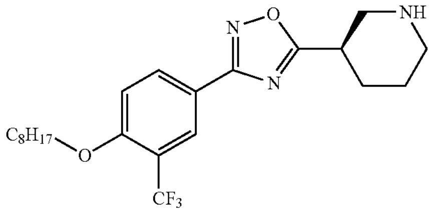 |

TABLE 1-continued
| Examples of Formula I Compounds | |
|---|---|
| Compound | Structure |
| 21e | 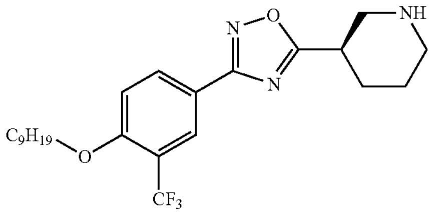 |
| 21f | 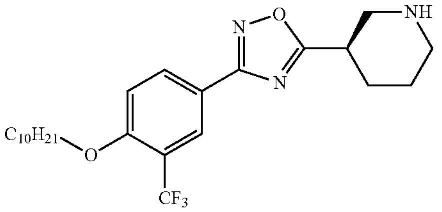 |
| 21g | 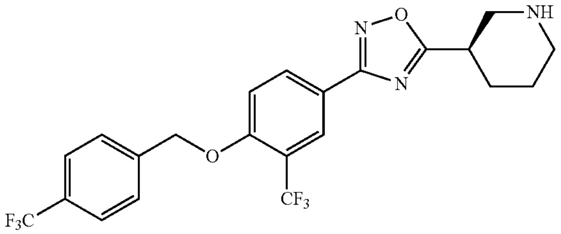 [SMILES: FC(F)(F)c1ccc(COc2ccc(-c3noc([C@@H]4CCCNC4)n3)cc2C(F)(F)F)cc1] |
| 21j | 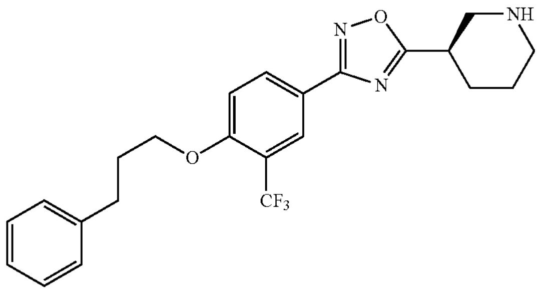 [SMILES: FC(F)(F)c1cc(-c2noc([C@@H]3CCCNC3)n2)ccc1OCCCc1ccccc1] |
| 28d | 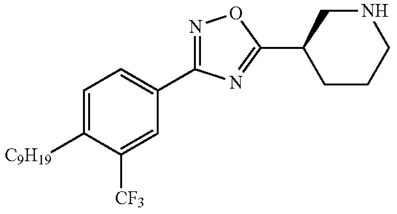 |
| 28e | 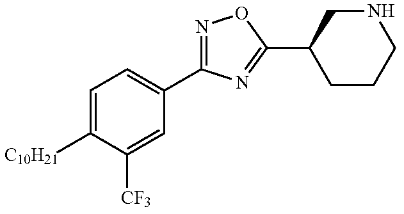 |

TABLE 1-continued
| Examples of Formula I Compounds | |
|---|---|
| Compound | Structure |
| 28f | 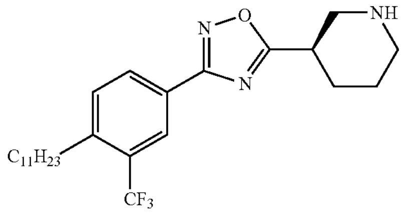 |
| 28g | 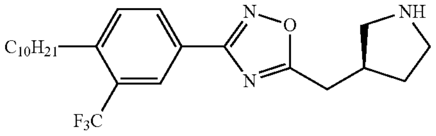 |
| 23a | 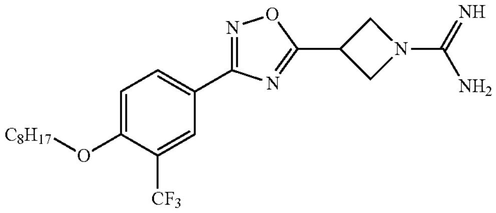 |
| 23b | 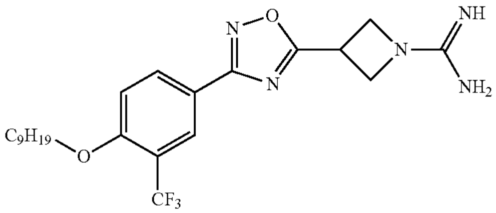 |
| 23c | 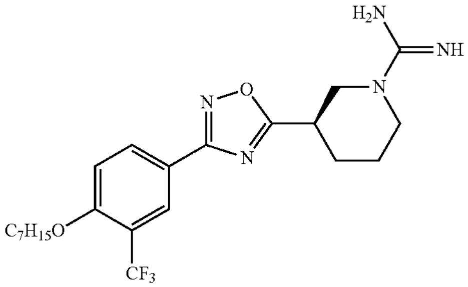 |
| 23d | 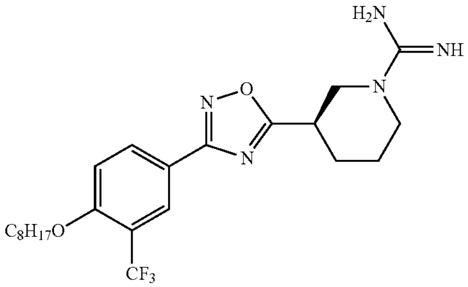 |

TABLE 1-continued
| Examples of Formula I Compounds | |
|---|---|
| Compound | Structure |
| 23e | 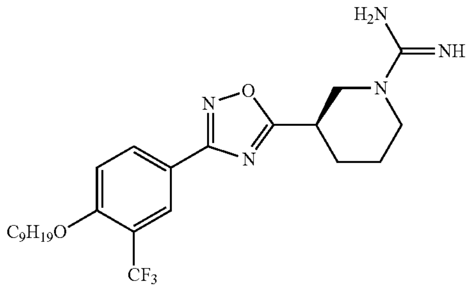 |
| 23f | 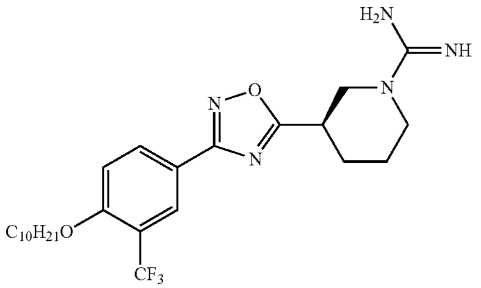 |
| 23g | 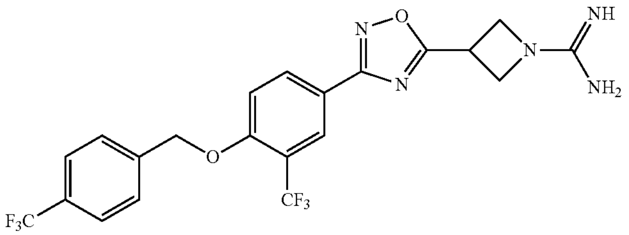 [SMILES: N=C(N)N1CC(c2nc(-c3ccc(OCc4ccc(C(F)(F)F)cc4)c(C(F)(F)F)c3)no2)C1] |
| 23h | 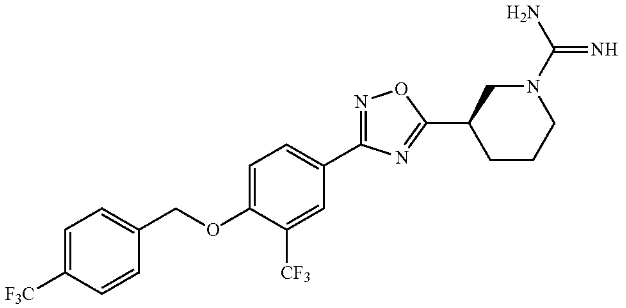 [SMILES: N=C(N)N1CCC[C@@H](c2nc(-c3ccc(OCc4ccc(C(F)(F)F)cc4)c(C(F)(F)F)c3)no2)C1] |
| 23i | 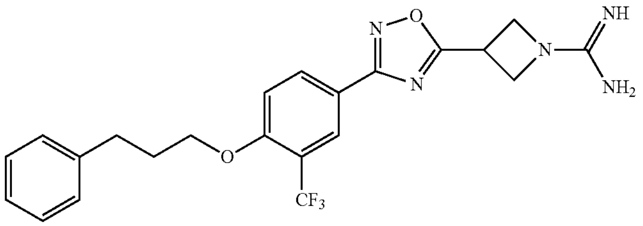 [SMILES: N=C(N)N1CC(c2nc(-c3ccc(OCCCc4ccccc4)c(C(F)(F)F)c3)no2)C1] |

TABLE 1-continued
| Examples of Formula I Compounds | |
|---|---|
| Compound | Structure |
| 23j | 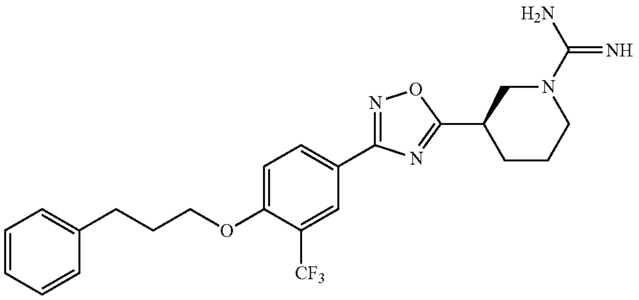 [SMILES: N=C(N)N1CCC[C@@H](c2nc(-c3ccc(OCCCc4ccccc4)c(C(F)(F)F)c3)no2)C1] |
| 30a | 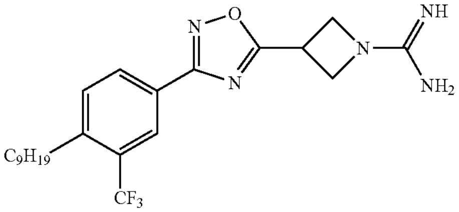 |
| 30b | 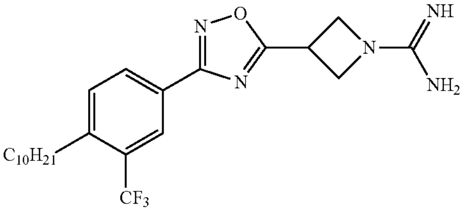 |
| 30c | 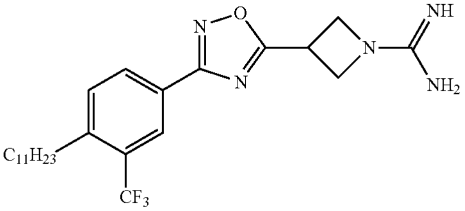 |
| 30d | 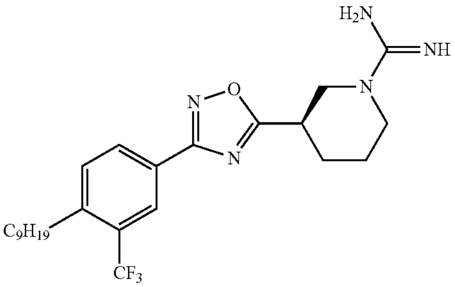 |
| 30e | 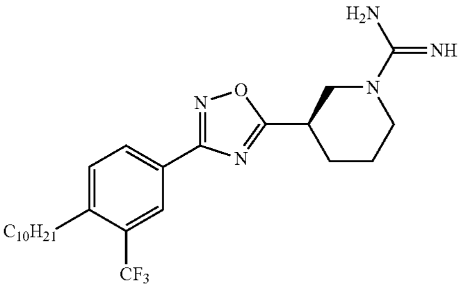 |

TABLE 1-continued
| Examples of Formula I Compounds | |
|---|---|
| Compound | Structure |
| 30f | 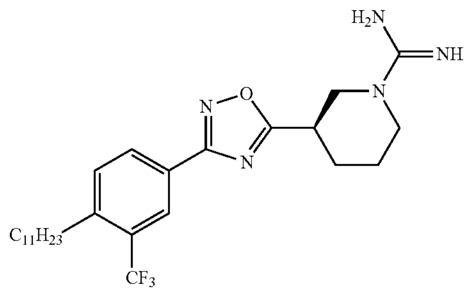 |
| 30g | 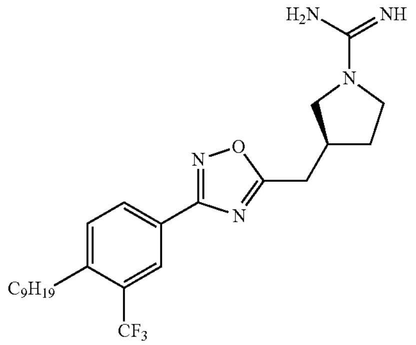 |
| 38a | 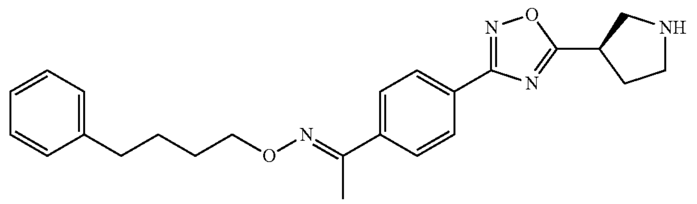 [SMILES: C/C(=N\OCCCCc1ccccc1)c1ccc(-c2noc([C@@H]3CCNC3)n2)cc1] |
| 38b | 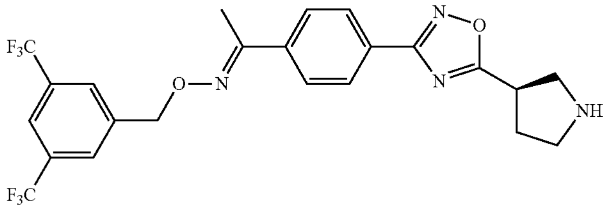 [SMILES: C/C(=N\OCc1cc(C(F)(F)F)cc(C(F)(F)F)c1)c1ccc(-c2noc([C@@H]3CCNC3)n2)cc1] |
| 38c | 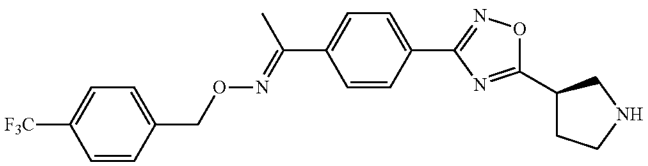 [SMILES: C/C(=N\OCc1ccc(C(F)(F)F)cc1)c1ccc(-c2noc([C@@H]3CCNC3)n2)cc1] |
| 38d | 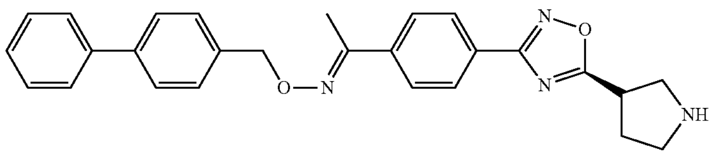 |

TABLE 1-continued
| Examples of Formula I Compounds | |
|---|---|
| Compound | Structure |
| 38g | 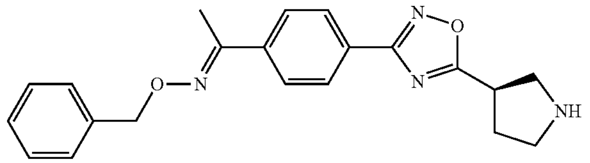 [SMILES: C/C(=N\OCc1ccccc1)c1ccc(-c2noc([C@@H]3CCNC3)n2)cc1] |
| 38h | 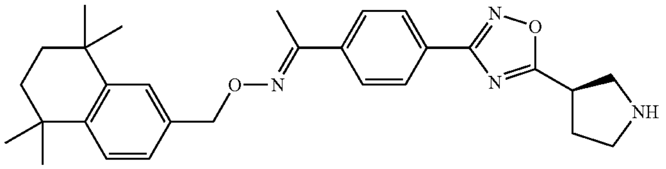 [SMILES: C/C(=N\OCc1ccc2c(c1)C(C)(C)CCC2(C)C)c1ccc(-c2noc([C@@H]3CCNC3)n2)cc1] |
| 38i | 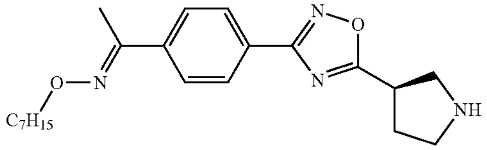 |
| 38j | 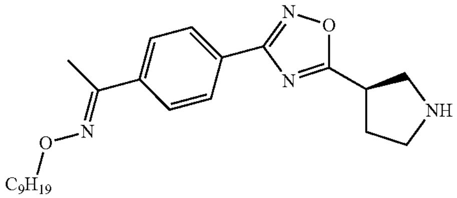 |
| 38k | 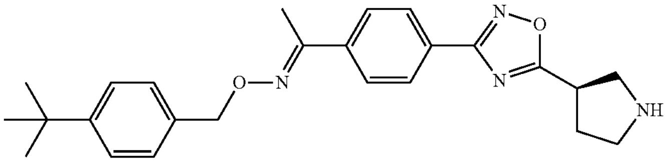 [SMILES: C/C(=N\OCc1ccc(C(C)(C)C)cc1)c1ccc(-c2noc([C@@H]3CCNC3)n2)cc1] |
| 38l | 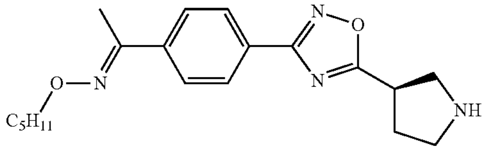 |
| 38n | 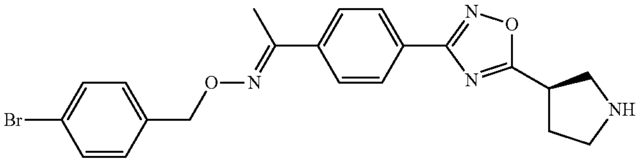 [SMILES: C/C(=N\OCc1ccc(Br)cc1)c1ccc(-c2noc([C@@H]3CCNC3)n2)cc1] |
| 38o | 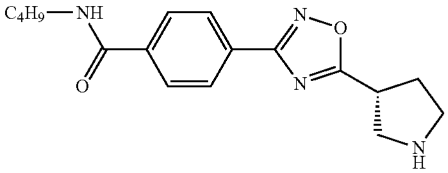 |

TABLE 1-continued
| Examples of Formula I Compounds | |
|---|---|
| Compound | Structure |
| 38p | 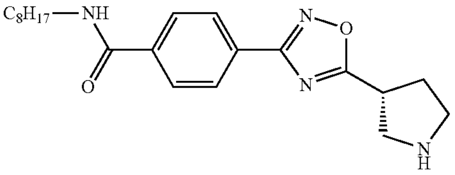 |
| 40a | 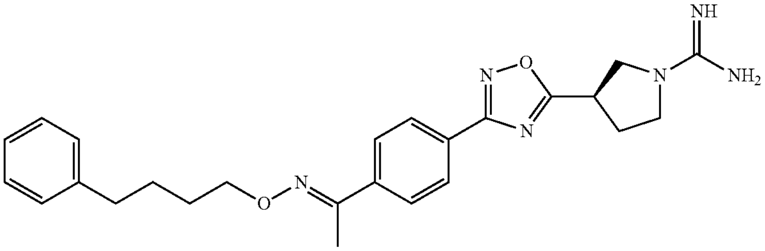 [SMILES: C/C(=N\OCCCCc1ccccc1)c1ccc(-c2noc([C@@H]3CCN(C(=N)N)C3)n2)cc1] |
| 40b | 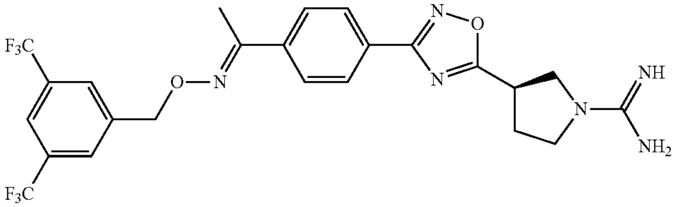 [SMILES: C/C(=N\OCc1cc(C(F)(F)F)cc(C(F)(F)F)c1)c1ccc(-c2noc([C@@H]3CCN(C(=N)N)C3)n2)cc1] |
| 40c | 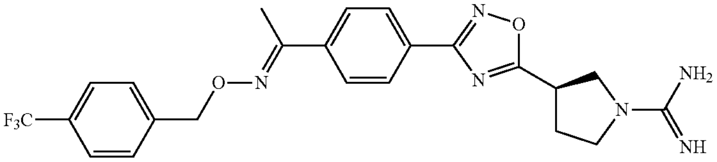 [SMILES: C/C(=N\OCc1ccc(C(F)(F)F)cc1)c1ccc(-c2noc([C@@H]3CCN(C(=N)N)C3)n2)cc1] |
| 40d | 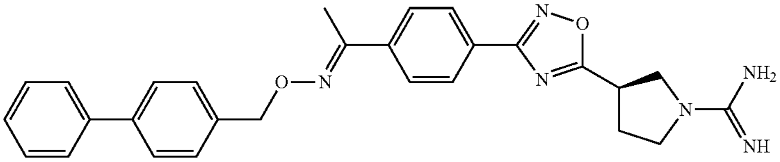 [SMILES: C/C(=N\OCc1ccc(-c2ccccc2)cc1)c1ccc(-c2noc([C@@H]3CCN(C(=N)N)C3)n2)cc1] |
| 40e | 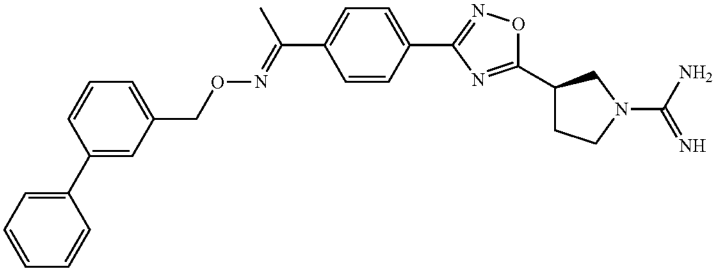 [SMILES: C/C(=N\OCc1cccc(-c2ccccc2)c1)c1ccc(-c2noc([C@@H]3CCN(C(=N)N)C3)n2)cc1] |
| 40f | 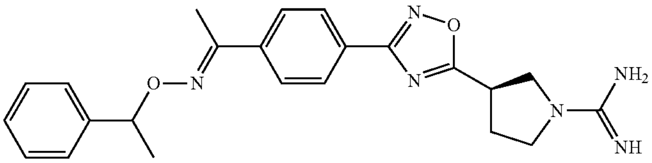 [SMILES: C/C(=N\OC(C)c1ccccc1)c1ccc(-c2noc([C@@H]3CCN(C(=N)N)C3)n2)cc1] |

TABLE 1-continued
| Examples of Formula I Compounds | |
| --- | --- |
| Compound | Structure |
| 40g | 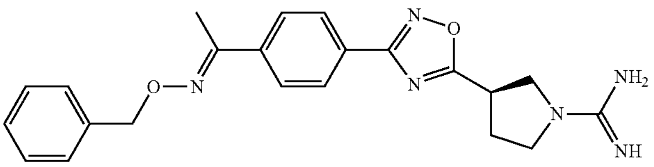 [SMILES: C/C(=N\OCc1ccccc1)c1ccc(-c2noc([C@@H]3CCN(C(=N)N)C3)n2)cc1] |
| 40h | 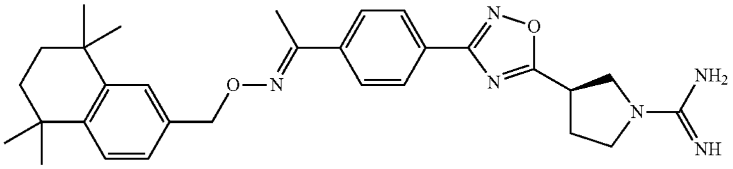 [SMILES: C/C(=N\OCc1ccc2c(c1)C(C)(C)CCC2(C)C)c1ccc(-c2noc([C@@H]3CCN(C(=N)N)C3)n2)cc1] |
| 40i | 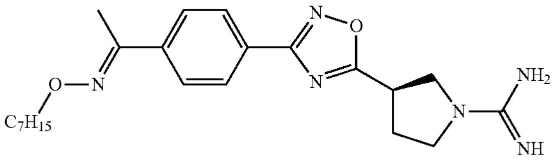 |
| 40j | 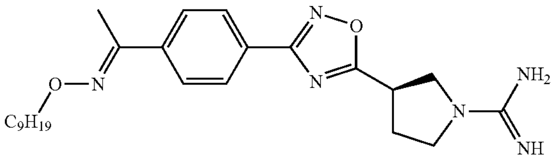 |
| 40k | 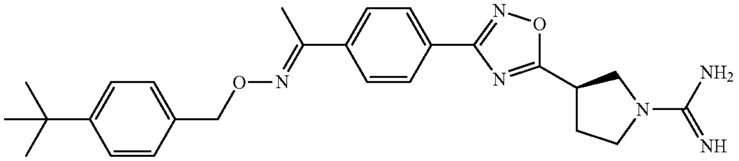 [SMILES: C/C(=N\OCc1ccc(C(C)(C)C)cc1)c1ccc(-c2noc([C@@H]3CCN(C(=N)N)C3)n2)cc1] |
| 40l | 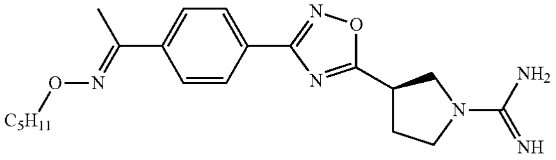 |
| 40m | 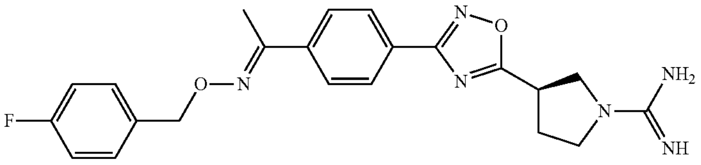 [SMILES: C/C(=N\OCc1ccc(F)cc1)c1ccc(-c2noc([C@@H]3CCN(C(=N)N)C3)n2)cc1] |
| 40n | 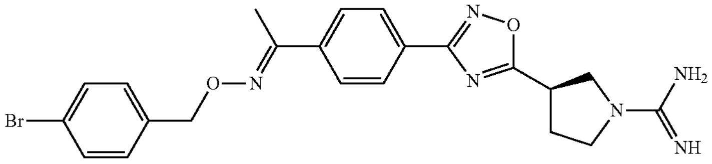 [SMILES: C/C(=N\OCc1ccc(Br)cc1)c1ccc(-c2noc([C@@H]3CCN(C(=N)N)C3)n2)cc1] |

TABLE 1-continued

| Examples of Formula I Compounds | |
|---|---|
| Compound | Structure |
| 40p | 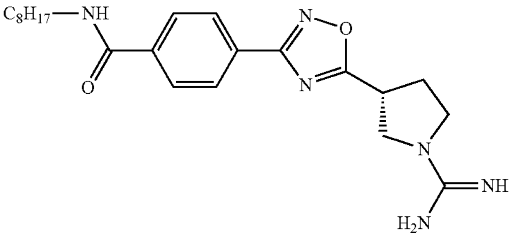 |

Pharmaceutical Composition

The disclosure also provides a pharmaceutical composition comprising a therapeutically effective amount of one or more compounds according to Formula I or a pharmaceutically acceptable salt, stereoisomer, and/or tautomer thereof in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Table 1 or a pharmaceutically acceptable salt, stereoisomer, and/or tautomer thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound (or a pharmaceutically acceptable salt, stereoisomer, and/or tautomer thereof that is administered is governed by such considerations, and is the minimum amount necessary to induce dose dependent lymphopenia and a modest decrease in plasma S1P, or to inhibit SPNS2 activity, or both. Such amount may be below the amount that is toxic to normal cells, or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment such dosage forms contain from about 5 mg to about 50 mg of a compound (or a pharmaceutically acceptable salt, stereoisomer, or tautomer thereof) of the present disclosure.

The disclosed compositions can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

Also encompassed by the present disclosure are pharmaceutical compositions suitable for single unit dosages that comprise a compound of the disclosure or its pharmaceutically acceptable stereoisomer, salt, or tautomer and a pharmaceutically acceptable carrier.

Compositions suitable for oral use may be prepared according to any method known to the art for the manufacture of pharmaceutical compositions. For instance, liquid formulations of the inventive compounds contain one or more agents selected from the group consisting of sweetening agents, flavoring agents, coloring agents and preserving agents in order to provide pharmaceutically palatable preparations of the SPNS2 inhibitor.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Methods of Use

S1P gradients are chemotactic, a property that enables correct positioning of immune cells, and they help to maintain endothelial barrier integrity. Accordingly, S1P gradients are manipulated for therapeutic benefit using Formula I compounds because they target the endothelial S1P exporter, SPNS2.

Thus, in one embodiment, the disclosure provides a method of inhibiting spinster homolog 2 (SPNS2). The method comprises contacting SPNS2 with an effective amount of a compound as described herein. In some embodiments, the contacting occurs in vitro. In other embodiments, the contacting occurs ex vivo or in vivo.

Another embodiment is a method of treating a patient afflicted by a neoplastic disease, comprising administering to the patient a therapeutically effective amount a compound as described herein. In some embodiments, the neoplastic disease is metastatic neoplasms.

An additional embodiment is a method of treating a patient afflicted with an allergic disease, comprising administering to the patient a therapeutically effective amount of a compound as described herein. An illustrative allergic disease is asthma.

Formula I compounds also are useful in a method of treating a patient afflicted with an autoimmune disease, comprising administering to the patient a therapeutically effective amount of the compound. In various embodiments, the autoimmune disease is chosen from multiple sclerosis, type I diabetes, inflammatory bowel diseases, Crohn's disease, ulcerative colitis, Grave's disease, Addison's disease, dermatomyositis, myasthenia gravis, systemic lupus erythematosus, scleroderma, and psoriasis. An exemplary autoimmune disease is multiple sclerosis. In accordance with some embodiments, multiple sclerosis comprises one or more progressive forms of multiple sclerosis as well as the remitting relapsing form of the disease.

Additional embodiments include a method of treating a patient afflicted with atherosclerosis or pulmonary arterial hypertension. The method comprises administering to the patient a therapeutically effective amount of a compound as described herein.

LITERATURE CITED IN THE DISCLOSURE

1. Chun J, Brinkmann V. A mechanistically novel, first oral therapy for multiple sclerosis: the development of fingolimod (FTY720, Gilenya). *Discovery Medicine* 12, 213-228 (2011) PMC3694367.
2. Cusack K P, Stoffel R H. S1P(1) receptor agonists: Assessment of selectivity and current clinical activity. *Current Opinion Drug Discovery & Development* 13, 481-488 (2010).
3. Schwab S R, Pereira J P, Matloubian M, Y. Xu Y, Huang Y, Cyster J G. Lymphocyte sequestration through S1P lyase inhibition and disruption of S1P gradients. *Science* 309, 1735-1739 (2005).
4. Mendoza A, Breat B, Ramoz-Perez W D, Pitt L A, Gobert M, Sunkara M, Lafaille J J, Morris A J, Schwab S R. The transporter SPNS2 is required for secretion of lymph but not plasma sphingosine-1-phosphate. *Cell Reports* 2, 1104-1110 (2012) PMC3616496.
5. Vu T M, Ishizu A-N, Foo J C, Toh X R, Zhang F, Whee D M, Torta F, Cazenave-Gassiot A, Matsumura T, Kim S, To S-AES, Suda T, Silver D L, Wenk M R, Nguyen L N. MFSD2B is essential for the sphingosine-1-phosphate export in erythrocytes and platelets. *Nature* 550, 524-528 (2017).
6. Kobayashi N, Kawasaki-Nishi S, Otsuka M, Hisano Y, Yamaguchi A, Nishi T. MSFD2B is a sphingosine 1-phosphate transporter in erythroid cells. *Scientific Reports* 8, 4969 (2018).
7. Camerer E, Regard J B, Cornelisssen I, Srinivasan Y, Duong D N, Palmer D, Pham T H, Wong J S, Pappu R, Coughlin S R. Sphingosine-1-phosphate in the plasma compartment regulates basal and inflammation-induced vascular leak in mice. *J Clinical Investigation* 119, 1871-1879 (2009).
8. Xiong Y, Hla T. S1P control of endothelial integrity. *Current Topics in Microbiology & Immunology* 378, 85-105 (2014) PMC4240614.
9. Yanagida K, Hla T. Vascular and immunobiology of the circulatory sphingosine 1-phosphate gradient. *Annual Review Physiology* 79, 67-91 (2016) PMC5500220.
10. Schumann J, Grevot A, Ledieu D, Wolf A, Schubart A, Piaia A, Sutter E, Côté S, Beerli C, Pognan F, Billich A, Moulin P, Walker U J. Reduced activity of sphingosine-1-phosphate lyase induces podocyte-related glomerular proteinuria, skin irritation, and platelet activation. *Toxicologic Pathology* 43, 694-703 (2015).
11. Prasad R, Hadjidemetriou I, Maharaj A, Meimaridou E, Buonocore F, Saleem M, Hurcombe J, Bierzynska A, Barbagelata E, Bergadá I, Cassinelli H, Das U, Krone R, Hacihamdioglu B, Sari E, Yesilkaya E, Storr H L, Clemente M, Fernandez-Cancio M, Camats N, Ram N, Achermann J C, Van Veldhoven P P, Guasti L, Braslavsky D, Guran T, Metherell L A. Sphingosine 1-phosphate lyase mutations cause primary adrenal insufficiency and steroid-resistant nephrotic syndrome. *J Clinical Investigation* 127, 942-953 (2017) PMC5330744.
12. Lovric S, Goncalves S, Gee H Y, Oskouian B, Srinivas H, Choi W I, Shril S, Ashraf S, Tan W, Rao J, Airik M, Schapiro D, Braun D A, Sadowski C E, Widmeier E, Jobst-Schwan T, Schmidt J M, Girik V, Capitani G, Suh J H, Lachaussée N, Arrondel C, Patat J, Gribouval O, Furlano M, Boyer O, Schmitt A, Vuiblet V, Hashmi S, Wilcken R, Bernier F P, Innes A M, Parboosingh J S, Lamont R E, Midgley J P, Wright N, Majewski J, Zenker M, Schaefer F, Kuss N, Greil J, Giese T, Schwarz K, Catheline V, Schanze D, Franke I, Sznajer Y, Truant A S, Adams B, Désir J, Biemann R, Pei Y, Ars E, Lloberas N, Madrid A, Dharnidharka V R, Connolly A M, Willing M C, Cooper M A, Lifton R P, Simons M, Riezman H, Antignac C, Saba J D, Hildebrandt F. Mutations in sphingosine-1-phosphate lyase cause nephrosis with ichthyosis and adrenal insufficiency. *J Clinical Investigation* 127, 912-928 (2017) PMC5330730.
13. van der Weyden L, Arends M J, Campbell A D, Bald T, Wardle-Jones H, Griggs N, Velasco-Herrera M D, Tuting T, Sansom O J, Karp N A, Clare S, Gleeson D, Ryder E, Galli A, Tuck E, Cambridge E L, Voet T, Macaulay I C, Wong K, Sanger Mouse Genetics Project, Spiegel S, Speak A O, Adams D J. Genome-wide in vivo screen identifies novel new regulators for metastatic colonization. *Nature* 541, 233-236 (2017) PMC5603286.

EXAMPLES

The present disclosure will be more fully understood by reference to the following examples. The examples should not, however, be construed as limiting the scope of the present disclosure.

Scheme 1-Example Synthesis for 3-(3-4-decylphenyl)-1,2,4-oxadiazol-5-yl)azetidine-1-carboximidamide hydrochloride (7b)

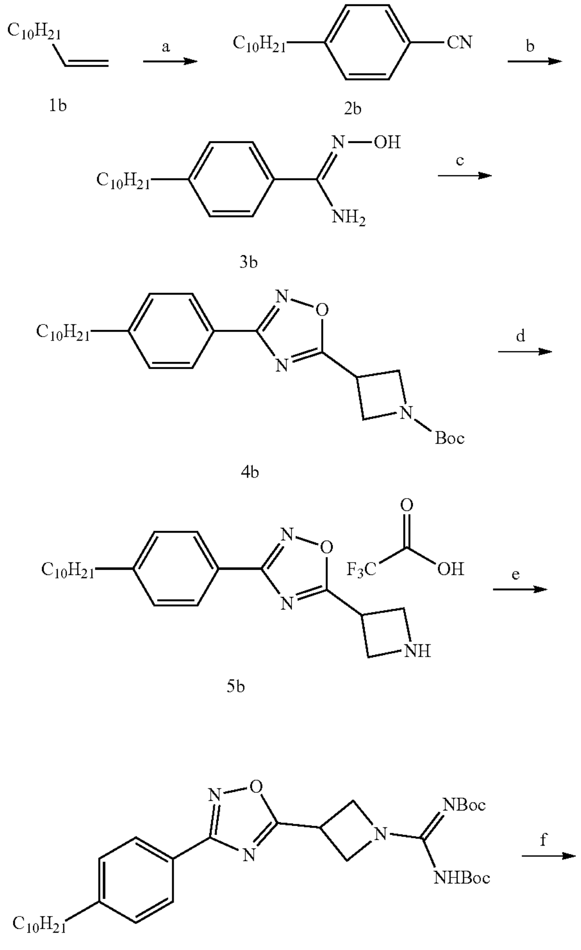

1b 2b 3b 4b 5b 6b

-continued

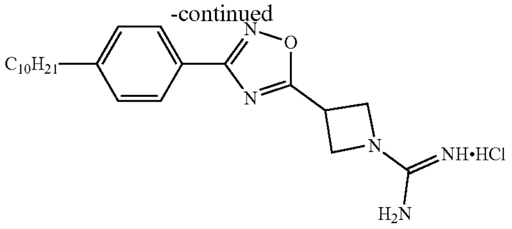

7b a. i) 9-BBN (1.5 equiv), THF, reflux ii) 4-iodobenzonitrile (1 equiv), $Pd(PPh_3)_2Cl_2$ (0.05 equiv), KOH (3 equiv), reflux; b. $NH_2OH$•HCl (2 equiv), TEA (3 equiv), EtOH, reflux; c. N-Boc-β-amino acid (1.1 equiv), HCTU (1.1 equiv), DIEA (1.8 equiv), DMF, 100° C.; d. TFA (30 equiv), DCM, rt; e. N,N'-Di-Boc-1H-pyrazole-1-carboxamidine (1 equiv), DIEA (15 equiv), MeCN, 50° C. μW; f. $HCl_{(g)}$, MeOH, rt.

General Procedure 1: Suzuki-Miyaura Cross Coupling

To a round bottom flask a containing alkene (1.1 equiv) in THF was added 9-BBN (1.5 equiv) and then heated to reflux until consumption of alkene as monitored by TLC (30-60 minutes). Aryl iodide (1 equiv) and $Pd(dppf)Cl_2$ (0.05 equiv) were then added to the mixture, followed by dropwise addition of a 3M $KOH_{(aq)}$ solution (3 equiv). The resulting mixture was then heated to reflux until consumption of aryl iodide as monitored by TLC (2-6 hours). Upon cooling to room temperature, the reaction mixture was filtered over a pad of celite, diluted in ethyl acetate, and washed with a brine solution. The organic layer was then dried over sodium sulfate and concentrated in vacuo to afford the crude product as a yellow oil, which was then purified by column chromatography with an appropriate hexanes:ethyl acetate solvent system to afford the pure product (2a-c, 4a, 4c, 4d).

General Procedure 2: Amidoxime Synthesis

To a round bottom flask containing ethanol was added 4-decylbenzonitrile (2b) (1 equiv), hydroxylamine hydrochloride (2 equiv), and triethylamine (3 equiv) under ambient air. The reaction mixture was then heated to reflux until complete as monitored by TLC (1-4 hours). The resulting solution was allowed to cool to room temperature, followed by concentration in vacuo, to afford the crude mixture as a solid. Purification by column chromatography (0-20% ethyl acetate in dichloromethane) afforded the pure amidoxime product (3a-3d).

General Procedure 3: 1,2,4-Oxadiazole Synthesis

Amidoxime (1 equiv), N-Boc protected β-amino acid (1.1 equiv), and DIEA (1.8 equiv) were added to a round bottom flask containing DMF at room temperature. HCTU (1.1 equiv) was then added and the resulting mixture was heated to 100° C. until completion as monitored by TLC (6-16 hours). Upon cooling to room temperature, the resulting mixture was diluted in ethyl acetate and washed with a saturated lithium bromide solution. The resulting aqueous layer was then extracted with ethyl acetate. The organic layers were then combined and washed with a brine solution, followed by drying over anhydrous sodium sulfate. Concentration in vacuo afforded the crude product, which was then purified by column chromatography using the appropriate ethyl acetate:hexanes solvent system to afford the pure 1,2,4-oxadiazole product (4a-u).

General Procedure 4: TFA Boc Deprotection

To a round bottom flask containing Boc-protected secondary amine (4b-4u) or diBoc protected guanidine compounds (6a-6u) (1 equiv) dissolved in dichloromethane was added TFA (30 equiv). The resulting solution was allowed to stir until consumption of starting material as monitored by TLC (1-6 hours). Concentration in vacuo and filtration of the resulting off-white solid, followed by washing with diethyl ether afforded either the secondary amine TFA salt (5b-u) or guanidine TFA salt compound (7b-7u).

General Procedure 5: Guanylation

TFA salt (5b-5xb) (1 equiv), DIEA (15 equiv), and (Z)-tert-butyl (((tert-butoxycarbonyl)imino)(1H-pyrazol-1-yl)methyl)carbamate (1 equiv) were added to a microwave vial containing MCCN at room temperature. The resulting solution was then placed in a CEM microwave synthesized and heated to 50° C. for 3 hours. After cooling down to room temperature, the solution was concentrated in vacuo to afford the crude mixture as a yellow oil, which was then purified by column chromatography using the appropriate ethyl acetate and hexanes solvent system to afford the diBoc protected guanidino compounds (6b-6xb).

General Procedure 6: HCl Boc Deprotection

DiBoc protected guanidino compound (6b-6xb) (1 equiv) was added to a round bottom flask and dissolved in methanol. $HCl_{(g)}$ was then bubbled into the solution for 1 minute. The resulting solution was allowed to stir at room temperature until consumption of Boc protected starting material as monitored by TLC (30-60 minutes). Concentration in vacuo afforded a white to off-white solid, which was then washed with diethyl ether to afford the pure guanidine compound as an HCl salt (7b-7xb).

4-undecylbenzonitrile (2a)

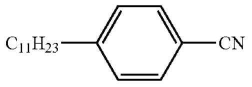

Synthesized from 4-iodobenzonitrile according to General Procedure 1. Purified by silica chromatography (60% ethyl acetate in hexanes). White solid (85%, 1500 mg). $^1$H NMR (400 MHz, $CDCl_3$) δ 7.53 (d, J=7.98, 2H), 7.26 (d, J=8.11, 2H), 2.64 (t, J=7.55, 2H), 1.60 (p, J=6.72, 2H), 1.33-1.22 (m, 16H), 0.87 (t, J=6.85, 3H); $^{13}$C NMR (101 MHz, $CDCl_3$) δ 148.61, 132.08, 129.21, 119.18, 109.49, 36.14, 31.96, 31.02, 29.67, 29.58, 29.46, 29.39, 29.22, 22.74, 14.17.

4-decylbenzonitrile (2b)

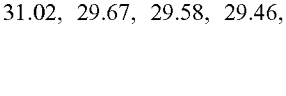

Synthesized from 4-iodobenzonitrile according to General Procedure 1. Purified by silica chromatography (2% ethyl acetate in hexanes). White solid (62%, 980 mg). $^1$H NMR (400 MHz, $CDCl_3$) δ 7.54 (d, J=8.2 Hz, 2H), 7.20 (d, J=8.2 Hz, 2H), 4.89 (brs, 2H), 2.62 (t, J=7.7 Hz, 2H), 1.67-1.55 (m, 2H), 1.37-1.19 (m, 14H), 0.88 (t, J=6.7 Hz, 3H). $^{13}$C NMR (101 MHz, $CDCl_3$) δ 152.8, 145.3, 129.9, 128.8, 125.9, 35.9, 32.0, 31.5, 29.8, 29.7, 29.6, 29.5, 29.4, 22.8, 14.3.

4-nonylbenzonitrile (2c)

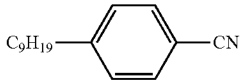

Synthesized from 4-iodobenzonitrile according to General Procedure 1. Purified by silica chromatography (10% ethyl acetate in hexanes). White solid (69%, 938 mg). $^{1}$H NMR (400 MHz, $CDCl_3$) δ 7.54 (d, J=7.89, 2H), 7.26 (d, J=8.14, 2H), 2.64 (t, J=7.95, 2H), 1.60 (p, J=7.58, 2H), 1.33-1.21 (m, 12H), 0.87 (t, J=6.70, 3H); $^{13}$C NMR (101 MHz, $CDCl_3$) δ 148.67, 132.13, 129.25, 119.26, 109.51, 36.18, 31.94, 31.06, 29.56, 29.49, 29.36, 29.25, 22.74, 14.19.

N'-hydroxy-4-iodobenzimidamide (3a)

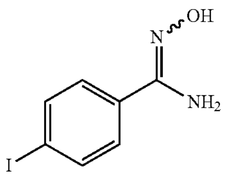 [SMILES: NC(=NO)c1ccc(I)cc1]

Synthesized according to General Procedure 2 using 4-iodobenzonitrile instead of 4-decylbenzonitrile. Isolated as a mixture of Z:E (7:1). White solid, 191 mg (66%) yield. $^{1}$H NMR (400 MHz, $CDCl_3$) δ 7.75 (d, J=8.6 Hz, 2H), 7.41 (d, J=8.6 Hz, 2H).

N'-hydroxy-4-iodobenzimidamide (3b)

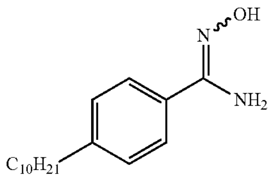

Synthesized according to General Procedure 2. Isolated as a mixture of Z:E (20:1). White solid, 560 mg (76%) yield. $^{1}$H NMR (400 MHz, $CDCl_3$) δ 7.54 (d, J=8.2 Hz, 2H), 7.20 (d, J=8.2 Hz, 2H), 4.89 (brs, 2H), 2.62 (t, J=7.7 Hz, 2H), 1.66-1.55 (m, 2H), 1.37 (m, 14H), 0.88 (t, J=6.7 Hz, 3H).

N'-hydroxy-4-undecylbenzimidamide (3c)

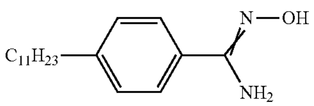

Synthesized according to General Procedure 2. Purified by silica chromatography (10% ethyl acetate in hexanes). White solid (45%, 774 mg). $^{1}$H NMR (400 MHz, $CDCl_3$) δ 7.52 (d, J=8.20, 2H), 7.25 (d, J=8.1, 2H), 1.58 (d, J=7.21, 2H), 1.31-1.19 (m, 16H), 0.85 (t, J=8.82, 3H); $^{13}$C NMR (101 MHz, $CDCl_3$) δ 148.61, 132.08, 129.21, 119.18, 109.49, 36.14, 31.96, 31.02, 29.67, 29.58, 29.46, 29.39, 29.22, 22.74, 14.17.

N'-hydroxy-4-nonylbenzimidamide (3d)

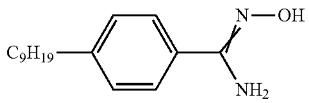

Synthesized according to General Procedure 2. Purified by silica chromatography (60% ethyl acetate in hexanes). White solid (69%, 741 mg). $^{1}$H NMR (400 MHz, Methanol-$d_4$) δ 7.54 (d, J=8.38. 2H), 7.21 (d, J=8.78, 2H), 2.63 (t, J=7.48, 2H), 1.62 (p, J=7.44, 2H), 1.35-1.26 (m, 12H), 0.90 (t, J=7.15, 3H); $^{13}$C NMR (101 MHz, Methanol-$d_4$) δ 155.67, 145.98, 131.54, 129.48, 127.24, 36.66, 33.06, 32.57, 30.70, 30.61, 30.45, 30.30, 23.73, 14.45.

tert-butyl 3-(3-(4-iodophenyl)-1,2,4-oxadiazol-5-yl) azetidine-1-carboxylate (4a')

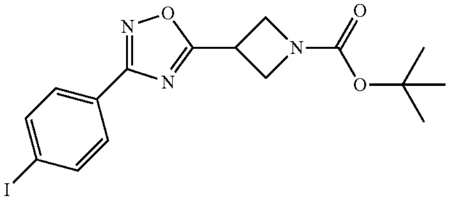 [SMILES: CC(C)(C)OC(=O)N1CC(c2nc(-c3ccc(I)cc3)no2)C1]

Synthesized according to General Procedure 3. Passed through a silica plug, eluting with 20% EtOAc in hexanes. Crude mixture dried in vacuo and carried forward to the next reaction without further purification.

tert-butyl 3-(3-(4-undecylphenyl)-1,2,4-oxadiazol-5-yl)azetidine-1-carboxylate (4a)

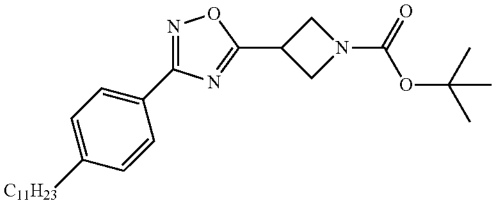

Synthesized according to General Procedure 1. Purified by silica chromatography (10% EtOAc in hexanes). Colorless oil, 162 mg (62%) yield. $^{1}$H NMR (400 MHz, $CDCl_3$) δ 7.98 (d, J=8.1 Hz, 2H), 7.29 (d, J=8.1 Hz, 2H), 4.41-4.29 (m, 4H), 4.09-4.00 (m, 1H), 2.66 (t, J=7.7 Hz, 2H), 1.68-1.59 (m, 2H), 1.47 (brs, 9H), 1.36-1.21 (m, 16H), 0.88 (t, J=6.8 Hz, 2H). $^{13}$C NMR (100 MHz, $CDCl_3$) δ 168.7, 156.0, 146.9, 129.1, 127.5, 123.9, 80.3, 53.2, 32.0, 31.4, 29.8, 29.8, 29.7, 29.6, 29.5, 29.4, 28.5, 29.4, 28.5, 25.9, 22.8, 14.3. HRMS: (ESI) $[M+H]^+$ calc. for $C_{22}H_{34}N_3O$, 356.2696, observed, 356.2690.

tert-butyl 3-(3-(4-decylphenyl)-1,2,4-oxadiazol-5-yl)azetidine-1-carboxylate (4b)

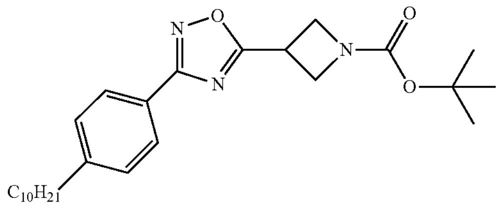

Synthesized according to General Procedure 1. Purified by silica chromatography (10% EtOAc in hexanes). Colorless oil, 130 mg (63%) yield. $^{1}$H NMR (400 MHz, $CDCl_3$) δ 7.99 (d, J=8.4 Hz, 2H), 7.29 (d, J=8.4 Hz, 2H), 4.40-4.29 (m, 4H), 4.14-3.99 (m, 1H), 2.66 (t, J=7.7 Hz, 2H), 1.88-1.78 (m, 1H), 1.68-1.58 (m, 3H), 1.47 (brs, 9H), 1.36-1.21 (m, 14H), 0.88 (t, J=6.8 Hz, 3H). $^{13}$C NMR (100 MHz, $CDCl_3$) δ 178.8, 168.7, 156.0, 146.8, 129.0, 127.5, 123.9, 80.2, 53.5, 36.0, 32.0, 31.3, 29.7, 29.6, 29.5, 29.4, 29.3, 28.4, 25.8, 22.7, 14.2.

tert-butyl 3-(3-(4-nonylphenyl)-1,2,4-oxadiazol-5-yl)azetidine-1-carboxylate (4c)

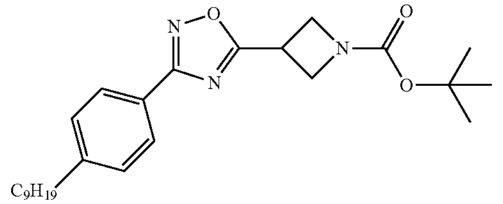

Synthesized according to General Procedure 1. Purified by silica chromatography (15% EtOAc in hexanes). Colorless oil, 172 mg (61%) yield. $^{1}$H NMR (400 MHz, $CDCl_3$) δ 7.98 (d, J=9.4 Hz 2H), 7.29 (d, J=9.4 Hz, 2H), 4.42-4.28 (m, 4H), 4.09-4.00 (m, 1H), 2.66 (t, J=7.7 Hz, 2H), 1.68-1.59 (m, 2H), 1.47 (brs, 9H), 1.38-1.19 (m, 12H), 0.87 (t, J=6.3 Hz, 3H). $^{13}$C NMR (100 MHz, $CDCl_3$) δ 178.9, 168.7, 156.0, 146.8, 129.1, 127.5, 123.9, 80.3, 53.3, 36.1, 32.0, 31.3, 29.7, 29.4, 29.4, 28.5, 25.9, 22.8, 14.2. HRMS: (ESI) $[M+Na]^+$ calc. for $C_{25}H_{37}N_3NaO_3$, 450.2727, observed, 450.2698.

tert-butyl 3-(3-(4-octylphenyl)-1,2,4-oxadiazol-5-yl)azetidine-1-carboxylate (4d)

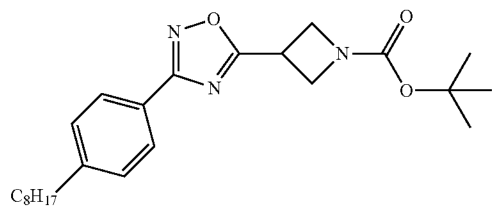

Synthesized according to General Procedure 1. Purified by silica chromatography (20% EtOAc in hexanes). Colorless oil, 60 mg (52%) yield. $^{1}$H NMR (400 MHz, $CDCl_3$) δ 7.99 (d, J=8.0 Hz, 2H), 7.29 (d, J=8.0 Hz, 2H), 4.42-4.29 (m, 4H), 4.09-4.00 (m, 1H), 2.66 (t, J=7.7 Hz, 2H), 1.68-1.59 (m, 2H), 1.47 (brs, 9H), 1.38-1.21 (m, 10H), 0.88 (t, J=6.7 Hz, 3H). $^{13}$C NMR (100 MHz, $CDCl_3$) δ 178.8, 168.6, 155.9, 146.7, 128.9, 127.4, 123.8, 80.1, 53.2, 31.8, 31.2, 29.4, 29.2, 29.2, 28.3, 25.7, 22.7, 14.1.

tert-butyl (S)-3-(3-(4-iodophenyl)-1,2,4-oxadiazol-5-yl)pyrrolidine-1-carboxylate (4e)

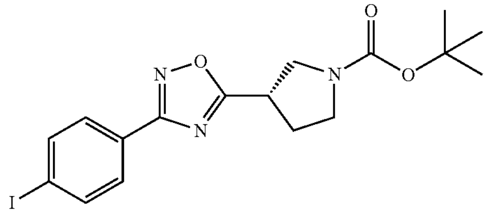 [SMILES: CC(C)(C)OC(=O)N1CC[C@H](c2nc(-c3ccc(I)cc3)no2)C1]

Synthesized according to General Procedure 3. Purified by silica chromatography (16% EtOAc in hexanes). Off-white solid, 280 mg (55%) yield. $^{1}$H NMR (400 MHz, $CDCl_3$) δ 7.83-7.74 (m, 4H), 3.91-3.43 (m, 7H), 2.44-2.27 (m, 2H), 1.46 (s, 9H). $^{13}$C NMR (100 MHz, $CDCl_3$) δ 179.8, 167.9, 154.2, 138.2, 129.0, 126.2, 98.1, 79.9, 49.5, 45.1, 36.7, 30.5, 29.7, 28.6. HRMS: (ESI) $[M+Na]^+$ calc. for $C_{17}H_{20}IN_3NaO_3$, 464.0442, observed, 464.0415.

tert-butyl (S)-3-(3-(4-decylphenyl)-1,2,4-oxadiazol-5-yl)pyrrolidine-1-carboxylate (4e')

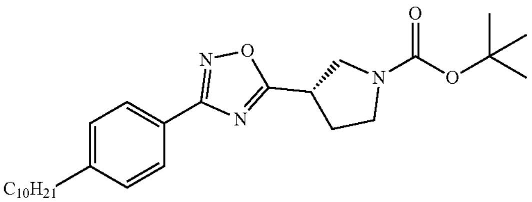

Synthesized according to General Procedure 1. Unable to separate from unreacted starting material, carried forward crude to the next reaction.

tert-butyl (S)-3-(3-(4-decylphenyl)-1,2,4-oxadiazol-5-yl)piperidine-1-carboxylate (4f)

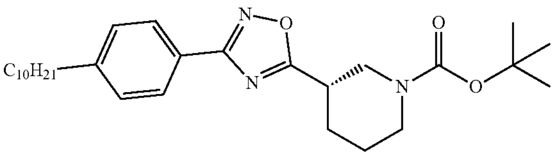

Synthesized according to General Procedure 3. Purified by silica chromatography (16% EtOAc in hexanes). Yellow solid, 252 mg (74%) yield. $^{1}$H NMR (400 MHz, $CDCl_3$) δ 7.98 (d, J=8.3 Hz, 2H), 7.28 (d, J=8.3 Hz, 2H), 4.55-4.11 (m, 1H), 4.02-3.92 (m, 1H), 3.43-3.10 (m, 2H), 3.05-2.87 (m, 1H), 2.65 (t, J=7.7 Hz, 2H), 2.31-2.19 (m, 1H), 1.96-1.77 (m, 2H), 1.69-1.52 (m, 3H), 1.46 (s, 9H), 1.39-1.17 (m, 14H), 0.88 (t, J=6.8 Hz, 3H). $^{13}$C NMR (100 MHz, $CDCl_3$) δ 179.8, 168.3, 154.6, 146.6, 129.0, 127.5, 124.2, 80.1, 46.5, 43.7, 36.0, 34.9, 32.0, 31.3, 29.7, 29.7, 29.6, 29.4, 29.3, 28.7, 28.5, 24.1, 22.8, 14.2. HRMS: (ESI) $[M+H]^+$ calc. for $C_{24}H_{36}N_3O_3$, 414.2751, observed, 414.2759.

tert-butyl (R)-3-(3-(4-decylphenyl)-1,2,4-oxadiazol-5-yl)pyrrolidine-1-carboxylate (4g)

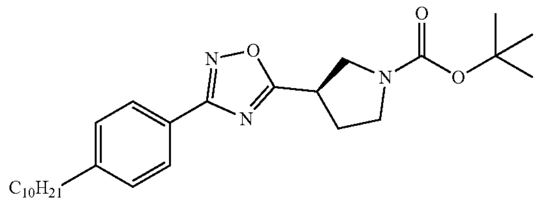

Synthesized according to General Procedure 3. Purified by silica chromatography (16% EtOAc in hexanes). Off-white solid, 148 mg (75%) yield. $^1$H NMR (400 MHz, $CDCl_3$) δ 7.97 (d, J=8.3 Hz, 2H), 7.28 (d, J=8.3 Hz, 2H), 3.95-3.41 (m, 6H), 2.65 (t, J=7.7 Hz, 2H), 2.44-2.29 (m, 2H), 1.68-1.58 (m, 2H), 1.48 (brs, 9H), 0.88 (t, J=6.8 Hz, 3H). $^{13}$C NMR (100 MHz, $CDCl_3$) δ 179.4, 168.4, 154.2, 146.6, 128.9, 127.4, 124.0, 79.8, 49.4, 45.1, 36.6, 36.0, 35.8, 31.9, 30.5, 30.4, 29.6, 29.6, 29.5, 29.4, 29.3, 28.5, 22.7, 14.2. HRMS: (ESI) $[M+H]^+$ calc. for $C_{27}H_{41}N_3NaO_3$, 478.3040, observed, 478.3065.

tert-butyl (R)-3-(3-(4-decylphenyl)-1,2,4-oxadiazol-5-yl)piperidine-1-carboxylate (4h)

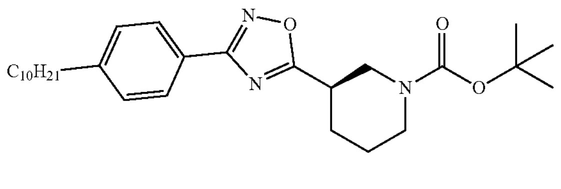

Synthesized by General Procedure 3. Purified by silica chromatography (16% EtOAc in hexanes). Yellow solid, 322 mg (76%) yield. $^1$H NMR (400 MHz, $CDCl_3$) δ 7.98 (d, J=8.3 Hz 2H), 7.28 (d, J=8.3 Hz, 2H), 4.55-4.12 (m, 2H), 4.01-3.92 (m, 1H), 3.43-3.26 (m, 1H), 3.19-3.09 (m, 1H), 3.04-2.90 (m, 1H), 2.65 (t, J=7.8 Hz, 2H), 2.30-2.20 (m, 1H), 1.95-1.78 (m, 2H), 1.69-1.54 (m, 3H), 1.46 (brs, 9H), 1.38-1.19 (m, 14H), 0.88 (t, J=6.8 Hz). $^{13}$C NMR (100 MHz, $CDCl_3$) δ 179.7, 168.3, 154.5, 146.5, 129.0, 127.4, 124.2, 80.0, 46.7, 43.6, 36.0, 34.9, 32.0, 31.3, 29.7, 29.7, 29.6, 29.4, 29.3, 28.6, 28.4, 24.1, 22.8, 14.2. HRMS: (ESI) $[M+H]^+$ calc. for $C_{28}H_{44}N_3O_3$, 470.3377, observed, 470.3386.

tert-butyl 3-((3-(4-decylphenyl)-1,2,4-oxadiazol-5-yl)methyl)azetidine-1-carboxylate (4j)

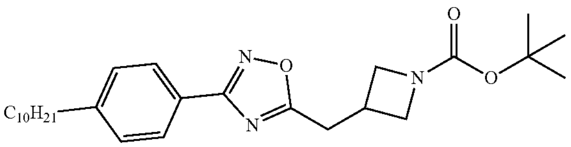

Synthesized according to General Procedure 3. Purified by silica chromatography (16% EtOAc in hexanes). Off-white solid, 160 mg (49%) yield. $^1$H NMR (400 MHz, $CDCl_3$) δ 7.96 (d, J=8.2 Hz, 2H), 7.28 (d, J=8.2 Hz, 2H), 4.16 (t, J=8.5 Hz, 2H), 3.79-3.74 (m, 2H), 3.24-3.19 (m, 2H), 3.13-3.03 (m, 1H), 2.65 (t, J=7.8 Hz, 2H), 1.67-1.58 (m, 2H), 1.44 (brs, 9H), 1.37-1.20 (m, 14H), 0.88 (t, J=6.8 Hz, 3H). $^{13}$C NMR (100 MHz, $CDCl_3$) δ 177.2, 168.4, 156.2, 146.6, 128.9, 127.4, 124.0, 79.6, 53.7, 36.0, 31.9, 31.3, 30.9, 29.6, 29.6, 29.5, 29.4, 29.3, 28.4, 26.4, 22.7, 14.2. HRMS: (ESI) $[M+Na]^+$ calc. for $C_{27}H_{41}N_3O_3Na$, 478.3046, observed, 478.2983.

tert-butyl 3-(3-(4-decylphenyl)-1,2,4-oxadiazol-5-yl) azepane-1-carboxylate (4k)

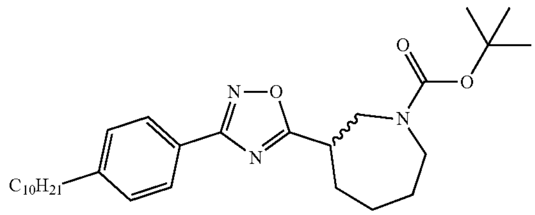

Synthesized according to General Procedure 3. Purified by silica chromatography (8% EtOAc in hexanes). Yellow oil, 125 mg (45%) yield. $^1$H NMR (400 MHz, $CDCl_3$) δ 7.98 (d, J=8.0 Hz, 2H), 7.28 (d, J=8.0 Hz, 2H), 4.34-4.00 (m, 1H), 3.82-3.66 (m, 1H), 3.60-3.29 (m, 2H), 3.27-3.07 (m, 1H), 2.65 (t, J=7.7 Hz, 2H), 2.18-2.06 (m, 1H), 2.01-1.82 (m, 3H), 1.75-1.53 (m, 4H), 1.50-1.42 (m, 9H), 1.37-1.21 (m, 14H), 0.88 (t, J=6.8 Hz, 3H). $^{13}$C NMR (100 MHz, $CDCl_3$) δ 180.8, 168.2, 155.5, 155.2, 146.5, 146.4, 129.0, 127.4, 124.3, 80.0, 79.7, 49.3, 49.3, 48.2, 47.7, 38.2, 37.5, 36.0, 32.0, 31.6, 31.4, 31.3, 29.7, 29.6, 29.4, 29.3, 28.5, 28.4, 28.3, 24.4, 24.2, 22.8, 14.2. HRMS: (ESI) $[M+Na]^+$ calc. for $C_{29}H_{46}N_3O_3$, 484.3534, observed, 484.3538.

tert-butyl (R)-3-((3-(4-decylphenyl)-1,2,4-oxadiazol-5-yl)methyl)pyrrolidine-1-carboxylate (4l)

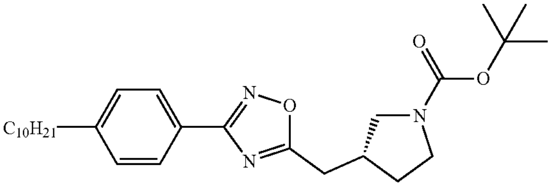

Synthesized according to General Procedure 3. Purified by silica chromatography (20% EtOAc in hexanes). Colorless oil, 121 mg (36%) yield. $^1$H NMR (400 MHz, $CDCl_3$) δ 7.97 (d, J=7.6 Hz, 2H), 7.29 (d, J=7.6 Hz, 2H), 3.76-3.28 (m, 3H), 3.19-2.95 (m, 3H), 2.82-2.69 (m, 1H), 2.66 (t, J=7.8 Hz, 2H), 2.18-2.08 (m, 1H), 1.76-1.58 (m, 3H), 1.47 (brs, 9H), 1.38-1.19 (m, 14), 0.88 (t, J=6.8 Hz, 3H). $^{13}$C NMR (100 MHz, $CDCl_3$) δ 178.0, 168.4, 154.5, 146.6, 129.0, 127.4, 124.1, 79.4, 51.1, 45.4, 36.9, 36.0, 32.0, 31.3, 30.8, 29.9, 29.7, 29.6, 29.5, 29.4, 29.3, 28.6, 22.8, 14.2. HRMS: (ESI) $[M+Na]^+$ calc. for $C_{28}H_{43}N_3NaO_3$, 492.3197, observed, 492.3200.

tert-butyl (S)-3-((3-(4-decylphenyl)-1,2,4-oxadiazol-5-yl)methyl)pyrrolidine-1-carboxylate (4p)

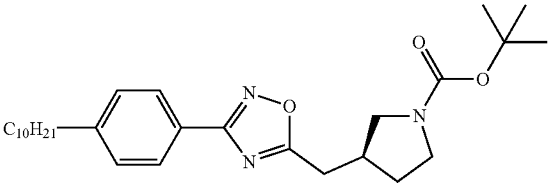

Synthesized by General Procedure 3. Purified by silica chromatography (20% EtOAc in hexanes). Yellow solid, 273 mg (64%) yield. $^1$H NMR (400 MHz, $CDCl_3$) δ 7.97 (d, J=7.6 Hz, 2H), 7.28 (d, J=7.6 Hz, 2H), 3.77-3.44 (m, 3H), 3.42-3.28 (m, 1H), 3.19-2.94 (m, 3H), 2.84-2.71 (m, 1H), 2.66 (t, J=7.7 Hz, 2H), 2.19-2.08 (m, 1H), 1.77-1.58 (m, 3H), 1.46 (brs, 9H), 1.38-1.19 (m, 14H), 0.88 (t, J=6.8 Hz, 3H). $^{13}$C NMR (100 MHz, $CDCl_3$) δ 178.0, 168.4, 154.5, 146.6, 129.0, 127.4, 124.1, 79.5, 50.8, 45.0, 36.8, 36.0, 32.0, 31.4, 31.3, 30.9, 29.9, 29.7, 29.7, 29.6, 29.4, 29.3, 28.6, 22.8, 14.2. HRMS: (ESI) $[M+Na]^+$ calc. for $C_{28}H_{43}N_3NaO_3$, 492.3197, observed, 492.3199.

tert-butyl (S)-3-((3-(4-decylphenyl)-1,2,4-oxadiazol-5-yl)methyl)piperidine-1-carboxylate (4q)

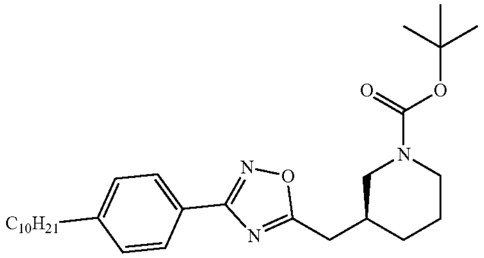

Synthesized according to General Procedure 3. Purified by silica chromatography (18% EtOAc in hexanes). Yellow oil, 280 mg (64%) yield. $^1$H NMR (400 MHz, $CDCl_3$) δ 7.98 (d, J=8.1 Hz, 2H), 7.27 (d, J=8.1 Hz, 2H), 4.16-3.79 (m, 2H), 2.99-2.76 (4H), 2.64 (t, J=7.7 Hz, 2H), 2.20-2.10 (m, 1H), 1.92-1.83 (m, 1H), 1.72-1.58 (m, 3H), 1.44 (brs, 9H), 1.36-1.19 (m, 14H), 0.87 (t, J=6.7 Hz, 3H). $^{13}$C NMR (100 MHz, $CDCl_3$) δ 178.0, 168.2, 154.6, 146.3, 128.8, 127.3, 124.1, 79.4, 48.8, 44.1, 35.9, 34.2, 31.9, 31.2, 30.3, 29.6, 29.5, 29.4, 29.3, 29.2, 22.6, 14.1. HRMS: (ESI) $[M+H]^+$ calc. for $C_{29}H_{46}N_3O_3$, 484.3534, observed, 484.3520.

tert-butyl (R)-3-(3-(3-decylphenyl)-1,2,4-oxadiazol-5-yl)pyrrolidine-1-carboxylate (4t)

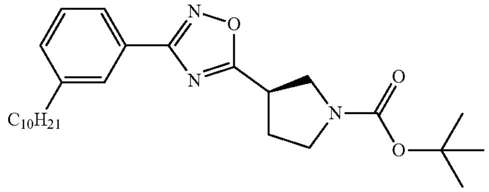

Synthesized according to General Procedure 3. Purified by silica chromatography (20% EtOAc in hexanes). Orange oil, 550 mg (52%) yield. $^1$H NMR (400 MHz, $CDCl_3$) δ 7.91-7.85 (m, 2H), 7.42-7.29 (m, 2H), 3.96-3.43 (m, 6H), 2.67 (t, J=7.7 Hz, 2H), 2.46-2.32 (m, 2H), 1.70-1.60 (m, 2H), 1.48 (brs, 9H), 1.37-1.18 (m, 14H), 0.88 (t, J=6.8 Hz, 3H). $^{13}$C NMR (100 MHz, $CDCl_3$) δ 179.4, 168.6, 154.3, 143.9, 131.5, 128.9, 127.5, 126.6, 124.9, 79.9, 49.5, 45.2, 36.7, 36.0, 32.0, 31.5, 30.5, 29.7, 29.7, 29.6, 29.4, 29.4, 28.6, 22.8, 14.2. HRMS: (ESI) $[M+H]^+$ calc. for $C_{27}H_{42}N_3O_3$, 456.3221, observed, 456.3208.

tert-butyl (R)-3-(3-(4-undecylphenyl)-1,2,4-oxadiazol-5-yl)pyrrolidine-1-carboxylate (4xa)

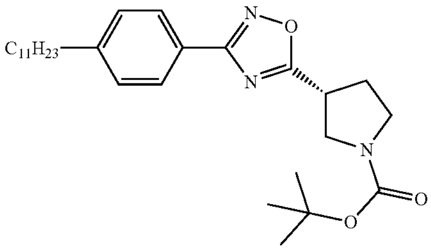

Synthesized according to General Procedure 3. Purified by silica chromatography (15% EtOAc in hexanes) Yellow oil (56%, 701 mg). $^1$H NMR (400 MHz, $CDCl_3$) δ 7.96 (d, J=8.05, 2H), 7.27 (d, J=8.34, 2H), 3.91-3.44 (m, 5H), 2.65 (t, J=7.82, 2H), 2.44-2.31 (m, 2H), 1.63 (p, J=7.55, 2H), 1.47 (s, 9H), 1.34-1.22 (m, 16H), 0.87 (t, J=7.03, 3H); $^{13}$C NMR (101 MHz, $CDCl_3$) δ 179.33, 168.51, 154.29, 146.71, 129.03, 127.48, 124.05, 79.89, 49.48, 45.16, 36.69, 36.07, 32.02, 31.34, 30.50, 29.76, 29.73, 29.68, 29.59, 29.45, 29.36, 28.59, 22.80, 14.24.

tert-butyl (R)-3-(3-(4-nonylphenyl)-1,2,4-oxadiazol-5-yl)pyrrolidine-1-carboxylate (4xb)

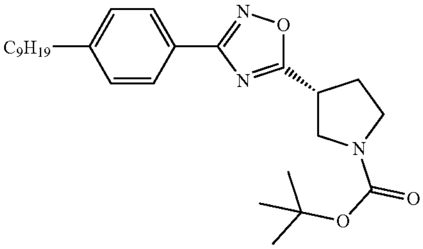

Synthesized according to General Procedure 3. Purified by silica chromatography (15% EtOAc in hexanes). Yellow oil (62%, 774 mg). $^1$H NMR (400 MHz, $CDCl_3$) δ 7.91 (d, J=8.24, 2H), 7.21 (d, J=8.24, 2H), 3.84-3.37 (m, 5H), 2.58 (t, J=7.82, 2H), 2.35-2.22 (m, 2H), 1.57 (p, J=7.45, 2H), 1.42 (s, 9H), 1.28-1.16 (m, 12H), 0.82 (t, J=6.90, 3H); $^{13}$C NMR (101 MHz, $CDCl_3$) δ 179.14, 168.24, 154.03, 146.42, 128.80, 127.27, 123.94, 79.55, 49.28, 44.97, 36.49, 35.87, 31.81, 31.15, 29.47, 29.41, 29.25, 29.18, 28.38, 22.60, 14.05.

tert-butyl (R)-(((tert-butoxycarbonyl)amino)(3-(3-(4-undecylphenyl)-1,2,4-oxadiazol-5-yl)piperidin-1-yl)methylene)carbamate (4ya)

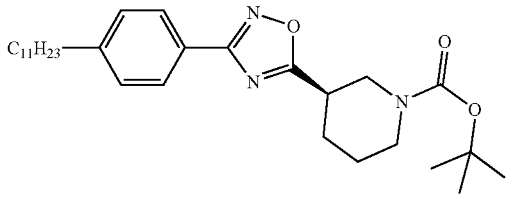

Synthesized according to General Procedure 3. Purified by silica chromatography (12% EtOAc in hexanes). Yellow oil (69%, 666 mg). $^1$H NMR (400 MHz, $CDCl_3$) δ 10.09 (brs, 1H), 7.94 (d, J=8.25, 2H), 7.26 (d, J=8.25, 2H), 4.36-3.94 (m, 2H), 3.47-3.36 (m, 2H), 3.21-3.13 (m, 1H), 2.63 (t, J=7.50, 2H), 2.33-2.23 (m, 1H), 2.00-1.90 (m, 1H), 1.83-1.69 (m, 1H), 1.61 (p, J=7.19, 2H), 1.48 (s, 18H), 1.33-1.21 (m, 16H), 0.85 (t, J=6.51, 3H); $^{13}$C NMR (101 MHz, $CDCl_3$) δ 179.49, 168.35, 154.95, 146.69, 129.06, 127.52, 124.11, 36.10, 34.68, 32.05, 31.36, 29.79, 29.76, 29.71, 29.62, 29.47, 29.38, 28.58, 28.28, 24.16, 22.82, 14.26.

tert-butyl (R)-(((tert-butoxycarbonyl)imino)(3-(3-(4-nonylphenyl)-1,2,4-oxadiazol-5-yl)piperidin-1-yl)methyl)carbamate (4yb)

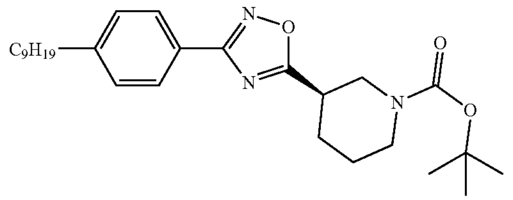

Synthesized according to General Procedure 3. Purified by silica chromatography (15% EtOAc in hexanes). Yellow oil (61%, 665 mg) $^1$H NMR (400 MHz, $CDCl_3$) δ 10.09 (s, 1H), 7.94 (d, J=8.04, 2H), 7.26 (d, J=8.16, 2H), 4.36-3.98 (m, 2H), 3.47-3.43 (m, 2H), 3.22-3.1 (m, 1H), 2.63 (t, J=7.60, 2H), 2.33-2.25 (m, 1H), 1.99-1.89 (m, 1H), 1.82-1.72 (m, 2H), 1.61 (p, J=7.45, 2H), 1.47 (s, 18H), 1.34-1.19 (m, 12H), 0.85 (t, J=6.74, 3H); $^{13}$C NMR (101 MHz, $CDCl_3$) δ 179.47, 168.33, 154.93, 146.68, 129.05, 127.50, 124.09, 49.92, 47.01, 36.08, 34.66, 32.00, 31.36, 29.66, 29.61, 29.44, 29.37, 28.56, 28.27, 24.14, 22.80, 14.25.

5-(azetidin-3-yl)-3-(4-undecylphenyl)-1,2,4-oxadiazole 2,2,2-trifluoroacetate (5a)

Synthesized according to General Procedure 4.

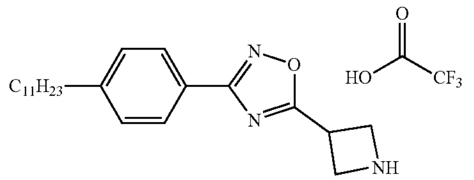

Purified by silica chromatography (8% MeOH in DCM). White solid, 90 mg (56%) yield. $^1$H NMR (400 MHz, $CD_3OD$) δ 7.94 (d, J=8.2 Hz, 2H), 7.28 (d, J=8.2 Hz, 2H), 4.58-4.43 (m, 5H), 2.63 (t, J=7.7 Hz, 2H), 1.66-1.55 (m, 2H), 1.35-1.17 (m, 16H), 0.85 (t, J=6.8 Hz, 2H). $^{13}$C NMR (100 MHz, $CD_3OD$) δ 178.9, 169.8, 148.1, 130.1, 128.4, 125.1, 50.8, 36.9, 33.1, 32.4, 30.8, 30.7, 30.7, 30.6, 30.5, 30.3, 29.9, 23.7, 14.5. HRMS: (ESI) $[M+H]^+$ calc. for $C_{22}H_{34}N_3O$, 356.2696, observed, 356.2718.

5-(azetidin-3-yl)-3-(4-decylphenyl)-1,2,4-oxadiazole 2,2,2-trifluoroacetate (5b)

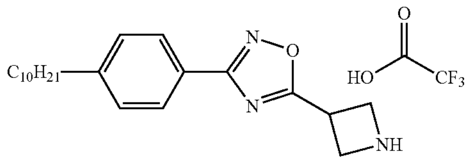

Synthesized according to General Procedure 4. Crude mixture dried in vacuo and carried forward to the next reaction without purification.

5-(azetidin-3-yl)-3-(4-nonylphenyl)-1,2,4-oxadiazole 2,2,2-trifluoroacetate (5c)

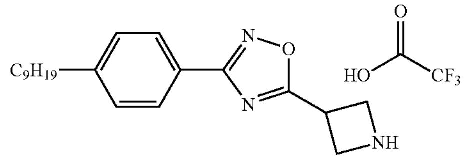

Synthesized according to General Procedure 4. Crude mixture dried in vacuo and carried forward to the next reaction without purification.

5-(azetidin-3-yl)-3-(4-octylphenyl)-1,2,4-oxadiazole 2,2,2-trifluoroacetate (5d)

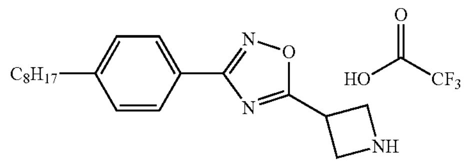

Synthesized according to General Procedure 4. Crude mixture dried in vacuo and carried forward to the next reaction without purification.

(S)-3-(3-(4-decylphenyl)-1,2,4-oxadiazol-5-yl)pyrrolidin-1-ium 2,2,2-trifluoroacetate (5e)

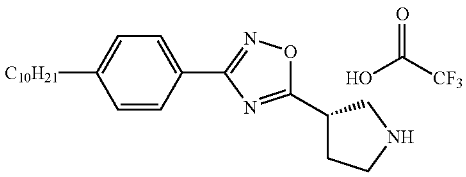

Synthesized according to General Procedure 4. Purified by silica chromatography (10% MeOH in DCM). White solid, 120 mg (94%) yield. $^{1}H$ NMR (400 MHz, $CD_3OD$) δ 7.95 (d, J=8.3 Hz, 2H), 7.30 (d, J=8.3 Hz, 2H), 4.00-3.92 (m, 1H), 3.74-3.58 (m, 2H), 3.46-3.33 (m, 2H), 2.65 (t, J=7.8 Hz, 2H), 2.58-2.49 (m, 1H), 2.42-2.32 (m, 1H), 1.67-1.58 (m, 2H), 1.38-1.20 (m, 14H), 0.88 (t, J=6.8 Hz, 3H). $^{13}C$ NMR (100 MHz, $CD_3OD$) δ 180.9, 169.5, 148.0, 130.0, 128.3, 125.2, 50.2, 46.8, 37.0, 36.8, 33.1, 32.4, 31.0, 30.7, 30.6, 30.5, 30.3, 23.7. 14.5. HRMS: (ESI) $[M+H]^+$ calc. for $C_{22}H_{34}N_3O$, 355.2618, observed, 355.2603.

(S)-3-(3-(4-decylphenyl)-1,2,4-oxadiazol-5-yl)piperidin-1-ium 2,2,2-trifluoroacetate (5f)

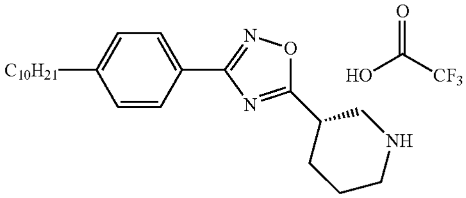

Synthesized according to General Procedure 4. Purified by silica chromatography (8% MeOH in DCM). White solid, 220 mg (85%) yield. $^{1}H$ NMR (400 MHz, $CD_3OD$) δ 7.94 (d, J=8.3 Hz, 2H), 7.29 (d, J=8.3 Hz, 2H), 3.81-3.75 (m, 1H), 3.65-3.57 (m, 2H), 3.47-3.37 (m, 2H), 3.15-3.06 (m, 1H), 2.63 (t, J=7.4 Hz, 2H), 2.39-2.29 (m, 1H), 2.05-1.89 (m, 3H), 1.66-1.56 (m, 2H), 1.37-1.19 (m, 14H), 0.87 (t, J=6.8 Hz, 3H). $^{13}C$ NMR (100 MHz, $CD_3OD$) δ 179.5, 169.4, 147.9, 130.0, 128.4, 125.1, 71.2, 46.2, 44.9, 36.8, 33.4, 33.0 32.4, 30.7, 30.6, 30.4, 30.3, 27.3, 23.7, 22.3, 14.5. HRMS: (ESI) $[M+H]^+$ calc. for $C_{23}H_{36}N_3O$, 370.2853, observed, 370.2831.

(R)-3-(3-(4-decylphenyl)-1,2,4-oxadiazol-5-yl)pyrrolidin-1-ium 2,2,2-trifluoroacetate (5g)

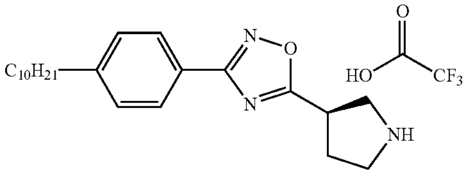

Synthesized according to General Procedure 4. Purified by silica chromatography (7% MeOH in DCM). White solid, 110 mg (70%) yield. $^{1}H$ NMR (400 MHz, $CD_3OD$) δ 7.95 (d, J=8.3 Hz, 2H), 7.30 (d, J=8.3 Hz, 2H), 4.02-3.94 (m, 1H), 3.76-3.69 (m, 1H), 3.67-3.61 (m, 1H), 3.48-3.35 (m, 2H), 2.65 (t, J=7.6 Hz, 2H), 2.60-2.50 (m, 1H), 1.67-1.57 (m, 2H), 1.37-1.20 (m, 14H), 0.88 (t, J=6.8 Hz, 3H). $^{13}C$ NMR (100 MHz, $CD_3OD$) δ 180.7, 169.5, 148.0, 130.0, 128.3, 125.2, 50.0, 46.8, 37.0, 36.8, 33.0, 32.4, 30.9, 30.7, 30.6, 30.4, 30.3, 23.7, 14.5. HRMS: (ESI) $[M+H]^+$ calc. for $C_{22}H_{34}N_3O$, 356.2702, observed, 356.2716.

(R)-3-(3-(4-decylphenyl)-1,2,4-oxadiazol-5-yl)piperidin-1-ium 2,2,2-trifluoroacetate (5h)

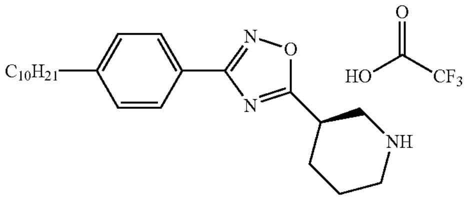

Synthesized according to General Procedure 4. Purified by silica chromatography (8% MeOH in DCM). White solid, 300 mg (91%) yield. $^{1}H$ NMR (400 MHz, $CD_3OD$) δ 7.97 (d, J=8.3 Hz, 2H), 7.32 (d, J=8.3 Hz, 2H), 3.82-3.75 (m, 1H), 3.65-3.57 (m, 1H), 3.51-3.37 (m, 2H), 3.15-3.08 (m, 1H), 2.67 (t, J=7.4 Hz, 2H), 2.42-2.30 (m, 1H), 2.07-1.89 (m, 3H), 1.66-1.56 (m, 2H), 1.38 0 1.19 (m, 14H), 0.89 (t, J=6.8 Hz, 3H). $^{13}C$ NMR (100 MHz, $CD_3OD$) δ 179.5, 169.5, 148.1, 130.1, 128.4, 125.1, 46.1, 45.0, 36.8, 33.3, 33.1, 32.4, 30.7, 30.6, 30.5, 30.3, 27.1, 23.7, 22.2, 14.5. HRMS: (ESI) $[M+H]^+$ calc. for $C_{23}H_{36}N_3O$, 370.2853, observed, 370.2842.

5-(azetidin-3-ylmethyl)-3-(4-decylphenyl)-1,2,4-oxadiazole 2,2,2-trifluoroacetate (5j)

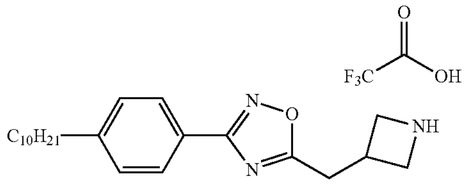

Synthesized according to General Procedure 4. 7.94 (d, J=8.3 Hz, 2H), 7.32 (d, J=8.3 Hz, 2H), 4.33-4.25 (m, 2H), 4.12-4.05 (m, 2H), 3.60-3.47 (m, 1H), 3.37 (d, J=7.6 Hz, 2H), 2.67 (t, J=7.7 Hz, 2H), 1.70-1.58 (m, 2H), 1.40-1.21 (m, 14H), 0.88 (t, J=6.7 Hz, 3H). HRMS: (ESI) $[M+H]^+$ calc. for $C_{22}H_{34}N_3O$, 356.2702, observed, 356.2729.

5-(azepan-3-yl)-3-(4-decylphenyl)-1,2,4-oxadiazole 2,2,2-trifluoroacetate (5k)

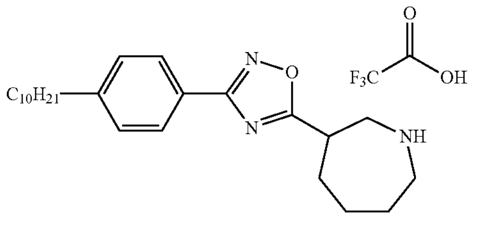

Synthesized according to General Procedure 4. Crude mixture dried in vacuo and carried forward to the next reaction without purification.

(R)-3-(4-decylphenyl)-5-(pyrrolidin-3-ylmethyl)-1,2,4-oxadiazole 2,2,2-trifluoroacetate (5l)

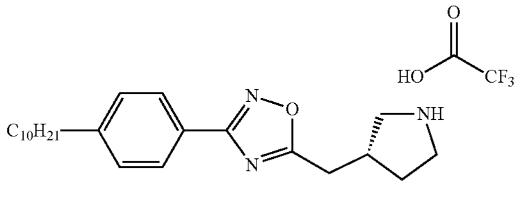

Synthesized according to General Procedure 4. White solid, 90 mg (72%) yield. $^{1}$H NMR (400 MHz, $CD_3OD$) δ 7.88 (d, J=8.3 Hz, 2H), 7.24 (d, J=8.3 Hz, 2H), 3.64-3.56 (m, 1H), 3.45-3.37 (m, 1H), 3.31-3.22 (m, 1H), 3.16-3.03 (m, 3H), 2.94-2.82 (m, 1H), 2.59 (t, J=7.7 Hz, 2H), 2.35-2.26 (m, 1H), 1.86-1.74 (m, 1H), 1.61-1.52 (m, 2H), 1.32-1.15 (m, 14H), 0.81 (t, J=6.8 Hz, 3H). $^{13}$C NMR (100 MHz, $CD_3OD$) δ 179.3, 169.5, 163.1, 147.9, 130.0, 128.3, 125.3, 119.6, 116.7, 50.6, 46.2, 36.8, 36.8, 33.0, 32.4, 31.0, 30.7, 30.6, 30.4, 30.3, 29.7, 23.7, 14.5. HRMS: (ESI) $[M+H]^+$ calc. for $C_{34}H_{54}N_5O_5$, 612.4119, observed, 612.4134.

(S)-3-(4-decylphenyl)-5-(pyrrolidin-3-ylmethyl)-1,2,4-oxadiazole 2,2,2-trifluoroacetate (5p)

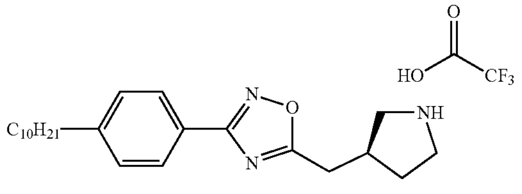

Synthesized according to General Procedure 4. White solid, 210 mg (75%) yield. $^{1}$H NMR (400 MHz, $CD_3OD$) δ 7.92 (d, J=8.2 Hz, 2H), 7.29 (d, J=8.2 Hz, 2H), 3.66-3.59 (m, 1H0, 3.47-3.40 (m, 1H), 3.34-3.25 (m, 2H), 3.21-3.14 (m, 2H), 3.13-3.05 (m, 1H), 2.65 (t, J=7.7 Hz, 2H), 2.39-2.30 (m, 1H), 1.89-1.77 (m, 1H), 1.67-1.57 (m, 2H), 1.36-1.19 (m, 14H), 0.86 (t, J=6.8 Hz, 3H). $^{13}$C NMR (100 MHz, $CD_3OD$) δ 179.3, 169.5, 148.1, 130.1, 128.3, 125.3, 50.7, 46.3, 36.8, 33.1, 32.4, 31.0, 30.7, 30.6, 30.5, 30.3, 29.7, 23.7, 14.5. HRMS: (ESI) $[M+H]^+$ calc. for $C_{23}H_{36}N_3O$, 370.2853, observed, 370.2856.

(S)-3-(4-decylphenyl)-5-(piperidin-3-ylmethyl)-1,2,4-oxadiazole 2,2,2-trifluoroacetate (5q)

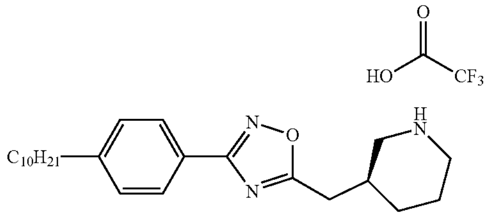

Synthesized according to General Procedure 4. White solid, 200 mg (69%) yield. $^{1}$H NMR (400 MHz, $CD_3OD$) δ 7.91 (d, J=8.2 Hz, 2H), 7.27 (d, J=8.2 Hz, 2H), 3.54-3.47 (m, 1H), 3.38-3.31 (m, 1H), 3.00 (d, J=7.0 Hz, 2H), 2.96-2.80 (m, 2H), 2.63 (t, J=7.7 Hz, 2H), 2.46-2.33 (m, 1H), 2.01-1.89 (m, 2H), 1.83-1.69 (m, 1H), 1.65-1.55 (m, 2H), 1.46-1.18 (m, 15H), 0.85 (t, J=6.8 Hz, 3H). $^{13}$C NMR (100 MHz, $CD_3OD$) δ 178.9, 169.5, 148.0, 130.1, 28.3, 125.3, 45.1, 36.8, 33.4, 33.1, 32.4, 30.9, 30.7, 30.6, 30.5, 30.3, 23.7, 23.1, 14.5. HRMS: (ESI) $[M+H]^+$ calc. for $C_{24}H_{38}N_3O$, 384.3009, observed, 348.3017.

(R)-3-(3-decylphenyl)-5-(pyrrolidin-3-yl)-1,2,4-oxadiazole 2,2,2-trifluoroacetate (5t)

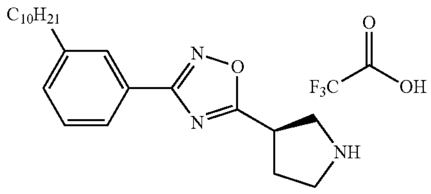

Synthesized according to General Procedure 4. Crude mixture dried in vacuo and taken forward into the next synthetic step without purification.

(R)-5-(pyrrolidin-3-yl)-3-(4-undecylphenyl)-1,2,4-oxadiazole hydrochloride (5xa)

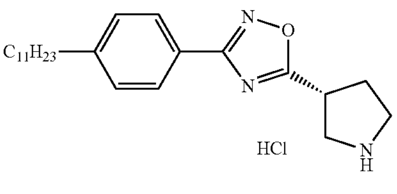

Synthesized according to General Procedure 6. Crude mixture dried in vacuo and carried forward to the next reaction without purification (R)-3-(4-nonylphenyl)-5-(pyrrolidin-3-yl)-1,2,4-oxadiazole hydrochloride (5xb)

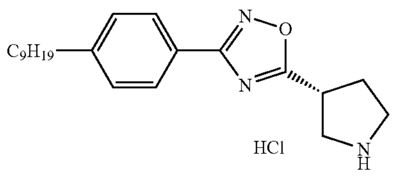

Synthesized according to General Procedure 5. Crude mixture dried in vacuo and carried forward to the next reaction without purification.

(R)-5-(piperidin-3-yl)-3-(4-undecylphenyl)-1,2,4-oxadiazole hydrochloride (5ya)

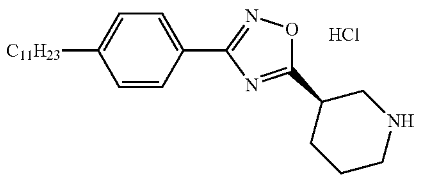

Synthesized according to General Procedure 6. Crude mixture dried in vacuo and carried forward to the next reaction without purification (R)-3-(4-nonylphenyl)-5-(piperidin-3-yl)-1,2,4-oxadiazole hydrochloride (5yb)

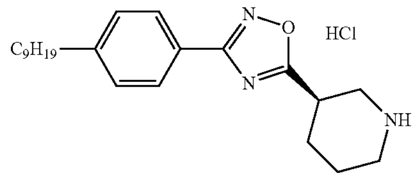

Synthesized according to General Procedure 6. Crude mixture dried in vacuo and carried forward to the next reaction without purification.

(R)-3-(6-(heptyloxy)naphthalen-2-yl)-5-(pyrrolidin-3-yl)-1,2,4-oxadiazole hydrochloride (5aa)

Synthesized according to General Procedure 6.

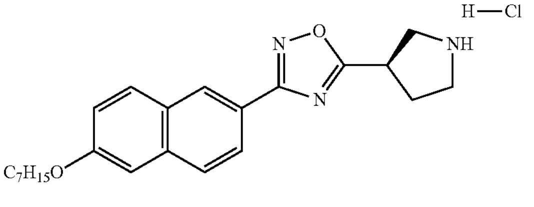

White solid (75%, 175 mg). $^1$H NMR (400 MHz, $CDCl_3$) δ 10.3 (brs, 1H), 8.52 (d, J=1.7 Hz, 1H), 8.04 (dd, J=8.6, 1.7 Hz, 1H), 7.83 (d, J=9.0 Hz, 1H), 7.77 (d, J=8.6 Hz, 1H), 7.18 (dd, J=8.9, 2.5 Hz, 1H), 7.12 (d, J=2.5 Hz, 1H), 4.07 (t, J=6.6 Hz, 2H), 4.01-3.91 (m, 2H), 3.88-3.78 (m, 2H), 3.69-3.58 (m, 2H), 2.71-2.59 (m, 1H), 2.55-2.43 (m, 1H), 1.90-1.79 (m, 2H), 1.55-1.44 (m, 2H), 1.43-1.25 (m, 6H), 0.90 (t, J=6.8 Hz, 3H). $^{13}$C NMR (101 MHz, $CDCl_3$) δ 180.0, 169.8, 160.1, 137.9, 131.2, 129.7, 128.7, 125.0, 122.6, 121.1, 111.4, 107.7, 69.2, 49.5, 46.6, 36.7, 33.0, 30.4, 30.3, 30.2, 27.2, 23.7, 14.4. HRMS: (ESI) $[M+H]^+$ calc. for $C_{23}H_{30}N_3O_2$, 380.2333, observed, 380.2331.

tert-butyl (Z)-(((tert-butoxycarbonyl)imino)(3-(3-(4-decylphenyl)-1,2,4-oxadiazol-5-yl)azetidin-1-yl)methyl)carbamate (6a)

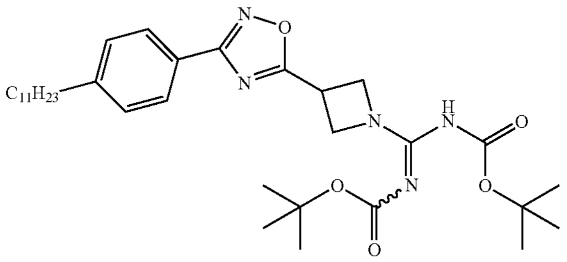

Synthesized by General Procedure 5. Purified by silica chromatography (15% EtOAc in hexanes). Colorless oil, 55 mg (51%) yield. $^1$H NMR (400 MHz, $CDCl_3$) δ 11.05 (s, 1H), 7.98 (d, J=8.2 Hz, 2H), 7.29 (d, J=8.2 Hz, 2H), 1.81-1.59 (m, 4H), 4.18-4.09 (m, 1H), 2.66 (t, J=7.7 Hz, 2H), 1.70-1.58 (m, 2H), 1.50 (brs, 18H), 1.38-1.19 (m, 16H), 0.88 (t, J=6.8 Hz, 3H). $^{13}$C NMR (100 MHz, $CDCl_3$) δ 178.3, 168.7, 162.9, 156.4, 149.8, 146.8, 129.1, 127.5, 123.8, 82.6, 79.9, 57.5, 54.7, 36.1, 32.0, 31.3, 29.8, 29.7, 29.7, 29.6, 29.4, 29.4, 28.3, 28.1, 26.6, 22.8, 14.2. HRMS: (ESI) $[M+H]^+$ calc. for $C_{33}H_{52}N_5O_5$, 598.3963, observed, 598.3956.

tert-butyl (((tert-butoxycarbonyl)imino)(3-(3-(4-decylphenyl)-1,2,4-oxadiazol-5-yl)azetidin-1-yl)methyl)carbamate (6b)

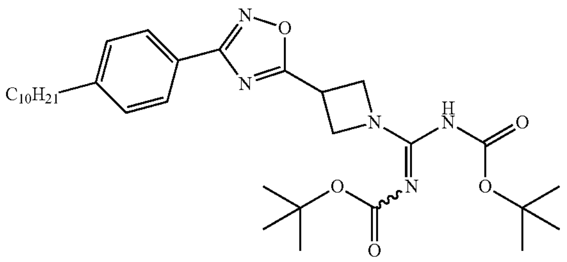

Synthesized by General Procedure 5. Purified by silica chromatography (15% EtOAc in hexanes). Colorless oil, 85 mg (53%) yield. $^1$H NMR (400 MHz, $CDCl_3$) δ 11.05 (brs, 1H), 7.98 (d, J=8.2 Hz, 2H), 7.29 (d, J=8.2 Hz, 2H), 4.83-4.58 (m, 4H), 4.19-4.09 (m, 1H), 2.66 (t, J=7.7 Hz, 2H), 1.69-1.58 (m, 2H), 1.50 (brs, 18H), 1.39-1.19 (m, 14H), 0.88 (t, J=6.8 Hz, 3H). $^{13}$C NMR (100 MHz, $CDCl_3$) δ 178.3, 168.6, 162.8, 156.3, 149.7, 146.7, 129.0, 127.4, 123.7, 82.5, 79.8, 57.6, 54.5, 36.0, 31.9, 31.2, 29.6, 29.6, 29.5, 29.3, 29.3, 28.2, 28.0, 26.5, 22.7, 14.1.

tert-butyl (((tert-butoxycarbonyl)imino)(3-(3-(4-nonylphenyl)-1,2,4-oxadiazol-5-yl)azetidin-1-yl) methyl)carbamate (6c)

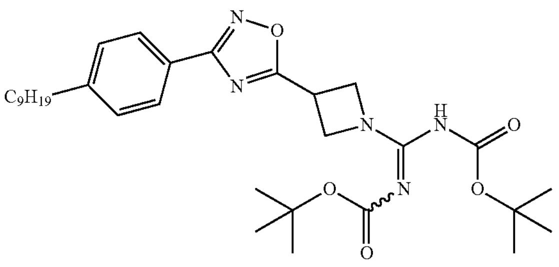

Synthesized by General Procedure 5. Purified by silica chromatography (5% EtOAc in $CHCl_3$). Colorless oil, 140 mg (84%) yield. $^1$H NMR (400 MHz, $CDCl_3$) δ 11.03 (s, 1H), 7.96 (d, J=8.2 Hz, 2H), 7.27 (d, J=8.1 Hz, 2H), 4.80-4.54 (m, 4H), 4.15-4.06 (m, 1H), 2.66 (t, J=7.7 Hz, 2H), 1.67-1.56 (m, 2H), 1.48 (brs, 18H), 1.36-1.18 (m, 12H), 0.85 (t, J=6.7 Hz, 3H). $^{13}$C NMR (100 MHz, $CDCl_3$) δ 178.3, 168.7, 163.0, 156.4, 149.8, 146.8, 129.0, 127.5, 123.8, 82.5, 79.8, 57.6, 54.8, 36.0, 32.0, 29.6, 29.6, 29.4, 29.3, 28.3, 28.1, 26.6, 22.7, 14.2. HRMS: (ESI) $[M+H]^+$ calc. for $C_{31}H_{48}N_5O_5$, 570.3650, observed, 570.3649.

tert-butyl (((tert-butoxycarbonyl)imino)(3-(3-(4-octylphenyl)-1,2,4-oxadiazol-5-yl)azetidin-1-yl) methyl)carbamate (6d)

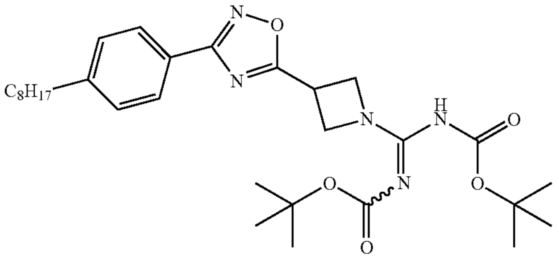

Synthesized by General Procedure 5. Purified by silica chromatography (14% EtOAc in hexanes). Colorless oil, 42 mg (65%) yield. $^1$H NMR (400 MHz, $CDCl_3$) δ 11.04 (s, 1H), 7.98 (d, J=8.2 Hz, 2H), 7.29 (d, J=8.2 Hz, 2H), 4.80-4.59 (m, 4H), 4.18-4.09 (m, 1H), 2.66 (t, J=7.7 Hz, 2H), 1.69-1.58 (m, 2H), 1.50 (brs, 18H), 1.40-1.20 (10H), 0.88 (t, J=6.8 Hz, 3H).

tert-butyl (S)-(((tert-butoxycarbonyl)imino)(3-(3-(4-decylphenyl)-1,2,4-oxadiazol-5-yl)pyrrolidin-1-yl) methyl)carbamate (6e)

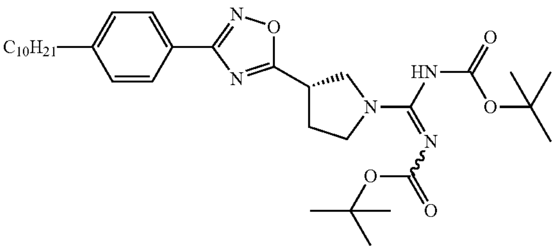

Synthesized by General Procedure 5. Purified by silica chromatography (20% EtOAc in hexanes). Colorless oil, 80 mg (48%) yield. $^1$H NMR (400 MHz, $CDCl_3$) δ 10.46 (brs, 1H), 7.96 (d, J=8.3 Hz, 2H), 7.28 (d, J=8.3 Hz, 2H), 4.20-3.95 (m, 2H), 3.91-3.66 (m, 3H), 2.66 (t, J=7.7 Hz, 2H), 2.51-2.35 (m, 2H), 1.69-1.57 (m, 2H), 1.58-1.44 (m, 18H), 1.39-1.19 (m, 14H), 0.88 (t, J=6.8 Hz, 3H). $^{13}$C NMR (100 MHz, $CDCl_3$) δ 178.4, 168.4, 154.3, 146.6, 128.9, 127.4, 123.8, 82, 79.5, 51.9, 48.5, 35.9, 31.9, 31.2, 29.6, 29.6, 29.5, 29.5, 29.3, 29.3, 29.2, 28.1, 28.1, 28.0, 22.7, 14.1. HRMS: (ESI) $[M+H]^+$ calc. for $C_{33}H_{52}N_5O_5$, 598.3963, observed, 598.3952.

tert-butyl (S)-(((tert-butoxycarbonyl)imino)(3-(3-(4-decylphenyl)-1,2,4-oxadiazol-5-yl)piperidin-1-yl) methyl)carbamate (6f)

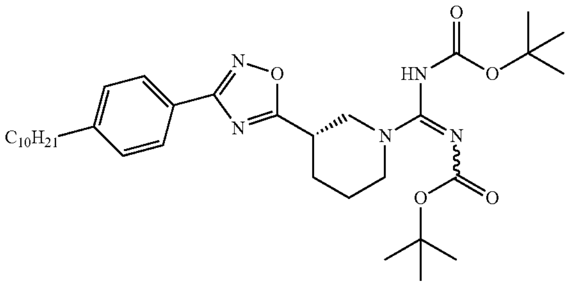

Synthesized by General Procedure 5. Purified by silica chromatography (20% EtOAc in hexanes). Colorless oil, 54 mg (51%) yield. $^1$H NMR (400 MHz, $CDCl_3$) δ 10.12 (brs, 1H), 7.97 (d, J=7.7 Hz, 2H), 7.28 (d, J=7.7 Hz, 2H), 4.44-3.92 (m, 2H), 3.45 (brs, 2H), 3.27-3.12 (m, 1H), 2.66 (t, J=7.8 Hz, 2H), 2.37-2.26 (m, 1H), 2.04-1.90 (m, 1H), 1.86-1.72 (m, 2H), 1.68-1.58 (m, 2H), 1.58-1.40 (m, 18), 1.39-1.17 (m, 14), 0.88 (t, J=6.6 Hz, 3H). $^{13}$C NMR (100 MHz, $CDCl_3$) δ 179.3, 168.2, 154.8, 146.5, 128.9, 127.4, 123.9, 49.6, 47.0, 35.9, 34.5, 31.9, 31.2, 29.6, 29.6, 29.5, 29.3, 29.2, 28.4, 28.1, 24.0, 22.7, 14.1. HRMS: (ESI) $[M+H]^+$ calc. for $C_{34}H_{54}N_5O_5$, 612.4119, observed, 612.4126.

tert-butyl (R)-(((tert-butoxycarbonyl)imino)(3-(3-(4-decylphenyl)-1,2,4-oxadiazol-5-yl)pyrrolidin-1-yl)methyl)carbamate (6g)

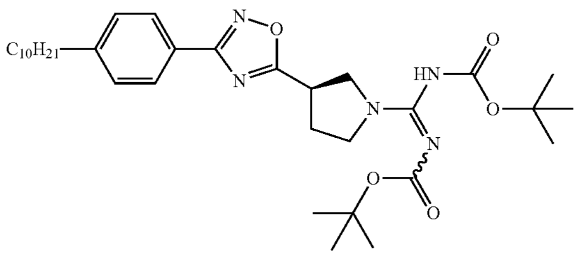

Synthesized by General Procedure 5. Purified by silica chromatography (20% EtOAc in hexanes). Colorless oil, 75 mg (59%) yield. $^1$H NMR (400 MHz, $CDCl_3$) δ 10.46 (brs, 1H), 7.96 (d, J=8.4 Hz, 2H), 7.28 (d, J=8.4 Hz, 2H), 4.17-3.97 (m, 2H), 3.86-3.69 (m, 3H), 2.66 (t, J=7.7 Hz, 2H), 2.51-2.36 (m, 2H), 1.68-1.59 (m, 2H), 1.50 (brs, 18H), 1.37-1.21 (m, 14H), 0.88 (t, J=6.8 Hz, 3H). $^{13}$C NMR (100 MHz, $CDCl_3$) δ 178.6, 168.6, 154.4, 146.8, 129.1, 127.5, 124.0, 82.3, 79.7, 52.0, 48.2, 36.1, 32.0, 31.4, 29.7, 29.7, 29.6, 29.5, 29.4, 28.3, 22.8, 14.3. HRMS: (ESI) $[M+H]^+$ calc. for $C_{33}H_{52}N_5O_5$, 598.3963, observed, 598.3990.

tert-butyl (R)-(((tert-butoxycarbonyl)imino)(3-(3-(4-decylphenyl)-1,2,4-oxadiazol-5-yl)piperidin-1-yl)methyl)carbamate (6h)

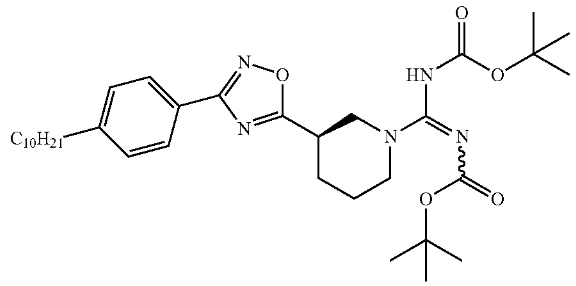

Synthesized by General Procedure 5. Purified by silica chromatography (24% EtOAc in hexanes). Colorless oil, 56 mg (44%) yield. $^1$H NMR (400 MHz, $CDCl_3$) δ 10.11 (brs, 1H), 7.97 (d, J=8.3 Hz, 2H), 7.28 (d, J=8.3 Hz, 2H), 4.41-3.94 (m, 2H), 3.45 (brs, 2H), 3.27-3.12 (m, 1H), 2.66 (t, J=7.7 Hz, 2H), 2.37-2.27 (m, 1H), 2.03-1.90 (m, 1H), 1.86-1.71 (m, 2H), 1.70-1.58 (m, 2H), 1.50 (brs, 18H), 1.37-1.20 (m, 14H), 0.88 (t, J=6.8 Hz, 3H). $^{13}$C NMR (100 MHz, $CDCl_3$) δ 179.5, 168.3, 154.9, 146.7, 129.0, 127.5, 124.1, 49.8, 47.1, 36.1, 34.6, 32.0, 31.4, 29.7, 29.7, 29.6, 29.4, 29.4, 28.5, 28.3, 28.1, 24.2, 22.8, 14.2. HRMS: (ESI) $[M+H]^+$ calc. for $C_{34}H_{54}N_5O_5$, 612.4125, observed, 612.4145.

tert-butyl (((tert-butoxycarbonyl)imino)(3-((3-(4-decylphenyl)-1,2,4-oxadiazol-5-yl)methyl)azetidin-1-yl)methyl)carbamate (6j)

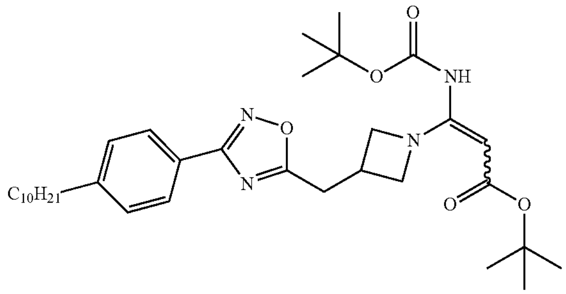

Synthesized by General Procedure 5. Purified by silica chromatography (25% EtOAc in hexanes). White solid, 42 mg (51%) yield. $^1$H NMR (400 MHz, $CDCl_3$) δ 10.93 (brs, 1H), 7.96 (d, J=8.2 Hz, 2H), 7.28 (d, J=8.2 Hz, 2H), 4.49 (t, J=9.1 Hz, 2), 4.17-4.05 (m, 2H), 3.28-3.14 (m, 3H), 2.66 (t, J=7.7 Hz, 2H), 1.68-1.58 (m, 2H), 1.49 (brs, 18H), 0.88 (t, J=6.8 Hz, 3H). $^{13}$C NMR (100 MHz, $CDCl_3$) δ 177.0, 168.5, 156.3, 146.7, 129.0, 127.5, 124.0, 36.1, 32.0, 31.4, 30.8, 29.7, 27.0, 29.6, 29.4, 29.4, 28.3, 27.2, 22.8, 14.2. HRMS: (ESI) $[M+H]^+$ calc. for $C_{33}H_{51}N_5O_5$, 597.3885, observed, 597.4002.

tert-butyl (((tert-butoxycarbonyl)imino)(3-(3-(4-decylphenyl)-1,2,4-oxadiazol-5-yl)azepan-1-yl)methyl)carbamate (6k)

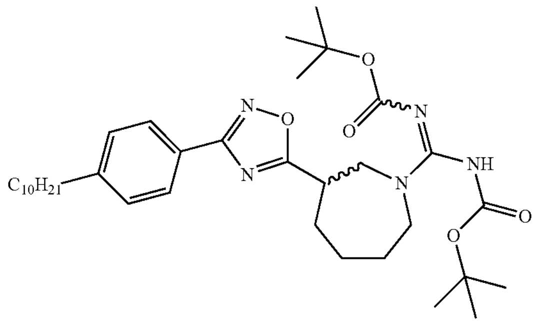

Synthesized by General Procedure 5. Purified by silica chromatography (10-20% EtOAc in hexanes). Colorless residue, 45 mg (40%) yield. $^1$H NMR (400 MHz, $CDCl_3$) δ 9.93 (brs, 1H), 7.97 (d, J=7.9 Hz, 2H), 7.28 (d, J=7.9 Hz), 3.94-3.50 (m, 4H), 2.65 (t, J=7.7 Hz, 2H), 2.23-2.14 (m, 1H), 2.01-1.75 (m, 4H), 1.68-1.55 (m, 4H), 1.46 (brs, 18H), 1.38-1.19 (m, 14H), 0.88 (t, J=6.8 Hz, 3H). $^{13}$C NMR (100 MHz, $CDCl_3$) δ 180.8, 168.2, 162.4, 155.1, 151.1, 146.6, 129.0, 127.5, 124.2, 82.0, 79.6, 50.5, 36.1, 32.0, 31.4, 29.7, 29.7, 29.6, 29.5, 29.4, 28.3, 24.2, 22.8, 14.3. HRMS: (ESI) $[M+H]^+$ calc. for $C_{35}H_{56}N_5O_5$, 626.4276, observed, 626.4303.

tert-butyl (R)-(((tert-butoxycarbonyl)amino)(3-((3-(4-decylphenyl)-1,2,4-oxadiazol-5-yl)methyl)pyrrolidin-1-yl)methylene)carbamate (6l)

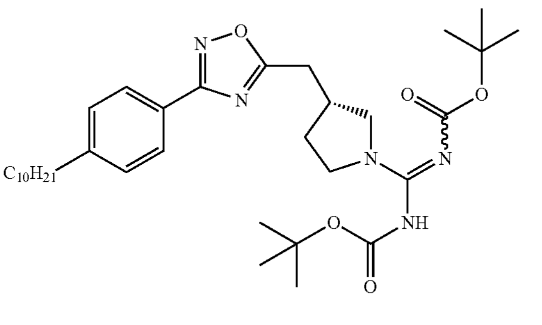

Synthesized by General Procedure 5. Purified by silica chromatography (24% EtOAc in hexanes). Colorless residue, 61 mg (54%) yield. $^1$H NMR (400 MHz, $CDCl_3$) δ 10.40 (brs, 1H0, 7.97 (d, J=8.0 Hz, 2H), 7.28 (d, J=8.0 Hz, 2H), 3.92-3.65 (m, 3H), 3.52-3.43 (m, 1H), 3.10-2.98 (m, 2H), 2.81 (brs, 1H), 2.66 (t, J=7.8 Hz, 2H), 2.25-2.15 (m, 1H), 1.82-1.70 (m, 1H), 1.69-1.58 (m, 2H), 1.49 (brs, 18H), 1.38-1.19 (m, 14H), 0.88 (t, J=6.8 Hz, 3H). $^{13}$C NMR (100 MHz, $CDCl_3$) δ 177.7, 168.5, 154.3, 146.7, 129.0, 127.4, 124.0, 53.9, 48.2, 36.0, 32.0, 31.3, 29.7, 29.7, 29.6, 29.4, 29.3, 28.2, 22.8, 14.2. HRMS: (ESI) $[M+H]^+$ calc. for $C_{34}H_{54}N_5O_5$, 612.4119, observed, 612.4162.

tert-butyl (S)-(((tert-butoxycarbonyl)imino)(3-((3-(4-decylphenyl)-1,2,4-oxadiazol-5-yl)methyl)pyrrolidin-1-yl)methyl)carbamate (6p)

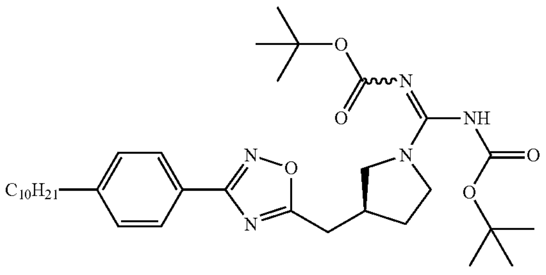

Synthesized by General Procedure 5. Purified by silica chromatography (24% EtOAc in hexanes). Colorless oil, 80 mg (66%) yield. $^1$H NMR (400 MHz, $CDCl_3$) δ 10.40 (brs, 1H0, 7.97 (d, J=8.0 Hz, 2H), 7.28 (d, J=8.0 Hz, 2H), 3.84 (brs, 1H), 3.75-3.65 (m, 2H), 3.52-3.43 (m, 1H), 3.10-2.98 (m, 2H), 2.81 (brs, 1H), 2.66 (t, J=7.8 Hz, 2H), 2.25-2.15 (m, 1H), 1.82-1.70 (m, 1H), 1.69-1.58 (m, 2H), 1.49 (brs, 18H), 1.38-1.19 (m, 14H), 0.88 (t, J=6.8 Hz, 3H). $^{13}$C NMR (100 MHz, $CDCl_3$) δ 177.6, 168.4, 154.3, 146.6, 129.0, 127.4, 124.0, 53.9, 48.2, 36.0, 32.0, 31.3, 29.7, 29.6, 29.5, 29.4, 29.3, 28.2, 22.8, 14.2. HRMS: (ESI) $[M+H]^+$ calc. for $C_{34}H_{54}N_5O_5$, 612.4119, observed, 612.4109.

tert-butyl (S)-(((tert-butoxycarbonyl)amino)(3-((3-(4-decylphenyl)-1,2,4-oxadiazol-5-yl)methyl)piperidin-1-yl)methylene)carbamate (6q)

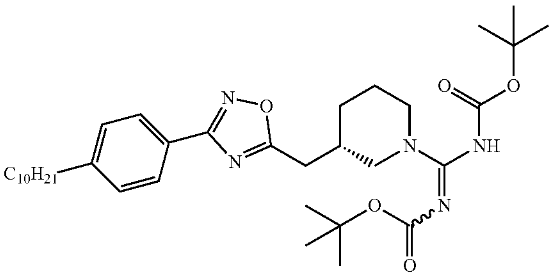

Synthesized by General Procedure 5. Purified by silica chromatography (20% EtOAc in hexanes). Colorless oil, 102 mg (67%) yield. $^1$H NMR (400 MHz, $CDCl_3$) δ 10.17 (brs, 1H), 7.97 (d, J=8.2 Hz, 2H), 7.28 (d, J=8.2 Hz, 2H), 4.10 (brs, 1H), 3.05-2.83 (m, 4H), 2.66 (t, J=7.7 Hz, 2H), 2.42-2.32 (m, 1H), 1.99-1.90 (m, 1H), 1.82-1.59 (m, 4H), 1.46 (brs, 18H), 1.38-1.21 (14H), 0.88 (t, J=6.8 Hz, 3H). $^{13}$C NMR (100 MHz, $CDCl_3$) δ 177.8, 168.4, 162.4, 155.3, 146.5, 129.0, 127.4, 124.2, 80.9, 52.1, 47.5, 36.0, 34.3, 32.0, 31.3, 30.4, 30.3, 29.7, 29.6, 29.4, 29.3, 28.2, 24.4. HRMS: (ESI) $[M+H]^+$ calc. for $C_{35}H_{56}N_5O_5$, 626.4276, observed, 626.4300.

tert-butyl (R)-(((tert-butoxycarbonyl)imino)(3-(3-(3-decylphenyl)-1,2,4-oxadiazol-5-yl)pyrrolidin-1-yl)methyl)carbamate (6t)

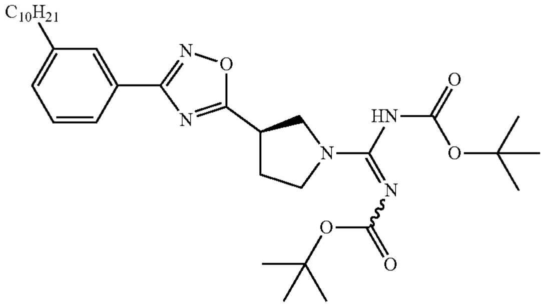

Synthesized by General Procedure 5. Purified by silica chromatography (10-25% EtOAc in hexanes). Colorless oil, 80 mg (50%) yield. $^1$H NMR (400 MHz, $CDCl_3$) δ 10.43 (brs, 1H), 7.89-7.83 (m, 2H), 7.40-7.28 (m, 2H), 4.16-3.99 (m, 2H), 3.86-3.69 (m, 3H), 2.66 (t, J=7.8 Hz, 2H), 2.50-2.37 (m, 2H), 1.68-1.60 (m, 2H), 1.49 (brs, 18H), 1.37-1.19 (m, 14H), 0.86 (t, J=6.8 Hz, 3H). $^{13}$C NMR (100 MHz, $CDCl_3$) δ 178.7, 168.7, 154.4, 143.9, 131.6, 128.9, 127.5, 126.5, 124.9, 80.8, 52.1, 48.1, 36.0, 32.0, 31.6, 29.7, 32.0, 31.6, 29.7, 29.7, 29.6, 29.4, 28.3, 22.8, 14.2. HRMS: (ESI) $[M+H]^+$ calc. for $C_{33}H_{52}N_5O_5$, 598.3963, observed, 598.3955 tert-butyl (R)-(((tert-butoxycarbonyl)imino)(3-(3-(4-undecylphenyl)-1,2,4-oxadiazol-5-yl)pyrrolidin-1-yl)methyl)carbamate (6ya)

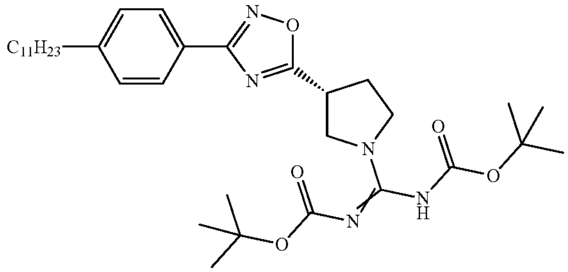

Synthesized according to General Procedure 5. Yellow oil (55% 327 mg). Purified by silica chromatography (20% EtOAc in hexanes). $^{1}H$ NMR (400 MHz, $CDCl_3$) δ 10.44 (brs, 1H), 7.94 (d, J=8.38, 2H), 7.28 (d, J=8.35, 2H), 4.14-3.69 (m, 5H), 2.65 (t, J=7.72, 2H), 2.49-2.37 (m, 2H), 1.63 (p, J=7.44, 2H), 1.50 (s, 18H), 1.35-1.22 (m, 16H), 0.87 (t, J=6.81, 3H); $^{13}C$ NMR (101 MHz, $CDCl_3$) δ 178.59, 168.59, 156.71, 154.41, 146.80, 129.07, 127.54, 123.97, 81.53, 36.11, 32.06, 31.37, 29.79, 29.76, 29.71, 29.62, 29.48, 29.40, 28.30, 28.29, 28.12, 22.83, 14.28.

tert-butyl (R)-(((tert-butoxycarbonyl)imino)(3-(3-(4-nonylphenyl)-1,2,4-oxadiazol-5-yl)pyrrolidin-1-yl)methyl)carbamate (6yb)

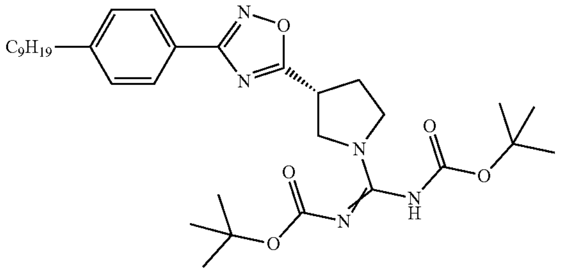

Synthesized according to General Procedure 5. Yellow oil (49%, 222 mg). Purified by silica chromatography (20% EtOAc in hexanes). $^{1}H$ NMR (400 MHz, $CDCl_3$) δ 10.45 (brs, 1H), 7.95 (d, J=7.96, 2H), 7.28 (d, J=7.96, 2H), 4.20-3.68 (m, 5H), 2.65 (t, J=7.66, 2H), 2.45-3.33 (m, 2H), 1.67-1.57 (m, 4H), 1.50 (s, 18H), 1.35-1.21 (m, 12H), 0.87 (t, J=6.80, 3H); $^{13}C$ NMR (101 MHz, $CDCl_3$) δ 178.59, 168.60, 154.41, 146.81, 129.08, 127.55, 123.97, 36.11, 32.03, 31.38, 29.68, 29.63, 29.46, 29.40, 28.37, 28.24, 22.82, 14.27.

tert-butyl (R)-(((tert-butoxycarbonyl)amino)(3-(3-(4-undecylphenyl)-1,2,4-oxadiazol-5-yl)piperidin-1-yl)methylene)carbamate (6xa)

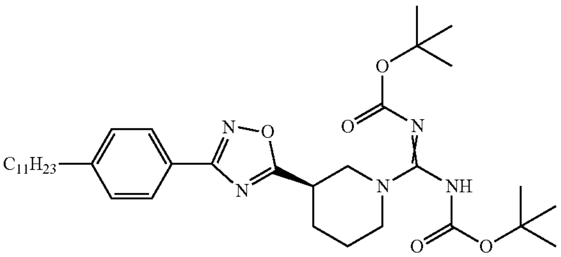

Synthesized according to General Procedure 5. Crude mixture dried in vacuo and carried forward to the next reaction without purification tert-butyl (R)-3-((tert-butoxycarbonyl)amino)-3-(3-(3-(4-nonylphenyl)-1,2,4-oxadiazol-5-yl)piperidin-1-yl)acrylate (6xb)

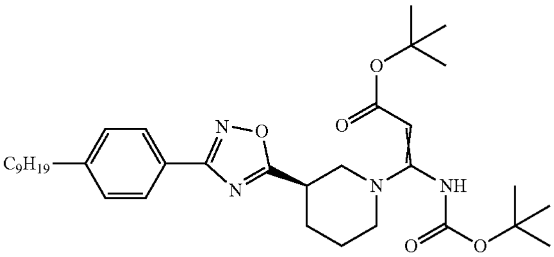

Synthesized according to General Procedure 5. Purified by silica chromatography (25% EtOAc in hexanes). Yellow oil (61%, 327 mg). $^{1}H$ NMR (400 MHz, $CDCl_3$) δ 10.09 (brs, 1H), 7.94 (d, J=7.99, 2H), 7.25 (d, J=7.89, 2H), 4.45-3.92 (m, 2H), 3.49-3.33 (m, 2H), 3.21-3.11 (m, 1H), 2.63 (t, J=7.56, 2H), 2.33-2.26 (m, 1H), 2.00-1.87 (m, 1H), 1.61 (p, J=6.49, 2H), 1.47 (s, 18H), 1.32-1.19 (m, 12H), 0.85 (t, J=6.89, 3H); $^{13}C$ NMR (101 MHz, $CDCl_3$) δ 179.32, 168.17, 154.77, 146.52, 128.89, 127.35, 123.93, 79.72, 49.67, 46.59, 35.93, 34.51, 31.85, 31.20, 29.50, 29.45, 29.28, 29.22, 28.40, 28.11, 23.99, 22.64, 14.09.

3-(3-(4-undecylphenyl)-1,2,4-oxadiazol-5-yl)azetidine-1-carboximidamide hydrochloride (7a)

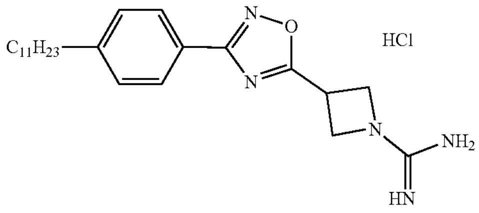

Synthesized by General Procedure 6. White solid, 15 mg (83%) yield. $^{1}H$ NMR (400 MHz, $CD_3OD$) δ 7.99 (d, J=8.2 Hz, 2H), 7.35 (d, J=8.2 Hz, 2H), 4.65 (t, J=8.7 Hz, 2H), 4.51-4.36 (m, 3H). 2.69 (t, J=7.7 Hz, 2H), 1.71-1.61 (m, 2H), 1.39-1.22 (m, 16H), 0.89 (t, J=6.8 Hz 3H). $^{13}$C NMR (100 MHz, $CD_3OD$) δ 180.1, 169.8, 158.3, 148.2, 130.2, 128.4, 125.2, 55.8, 36.9, 33.1, 32.4, 30.7, 30.7, 32.4, 30.7, 30.7, 30.6, 30.5, 30.3, 27.2, 23.7, 14.5. HRMS: (ESI) $[M+H]^+$ calc. for $C_{23}H_{36}N_5O$, 398.2914, observed, 398.2938.

3-(3-(4-decylphenyl)-1,2,4-oxadiazol-5-yl)azetidine-1-carboximidamide hydrochloride (7b)

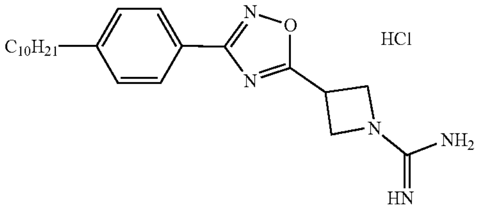

Synthesized by General Procedure 6. White solid, 55 mg (95%) yield. $^1$H NMR (400 MHz, $CD_3OD$) δ 7.96 (d, J=7.9 Hz, 2H), 7.31 (d, J=7.9 Hz, 2H), 4.64 (t, J=8.7 Hz, 2H), 4.49-4.34 (m, 3H), 2.65 (t, J=8.7 Hz, 2H), 1.68-1.58 (m, 2H), 1.36-1.21 (m, 14H), 0.87 (t, J=6.7 Hz, 3H). HRMS: (ESI) $[M+H]^+$ calc. for $C_{22}H_{34}N_5O$, 384.2758, observed, 384.2790.

3-(3-(4-nonylphenyl)-1,2,4-oxadiazol-5-yl)azetidine-1-carboximidamide hydrochloride (7c)

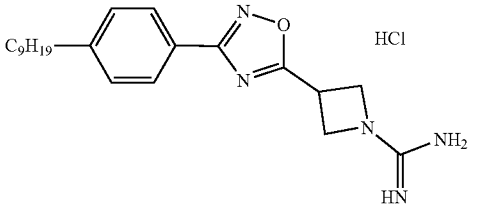

Synthesized by General Procedure 6. White solid, 90 mg (quant.) yield. $^1$H NMR (400 MHz, $CD_3OD$) δ 7.96 (d, J=7.8 Hz, 2H), 7.31 (d, J=7.8 Hz, 2H), 4.66 (t, J=8.4 Hz, 2H), 4.52-4.35 (m, 3H), 2.66 (t, J=7.6 Hz, 2H), 1.68-1.57 (m, 2H), 1.38 (m, 12H), 0.88 (t, J=6.7 Hz, 3H). $^{13}$C NMR (100 MHz, $CD_3OD$) δ 180.0, 169.7, 158.2, 148.1, 130.1, 128.4, 125.1, 55.9, 36.8, 33.0, 32.4, 30.7, 30.6, 30.4, 30.3, 27.1, 23.7, 14.5. HRMS: (ESI) $[M+H]^+$ calc. for $C_{21}H_{32}N_5O$, 370.2601, observed, 370.2612.

3-(3-(4-octylphenyl)-1,2,4-oxadiazol-5-yl)azetidine-1-carboximidamide hydrochloride (7d)

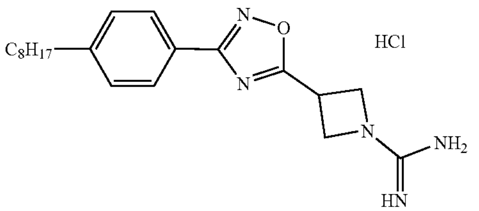

Synthesized by General Procedure 6. White solid, 21 mg (72%) yield. $^1$H NMR (400 MHz, $CD_3OD$) δ 7.97 (d, J=7.9 Hz, 2H), 7.33 (d, J=7.9 Hz, 2H), 4.63 (t, J=8.8 Hz, 2H), 4.49-4.34 (m, 3H), 2.67 (t, J=7.7 Hz, 2H), 1.70-1.58 (m, 2H), 1.41-1.20 (m, 10H), 0.88 (t, J=6.6 Hz, 2H). $^{13}$C NMR (100 MHz, $CD_3OD$) δ 180.1, 169.8, 158.3, 148.2, 130.2 128.4, 125.2, 55.8, 36.9, 33.0, 32.5, 30.6, 30.4, 30.3, 27.1, 23.7, 14.4. HRMS: (ESI) $[M+H]^+$ calc. for $C_{20}H_{30}N_5$, 356.2445, observed, 356.2444.

(S)-amino(3-(3-(4-decylphenyl)-1,2,4-oxadiazol-5-yl)pyrrolidin-1-yl)methaniminium chloride (7e)

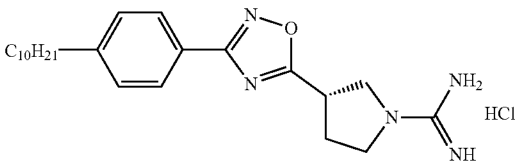

Synthesized by General Procedure 6. White solid, 32 mg (88%) yield. $^1$H NMR (400 MHz, $CD_3OD$) δ 7.93 (d, J=7.9 Hz, 2H), 7.31 (d, J=7.9 Hz, 2H), 4.09-3.85 (m, 3H), 3.72-3.60 (m, 2H), 2.68-2.57 (m, 3H), 2.52-2.42 (m, 1H), 1.68-1.58 (m, 2H), 1.37-1.20 (m, 14H), 0.87 (t, J=6.8, 3H). $^{13}$C NMR (100 MHz, $CD_3OD$) δ 180.3, 169.6, 156.4, 148.1, 130.1, 128.3, 125.2, 51.3, 47.7, 37.3, 36.8, 33.1, 32.4, 30.7, 30.6, 30.5, 30.4, 30.3, 23.7, 14.5. HRMS: (ESI) $[M+H]^+$ calc. for $C_{23}H_{36}N_5O$, 398.2914, observed, 398.2911.

(S)-amino(3-(3-(4-decylphenyl)-1,2,4-oxadiazol-5-yl)piperidin-1-yl)methaniminium chloride (7f)

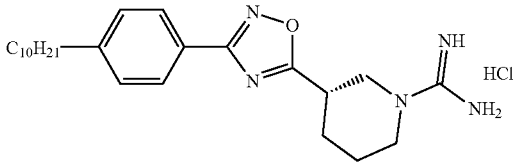

Synthesized by General Procedure 6. White solid, 30 mg (82%) yield. $^1$H NMR (400 MHz, $CD_3OD$) δ 7.96 (d, J=8.1 Hz, 2H), 7.33 (d, J=8.1 Hz), 4.08-4.02 (m, 1H), 3.88-3.80 (m, 1H), 3.72-3.64 (m, 1H), 3.50-3.42 (m, 2H), 2.68 (t, J=7.4 Hz, 2H), 2.38-2.28 (m, 1H), 2.17-2.06 (m, 1H), 1.93-1.83 (m, 1H), 1.82-1.72 (m, 1H), 1.70-1.60 (m, 2H), 1.40-1.21 (m, 14H), 0.89 (t, J=6.8 Hz, 3H). $^{13}$C NMR (100 MHz, $CD_3OD$) δ 180.7, 169.4, 158.2, 148.1, 130.1, 128.3, 125.3, 111.4, 49.0, 47.4, 36.8, 35.2, 33.1, 32.5, 30.7, 30.6, 30.5, 30.3, 28.6, 24.2, 23.7, 14.5. HRMS: (ESI) $[M+H]^+$ calc. for $C_{23}H_{36}N_5O$, 411.2993, observed, 411.3014.

(R)-amino(3-(3-(4-decylphenyl)-1,2,4-oxadiazol-5-yl)pyrrolidin-1-yl)methaniminium chloride (7g)

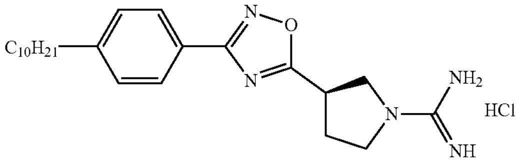

Synthesized by General Procedure 6. White solid, 25 mg (69%) yield. $^1$H NMR (400 MHz, $CD_3OD$) δ 7.93 (d, J=8.1 Hz, 2H), 7.31 (d, J=8.1 Hz, 2H), 4.09-3.94 (m, 2H), 3.92-3.85 (m, 1H), 3.72-3.60 (m, 2H), 2.69-2.56 (m, 3H), 2.52-2.41 (m, 1H), 1.68-1.57 (m, 2H), 1.37-1.20 (m, 14H), 0.87 (t, J=6.8 Hz, 3H). $^{13}$C NMR (100 MHz, $CD_3OD$) δ 180.3, 169.6, 156.4, 148.1, 130.1, 128.3, 125.2, 51.3, 47.7, 37.3, 36.8, 33.1, 32.4, 30.7, 30.6, 30.5, 30.4, 30.3, 23.7, 14.5. LC/MS: (ESI) $[M+H]^+$ calc. for $C_{23}H_{36}N_5O$, 398.29, observed, 398.33.

(R)-amino(3-(3-(4-decylphenyl)-1,2,4-oxadiazol-5-yl)piperidin-1-yl)methaniminium chloride (7h)

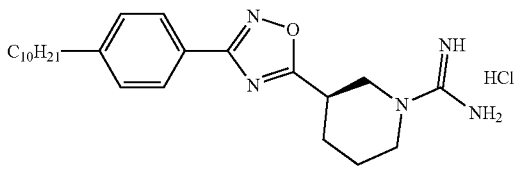

Synthesized by General Procedure 6. White solid, 30 mg (82%) yield. $^1$H NMR (400 MHz, $CD_3OD$) δ 7.96 (d, J=8.2 Hz, 2H), 7.33 (d, J=8.2 Hz, 2H), 4.8-4.01 (m, 1H), 3.88-3.81 (m, 1H), 3.72-3.64 (m, 2H), 3.51-3.41 (m, 2H), 2.68 (t, J=7.7 Hz, 2H), 2.38-2.28 (m, 1H), 2.17-2.06 (m, 1H), 1.93-1.71 (m, 2H), 1.70-1.60 (m, 2H), 1.39-1.21 (m, 14H), 0.89 (t, J=6.8 Hz, 3H). $^{13}$C NMR (100 MHz, $CD_3OD$) δ 180.7, 169.4, 158.2, 148.1, 130.1, 128.3, 125.3, 49.0 47.4, 36.8, 35.2, 33.1, 32.5, 30.7, 30.6, 30.5, 30.3, 28.6, 24.2, 23.7, 14.5. LC/MS: (ESI) $[M+H]^+$ calc. for $C_{24}H_{38}N_5O$, 412.60, observed, 412.35.

3-((3-(4-decylphenyl)-1,2,4-oxadiazol-5-yl)methyl) azetidine-1-carboximidamide 2,2,2-trifluoroacetate (7j)

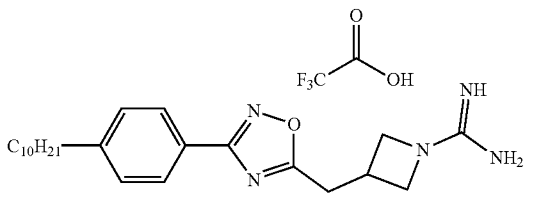

Synthesized by General Procedure 4. White solid, 20 mg (75%) yield. $^1$H NMR (400 MHz, $CD_3OD$) δ 7.93 (d, J=8.2 Hz, 2H), 7.32 (d, J=8.0 Hz, 2H), 4.40-4.34 (m, 2H), 4.03 (dd, J=8.7, 4.5 Hz, 2H), 3.41-3.32 (m, 2H), 2.67 (t, J=7.7 Hz, 2H), 1.68-1.59 (m, 2H), 1.48-1.41 (m, 1H), 1.38-1.22 (m, 14H), 0.88 (t, J=6.7 Hz, 3H). $^{13}$C NMR (100 MHz, $CD_3OD$) δ 179.0, 169.5, 158.2, 148.1, 130.1, 128.3, 125.3, 56.3, 36.8, 33.1, 32.5, 30.7, 32.5, 30.7, 30.6, 30.5, 30.5, 30.3, 27.7, 23.7, 14.5. HRMS: (ESI) $[M+H]^+$ calc. for $C_{23}H_{36}N_5O$, 398.2914, observed, 398.2911.

3-(3-(4-decylphenyl)-1,2,4-oxadiazol-5-yl)azepane-1-carboximidamide 2,2,2-trifluoroacetate (7k)

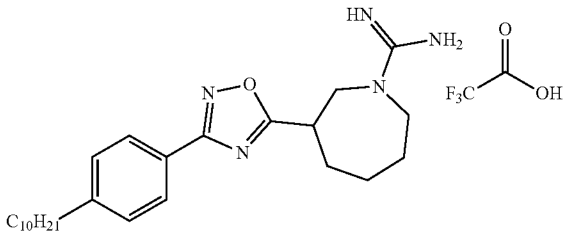

Synthesized by General Procedure 4. White solid, 25 mg (82%) yield. $^1$H NMR (400 MHz, $CD_3OD$) δ 7.94 (d, J=8.2 Hz, 2H), 7.33 (d, J=8.2 Hz, 2H), 4.19-4.10 (m, 1H), 4.00-3.90 (m, 1H), 3.77-3.61 (m, 2H), 3.61-3.57 (m, 1H), 7.61 (t, J=7.6 Hz, 2H), 2.26-2.15 (m, 1H), 2.04-1.58 (m, 7H), 1.42-1.20 (m, 14H), 0.89 (t, J=6.8 Hz, 3H). $^{13}$C NMR (100 MHz, $CD_3OD$) δ 181.6, 169.3, 158.3, 148.2, 130.1, 128.3, 125.3, 51.0, 50.9, 38.1, 36.8, 33.1, 32.5, 32.2, 30.7, 30.6, 30.5, 30.3, 27.9, 25.2, 23.7, 14.5. HRMS: (ESI) $[M+H]^+$ calc. for $C_{25}H_{40}N_5O$, 426.3227, observed, 426.3241.

(R)-3-(3-(6-(heptyloxy)naphthalen-2-yl)-1,2,4-oxadiazol-5-yl)pyrrolidine-1-carboximidamide hydrochloride (7kk)

Synthesized according to General Procedure 6.

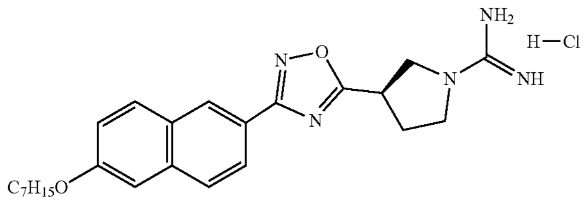

White solid (57%, 16 mg). $^1$H NMR (400 MHz, $CDCl_3$) δ 8.48 (s, 1H), 8.02 (dd, J=8.6, 1.7 Hz, 1H), 7.85 (dd, J=8.8, 2.4 Hz, 2H), 7.27 (d, J=2.4 Hz, 1H), 7.20 (dd, J=9.0, 2.5 Hz, 1H), 4.14-3.88 (m, 5H), 3.75-3.61 (m, 2H), 2.69-2.59 (m, 1H), 2.57-2.45 (m, 1H), 1.89-1.78 (m, 2H), 1.59-1.48 (m, 2H), 1.45-1.29 (m, 6H), 0.92 (t, J=6.8 Hz, 3H). $^{13}$C NMR (101 MHz, $CDCl_3$) δ 180.3, 169.8, 160.1, 156.4, 137.8, 131.2, 129.7, 128.7, 128.7, 125.0, 122.6, 121.1, 107.7, 69.2, 51.3, 47.7, 37.3, 33.0, 30.5, 30.3, 30.2, 27.2, 23.7, 14.4. HRMS: (ESI) $[M+H]^+$ calc. for $C_{24}H_{32}N_5O_2$, 422.2551, observed, 422.2552.

(R)-3-((3-(4-decylphenyl)-1,2,4-oxadiazol-5-yl) methyl)pyrrolidine-1-carboximidamide hydrochloride (7l)

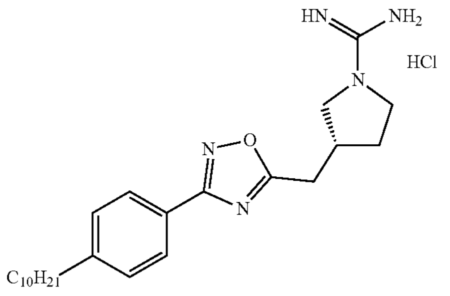

Synthesized by General Procedure 6. White solid, 30 mg (74%) yield. $^{1}H$ NMR (400 MHz, $CD_3OD$) δ 7.94 (d, J=8.1 Hz, 2H), 7.29 (d, J=8.1 Hz, 2H), 3.8-3.72 (m, 1H), 3.61-3.53 (m, 1H), 3.51-3.41 (m, 1H), 3.28-3.09 (m, 3H), 3.00-2.88 (m, 1H), 2.65 (t, J=7.7 Hz, 2H), 2.38-2.28 (m, 1H), 1.98-1.86 (m, 1H), 1.68-1.57 (m, 2H), 1.38-1.19 (m, 14H), 0.87 (t, J=6.7 Hz, 3H). $^{13}C$ NMR (100 MHz, $CD_3OD$) δ 179.6, 169.5, 156.2, 148.0, 130.1, 128.3, 125.4, 52.8, 47.7, 37.6, 36.8, 33.1, 32.5, 31.7, 30.7, 30.6, 30.5, 30.3, 23.7, 14.5. HRMS: (ESI) $[M+H]^+$ calc. for $C_{24}H_{38}N_5O$, 412.3071, observed, 412.3097.

(S)-3-((3-(4-decylphenyl)-1,2,4-oxadiazol-5-yl) methyl)pyrrolidine-1-carboximidamide 2,2,2-trifluoroacetate (7p)

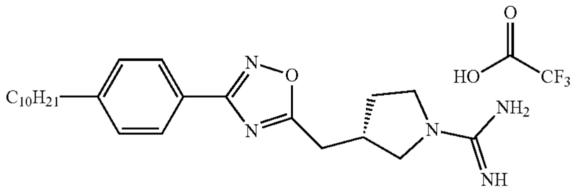

Synthesized by General Procedure 4. White solid, 42 mg (61%) yield. $^{1}H$ NMR (400 MHz, $CD_3OD$) δ 7.94 (d, J=8.4 Hz, 2H), 7.32 (d, J=8.4 Hz, 2H), 3.78-3.73 (m, 1H), 3.61-3.54 (m, 1H), 3.50-3.42 (m, 1H), 3.27-3.09 (m, 3H), 3.01-2.90 (m, 1H), 2.67 (t, J=7.7 Hz, 2H), 2.37-2.30 (m, 1H), 1.98-1.86 (m, 1H), 1.69-1.59 (m, 2H), 1.38-1.20 (m, 14H), 0.88 (t, J=6.9 Hz, 3H). $^{13}C$ NMR (100 MHz, $CD_3OD$) δ 179.7, 169.6, 156.3, 148.1, 130.1, 128.3, 125.4, 52.8, 47.7, 37.6, 36.9, 33.1, 32.5, 31.8, 30.7, 30.6, 30.5, 30.3, 29.8, 23.7, 14.5. HRMS: (ESI) $[M+H]^+$ calc. for $C_{24}H_{38}N_5O$, 412.3071, observed, 412.3058.

(S)-3-((3-(4-decylphenyl)-1,2,4-oxadiazol-5-yl) methyl)piperidine-1-carboximidamide 2,2,2-trifluoroacetate (7q)

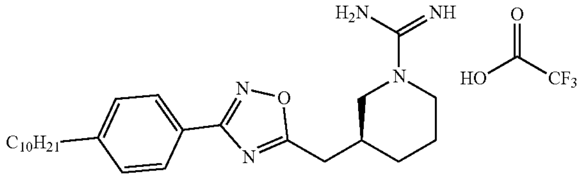

Synthesized by General Procedure 4. White solid, 55 mg (64%) yield. $^{1}H$ NMR (400 MHz, $CD_3OD$) δ 7.93 (d, J=8.2 Hz, 2H), 7.31 (d, J=8.2 Hz, 2H), 3.95-3.87 (m, 1H), 3.81-3.74 (m, 1H), 3.18-3.09 (m, 1H), 3.08-2.91 (m, 3H), 2.66 (t J=7.7 Hz, 2H), 2.30-2.18 (m, 1H), 2.03-1.94 (m, 1H), 1.87-1.78 (m, 1H), 1.68-1.56 (m, 3H), 1.52-1.40 (m, 1H), 1.37-1.20 (m, 14H), 0.87 (t, J=6.9 Hz, 3H). $^{13}C$ NMR (100 MHz, $CD_3OD$) δ 179.5, 169.5, 157.9, 148.0, 130.1, 28.3, 125.4, 51.7, 47.5, 36.8, 35.4, 33.1, 32.5, 30.7, 30.6, 30.6, 30.5, 30.5, 30.3, 25.2, 23.7, 14.5. HRMS: (ESI) $[M+H]^+$ calc. for $C_{25}H_{40}N_5O$, 426.3227, observed, 426.3241.

(R)-3-(3-(3-decylphenyl)-1,2,4-oxadiazol-5-yl)pyrrolidine-1-carboximidamide hydrochloride (7t)

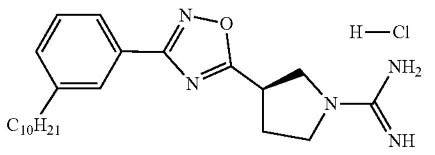

Synthesized by General Procedure 6. Colorless solid, 53 mg (quant) yield. $^{1}H$ NMR (400 MHz, $CD_3OD$) δ 7.90-7.82 (m, 2H), 7.44-7.34 (m, 2H), 4.11-3.96 (m, 2H), 3.93-3.87 (m, 1H), 3.74-3.61 (m, 2H), 2.71-2.58 (m, 3H), 2.54-2.43 (m, 1H), 1.69-1.59 (m, 2H), 1.40-1.18 (m, 14H), 0.88 (t, J=6.8 Hz, 3H). $^{13}C$ NMR (100 MHz, $CD_3OD$) δ 180.4, 169.7, 156.4, 145.1, 132.7, 130.0, 128.2, 127.7, 125.8, 51.3, 47.7, 37.3, 36.7, 33.1, 32.6, 30.7, 30.6, 30.5, 30.4, 30.3, 23.7, 14.5. HRMS: (ESI) $[M+H]^+$ calc. for $C_{23}H_{36}N_5O$, 398.2914, observed, 398.2918.

(R)-3-(3-(4-undecylphenyl)-1,2,4-oxadiazol-5-yl) pyrrolidine-1-carboximidamide hydrochloride (7xa)

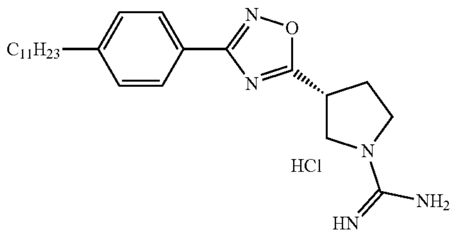

Synthesized according to General Procedure 6. White solid (45%, 103 mg). $^{1}H$ NMR (400 MHz, Methanol-$d_4$) δ 7.95 (d, J=8.04, 2H), 7.34 (d, J=8.04, 2H), 4.09-3.86 (m, 3H), 3.72-3.59 (m, 2H), 2.71-2.57 (m, 3H), 2.54-2.44 (m, 1H), 1.65 (p, J=7.30, 2H), 1.38-1.23 (m, 16H), 0.89 (t, J=6.68, 3H); $^{13}$C NMR (101 MHz, Methanol-$d_4$) δ 178.88, 168.21, 154.99, 146.77, 128.70, 126.90, 123.77, 49.84, 46.20, 35.87, 35.42, 31.64, 31.01, 29.30, 29.25, 29.12, 29.09, 29.04, 28.85, 22.31, 13.01; HRMS (ESI+): Calcd for $C_{24}H_{39}N_5O$ $[M+H]^+$: 412.3071, Found: 412.3078.

(R)-3-(3-(4-nonylphenyl)-1,2,4-oxadiazol-5-yl)pyrrolidine-1-carboximidamide hydrochloride (7xb)

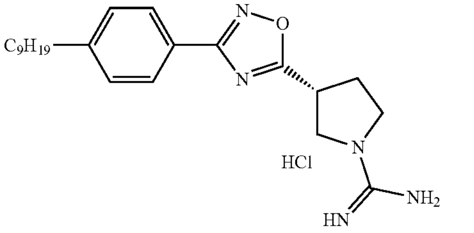

Synthesized according to General Procedure 6. White solid (62%, 99 mg). $^1$H NMR (400 MHz, Methanol-$d_4$) δ 7.95 (d, J=8.05, 2H), 7.34 (d, J=8.05, 2H), 4.09-3.86 (m, 3H), 3.72-3.60 (m, 2H), 2.71-2.57 (m, 3H), 2.54-2.44 (m, 1H), 1.65 (p, J=7.10, 2H), 1.41-1.20 (m, 12H), 0.89 (t, J=7.11, 3H); $^{13}$C NMR (101 MHz, Methanol-$d_4$) δ 180.31, 169.64, 156.42, 148.21, 130.13, 128.34, 125.20, 51.27, 47.63, 37.30, 36.85, 33.04, 32.45, 30.67, 30.58, 30.52, 30.43, 30.32, 23.7414.43; HRMS (ESI+): Calcd for $C_{22}H_{35}N_5O$ $[M+H]^+$: 384.2758, Found: 384.2750.

(R)-3-(3-(4-undecylphenyl)-1,2,4-oxadiazol-5-yl)piperidine-1-carboximidamide hydrochloride (7ya)

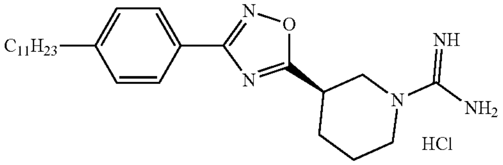

Synthesized according to General Procedure 6. White solid (33%, 223 mg). $^1$H NMR (400 MHz, Methanol-$d_4$) δ 7.96 (d, J=8.09, 2H), 7.34 (d, J=8.15, 2H), 4.07-4.00 (m, 1H) 3.87-3.81 (m, 1H), 3.70-3.63 (m, 1H), 3.50-3.42 (m, 2H), 2.68 (d, J=7.76, 2H), 2.37-2.28 (m, 1H), 2.17-2.07 (m, 1H), 1.92-1.72 (m, 2H), 1.65 (p, J=6.68, 2H), 1.38-1.20 (m, 16H), 0.89 (t, J=6.86, 3H); $^{13}$C NMR (101 MHz, Methanol-$d_4$) δ 180.66, 169.45, 158.21, 148.16, 130.14, 128.33, 125.28, 48.96, 47.39, 36.85, 35.24, 33.07, 32.46, 30.73, 30.69, 30.56, 30.48, 30.30, 28.55, 24.14, 23.74, 14.45; HRMS (ESI+): Calcd for $C_{25}H_{41}N_5O$ $[M+H]^+$: 426.3227, Found: 426.3229.

(R)-3-(3-(4-nonylphenyl)-1,2,4-oxadiazol-5-yl)piperidine-1-carboximidamide hydrochloride (7yb)

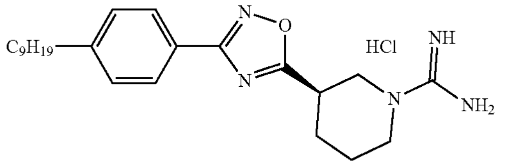

Synthesized according to General Procedure 6. White solid (85%, 202 mg). $^1$H NMR (400 MHz, Methanol-$d_4$) δ 7.95 (d, J=7.68, 2H), 7.33 (d, J=7.26, 2H), 4.07-3.99 (m, 1H), 3.88-3.78 (m, 1H), 3.70-3.62 (m, 1H), 3.50-3.40 (m, 2H), 2.68 (t, J=7.69, 2H), 2.36-2.27 (m, 1H), 2.16-2.05 (m, 1H), 1.91-1.58 (m, 4H), 1.39-1.21 (m, 12H), 0.89 (t, J=6.79, 3H); $^{13}$C NMR (101 MHz, Methanol-$d_4$) δ 180.66, 169.44, 158.22, 148.14, 130.13, 128.33. 125.29, 48.95, 47.38, 36.85, 35.23, 33.05, 32.46, 30.67, 30.58, 30.43, 30.31, 28.96, 24.15, 23.74, 14.44; HRMS (ESI+): Calcd for $C_{23}H_{37}N_5O$ $[M+H]^+$: 398.2914, Found: 398.2922.

Scheme 2 - Synthetic Route to 15a-j

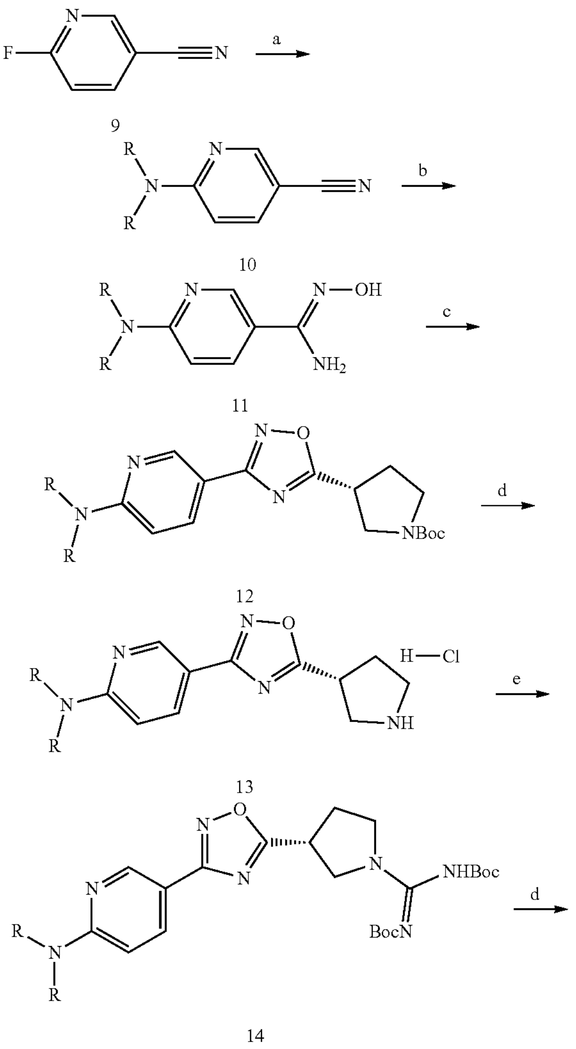

-continued

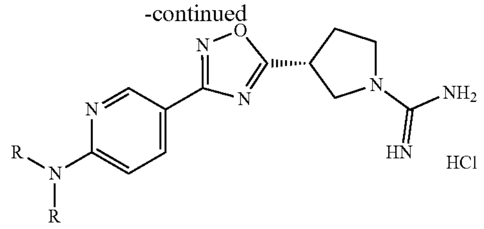

15 a. i) NAH (1.5 equiv), DMF, 100° C.;
b. $NH_2OH$•HCl (2 equiv), TEA (3 equiv), EtOH, reflux;
c. N-Boc-β-amino acid (1.1 equiv), HTCU (1.1 equiv), DIEA (1.8 equiv), DMF, 100° C.;
d. TFA (30 equiv), DCM, rt;
e. N,N'-Di-Boc-1H-pyrazole-1-carboxamidine (1 equiv), DIEA (15 equiv), MeCN, 50° C. μW;
f. $HCl_{(g)}$, MeOH, rt.

General Procedure A: $S_NAR$

To a round bottom flask containing DMF was added 6-fluoronicotinonitrile (1 equiv), piperidine (1 equiv), and the mixture was cooled to 0° C. in a brine ice bath. Sodium hydride (1.5 equiv) was then added and the reaction was allowed to warm to room temperature, followed by heating to 100° C. until consumption of starting material was observed as monitored by TLC (2-4 hours). Upon cooling to room temperature, the mixture was diluted in ethyl acetate and extracted with brine solution. The organic layers were then collected and dried over anhydrous sodium sulfate. Concentration in vacuo afforded the crude product as an oil, which was then purified by column chromatography (10-35% ethyl acetate in hexanes).

General Procedure B: Amidoxime Synthesis

To a round bottom flask containing ethanol was added 4-decylbenzonitrile (1 equiv), hydroxylamine hydrochloride (2 equiv), and trimethylamine (3 equiv) under ambient air. The reaction mixture was then heated to reflux until complete as monitored by TLC (1-4 hours). The resulting solution was allowed to cool to room temperature, followed by concentration in vacuo, to afford the crude mixture as a solid. Purification by column chromatography (0-20% ethyl acetate in dichloromethane) afforded the pure amidoxime product.

General Procedure C: 1,2,4-Oxadiazole Synthesis

Amidoxime (1 equiv), N-Boc protected β-amino acid (1.1 equiv), and DIEA (1.8 equiv) were added to a round bottom flask containing DMF at room temperature. HCTU (1.1 equiv) was then added and the resulting mixture was heated to 100° C. until completion as monitored by TLC (6-16 hours). Upon cooling to room temperature, the resulting mixture was diluted in ethyl acetate and washed with a saturated lithium bromide solution. The resulting aqueous layer was then extracted with ethyl acetate. The organic layers were then combined and washed with a brine solution, followed by drying over anhydrous sodium sulfate. Concentration in vacuo afforded the crude product, which was then purified by column chromatography using the appropriate ethyl acetate:hexanes solvent system.

General Procedure D: TFA Boc Deprotection

To a round bottom flask containing Boc-protected starting material (1 equiv) dissolved in dichloromethane was added TFA (30 equiv). The resulting solution was allowed to stir until consumption of starting material as monitored by TLC (1-6 hours). Concentration in vacuo and filtration of the resulting off-white solid, followed by washing with diethyl ether afforded the pure TFA salt.

General Procedure E: Guanylation

TFA salt (1 equiv), DIEA (15 equiv), and (Z)-tert-butyl (((tert-butoxycarbonyl)imino)(1H-pyrazol-1-yl)methyl)carbamate (1 equiv) were added to a microwave vial containing MCCN at room temperature. The resulting solution was then placed in a CEM microwave synthesized and heated to 50° C. for 3 hours. After cooling down to room temperature, the solution was concentrated in vacuo to afford the crude mixture as a yellow oil, which was then purified by column chromatography using the appropriate ethyl acetate and hexanes solvent system.

General Procedure F: HCl Boc Deprotection

Boc protected starting material (1 equiv) was added to a round bottom flask and dissolved in methanol. $HCl_{(g)}$ was then bubbled into the solution for 1 minute. The resulting solution was allowed to stir at room temperature until consumption of Boc protected starting material as monitored by TLC (30-60 minutes). Concentration in vacuo afforded a white to off-white solid, which was then washed with diethyl ether to afford the pure HCl salt.

6-(piperidin-1-yl)nicotinonitrile (10a)

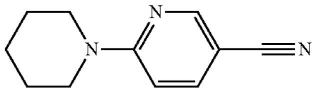 [SMILES: N#Cc1ccc(N2CCCCC2)nc1]

Synthesized according to General Procedure A. Red solid (89%, 645 mg). $^1H$ NMR (400 MHz, $CDCl_3$) δ 8.34 (s, 1H), 7.52 (d, J=9.26, 1H), 6.55 (d, J=9.09, 1H), 3.62 (t, J=5.64, 4H), 1.70-1.54 (m 6H); $^{13}C$ NMR (101 MHz, $CDCl_3$) δ 159.16, 152.76, 139.49, 118.96, 105.54, 95.10, 45.67, 25.48, 24.51.

N'-hydroxy-6-(piperidin-1-yl)nicotinimidamide (11a)

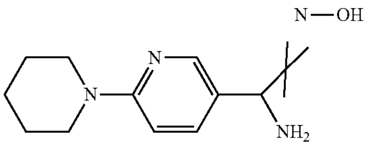

Synthesized according to General Procedure B. Crude mixture dried in vacuo and carried forward to the next reaction without purification.

tert-butyl (R)-3-(3-(6-(piperidin-1-yl)pyridin-3-yl)-1,2,4-oxadiazol-5-yl)pyrrolidine-1-carboxylate (12a)

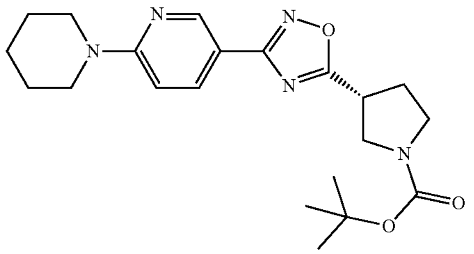 [SMILES: CC(C)(C)OC(=O)N1CC[C@@H](c2nc(-c3ccc(N4CCCCC4)nc3)no2)C1]

Synthesized according to General Procedure C. Purified by silica chromatography (40% EtOAc in hexanes). Yellow oil (66%, 708 mg). $^{1}$H NMR (400 MHz, $CDCl_3$) δ 8.73 (s, 1H), 7.95 (d, J=8.24, 1H), 6.62 (d, J=8.99, 1H), 3.84-3.50 (m, 9H), 2.38-2.24 (m, 2H), 1.66-1.54 (m, 6H), 1.41 (s, 9H); $^{13}$C NMR (101 MHz, $CDCl_3$) δ 178.88, 166.89, 160.11, 154.34, 147.89, 135.98, 110.51, 106.16, 79.98, 49.17, 45.97, 45.10, 36.50, 29.53, 28.42, 25.49, 24.63.

(R)-3-(6-(piperidin-1-yl)pyridin-3-yl)-5-(pyrrolidin-3-yl)-1,2,4-oxadiazole hydrochloride (13a)

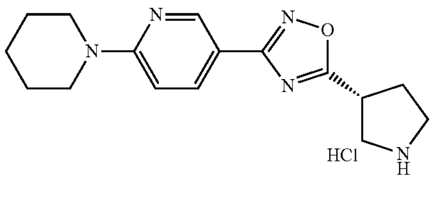 [SMILES: c1cc(N2CCCCC2)ncc1-c1noc([C@@H]2CCNC2)n1 ; Cl]

Synthesized according to General Procedure D. White solid (80%, 475 mg). $^{1}$H NMR (400 MHz, Methanol-$d_4$) δ 8.70 (s, 1H), 8.05 (d, J=8.88, 1H), 6.87 (d, J=9.13, 1H), 4.05 (p, J=7.17, 1H), 3.84-3.63 (m, 6H), 3.54-3.45 (m, 2H), 2.65-2.54 (m, 1H), 2.47-2.38 (m, 1H), 1.76-1.59 (m, 6H); $^{13}$C NMR (101 MHz, Methanol-$d_4$) δ 178.44, 166.64, 160.07, 147.14, 135.69, 110.18, 106.43, 48.15, 45.66, 45.21, 35.26, 29.08, 25.23, 24.32.

tert-butyl (R)-(((tert-butoxycarbonyl)amino)(3-(3-(6-(piperidin-1-yl)pyridin-3-yl)-1,2,4-oxadiazol-5-yl) pyrrolidin-1-yl)methylene)carbamate (14a)

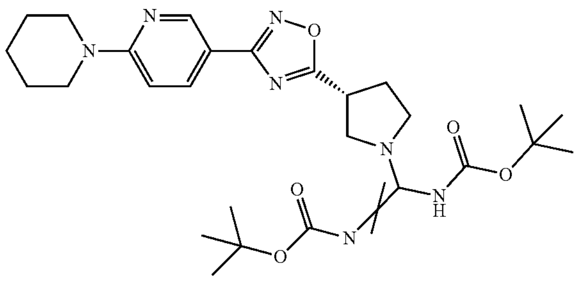 [SMILES: CC(C)(C)OC(=O)NC(N1CC[C@@H](c2nc(-c3ccc(N4CCCCC4)nc3)no2)C1)C(C)(C)NC(=O)OC(C)(C)C]

Synthesized according to General Procedure E. Crude mixture dried in vacuo and carried forward to the next reaction without purification.

(R)-3-(3-(6-(piperidin-1-yl)pyridin-3-yl)-1,2,4-oxadiazol-5-yl)pyrrolidine-1-carboximidamide hydrochloride (15a)

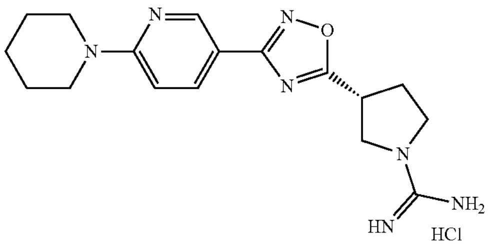 [SMILES: N=C(N)N1CC[C@@H](c2nc(-c3ccc(N4CCCCC4)nc3)no2)C1 ; Cl]

Synthesized according to General Procedure F. White solid (51%, 205 mg). $^{1}$H NMR (400 MHz, Methanol-$d_4$) δ 8.68 (s, 1H), 8.08 (d, J=9.15, 1H), 6.86 (d, J=8.40, 1H), 4.07-3.84 (m, 3H), 3.71-3.58 (m, 6H), 2.66-2.40 (m, 2H), 1.74-1.58 (m, 6H); $^{13}$C NMR (101 MHz, Methanol-$d_4$) δ 178.61, 166.65, 160.08, 154.97, 147.09, 135.69, 110.27, 106.47, 49.89, 46.27, 45.69, 35.84, 29.09, 25.24, 24.33; HRMS (ESI+): Calcd for $C_{17}H_{25}N_7O$ [M+H]: 342.2037, Found: 342.2042.

5-methyl-N-octylpyridin-2-amine (10b)

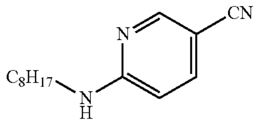

Synthesized according to General Procedure A. Crude mixture dried in vacuo and carried forward to the next reaction without purification.

N'-hydroxy-6-(octylamino)nicotinimidamide (11b)

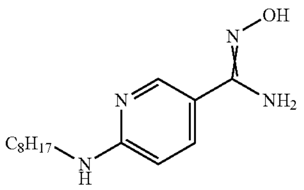

Synthesized according to General Procedure B. Crude mixture dried in vacuo and carried forward to the next reaction without purification.

tert-butyl (R)-3-(3-(6-(octylamino)pyridin-3-yl)-1,2,4-oxadiazol-5-yl)pyrrolidine-1-carboxylate (12b)

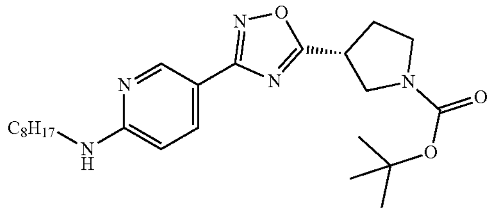

Synthesized according to General Procedure C. Purified by silica chromatography (25% EtOAc in hexanes). Yellow oil (61%, 333 mg). $^{1}$H NMR (400 MHz, $CDCl_3$) δ 8.70 (s, 1H), 7.98 (d, J=8.81, 1H), 6.39 (d, J=8.90, 1H), 5.06 (brs, 1H), 3.85-3.44 (m, 5H), 3.25 (q, J=6.31, 2H), 2.38-2.24 (m, 2H), 1.58 (p, J=6.74, 2H), 1.42 (s, 9H), 1.37-1.17 (m, 10H), 0.82 (t, J=6.69, 3H); $^{13}$C NMR (101 MHz, $CDCl_3$) δ 179.03, 167.02, 160.25, 154.31, 148.24, 136.28, 111.62, 106.02, 79.88, 49.45, 45.14, 42.29, 36.65, 31.87, 29.68, 29.48, 29.40, 29.30, 28.56, 27.09, 22.72, 14.18.

(R)—N-octyl-5-(5-(pyrrolidin-3-yl)-1,2,4-oxadiazol-3-yl)pyridin-2-amine hydrochloride (13b)

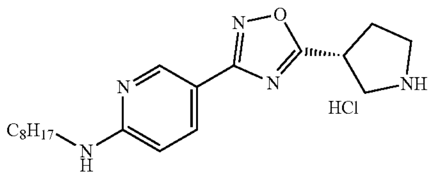

Synthesized according to General Procedure D. White solid (78%, 121 mg). $^1$H NMR (400 MHz, Methanol-$d_4$) δ 8.47 (s, 1H), 8.34 (d, J=7.59, 2H), 7.24 (d, J=9.19, 1H), 4.13 (p, J=7.00, 1H), 3.88-3.74 (m, 2H), 3.57-3.50 (m, 2H), 3.46 (t, J=7.11, 2H), 2.68-2.58 (m, 1H), 2.49-2.38 (m, 1H), 1.75 (p, J=7.38, 2H), 1.50-1.28 (m, 10H), 0.88 (t, J=6.56, 3H); $^{13}$C NMR (101 MHz, cdcl$_3$) δ 183.42, 168.34, 157.41, 142.84, 138.97, 119.08, 115.97, 49.05, 46.40, 39.19, 35.48, 32.86, 31.77, 30.45, 26.23, 16.99.

tert-butyl (R)-(((tert-butoxycarbonyl)imino)(3-(3-(6-(octylamino)pyridin-3-yl)-1,2,4-oxadiazol-5-yl)pyrrolidin-1-yl)methyl)carbamate (14b)

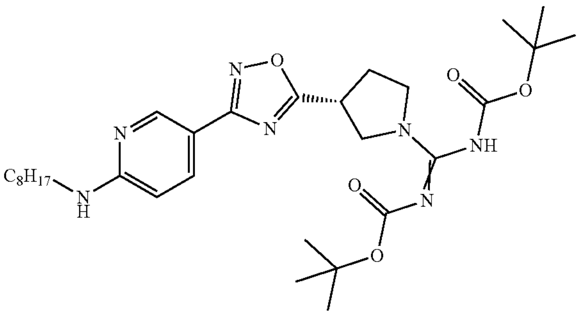

Synthesized according to General Procedure E. Crude mixture dried in vacuo and carried forward to the next reaction without purification (R)-3-(3-(6-(octylamino)pyridin-3-yl)-1,2,4-oxadiazol-5-yl)pyrrolidine-1-carboximidamide hydrochloride (15b)

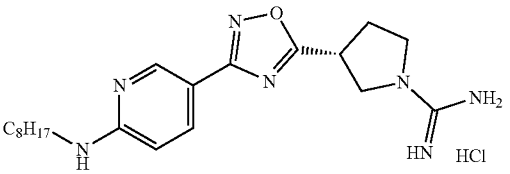

Synthesized according to General Procedure F. White solid (46%, 97 mg). $^1$H NMR (400 MHz, Methanol-$d_4$) δ 8.59 (s, 1H), 7.94, (d J=8.84, 1H), 6.60 (d, J=8.83, 1H), 4.06-3.85 (m, 3H), 3.71-3.61 (m, 2H), 3.35-3.30 (m, 3H), 2.65-2.56 (m, 1H), 2.51-2.41 (m, 1H), 1.62 (p, J=7.00, 2H), 1.45-1.26 (m, 10H), 0.89 (t, J=6.87, 3H); $^{13}$C NMR (101 MHz, Methanol-$d_4$) δ 178.54, 166.73, 160.41, 154.95, 146.98, 146.98, 134.98, 110.19, 108.45, 49.87, 46.24, 41.04, 35.82, 31.96, 29.08, 28.99, 28.91, 26.72, 22.28, 13.01; HRMS (ESI+): Calcd for $C_{20}H_{33}N_7O$ $[M+H]^+$: 386.2663, Found: 386.2666.

6-((3-fluoro-4-(trifluoromethoxy)phenyl)amino) nicotinonitrile (10c)

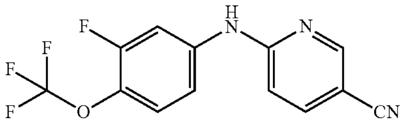 [SMILES: N#Cc1ccc(Nc2ccc(OC(F)(F)F)c(F)c2)nc1]

Synthesized according to General Procedure A. Pink solid (46%, 138 mg) $^1$H NMR (400 MHz, Methanol-$d_4$) δ 8.54 (s, 1H), 8.02 (d, J=13.20, 1H), 7.81 (d, J=8.30, 1H), 7.39-7.28 (m, 2H), 6.87 (d, J=8.56, 1H); $^{13}$C NMR (101 MHz, Methanol-$d_4$) δ 158.39, 156.77, 154.31, 153.27, 141.87, 141.77, 140.44, 140.39, 131.55, 131.53, 131.51, 131.49, 131.42, 131.40, 131.38, 131.36, 125.78, 124.78, 123.23, 120.67, 118.87, 118.12, 115.90, 115.87, 112.06, 108.78, 108.54, 100.33.

6-((3-fluoro-4-(trifluoromethoxy)phenyl)amino)-N'-hydroxynicotinimidamide (11c)

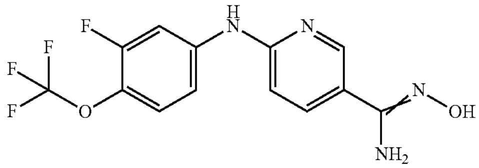 [SMILES: NC(=NO)c1ccc(Nc2ccc(OC(F)(F)F)c(F)c2)nc1]

Synthesized according to General Procedure B. Crude mixture dried in vacuo and carried forward to the next reaction without purification.

tert-butyl (R)-3-(3-(6-((3-fluoro-4-(trifluoromethoxy)phenyl)amino)pyridin-3-yl)-1,2,4-oxadiazol-5-yl)piperidine-1-carboxylate (12c)

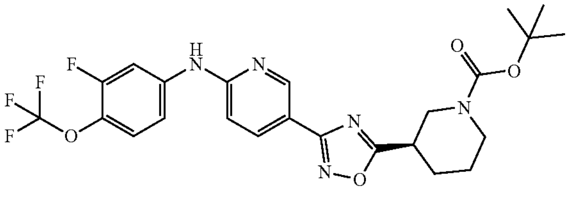 [SMILES: CC(C)(C)OC(=O)N1CCC[C@@H](c2nc(-c3ccc(Nc4ccc(OC(F)(F)F)c(F)c4)nc3)no2)C1]

Synthesized according to General Procedure C. Purified by silica chromatography (30% EtOAc in hexanes) Pink solid (66%, 112 mg). $^1$H NMR (400 MHz, CDCl$_3$) δ 8.90 (s, 1H), 8.13 (s, 1H), 7.64 (d, J=12.62, 1H), 7.50 (brs, 1H), 7.24-7.12 (m, 2H), 6.84 (d, J=8.59, 1H), 4.48-3.84 (m, 2h), 3.45-2.95 (m, 3H), 2.29-2.17 (m, 1H), 1.95-1.77 (m, 2H), 1.66-1.37 (m, 10H); $^{13}$C NMR (101 MHz, CDCl$_3$) δ 179.95, 166.39, 156.65, 156.14, 154.72, 153.65, 147.89, 147.81, 140.26, 140.17, 136.54, 131.17, 131.14, 131.04, 131.02, 124.52, 124.34, 121.95, 119.39, 116.82, 115.22, 115.19, 115.16, 109.59, 108.57, 108.34, 80.33, 46.83, 43.69, 34.86, 28.48.

(R)—N-(3-fluoro-4-(trifluoromethoxy)phenyl)-5-(5-(piperidin-3-yl)-1,2,4-oxadiazol-3-yl)pyridin-2-amine hydrochloride (13c)

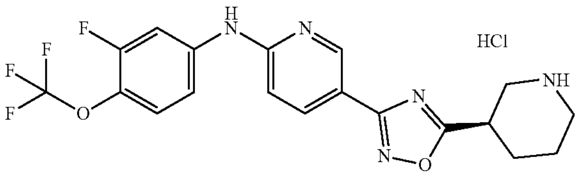 [SMILES: Fc1cc(Nc2ccc(-c3noc([C@@H]4CCCNC4)n3)cn2)ccc1OC(F)(F)F ; Cl]

Synthesized according to General Procedure D. White solid (91%, 89 mg). $^{1}H$ NMR (400 MHz, Methanol-$d_4$) δ 8.68 (s, 1H), 8.43 (d, J=8.81, 1H), 7.76 (d, J=11.16, 1H), 7.53-7.40 (m, 2H), 7.28 (d, J=9.04, 1H), 3.82-3.68 (m, 2H), 3.54-3.39 (m, 2H), 3.21-3.14 (m, 1H), 2.43-2.33 (m, 1H), 2.07-1.96 (m, 3H); $^{13}C$ NMR (101 MHz, Methanol-$d_4$) δ 180.24, 166.29, 157.35, 155.49, 154.84, 141.27, 140.83, 138.92, 138.82, 134.59, 134.47, 126.12, 125.74, 123.18, 120.62, 120.10, 120.07, 118.06, 115.84, 114.92, 112.75, 112.53, 46.03, 45.00, 33.24, 27.02, 22.06.

tert-butyl (R)-(((tert-butoxycarbonyl)amino)(3-(3-(6-((3-fluoro-4-(trifluoromethoxy)phenyl)amino)pyridin-3-yl)-1,2,4-oxadiazol-5-yl)piperidin-1-yl)methylene)carbamate (14c)

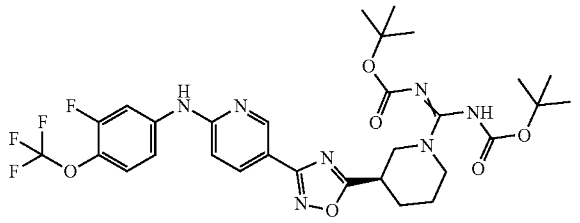 [SMILES: CC(C)(C)OC(=O)N=C(NC(=O)OC(C)(C)C)N1CCC[C@@H](c2nc(-c3ccc(Nc4ccc(OC(F)(F)F)c(F)c4)nc3)no2)C1]

Synthesized by General Procedure E. Purified by silica chromatography (35% EtOAc in hexanes). White solid (52%, 67 mg). $^{1}H$ NMR (400 MHz, $CDCl_3$) δ 9.98 (brs, 1H), 8.80 (s, 1H), 8.12-7.99 (m, 2H), 7.71 (d, J=12.24, 1H), 7.20-7.11 (m, 2H), 6.83 (d, J=9.12, 1H), 4.27-3.22 (m, 5H), 2.26-2.16 (m, 1H), 2.07-1.93 (m, 1H), 1.76-1.35 (m, 20H); $^{13}C$ NMR (101 MHz, $CDCl_3$) δ 179.35, 166.09, 156.64, 155.87, 155.49, 153.38, 153.26, 147.56, 140.36, 140.27, 135.92, 130.68, 130.66, 130.55, 130.53, 124.42, 123.90, 121.85, 119.28, 116.71, 114.74, 114.71, 114.31, 109.88, 108.15, 107.92, 105.05, 82.87, 49.16, 47.12, 34.35, 28.13, 28.12, 23.71.

(R)-3-(3-(6-((3-fluoro-4-(trifluoromethoxy)phenyl)amino)pyridin-3-yl)-1,2,4-oxadiazol-5-yl)piperidine-1-carboximidamide hydrochloride (15g)

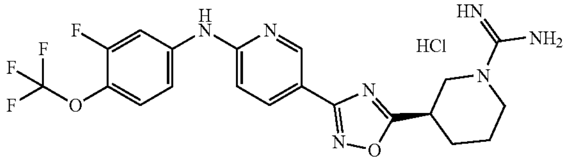 [SMILES: N=C(N)N1CCC[C@@H](c2nc(-c3ccc(Nc4ccc(OC(F)(F)F)c(F)c4)nc3)no2)C1 ; Cl]

Synthesized according to General Procedure F. White solid (90%, 46 mg). $^{1}H$ NMR (400 MHz, Methanol-$d_4$) δ 8.82 (s, 1H), 8.11 (d, J=8.11, 1H), 8.03 (d, J=12.45, 1H), 7.34-7.26 (m, 2H), 6.92 (d, J=8.81, 1H), 4.04-3.97 (m, 1H), 3.88-3.80 (m, 1H), 3.69-3.60 (m, 1H), 3.50-3.39 (m, 2H), 2.34-2.25 (m, 1H), 2.14-2.04 (m, 1H), 1.89-1.69 (m, 2H); $^{13}C$ NMR (126 MHz, Methanol-$d_4$) δ 179.31, 166.32, 157.21, 156.90, 156.84, 155.35, 153.39, 146.69, 141.51, 141.43, 135.45, 129.64, 129.54, 123.75, 123.57, 121.72, 119.68, 117.64, 114.31, 114.29, 114.05, 111.04, 106.89, 106.70, 47.53, 46.02, 33.79, 27.10, 22.68

6-morpholinonicotinonitrile (10d)

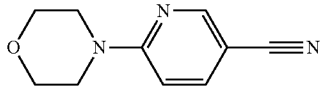 [SMILES: N#Cc1ccc(N2CCOCC2)nc1]

Synthesized according to General Procedure A. White solid (84%, 840 mg). $^{1}H$ NMR (400 MHz, Methanol-$d_4$) δ 8.38 (s, 1H), 7.71 (d, J=9.08, 1H), 6.81 (d, J=9.22, 1H), 3.75-3.71 (m, 4H), 3.65-3.61 (m, 4H); $^{13}C$ NMR (101 MHz, Methanol-$d_4$) δ 159.74, 152.14, 139.66, 117.90, 105.96, 96.22, 66.12, 44.47.

N'-hydroxy-6-morpholinonicotinimidamide (11d)

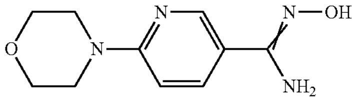

Synthesized according to General Procedure B. Crude mixture dried in vacuo and carried forward to the next reaction without purification.

tert-butyl (R)-3-(3-(6-morpholinopyridin-3-yl)-1,2,4-oxadiazol-5-yl)pyrrolidine-1-carboxylate (12d)

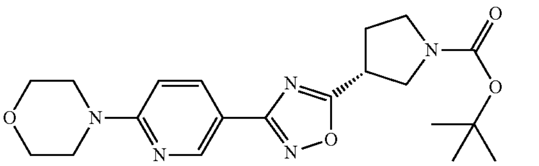 [SMILES: CC(C)(C)OC(=O)N1CC[C@@H](c2nc(-c3ccc(N4CCOCC4)nc3)no2)C1]

Synthesized according to General Procedure C. Crude mixture dried in vacuo and carried forward to the next reaction without purification.

(R)-4-(5-(5-(pyrrolidin-3-yl)-1,2,4-oxadiazol-3-yl)pyridin-2-yl)morpholine hydrochloride (13d)

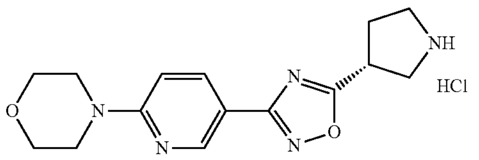 [SMILES: c1cc(N2CCOCC2)ncc1-c1noc([C@@H]2CCNC2)n1 ; Cl]

Synthesized according to General Procedure D. White solid (86%, 640 mg). $^{1}$H NMR (400 MHz, Methanol-$d_4$) δ 8.65 (s, 1H), 8.38 (d, J=9.50, 1H), 7.33 (d, J=9.57, 1H), 4.13 (p, J=7.29, 1H), 3.88-3.74 (m, 9H), 3.68 (d, J=11.14, 1H), 3.60-3.48 (m, 2H), 2.69-2.59 (m, 1H), 2.50-2.40 (m, 1H); $^{13}$C NMR (101 MHz, Methanol-$d_4$) δ 180.61, 166.49, 157.06, 141.42, 140.17, 113.73, 112.23, 67.07, 49.37, 47.17, 46.55, 36.64, 30.35.

tert-butyl (R)-(((tert-butoxycarbonyl)amino)(3-(3-(6-morpholinopyridin-3-yl)-1,2,4-oxadiazol-5-yl)pyrrolidin-1-yl)methylene)carbamate (14d)

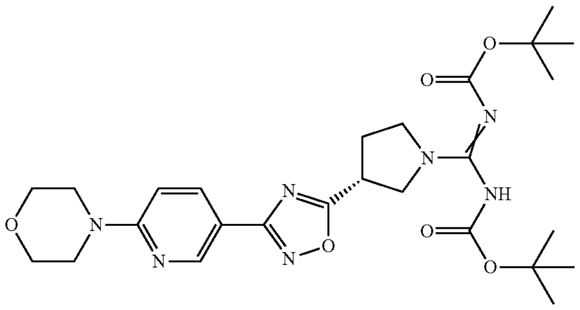 [SMILES: CC(C)(C)OC(=O)N=C(NC(=O)OC(C)(C)C)N1CC[C@@H](c2nc(-c3ccc(N4CCOCC4)nc3)no2)C1]

Synthesized according to General Procedure E. Crude mixture dried in vacuo and carried forward to the next reaction without purification (R)-3-(3-(6-morpholinopyridin-3-yl)-1,2,4-oxadiazol-5-yl)pyrrolidine-1-carboximidamide hydrochloride (15d)

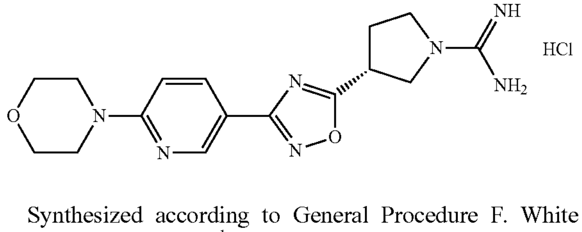

Synthesized according to General Procedure F. White solid (22%, 112 mg). $^{1}$H NMR (400 MHz, Methanol-$d_4$) δ 8.72 (s, 1H), 8.09 (d, J=9.13, 1H), 6.89 (d, J=8.50, 1H), 4.06-3.85 (m, 3H), 3.79-3.74 (m, 4H), 3.68-3.57 (m, 6H), 2.65-2.55 (m, 1H), 2.50-2.40 (m, 1H); $^{13}$C NMR (101 MHz, Methanol-$d_4$) δ 178.77, 166.55, 160.43, 154.95, 146.97, 135.83, 111.73, 106.50, 66.23, 49.87, 46.24, 44.88, 35.83, 29.08

6-((2-chlorophenyl)amino)nicotinonitrile (10e)

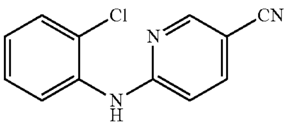 [SMILES: N#Cc1ccc(Nc2ccccc2Cl)nc1]

Synthesized according to General Procedure A. Yellow solid (45%, 225 mg) $^{1}$H NMR (400 MHz, $CDCl_3$) δ 8.48 (s, 1H), 7.96 (d, J=8.29, 1H), 7.68 (d, J=9.19, 1H), 7.44 (d, J=8.24, 1H), 7.39 (brs, 1H), 7.30 (t, J=8.00, 1H), 7.09 (t, J=7.64, 1H), 6.77 (d, J=8.71, 1H); $^{13}$C NMR (101 MHz, $CDCl1_3$) δ 157.27, 152.85, 140.26, 135.39, 129.99, 127.75, 125.67, 125.21, 122.70, 117.89, 108.97, 100.07.

6-((2-chlorophenyl)amino)-N'-hydroxynicotinimidamide (11e)

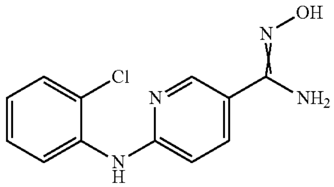 [SMILES: NC(=NO)c1ccc(Nc2ccccc2Cl)nc1]

Synthesized according to General Procedure B. Crude mixture dried in vacuo and carried forward to the next reaction without purification.

tert-butyl (R)-3-(3-(6-((2-chlorophenyl)amino)pyridin-3-yl)-1,2,4-oxadiazol-5-yl)pyrrolidine-1-carboxylate (12e)

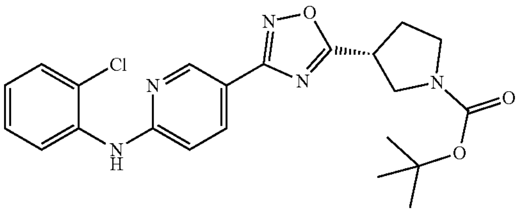 [SMILES: CC(C)(C)OC(=O)N1CC[C@@H](c2nc(-c3ccc(Nc4ccccc4Cl)nc3)no2)C1]

Synthesized according to General Procedure C. Purified by silica chromatography (20% EtOAc in hexanes). Yellow oil (58%, 146 mg). $^{1}$H NMR (400 MHz, $CDCl_3$) δ 8.92 (s, 1H), 8.13 (d, J=8.79, 1H), 8.08 (d, J=8.43 1H), 7.41 (d, J=8.00, 1H), 7.28 (t, J=7.43, 1H), 7.13 (brs, 1H), 7.00 (t, J=8.00, 1H), 6.89 (d, J=8.43, 1H), 3.91-3.43 (m, 5H), 2.43-2.32 (m, 2H), 1.47 (s, 9H); $^{13}$C NMR (101 MHz, $CDCl_3$) δ 179.31, 171.12, 166.49, 156.68, 147.96, 136.36, 136.28, 129.62, 127.52, 124.13, 123.61, 120.99, 114.76, 109.28, 79.82, 49.36, 45.02, 31.53, 28.43, 22.60.

(R)—N-(2-chlorophenyl)-5-(5-(pyrrolidin-3-yl)-1,2,4-oxadiazol-3-yl)pyridin-2-amine hydrochloride (13e)

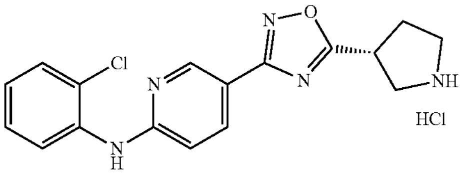 [SMILES: Clc1ccccc1Nc1ccc(-c2noc([C@@H]3CCNC3)n2)cn1 ; Cl]

Synthesized according to General Procedure D. Crude mixture dried in vacuo and carried forward to the next reaction without purification tert-butyl (R)-(((tert-butoxycarbonyl)imino)(3-(3-(6-((2-chlorophenyl)amino)pyridin-3-yl)-1,2,4-oxadiazol-5-yl)pyrrolidin-1-yl)methyl)carbamate (14e)

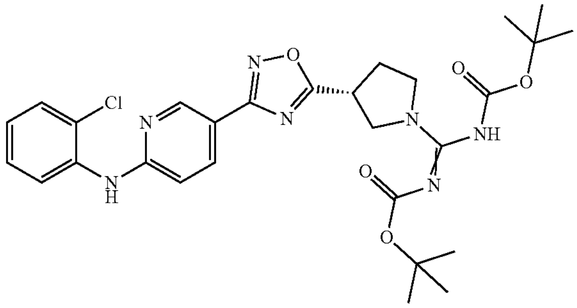 [SMILES: CC(C)(C)OC(=O)N=C(NC(=O)OC(C)(C)C)N1CC[C@@H](c2nc(-c3ccc(Nc4ccccc4Cl)nc3)no2)C1]

Synthesized according to General Procedure E. Yellow oil (48%, 114 mg). $^1$H NMR (400 MHz, $CDCl_3$) δ 10.45 (brs, 1H), 8.90 (s, 1H), 8.18-8.09 (m, 2H), 7.42 (d, J=8.12, 1H), 7.29 (t, J=8.18, 1H), 7.10 (brs, 1H), 7.01 (t, J=7.17, 1H), 6.91 (d, J=8.70, 1H), 4.16-3.71 (m, 5H), 2.50-2.35 (m, 2H), 1.52-1.47 (m, 18H); $^{13}$C NMR (101 MHz, $cdcl_3$) δ 178.58, 166.54, 162.45, 156.66, 154.23, 150.36, 148.04, 136.40, 129.62, 127.54, 124.05, 123.58, 120.91, 114.73, 109.27, 79.59, 31.20, 29.66, 28.02.

(R)-3-(3-(6-((2-chlorophenyl)amino)pyridin-3-yl)-1,2,4-oxadiazol-5-yl)pyrrolidine-1-carboximidamide hydrochloride (15e)

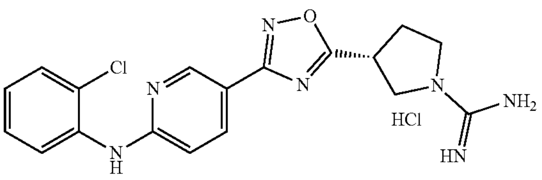 [SMILES: N=C(N)N1CC[C@@H](c2nc(-c3ccc(Nc4ccccc4Cl)nc3)no2)C1 ; Cl]

Synthesized according to General Procedure F. White solid (40%, 33 mg). $^1$H NMR (400 MHz, Methanol-$d_4$) δ 8.70 (s, 1H), 8.12 (d, J=9.72, 1H), 7.85 (d, J=8.54, 1H), 7.45 (d, J=7.91, 1H), 7.30 (t, J=7.45, 1H), 7.11 (t, J=7.91, 1H), 6.93 (d, J=8.48, 1H), 4.03 (p, J=6.69, 1H), 3.98-3.83 (m, 2H), 3.70-3.57 (m, 2H), 2.64-2.54 (m, 1H), 2.50-2.40 (m, 1H); $^{13}$C NMR (101 MHz, Methanol-$d_4$) δ 178.93, 166.45, 158.04, 154.97, 146.80, 136.48, 135.90, 129.52, 127.15, 124.88, 124.58, 113.62, 109.84, 49.87, 46.24, 35.85, 29.08; HRMS (ESI+)$^+$: Calcd for $C_{20}H_{20}ClN_7O$ $[M+H]^+$: 384.1334, Found: 384.1312.

6-((2,5-dibromophenyl)amino)nicotinonitrile (10f)

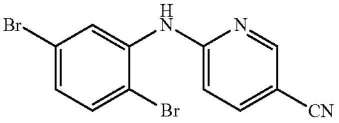 [SMILES: N#Cc1ccc(Nc2cc(Br)ccc2Br)nc1]

Synthesized according to General Procedure A. White solid (56%, 84 mg). $^1$H NMR (400 MHz, $CDCl_3$) δ 8.54 (s, 1H), 8.37 (s, 1H), 7.74 (d, J=8.98, 1H), 7.43 (d, J=8.98, 1H), 7.19 (brs, 1H), 7.10 (d, J=7.83, 1H), 6.82 (d, J=8.43, 1H); $^{13}$C NMR (101 MHz, $CDCl_3$) δ 156.31, 152.65, 140.29, 137.71, 133.72, 127.64, 124.31, 121.82, 117.50, 113.38, 109.95, 100.94.

6-((2,5-dibromophenyl)amino)-N'-hydroxynicotinimidamide (11f)

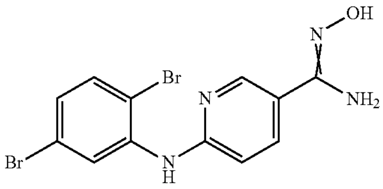 [SMILES: NC(=NO)c1ccc(Nc2cc(Br)ccc2Br)nc1]

Synthesized according to General Procedure B. Crude mixture dried in vacuo and carried forward to the next reaction without purification.

tert-butyl (R)-3-(3-(6-((2,5-dibromophenyl)amino)pyridin-3-yl)-1,2,4-oxadiazol-5-yl)pyrrolidine-1-carboxylate (12f)

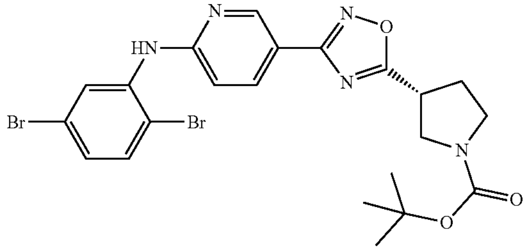 [SMILES: CC(C)(C)OC(=O)N1CC[C@@H](c2nc(-c3ccc(Nc4cc(Br)ccc4Br)nc3)no2)C1]

Synthesized according to General Procedure C. Purified by silica chromatography (20% EtOAc in hexanes). Yellow oil (49%, 66 mg). $^1$H NMR (400 MHz, $CDCl_3$) δ 8.97 (s, 1H), 8.49 (s, 1H), 8.18 (d, J=8.90, 1H), 7.40 (d, J=8.64, 1H), 7.10 (brs, 1H), 7.03 (d, J=8.70, 1H), 6.89 (d, J=8.57, 1H), 3.84-3.45 (m, 5H), 2.45-2.30 (m, 2H), 1.49 (s, 9H); $^{13}$C NMR (101 MHz, $CDCl_3$) δ 179.59, 166.51, 156.05, 154.26, 147.98, 138.79, 136.62, 133.65, 126.44, 123.12, 121.93, 115.65, 112.42, 110.41, 79.95, 49.43, 45.08, 36.54, 29.91, 28.60.

(R)—N-(2,5-dibromophenyl)-5-(5-(pyrrolidin-3-yl)-1,2,4-oxadiazol-3-yl)pyridin-2-amine hydrochloride (13f)

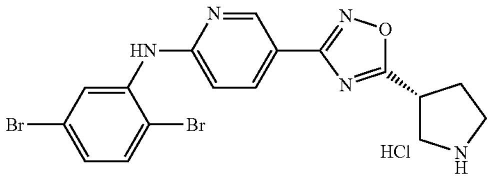 [SMILES: Brc1ccc(Br)c(Nc2ccc(-c3noc([C@@H]4CCNC4)n3)cn2)c1 ; Cl]

Synthesized according to General Procedure D. Crude mixture dried in vacuo and carried forward to the next reaction without purification tert-butyl (R)-(((tert-butoxycarbonyl)amino)(3-(3-(6-((2,5-dibromophenyl)amino)pyridin-3-yl)-1,2,4-oxadiazol-5-yl)pyrrolidin-1-yl)methylene)carbamate (14f)

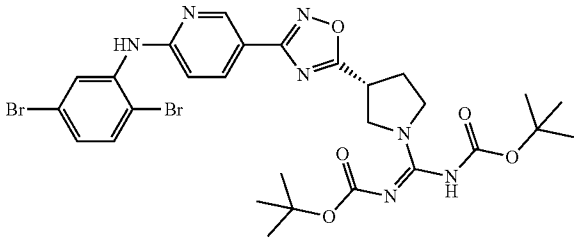 [SMILES: CC(C)(C)OC(=O)/N=C(/NC(=O)OC(C)(C)C)N1CC[C@@H](c2nc(-c3ccc(Nc4cc(Br)ccc4Br)nc3)no2)C1]

Synthesized by General Procedure E. Purified by silica chromatography (26% EtOAc in hexanes). Yellow oil (41%, 71 mg). $^1$H NMR (400 MHz, $CDCl_3$) δ 10.42 (brs, 1H), 8.94 (s, 1H), 8.47 (s, 1H), 8.16 (d, J=8.76, 1H), 7.39 (d, J=8.57, 1H), 7.12 (brs, 1H), 7.01 (d, J=8.55, 1H), 6.88 (d, J=8.57, 1H), 4.09-3.69 (m, 5H), 2.48-2.35 (m, 2H), 1.48 (s, 18H); $^{13}$C NMR (101 MHz, $CDCl_3$) δ 178.85, 171.18, 166.54, 162.56, 156.11, 154.32, 150.51, 148.01, 138.81, 136.60, 133.64, 126.45, 123.21, 121.90, 115.52, 112.49, 110.37, 82.27, 79.68, 51.92, 48.03, 31.32, 28.34, 28.16.

(R)-3-(3-(6-((2,5-dibromophenyl)amino)pyridin-3-yl)-1,2,4-oxadiazol-5-yl)pyrrolidine-1-carboximidamide hydrochloride (15f)

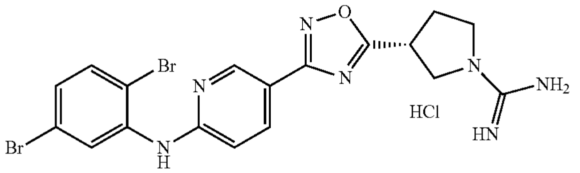 [SMILES: N=C(N)N1CC[C@@H](c2nc(-c3ccc(Nc4cc(Br)ccc4Br)nc3)no2)C1 ; Cl]

Synthesized according to General Procedure F. White solid (69%, 38 mg). $^1$H NMR (400 MHz, Methanol-$d_4$) δ 8.77 (s, 1H), 8.19 (m, 2H), 7.54 (d, J=8.67, 1H), 7.17 (d, J=7.67, 1H), 7.03 (d, J=8.67, 1H), 4.09-3.85 (m, 3H), 3.73-3.59 (m, 2H), 2.64-2.56 (m, 1H), 2.52-2.43 (m, 1H); $^{13}$C NMR (101 MHz, Methanol-$d_4$) δ 180.43, 167.78, 158.70, 156.36, 148.09, 140.71, 137.43, 135.27, 128.76, 127.73, 122.23, 116.21, 115.83, 112.12, 51.31, 47.67, 37.27, 30.50.

6-((3-(tert-butyl)phenyl)amino)nicotinonitrile (10g)

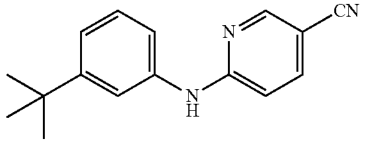 [SMILES: CC(C)(C)c1cccc(Nc2ccc(C#N)cn2)c1]

Synthesized according to General Procedure A. Yellow solid (68%, 204 mg) $^1$H NMR (400 MHz, $CDCl_3$) δ 8.43 (s, 1H), 7.62 (d, J=8.83, 1H), 7.32 (t, J=7.81, 1H), 7.27 (s, 1H), 7.22 (d, J=7.81, 1H), 7.16 (d, J=7.82, 1H), 7.11 (brs, 1H), 6.77 (d, J=8.83, 1H), 1.31 (s, 9H); $^{13}$C NMR (101 MHz, $CDCl_3$) δ 158.29, 153.08, 153.00, 140.26, 137.68, 129.21, 122.45, 119.85, 119.67, 118.06, 106.95, 98.78, 77.30, 76.98, 76.67, 34.79, 31.23.

6-((3-(tert-butyl)phenyl)amino)-N'-hydroxynicotinimidamide (11g)

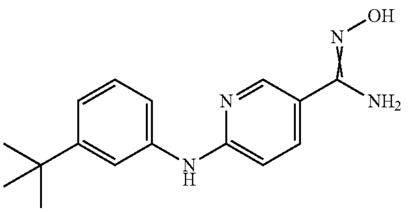 [SMILES: CC(C)(C)c1cccc(Nc2ccc(C(N)=NO)cn2)c1]

Synthesized according to General Procedure B. Crude mixture dried in vacuo and carried forward to the next reaction without purification tert-butyl (R)-3-(3-(6-((3-(tert-butyl)phenyl)amino)pyridin-3-yl)-1,2,4-oxadiazol-5-yl)pyrrolidine-1-carboxylate (12g)

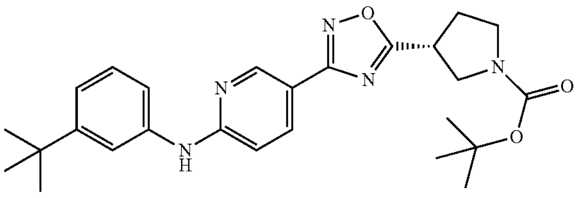 [SMILES: CC(C)(C)OC(=O)N1CC[C@@H](c2nc(-c3ccc(Nc4cccc(C(C)(C)C)c4)nc3)no2)C1]

Synthesized according to General Procedure C. Purified by silica chromatography (20% EtOAc in hexanes). Yellow oil (65%, 146 mg) $^1$H NMR (400 MHz, $CDCl_3$) δ 8.84 (s, 1H), 8.06 (d, J=8.91, 1H), 7.55 (d, J=12.70, 1H), 7.31 (s, 1H), 7.27 (d, J=8.05, 1H), 7.18 (d, J=8.05, 1H), 7.14 (d, J=8.05, 1H), 6.90 (d, J=9.08, 1H), 3.98-3.41 (m, 6H), 2.41-2.25 (m, 1H), 1.43 (s, 9H), 1.30 (s, 1H); $^{13}$C NMR (101

MHz, $CDCl_3$) δ 179.11, 166.64, 158.22, 154.15, 152.76, 148.24, 138.98, 136.42, 129.00, 121.23, 119.02, 118.78, 113.44, 107.18, 79.79, 34.74, 31.26, 28.45.

(R)—N-(3-(tert-butyl)phenyl)-5-(5-(pyrrolidin-3-yl)-1,2,4-oxadiazol-3-yl)pyridin-2-amine hydrochloride (13g)

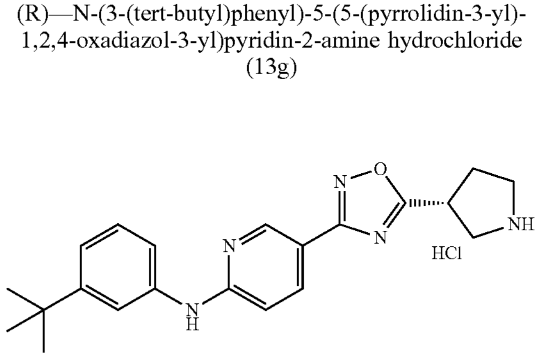

Synthesized according to General Procedure D. White solid (95%, 171 mg). $^1$H NMR (400 MHz, Methanol-$d_4$) δ 8.55 (s, 1H), 8.47 (d, J=8.78, 1H), 7.53-7.41 (m, 3H), 7.37-7.28 (m, 2H), 4.14 (p, J=7.06, 1H), 3.89-3.74 (m, 2H), 3.61-3.49 (m, 2H), 2.69-2.59 (m, 1H), 2.50-2.40 (m, 1H), 1.37 (s, 9H); $^{13}$C NMR (101 MHz, Methanol-$d_4$) δ 180.83, 165.97, 155.09, 154.93, 141.57, 138.60, 136.37, 131.07, 125.98, 122.60, 122.36, 115.41, 114.86, 49.31, 46.49, 36.63, 35.79, 31.60, 30.32.

tert-butyl (R)-(((tert-butoxycarbonyl)amino)(3-(3-(6-((3-(tert-butyl)phenyl)amino)pyridin-3-yl)-1,2,4-oxadiazol-5-yl)pyrrolidin-1-yl)methylene)carbamate (14g)

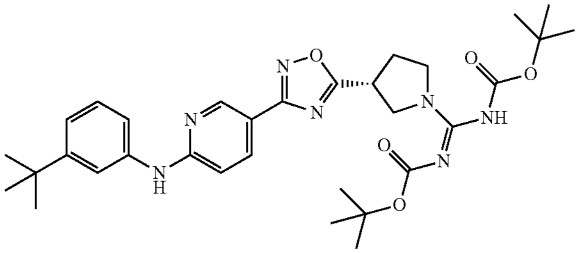 [SMILES: CC(C)(C)OC(=O)/N=C(/NC(=O)OC(C)(C)C)N1CC[C@@H](c2nc(-c3ccc(Nc4cccc(C(C)(C)C)c4)nc3)no2)C1]

Synthesized by General Procedure E. Purified by silica chromatography (30% ethyl acetate in hexanes). Yellow oil (39%, 101 mg). $^1$H NMR (400 MHz, $CDCl_3$) δ 10.42 (brs, 1H), 8.85 (s, 1H), 8.06 (d, J=8.98, 1H), 7.59 (brs, 1H), 7.34 (s, 1H), 7.29 (d, J=7.61, 1H), 7.22 (d, J=7.61, 1H), 7.15, (d, J=7.90, 1H), 6.91 (d, J=8.64, 1H), 4.14-3.66 (m, 5H), 2.47-3.33 (m, 2H), 1.48 (s, 18H), 1.32 (s, 8H); $^{13}$C NMR (101 MHz, $CDCl_3$) δ 178.51, 171.20, 166.83, 158.37, 154.30, 152.83, 150.52, 148.42, 139.19, 136.52, 129.10, 121.25, 119.07, 118.84, 113.48, 107.40, 82.28, 79.68, 52.03, 43.09, 34.86, 31.39, 28.34, 28.15.

(R)-3-(3-(6-((3-(tert-butyl)phenyl)amino)pyridin-3-yl)-1,2,4-oxadiazol-5-yl)pyrrolidine-1-carboximidamide hydrochloride (15g)

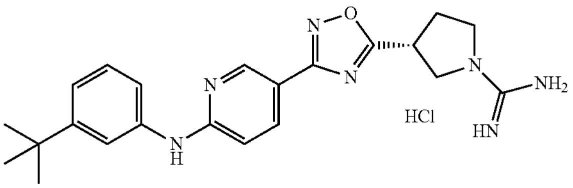 [SMILES: CC(C)(C)c1cccc(Nc2ccc(-c3noc([C@@H]4CCN(C(=N)N)C4)n3)cn2)c1 ; Cl]

Synthesized according to General Procedure F. White solid (55%, 40 mg). $^1$H NMR (400 MHz, Methanol-$d_4$) δ 8.70 (s, 1H), 8.04 (d, J=9.20, 1H), 7.53 (s, 1H), 7.43 (d, J=8.00, 1H), 7.22 (t, J=8.15, 1H), 7.07 (d, J=8.00, 1H), 6.87 (d, J=8.45, 1H), 4.04-3.82 (m, 3H), 3.69-3.58 (m, 2H), 2.63-2.53 (m, 1H), 2.48-2.37 (m, 1H), 1.31 (s, 9H); $^{13}$C NMR (101 MHz, Methanol-$d_4$) δ 178.75, 166.52, 158.16, 154.93, 151.80, 146.89, 139.77, 135.39, 128.16, 119.57, 117.29, 117.23, 112.57, 109.74, 47.87, 46.24, 35.82, 34.14, 30.36, 29.06; HRMS (ESI+)$^+$: Calcd for $C_{22}H_{28}N_7O$ $[M+H]^+$: 406.2350, Found: 406.2369.

6-((4-decylphenyl)amino)nicotinonitrile (10h)

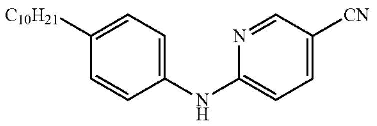

Synthesized according to General Procedure A. Crude mixture dried in vacuo and carried forward to the next reaction without purification.

6-((4-decylphenyl)amino)-N'-hydroxynicotinimidamide (11h)

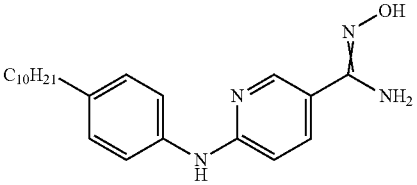

Synthesized according to General Procedure B. Crude mixture dried in vacuo and carried forward to the next reaction without purification.

tert-butyl (R)-3-(3-(6-((4-decylphenyl)amino)pyridin-3-yl)-1,2,4-oxadiazol-5-yl)pyrrolidine-1-carboxylate (12h)

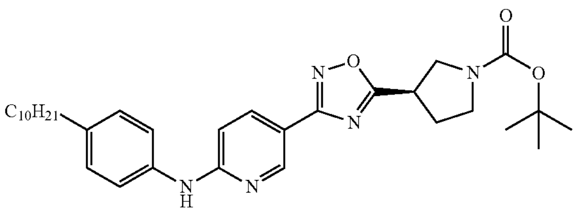

Synthesized according to General Procedure C. Purified by silica chromatography (12% EtOAc in hexanes). Yellow oil (48%, 202 mg). $^1$H NMR (400 MHz, $CDCl_3$) δ 8.84 (s, 1H), 8.05 (d, J=8.88, 1H), 7.43 (brs, 1H), 7.25 (d, J=8.17, 2H), 7.17 (d, J=8.52, 2H), 6.86 (d, J=8.78, 1H), 3.91-3.43 (m, 5H), 2.58 (t, J=7.77, 2H), 2.43-2.27 (m, 2H), 1.60 (p, J=6.99, 2H), 1.47 (s, 9H), 1.33-1.21 (m, 14H), 0.87 (t, J=6.57, 3H); $^{13}$C NMR (101 MHz, $CDCl_3$) δ 179.14, 166.70, 158.35, 154.18, 148.24, 138.97, 136.85, 136.35, 129.30, 121.88, 113.36, 107.20, 79.78, 49.36, 45.06, 35.39, 31.88, 31.52, 29.61, 29.59, 29.58, 29.50, 29.31, 29.29, 28.47, 22.66, 14.10.

(R)—N-(4-decylphenyl)-5-(5-(pyrrolidin-3-yl)-1,2,4-oxadiazol-3-yl)pyridin-2-amine hydrochloride (13h)

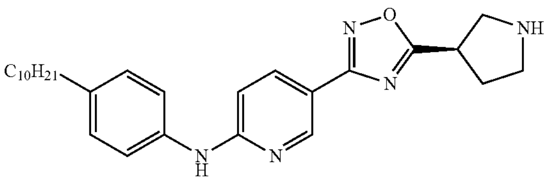

Synthesized according to General Procedure D. Yellow solid (84%, 150 mg). $^1$H NMR (400 MHz, $CDCl_3$) δ 10.41 (brs, 1H), 10.02 (brs, 1H), 8.87 (s, 1H), 8.09 (d, J=8.017, 2H), 8.03 (brs, 1H), 7.28-7.17 (m, 3H), 7.07 (d, J=8.51, 1H), 4.14-3.61 (m, 5H), 2.71-2.54 (m, 3H), 2.47-2.39 (m, 1H), 1.58 (p, J=7.55, 2H), 1.35-1.23 (m, 14H), 0.88 (t, J=6.81, 3H); $^{13}$C NMR (101 MHz, $CDCl_3$) δ 179.07, 164.56, 154.11, 142.60, 140.68, 138.93, 132.95, 130.00, 124.19, 113.13, 111.48, 48.38, 45.23, 35.70, 35.60, 31.97, 31.49, 29.70, 29.69, 29.57, 29.43, 29.41, 22.76, 14.21.

tert-butyl (R)-(((tert-butoxycarbonyl)amino)(3-(3-(6-((4-decylphenyl)amino)pyridin-3-yl)-1,2,4-oxadiazol-5-yl)pyrrolidin-1-yl)methylene)carbamate (14h)

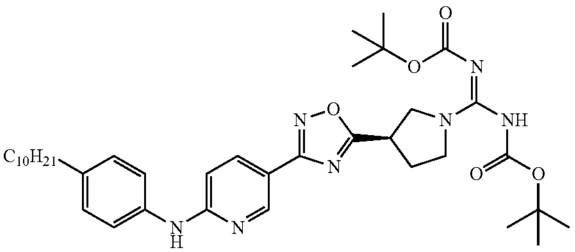

Synthesized by General Procedure E. Purified by silica chromatography (30% ethyl acetate in hexanes). Yellow oil (41%, 87 mg). $^1$H NMR (400 MHz, $CDCl_3$) δ 10.44 (s, 1H), 8.84 (s, 1H), 8.05 (d, J=8.99, 1H), 7.26 (d, J=8.01, 2H), 7.17 (d, J=8.29, 2H), 7.10 (s, 1H), 6.85 (d, J=9.00, 1H), 4.15-3.66 (m, 5H), 2.59 (t, J=7.89, 2H), 2.48-2.36 (m, 2H), 1.60 (p, J=6.94, 2H), 1.52-1.46 (m, 18H), 1.34-1.23 (m, 14H), 0.87 (t, J=7.00, 3H); $^{13}$C NMR (101 MHz, $CDCl_3$) δ 178.34, 166.70, 162.43, 158.21, 154.20, 150.38, 148.29, 139.00, 136.72, 136.35, 129.28, 121.85, 113.32, 107.15, 82.15, 79.58, 35.36, 31.86, 31.52, 31.20, 29.59, 29.57, 29.48, 29.30, 29.27, 28.37, 28.21, 28.01, 22.65, 14.09.

(R)-3-(3-(6-((4-decylphenyl)amino)pyridin-3-yl)-1,2,4-oxadiazol-5-yl)pyrrolidine-1-carboximidamide hydrochloride (15h)

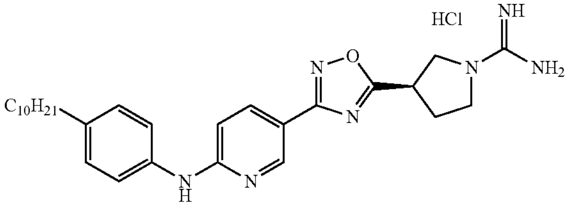

Synthesized according to General Procedure F. White solid (76%, 50 mg) $^1$H NMR (400 MHz, Methanol-$d_4$) δ 8.72 (s, 1H), 8.07 (d, J=9.17, 1H), 7.44 (d, J=8.30, 2H), 7.15 (d, J=7.50, 2H), 6.86 (d, J=8.50, 1H), 4.08-3.86 (m, 3H), 3.71-3.59 (m, 2H), 2.66-2.56 (m, 3H), 2.53-2.43 (m, 1H), 1.61 (p, J=6.69, 2H), 1.37-1.23 (m, 14H), 0.90 (t, J=6.89, 3H); $^{13}$C NMR (101 MHz, Methanol-$d_4$) δ 180.18, 168.02, 159.75, 156.41, 148.44, 139.04, 138.88, 136.81, 129.90, 121.84, 113.86, 110.92, 51.30, 47.86, 37.28, 36.36, 33.08, 32.87, 30.76, 30.74, 30.64, 30.50, 30.47, 30.31, 23.75, 14.46; HRMS (ESI+): Calcd for $C_{28}H_{40}N_7O$ $[M+H]^+$: 490.3289, Found: 490.3286.

6-((4-butylphenyl)amino)nicotinonitrile (10i)

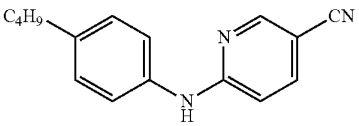

Synthesized according to General Procedure A. Crude mixture dried in vacuo and carried forward to the next reaction without purification.

6-((4-butylphenyl)amino)-N'-hydroxynicotinimidamide (11i)

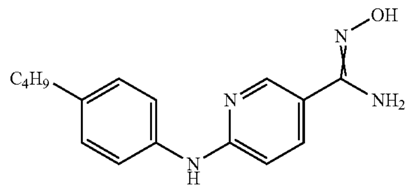

Synthesized according to General Procedure B. Crude mixture dried in vacuo and carried forward to the next reaction without purification.

tert-butyl (R)-3-(3-(6-((4-butylphenyl)amino)pyridin-3-yl)-1,2,4-oxadiazol-5-yl)pyrrolidine-1-carboxylate (12i)

Synthesized according to General Procedure C. Crude mixture dried in vacuo and carried forward to the next reaction without purification.

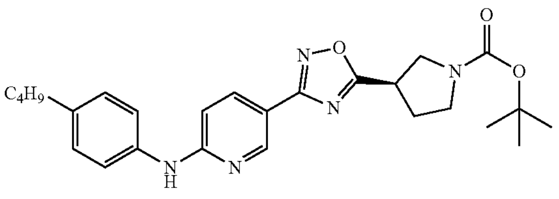

(R)—N-(4-butylphenyl)-5-(5-(pyrrolidin-3-yl)-1,2,4-oxadiazol-3-yl)pyridin-2-amine hydrochloride (13i)

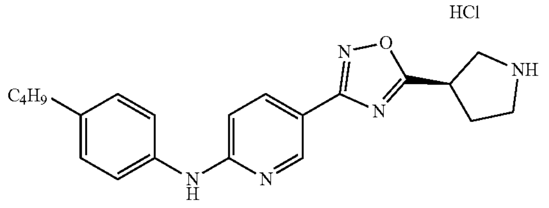

Synthesized according to General Procedure D. White solid (96% 44 mg). $^{1}$H NMR (400 MHz, Methanol-$d_4$) δ 8.54 (s, 1H), 8.39 (d, J=8.13, 1H), 7.43-7.31 (m, 4H), 7.23 (d, J=8.91, 1H), 4.13 (p, J=7.35, 1H), 3.88-3.75 (m, 2H), 3.60-3.49 (m, 2H), 2.69-2.59 (m, 3H), 2.49-2.40 (m, 1H), 1.63 (p, J=7.56, 2H), 1.39 (sx, J=7.40, 2H), 0.96 (t, J=7.31, 3H); $^{13}$C NMR (101 MHz, Methanol-$d_4$) δ 179.28, 164.85, 154.18, 141.86, 139.43, 138.53, 133.40, 129.72, 123.44, 113.42, 113.24, 47.93, 45.12, 35.24, 34.76, 33.47, 28.95, 21.93, 12.89.

tert-butyl (R)-(((tert-butoxycarbonyl)amino)(3-(3-(6-((4-butylphenyl)amino)pyridin-3-yl)-1,2,4-oxadiazol-5-yl)pyrrolidin-1-yl)methylene)carbamate (14i)

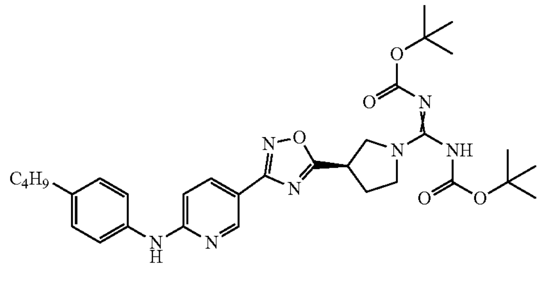

Synthesized by General Procedure E. Crude mixture dried in vacuo and carried forward to the next reaction without purification.

(R)-3-(3-(6-((4-butylphenyl)amino)pyridin-3-yl)-1,2,4-oxadiazol-5-yl)pyrrolidine-1-carboximidamide hydrochloride (15i)

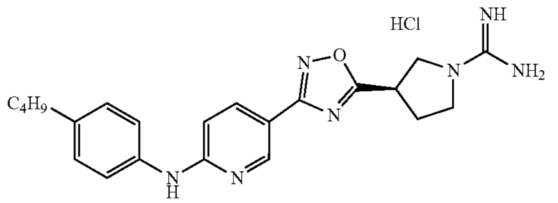

Synthesized according to General Procedure F. White solid (15% 11 mg). $^{1}$H NMR (400 MHz, Methanol-$d_4$) δ 8.69 (s, 1H), 8.03 (d, J=8.68, 1H), 7.12 (d, J=8.68, 1H), 6.85 (d, J=8.68, 1H), 4.04-3.82 (m, 3H), 3.69-3.57 (m, 2H), 2.64-2.51 (m, 3H), 2.49-2.39 (m, 1H), 1.58 (sx, J=7.68, 2H), 1.35 (p, J=7.47, 2H), 0.93 (t, J=7.42, 3H); $^{13}$C NMR (101 MHz, Methanol-$d_4$) δ 180.10, 167.96, 159.64, 156.36, 148.36, 139.06, 138.70, 136.77, 129.85, 121.71, 113.85, 110.97, 51.27, 47.66, 37.24, 36.06, 35.08, 30.47, 23.32, 14.32; HRMS (ESI+): Calcd for $C_{22}H_{28}N_7O$ $[M+H]^+$: 406.2350, Found: 406.2353.

Synthesis of Compound 15j 4-(3-phenylpropoxy)benzonitrile (16a)

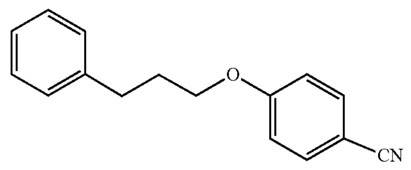 [SMILES: N#Cc1ccc(OCCCc2ccccc2)cc1]

To a round bottom flask containing THF was added 4-fluorobenzonitrile (1 equiv), 3-phenylpropanol (1 equiv), and the mixture was cooled to 0° C. in a brine ice bath. Sodium hydride (2 equiv) was then added and the reaction was allowed to warm to room temperature, followed by heating to reflux until consumption of starting material was observed as monitored by TLC (2-4 hours). Upon cooling to room temperature, ethyl acetate was added, followed by extraction with water. The organic layers were combined and dried over anhydrous sodium sulfate. Concentration in vacuo afforded the crude product as an oil, which was then purified by column chromatography (10% ethyl acetate in hexanes). $^{1}$H NMR (400 MHz, $CDCl_3$) δ 7.57 (d, J=8.47, 2H), 7.33-7.29 (t, J=7.18, 2H), 7.26-7.21 (m, 3H), 6.39 (d, J=9.00, 2H), 4.00 (t, J=6.15, 2H), 2.82 (t, J=7.27, 2H), 2.14 (p, J=6.90, 2H); $^{13}$C NMR (101 MHz, $CDCl_3$) δ 162.30, 141.01, 133.97, 128.51, 128.48, 126.12, 119.31, 115.19, 103.78, 67.23, 31.98, 30.49.

N'-hydroxy-4-(3-phenylpropoxy)benzimidamide (11j)

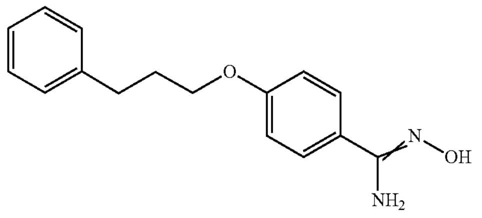 [SMILES: NC(=NO)c1ccc(OCCCc2ccccc2)cc1]

White solid (54%, 182 mg). 1H NMR (400 MHz, Methanol-d4) δ 7.53 (d, J=8.79, 2H), 7.26-7.11 (m, 5H), 6.89 (d, J=8.93, 2H), 3.95 (t, J=6.16, 2H), 2.77 (t, J=7.70, 2H), 2.09-2.01 (m, 2H); 13C NMR (101 MHz, Methanol-d4) δ 161.79, 155.56, 142.84, 129.54, 129.42, 128.67, 126.94, 126.35, 115.30, 67.99, 33.08, 32.14.

tert-butyl 3-(3-(4-(3-phenylpropoxy)phenyl)-1,2,4-oxadiazol-5-yl)azetidine-1-carboxylate (12j)

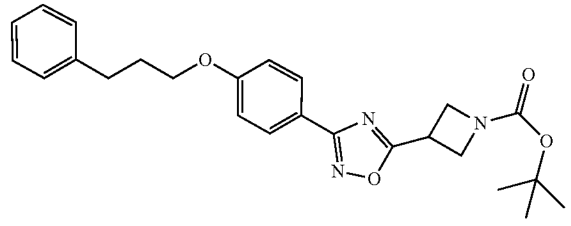 [SMILES: CC(C)(C)OC(=O)N1CC(c2nc(-c3ccc(OCCCc4ccccc4)cc3)no2)C1]

Synthesized according to General Procedure 3. Purified by silica chromatography (15% EtOAc in hexanes). Yellow oil (65%, 194 mg). $^{1}$H NMR (400 MHz, $CDCl_3$) δ 8.01 (d, J=8.37, 2H), 7.29 (t, J=7.55, 2H), 7.23-7.18 (m, 3H), 6.97 (d, J=9.07, 2H), 4.40-4.29 (m, 4H), 4.04-3.99 (m, 3H), 2.82 (t, J=7.54, 2H), 2.13 (p, J=6.90, 2H), 1.47 (s, 9H); $^{13}$C NMR (101 MHz, $CDCl_3$) δ 178.63, 168.26, 161.48, 155.89, 141.26, 129.04, 128.48, 128.43, 125.99, 118.77, 114.78, 80.13, 66.97, 32.05, 30.68, 28.34, 25.71.

5-(azetidin-3-yl)-3-(4-(3-phenylpropoxy)phenyl)-1,2,4-oxadiazole hydrochloride (13j)

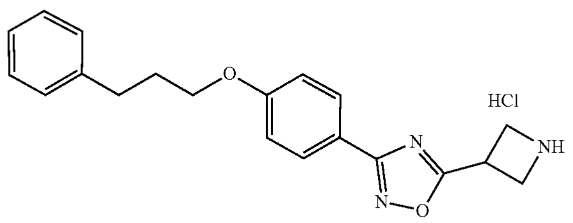 [SMILES: c1ccc(CCCOc2ccc(-c3noc(C4CNC4)n3)cc2)cc1 ; Cl]

Synthesized according to General Procedure 6. White solid (93%, 155 mg). $^{1}$H NMR (400 MHz, Methanol-$d_4$) δ 8.02 (d, J=8.21, 2H), 7.30-7.14 (m, 4H), 7.05 (d, J=8.87, 2H), 4.59-4.43 (m, 5H), 4.05 (t, J=6.18, 2H), 2.82 (t, J=7.08, 2H), 2.11 (p, J=7.08, 2H); $^{13}$C NMR (101 MHz, Methanol-$d_4$) δ 178.83, 169.61, 163.27, 142.78, 130.07, 129.54, 129.45, 126.99, 119.84, 115.99, 68.22, 51.02, 33.07, 32.08, 30.00.

tert-butyl-(((tert-butoxycarbonyl)amino)(3-(3-(4-(3-phenylpropoxy)phenyl)-1,2,4-oxadiazol-5-yl)azetidin-1-yl)methylene)carbamate (14j)

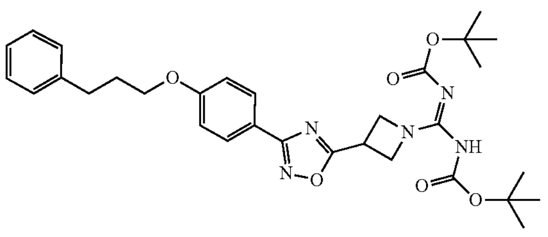 [SMILES: CC(C)(C)OC(=O)/N=C(/NC(=O)OC(C)(C)C)N1CC(c2nc(-c3ccc(OCCCc4ccccc4)cc3)no2)C1]

Synthesized by General Procedure 5. Purified by silica chromatography (20% ethyl acetate in hexanes). Yellow oil (36%, 56 mg) $^{1}$H NMR (400 MHz, $CDCl_3$) δ 11.04 (s, 1H), 7.99 (d, J=9.09, 2H), 7.31-7.18 (m, 5H), 6.97 (d, J=8.67, 2H), 4.76-4.57 (m, 4H), 4.10 (p, J=7.49, 1H), 4.01 (t, J=6.37, 2H), 2.82 (t, J=7.09, 2H), 2.13 (p, J=6.69, 2H), 1.50 (s, 18H); $^{13}$C NMR (101 MHz, $CDCl_3$) δ 178.21, 168.39, 161.61, 156.37, 141.37, 129.19, 128.59, 128.55, 126.10, 118.81, 114.88, 77.36, 67.07, 32.17, 30.79, 28.21, 26.61.

3-(3-(4-(3-phenylpropoxy)phenyl)-1,2,4-oxadiazol-5-yl)azetidine-1-carboximidamide hydrochloride (15j)

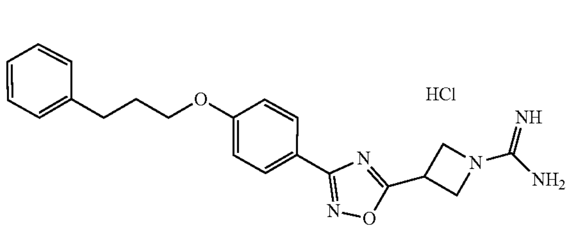 [SMILES: N=C(N)N1CC(c2nc(-c3ccc(OCCCc4ccccc4)cc3)no2)C1 ; Cl]

Synthesized according to General Procedure 6. White solid (50%, 24 mg) $^{1}$H NMR (400 MHz, Methanol-$d_4$) δ 8.00 (d, J=8.45, 2H), 7.28-7.14 (m, 5H), 7.03 (d, J=7.42, 2H), 4.62 (t, J=8.94, 2H), 4.46 (t, J=7.88, 2H), 4.41-4.32 (m, 1H), 4.03 (t, J=6.23, 2H), 2.81 (t, J=7.85, 2H), 2.10 (p, J=7.05, 2H); $^{13}C$ NMR (101 MHz, Methanol-$d_4$) δ 179.86, 169.56, 163.18, 158.32, 142.76, 142.76, 130.04, 129.53, 129.44, 126.98, 119.92, 115.95, 68.19, 55.76, 33.06, 32.06, 27.09.

Scheme 3-Synthetic Route to 23a-j

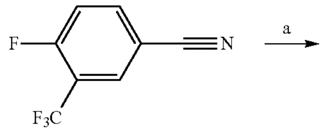

17

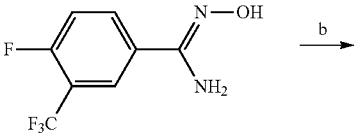

18

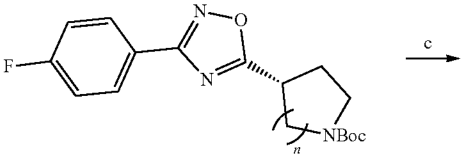

19a-b

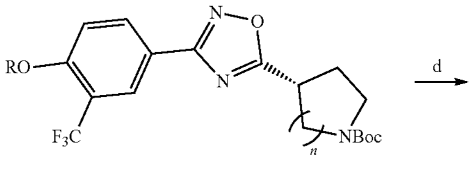

20a-j

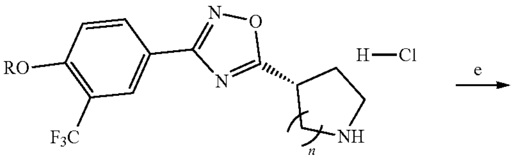

21a-j

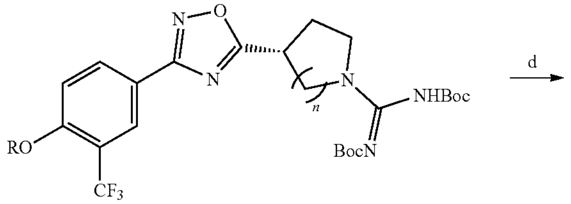

22a-j

-continued

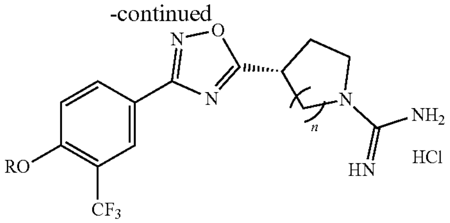

23a-j a. $NH_2OH$•HCl (2 equiv), TEA (3 equiv), EtOH, reflux; b. N-Boc-β-amino acid (1.1 equiv), HCTU (1.1 equiv), DIEA (1.8 equiv), DMF, 100° C.; c. NaH (2 equiv), ROH (1.1 equiv), THF, reflux; d. $HCl_{(g)}$, MeOH, rt; e. N,N'-Di-Boc-1H-pyrazole-1-carboxamidine (1 equiv), DIEA (15 equiv), MeCN, 50°C. µW.

General Procedure 1A: $S_NAR$

To a round bottom flask containing THF was added 19a or 19b (1 equiv), primary alcohol (1.1 equiv), and the mixture was cooled to 0° C. in a brine ice bath. Sodium hydride (2 equiv) was then added and the reaction was allowed to warm to room temperature, followed by heating to reflux until consumption of starting material was observed as monitored by TLC (4-6 hours). Upon cooling to room temperature, methanol was added to quench any unreacted sodium hydride. Concentration in vacuo afforded the crude product as an oil, which was then purified by column chromatography (ethyl acetate in hexanes) to afford products 20a-j.

General Procedure 1B: Amidoxime Synthesis

To a round bottom flask containing ethanol was added 17 (1 equiv), hydroxylamine hydrochloride (2 equiv), and trimethylamine (3 equiv) under ambient air. The reaction mixture was then heated to reflux until complete as monitored by TLC (1-4 hours). The resulting solution was allowed to cool to room temperature, followed by concentration in vacuo, to afford the crude mixture as a solid. Purification by column chromatography (0-20% ethyl acetate in dichloromethane) afforded the pure amidoxime product 18.

General Procedure 1C: 1,2,4-Oxadiazole Synthesis

Amidoxime 18 (1 equiv), N-Boc protected β-amino acid (1.1 equiv), and DIEA (1.8 equiv) were added to a round bottom flask containing DMF at room temperature. HCTU (1.1 equiv) was then added and the resulting mixture was heated to 100° C. until completion as monitored by TLC (6-16 hours). Upon cooling to room temperature, the resulting mixture was diluted in ethyl acetate and washed with a saturated lithium bromide solution. The resulting aqueous layer was then extracted with ethyl acetate. The organic layers were then combined and washed with a brine solution, followed by drying over anhydrous sodium sulfate. Concentration in vacuo afforded the crude product, which was then purified by column chromatography (0-30% ethyl acetate in hexanes) to afford the pure 1,2,4-oxadiazole product 19a or 19b.

General Procedure 1D: HCl Boc Deprotection

Boc protected secondary amine (20a-j) or diBoc-protected guanidine compound 22a-j (1 equiv) was added to a round bottom flask and dissolved in methanol. HCl) was then bubbled into the solution for 1 minute. The resulting solution was allowed to stir at room temperature until consumption of Boc protected starting material as monitored by TLC (30-60 minutes). Concentration in vacuo afforded a white to off-white solid, which was then washed with diethyl ether to afford the secondary amine (21a-j) or guanidine compounds (23a-j) as pure HCl salts.

General Procedure 1E: Guanylation

HCl salt 21a-j (1 equiv), DIEA (15 equiv), and (Z)-tert-butyl (((tert-butoxycarbonyl)imino)(1H-pyrazol-1-yl) methyl)carbamate (1 equiv) were added to a microwave vial containing MeCN at room temperature. The resulting solution was then placed in a CEM microwave synthesized and heated to 50° C. for 3 hours. After cooling down to room temperature, the solution was concentrated in vacuo to afford the crude mixture as a yellow oil, which was then purified by column chromatography (0-30% ethyl acetate in hexanes) to afford diBoc protected guanidine product (22a-j).

4-fluoro-N'-hydroxy-3-(trifluoromethyl)benzimidamide (18)

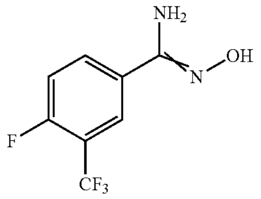

Synthesized according to General Procedure 1B. Purified by silica chromatography (40% EtOAc in hexanes). White solid (39%, 691 mg) $^1$H NMR (400 MHz, $CDCl_3$) δ 8.91 (brs, 1H), 7.90 (d, J=6.61, 1H), 7.84-7.80 (m, 1H), 4.92 (brs, 2H).

tert-butyl 3-(3-(4-fluoro-3-(trifluoromethyl)phenyl)-1,2,4-oxadiazol-5-yl)azetidine-1-carboxylate (19a)

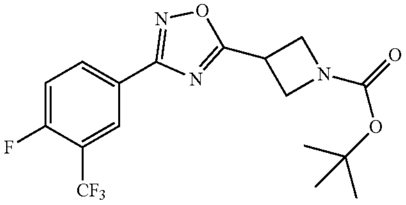 [SMILES: CC(C)(C)OC(=O)N1CC(c2nc(-c3ccc(F)c(C(F)(F)F)c3)no2)C1]

Synthesized according to General Procedure 1C. Purified by silica chromatography (20% EtOAc in hexanes). Yellow oil (85%, 91 mg). $^1$H NMR (400 MHz, $CDCl_3$) δ 8.28 (d, J=6.77, 1H), 8.24-8.20 (m, 1H), 7.27 (t, J=9.11, 1H), 4.36-4.24 (m, 4H), 4.06-3.99 (m, 1H), 1.41 (s, 9H)

tert-butyl (R)-3-(3-(4-fluoro-3-(trifluoromethyl)phenyl)-1,2,4-oxadiazol-5-yl)piperidine-1-carboxylate (19b)

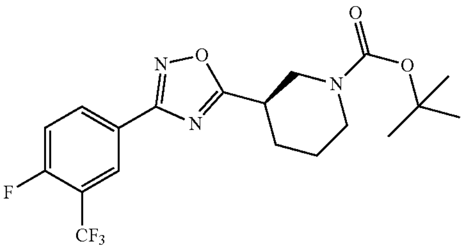 [SMILES: CC(C)(C)OC(=O)N1CCC[C@@H](c2nc(-c3ccc(F)c(C(F)(F)F)c3)no2)C1]

Synthesized according to General Procedure 1C. Purified by silica chromatography (20% EtOAc in hexanes). Yellow oil (59%, 283 mg). $^1$H NMR (400 MHz, $CDCl_3$) δ 8.24 (d, J=6.78, 1H), 8.26-8.22 (m, 1H), 4.47-4.04 (m, 1H), 3.95-3.85 (m, 1H), 3.38-2.92 (m, 3H), 2.26-2.18 (m, 1H), 1.95-1.77 (m, 2H), 1.65-1.54 (m, 1H), 1.43 (s, 9H).

tert-butyl 3-(3-(4-(octyloxy)-3-(trifluoromethyl)phenyl)-1,2,4-oxadiazol-5-yl)azetidine-1-carboxylate (20a)

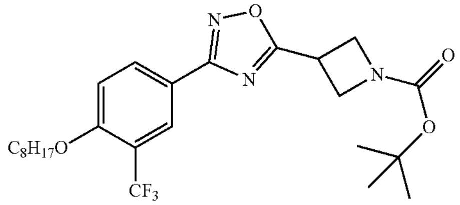

Synthesized according to General Procedure 1A. Purified by silica chromatography (20% EtOAc in hexanes). Yellow oil (53%, 17 mg). $^1$H NMR (400 MHz, $CDCl_3$) δ 8.30 (s, 1H), 8.20 (d, J=8.76, 1H), 7.08 (d, J=8.84, 1H), 4.42-4.30 (m 4H), 4.14-4.00 (m, 3H), 1.85 (p, J=7.56, 2H), 1.47 (s, 9H), 1.39-1.25 (m, 8H), 0.89 (t, J=6.86, 3H).

tert-butyl 3-(3-(4-(nonyloxy)-3-(trifluoromethyl)phenyl)-1,2,4-oxadiazol-5-yl)azetidine-1-carboxylate (20b)

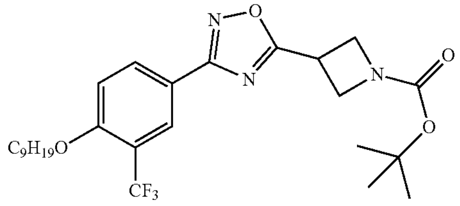

Synthesized according to General Procedure 1A. Purified by silica chromatography (20% EtOAc in hexanes). Colorless oil (58%, 115 mg). $^1$H NMR (400 MHz, $CDCl_3$) δ 8.26 (s, 1H), 8.16 (d, J=9.09, 1H), 7.05 (d, J=9.05, 1H), 4.44-4.27 (m, 4H), 4.11-3.98 (m, 3H), 1.86-1.77 (m, 2H), 1.45 (s, 9H), 1.35-1.21 (m, 12H), 0.88-0.82 (m, 3H).

tert-butyl (R)-3-(3-(4-(heptyloxy)-3-(trifluoromethyl)phenyl)-1,2,4-oxadiazol-5-yl)piperidine-1-carboxylate (20c)

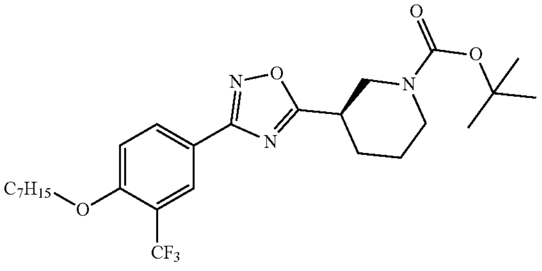

Synthesized according to General Procedure 1A. Purified by silica chromatography (20% EtOAc in hexanes). Yellow oil (71%, 325 mg). $^{1}$H NMR (400 MHz, $CDCl_3$) δ 8.29 (s, 1H), 8.18 (d, J=8.69, 1H), 7.07 (d, J=8.62, 1H), 4.51-4.05 (m, 3H), 4.00-3.90 (m, 1H), 3.49-3.97 (m, 3H), 2.30-2.22 (m, 1H), 1.97-1.80 (m, 4H), 1.68-1.55 (m, 1H), 1.55-1.45 (m, 11H), 1.44-1.20 (m, 6H).

tert-butyl (R)-3-(3-(4-(octyloxy)-3-(trifluoromethyl)phenyl)-1,2,4-oxadiazol-5-yl)piperidine-1-carboxylate (20d)

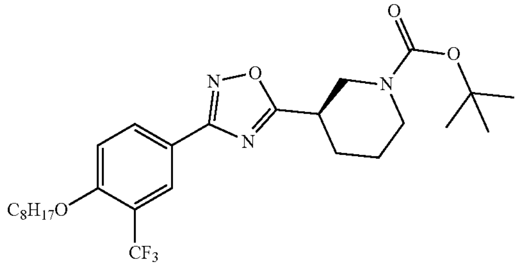

Synthesized according to General Procedure 1A. Purified by silica chromatography (10% EtOAc in hexanes). White solid (52%, 130 mg). $^{1}$H NMR (400 MHz, $CDCl_3$) δ 8.29 (s, 1H), 8.18 (d, J=8.66, 1H), 7.07, (d, J=8.75, 1H), 4.50-4.15 (m, 3H), 4.11 (t, J=6.33, 1H), 3.44-3.11 (m, 2H), 3.01 (brs, 1H), 2.29-2.21 (m, 1H), 1.94-1.80 (m, 4H), 1.69-1.56 (m, 1H), 1.52-1.41 (m, 11H), 1.38-1.25 (m, 8H), 0.89 (t, J=6.78, 3H).

tert-butyl (R)-3-(3-(4-(nonyloxy)-3-(trifluoromethyl)phenyl)-1,2,4-oxadiazol-5-yl)piperidine-1-carboxylate (20e)

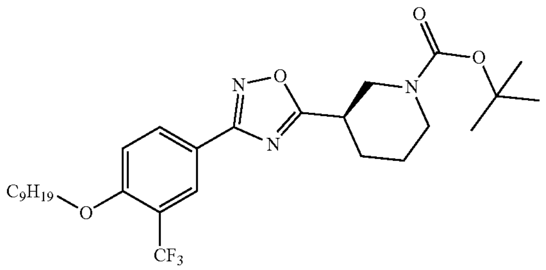

Synthesized according to General Procedure 1A. Purified by silica chromatography (10% EtOAc in hexanes). Yellow oil (63%, 156 mg). $^{1}$H NMR (400 MHz, $CDCl_3$) δ 9.05 (1H), 7.32-7.27 (m, 2H), 7.23-7.18 (m, 3H), 8.27 (s, 1H), 8.17 (d, J=8.61), 7.05 (d, J=8.50, 1H), 4.49-4.06 (m, 3H), 4.02-3.87 (m, 1H), 3.45-2.92 (m, 3H), 2.31-2.13 (m, 1H), 1.96-1.73 (m, 4H), 1.65-1.55 (m, 1H), 1.45 (s, 9H), 1.38-1.22 (m, 12H), 0.86 (t, J=6.86, 3H).

tert-butyl (R)-3-(3-(4-(decyloxy)-3-(trifluoromethyl)phenyl)-1,2,4-oxadiazol-5-yl)piperidine-1-carboxylate (20f)

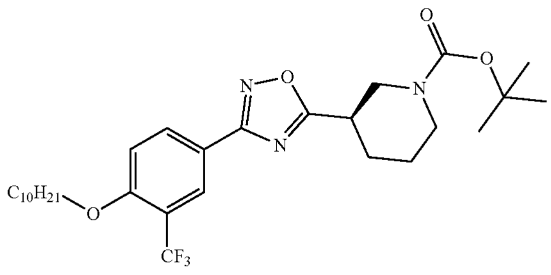

Synthesized according to General Procedure 1A. Purified by silica chromatography (20% EtOAc in hexanes). White solid (80%, 565 mg). $^{1}$H NMR (400 MHz, $CDCl_3$) δ 8.29 (s, 1H), 8.18 (d, J=8.70, 1H), 7.07 (d, J=8.71, 1H), 4.48-4.08 (m, 3H), 4.00-3.92 (m, 1H), 3.47-3.94 (m, 3H), 3.31-3.21 (m, 1H), 1.98-1.87 (m, 4H), 1.68-1.57 (m, 1H), 1.53-1.44 (m, 11H), 1.39-1.24 (m, 12H), 0.88 (t, J=6.86, 3H).

tert-butyl 3-(3-(3-(trifluoromethyl)-4-((4-(trifluoromethyl)benzyl)oxy)phenyl)-1,2,4-oxadiazol-5-yl)azetidine-1-carboxylate (20g)

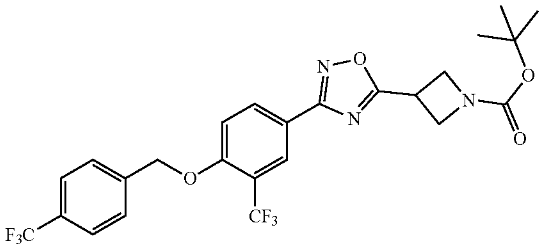 [SMILES: CC(C)(C)OC(=O)N1CC(c2nc(-c3ccc(OCc4ccc(C(F)(F)F)cc4)c(C(F)(F)F)c3)no2)C1]

Synthesized according to General Procedure 1A. Purified by silica chromatography (20% EtOAc in hexanes). Colorless oil (76%, 160 mg). $^{1}$H NMR (400 MHz, $CDCl_3$) δ 8.35 (s, 1H), 8.21 (d, J=8.65, 1H), 7.67 (d, J=8.46, 2H), 7.58 (d, J=8.16, 2H), 5.30 (s, 1H), 4.41-4.29 (m, 4H), 4.08-4.01 (m, 1H), 1.47 (s, 9H).

tert-butyl (R)-3-(3-(3-(trifluoromethyl)-4-((4-(trifluoromethyl)benzyl)oxy)phenyl)-1,2,4-oxadiazol-5-yl)piperidine-1-carboxylate (20h)

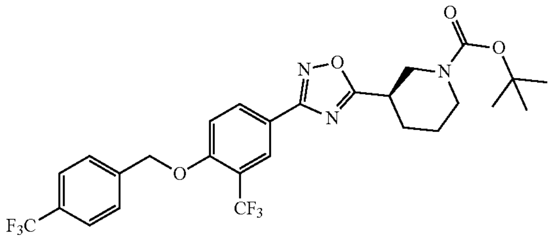 [SMILES: CC(C)(C)OC(=O)N1CCC[C@@H](c2nc(-c3ccc(OCc4ccc(C(F)(F)F)cc4)c(C(F)(F)F)c3)no2)C1]

Synthesized according to General Procedure 1A. Purified by silica chromatography (20% EtOAc in hexanes). White solid (78%, 216 mg). $^1$H NMR (400 MHz, $CDCl_3$) δ 8.33 (s, 1H), 8.19 (d, J=8.80, 1H), 7.65 (d, J=8.62, 2H), 7.57 (d, J=8.33, 2H), 7.10 (d, J=8.82, 1H), 5.29 (s, 2H), 4.46-3.89 (m, 2H), 3.50-2.99 (m, 4H), 2.26-2.18 (m, 1H), 1.95-1.78 (m, 2H), 1.68-1.39 (m, 10H).

tert-butyl 3-(3-(4-(3-phenylpropoxy)-3-(trifluoromethyl)phenyl)-1,2,4-oxadiazol-5-yl)azetidine-1-carboxylate (20i)

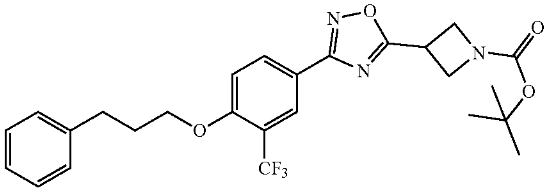 [SMILES: CC(C)(C)OC(=O)N1CC(c2nc(-c3ccc(OCCCc4ccccc4)c(C(F)(F)F)c3)no2)C1]

Synthesized according to General Procedure 1A. Purified by silica chromatography (20% EtOAc in hexanes). Colorless oil (64%, 25 mg). $^1$H NMR (400 MHz, $CDCl_3$) δ 8.32 (s, 1H), 8.19 (d, J=9.05, 1H), 7.32-7.27 (m, 2H), 7.23-7.18 (m, 3H), 7.03 (d, J=8.88, 1H), 4.41-4.30 (m, 4H), 4.11-4.02 (m, 3H), 2.86 (t, J=7.33, 2H), 2.17 (p, J=7.04, 2H), 1.47 (s, 9H).

tert-butyl (R)-3-(3-(4-(3-phenylpropoxy)-3-(trifluoromethyl)phenyl)-1,2,4-oxadiazol-5-yl)piperidine-1-carboxylate (20j)

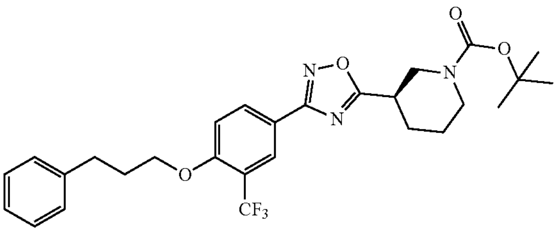 [SMILES: CC(C)(C)OC(=O)N1CCC[C@@H](c2nc(-c3ccc(OCCCc4ccccc4)c(C(F)(F)F)c3)no2)C1]

Synthesized according to General Procedure 1A. Purified by silica chromatography (20% EtOAc in hexanes). White solid (72%, 175 mg). $^1$H NMR (400 MHz, $CDCl_3$) δ 8.31 (s, 1H), 8.17 (d, J=8.88, 1H), 7.31-7.26 (m, 2H), 7.22-7.17 (m, 3H), 7.01 (d, J=8.81, 1H), 4.49-3.89 (m, 4H), 3.45-2.84 (m, 5H), 2.29-2.21 (m, 2H), 2.16 (p, J=7.03, 2H), 1.94-1.80 (m, 2H), 1.68-1.55 (m, 1H), 1.47 (s, 9H).

5-(azetidin-3-yl)-3-(4-(octyloxy)-3-(trifluoromethyl)phenyl)-1,2,4-oxadiazole hydrochloride (21a)

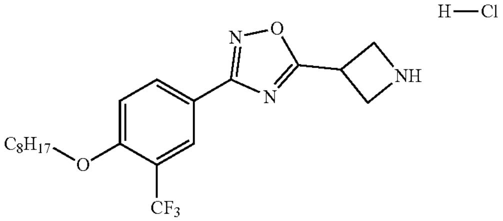

Synthesized according to General Procedure 1D. Crude mixture dried in vacuo and carried forward to the next reaction without purification.

5-(azetidin-3-yl)-3-(4-(nonyloxy)-3-(trifluoromethyl)phenyl)-1,2,4-oxadiazole hydrochloride (21b)

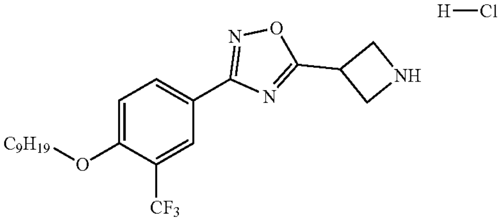

Synthesized according to General Procedure 1D. Crude mixture dried in vacuo and carried forward to the next reaction without purification.

(R)-3-(4-(heptyloxy)-3-(trifluoromethyl)phenyl)-5-(piperidin-3-yl)-1,2,4-oxadiazole hydrochloride (21c)

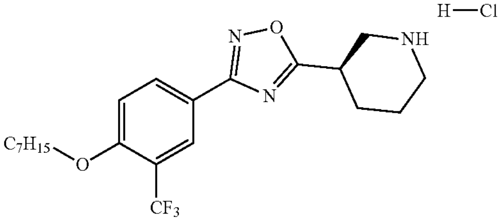

Synthesized according to General Procedure 1D. White Solid, 242 mg, (85%). $^1$H NMR (400 MHz, Chloroform-d) δ 8.23 (d, J=1.9 Hz, 1H), 8.14 (dd, J=8.7, 2.0 Hz, 1H), 7.03 (d, J=8.8 Hz, 1H), 4.08 (t, J=6.4 Hz, 2H), 3.71 (dd, J=12.8, 3.7 Hz, 1H), 3.55 (tt, J=10.5, 3.9 Hz, 1H), 3.40-3.31 (m, 1H), 3.18 (t, J=11.5 Hz, 1H), 2.90 (m, 1H), 2.40-2.25 (m, 1H), 1.99-1.75 (m, 5H), 1.47 (p, J=6.9 Hz, 2H), 1.41-1.22 (m, 6H), 0.88 (t, J=6.9 Hz, 3H); HRMS (ESI): Calcd for $C_{21}H_{29}F_3N_3O_2[M+H]^+$: 412.2206, Found: 412.2197.

(R)-3-(4-(octyloxy)-3-(trifluoromethyl)phenyl)-5-(piperidin-3-yl)-1,2,4-oxadiazole hydrochloride (21d)

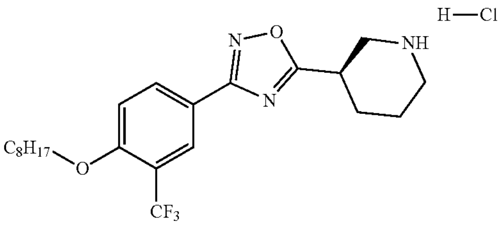

Synthesized according to General Procedure 1D. White Solid, 105 mg, 92%. $^1$H NMR (400 MHz, Methanol-$d_4$) δ 8.30-8.20 (m, 2H), 7.32 (d, J=8.8 Hz, 1H), 4.17 (t, J=6.2 Hz, 2H), 3.79 (dd, J=12.6, 3.9 Hz, 1H), 3.70-3.61 (m, 1H), 3.50 (dd, J=12.6, 9.9 Hz, 1H), 3.41 (dt, J=12.6, 4.1 Hz, 1H), 3.20-3.10 (m, 1H), 2.43-2.33 (m, 1H), 2.08-1.93 (m, 3H), 1.88-1.78 (m, 2H), 1.52 (p, J=7.0 Hz, 2H), 1.43-1.27 (m, 8H), 0.90 (t, J=7.0 Hz, 3H); HRMS (ESI): Calcd for $C_{22}H_{31}F_3N_3O_2[M+H]^+$: 426.2363, Found: 426.2351.

(R)-3-(4-(nonyloxy)-3-(trifluoromethyl)phenyl)-5-(piperidin-3-yl)-1,2,4-oxadiazole hydrochloride: (21e)

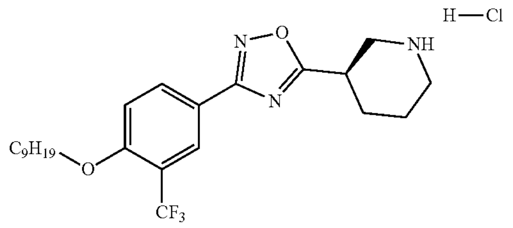

Synthesized according to General Procedure 1D. White Solid, 121 mg, 88%. $^1$H NMR (400 MHz, Methanol-$d_4$) δ 8.30-8.16 (m, 2H), 7.31 (d, J=8.9 Hz, 1H), 4.17 (t, J=6.2 Hz, 2H), 3.77 (dd, J=12.6, 3.9 Hz, 1H), 3.68-3.59 (m, 1H), 3.47 (dd, J=12.6, 10.0 Hz, 1H), 3.40 (dt, J=12.8, 4.0 Hz, 1H), 3.18-3.08 (m, 1H), 2.42-2.33 (m, 1H), 2.08-1.91 (m, 3H), 1.87-1.78 (m, 2H), 1.52 (p, J=7.0 Hz, 2H), 1.42-1.25 (m, 8H), 0.89 (t, J=6.9 Hz, 3H); HRMS (ESI): Calcd for $C_{23}H_{33}F_3N_3O_2[M+H]^+$: 440.2519, Found: 440.2559.

(R)-3-(4-(decyloxy)-3-(trifluoromethyl)phenyl)-5-(piperidin-3-yl)-1,2,4-oxadiazole hydrochloride: (21f)

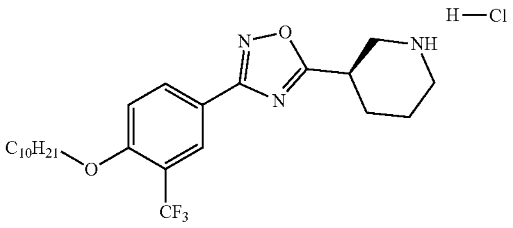

Synthesized according to General Procedure 1D. White Solid, 418 mg, 84%. $^1$H NMR (400 MHz, Methanol-$d_4$) δ 8.25 (m, 2H), 7.32 (d, J=8.8 Hz, 1H), 4.18 (t, J=6.2 Hz, 2H), 3.75 (dd, J=12.6, 3.9 Hz, 1H), 3.67-3.56 (m, 1H), 3.45 (dd, J=12.6, 9.9 Hz, 1H), 3.38 (dt, J=12.7, 4.0 Hz, 1H), 3.17-3.05 (m, 1H), 2.42-2.33 (m, 1H), 2.07-1.90 (m, 3H), 1.82 (p, J=12.5, 6.4 Hz, 2H), 1.52 (p, J=7.0 Hz, 2H), 1.41-1.24 (m, 12H), 0.89 (t, J=6.9 Hz, 3H); HRMS (ESI): Calcd for $C_{24}H_{35}F_3N_3O_2[M+H]^+$: 454.2676, Found: 454.2690.

5-(azetidin-3-yl)-3-(3-(trifluoromethyl)-4-((4-(trifluoromethyl)benzyl)oxy)phenyl)-1,2,4-oxadiazole hydrochloride (21g)

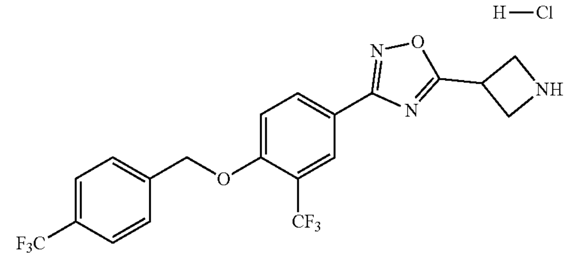

Synthesized according to General Procedure 1D. Crude mixture dried in vacuo and carried forward to the next reaction without purification.

(R)-5-(piperidin-3-yl)-3-(3-(trifluoromethyl)-4-((4-(trifluoromethyl)benzyl)oxy)phenyl)-1,2,4-oxadiazole hydrochloride: (21h)

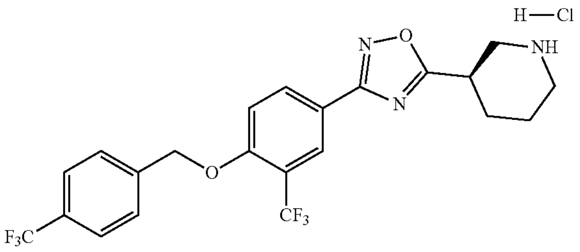

Synthesized according to General Procedure 1D. White Solid, 166 mg, 86%. $^1$H NMR (400 MHz, Methanol-$d_4$) δ 8.33-8.27 (m, 2H), 7.70 (q, J=8.4 Hz, 4H), 7.44 (d, J=8.6 Hz, 1H), 5.43 (s, 2H), 3.78 (dd, J=12.5, 3.8 Hz, 1H), 3.64 (tt, J=9.5, 3.9 Hz, 1H), 3.50 (dd, J=12.5, 9.9 Hz, 1H), 3.40 (dt, J=12.7, 4.2 Hz, 1H), 3.19-3.11 (m, 1H), 2.43-2.34 (m, 1H), 2.08-1.88 (m, 3H); HRMS (ESI): Calcd for $C_{22}H_{20}F_6N_3O_2$ $[M+H]^+$: 472.1454, Found: 472.1434.

5-(azetidin-3-yl)-3-(4-(3-phenylpropoxy)-3-(trifluoromethyl)phenyl)-1,2,4-oxadiazole hydrochloride (21i)

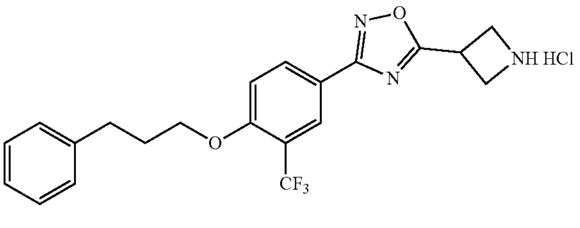

Synthesized according to General Procedure 1D. Crude mixture dried in vacuo and carried forward to the next reaction without purification.

(R)-3-(4-(3-phenylpropoxy)-3-(trifluoromethyl)phenyl)-5-(piperidin-3-yl)-1,2,4-oxadiazole hydrochloride: (21j)

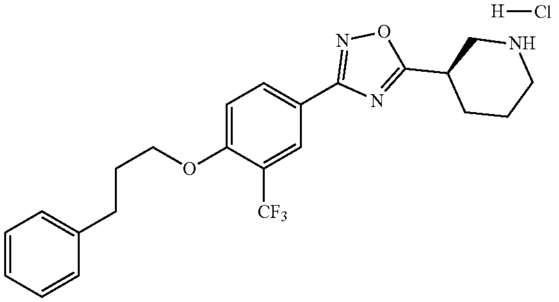

Synthesized according to General Procedure 1D. White Solid, 129 mg, 84%. $^1$H NMR (400 MHz, Methanol-$d_4$) δ 8.30-8.20 (m, 2H), 7.29-7.12 (m, 6H), 4.13 (t, J=5.9 Hz, 2H), 3.79 (dd, J=12.7, 3.9 Hz, 1H), 3.70-3.59 (m, 1H), 3.49 (dd, J=12.6, 9.9 Hz, 1H), 3.41 (dt, J=12.7, 4.1 Hz, 1H), 3.22-3.09 (m, 1H), 2.83 (t, J=7.5 Hz, 2H), 2.42-2.32 (m, 1H), 2.12 (p, J=6.5 Hz, 2H), 2.06-1.92 (m, 3H); HRMS (ESI): Calcd for $C_{23}H_{25}F_3N_3O_2$ $[M+H]^+$: 432.1893, Found: 432.1898.

tert-butyl (E)-(((tert-butoxycarbonyl)amino)(3-(3-(4-(octyloxy)-3-(trifluoromethyl)phenyl)-1,2,4-oxadiazol-5-yl)azetidin-1-yl)methylene)carbamate (22a)

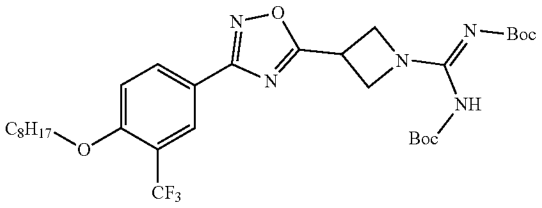

Synthesized according to General Procedure 1E. Yellow oil, 13 mg (50%) yield. $^1$H NMR (400 MHz, $CDCl_3$) δ 11.01 (brs, 1H), 8.29 (s, 1H), 8.19 (dd, J=8.7, 2.2 Hz, 1H), 7.07 (d, J=8.8 Hz, 1H), 4.77-4.58 (m, 4H), 4.11 (t, J=6.3 Hz, 3H), 1.89-1.79 (m, 2H), 1.51 (m, 18H), 1.41-1.20 (m, 10H), 0.88 (t, J=6.8 Hz, 3H).

tert-butyl (E)-(((tert-butoxycarbonyl)amino)(3-(3-(4-(nonyloxy)-3-(trifluoromethyl)phenyl)-1,2,4-oxadiazol-5-yl)azetidin-1-yl)methylene)carbamate (22b)

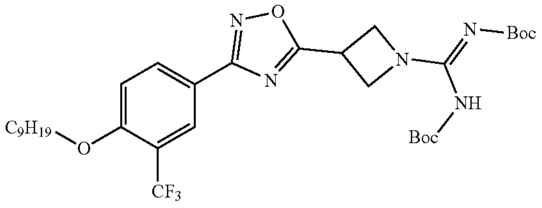

Synthesized according to General Procedure 1E. Yellow oil, 50 mg (69%) yield. $^1$H NMR (400 MHz, $CDCl_3$) δ 11.13 (brs, 1H), 8.29 (s, 1H), 8.19 (dd, J=8.7, 2.2 Hz, 1H), 7.07 (d, J=8.7 Hz, 1H), 4.81-4.66 (m, 2H), 4.61 (dd, J=10.1, 6.2 Hz, 2H), 4.17-4.07 (m, 3H), 1.88-1.80 (m, 2H), 1.49 (brs, 18H), 1.42-1.17 (m, 12H), 0.88 (t, J=6.7 Hz, 3H).

tert-butyl (R,Z)-(((tert-butoxycarbonyl)amino)(3-(3-(4-(heptyloxy)-3-(trifluoromethyl)phenyl)-1,2,4-oxadiazol-5-yl)piperidin-1-yl)methylene)carbamate (22c)

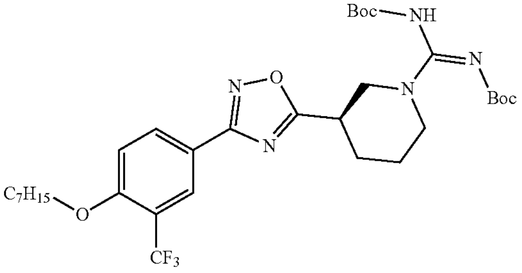

Synthesized according to General Procedure 1E. Yellow oil, 52 mg (69%) yield. $^1$H NMR (400 MHz, $CDCl_3$) δ 10.18 (brs, 1H), 8.27 (s, 1H), 8.16 (dd, J=8.7, 2.2 Hz, 1H), 7.05 (d, J=8.8 Hz, 1H), 4.51-4.14 (m, 2H), 4.10 (t, J=6.4 Hz, 2H), 3.50-3.39 (m, 1H), 3.38-3.27 (m, 1H), 3.15-3.05 (m, 1H), 2.39-2.29 (m, 1H), 1.97-1.71 (m, 4H), 1.49 (brs, 18H), 1.41-1.18 (m, 8H), 0.90 (t, J=6.9 Hz, 3H).

tert-butyl (R,Z)-(((tert-butoxycarbonyl)amino)(3-(3-(4-(octyloxy)-3-(trifluoromethyl)phenyl)-1,2,4-oxadiazol-5-yl)piperidin-1-yl)methylene)carbamate (22d)

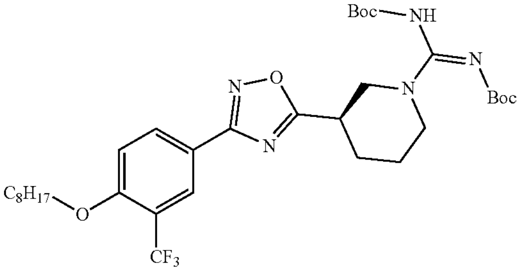

Synthesized according to General Procedure 1E. Yellow oil, 48 mg (66%) yield. $^1$H NMR (400 MHz, $CDCl_3$) δ 10.13 (brs, 1H), 8.26 (s, 1H), 8.16 (d, J=10.1 Hz, 1H), 7.05 (d, J=8.7 Hz, 1H), 4.52-4.13 (m, 2H), 4.09 (t, J=6.3 Hz, 2H), 3.52-3.27 (m, 2H), 3.18-3.05 (m, 1H), 2.38-2.28 (m 1H), 1.94-1.73 (m, 4H), 1.48 (brs, 18H), 1.39-1.17 (m, 10H), 0.87 (t, J=6.7 Hz, 3H).

tert-butyl (R)-(((tert-butoxycarbonyl)amino)(3-(3-(4-(nonyloxy)-3-(trifluoromethyl)phenyl)-1,2,4-oxadiazol-5-yl)piperidin-1-yl)methylene)carbamate (22e)

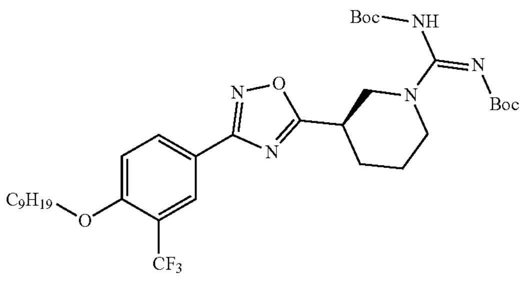

Synthesized according to General Procedure 1E. Yellow oil, 50 mg (69%) yield. $^1$H NMR (400 MHz, $CDCl_3$) δ 10.16 (brs, 1H), 8.29 (s, 1H), 8.18 (dd, J=8.7, 2.1 Hz, 1H), 7.07 (d, J=8.7 Hz, 1H), 4.49-4.15 (m, 2H), 4.11 (t, J=6.4 Hz, 2H), 3.52-3.39 (m, 1H), 3.33 (dd, J=13.2, 10.3, 1H), 2.40-2.28 (m, 1H), 1.97-1.73 (m, 4H), 1.50 (brs, 18H), 1.42-1.20 (m, 12H), 0.88 (t, J=6.7 Hz, 3H).

tert-butyl (R)-(((tert-butoxycarbonyl)amino)(3-(3-(4-(decyloxy)-3-(trifluoromethyl)phenyl)-1,2,4-oxadiazol-5-yl)piperidin-1-yl)methylene)carbamate (22f)

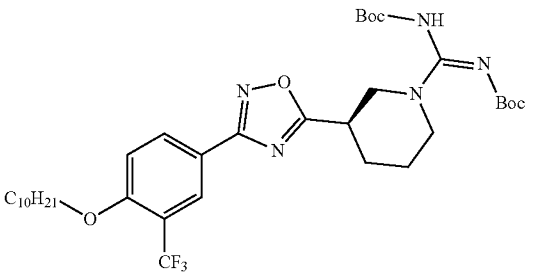

Synthesized according to General Procedure 1E. Yellow oil, 48 mg (67%) yield. $^1$H NMR (400 MHz, $CDCl_3$) δ 10.17 (brs, 1H), 8.28 (s, 1H), 8.18 (dd, J=8.7, 2.2 Hz, 1H), 7.07 (d, J=8.7 Hz, 1H), 4.49-4.14 (m, 2H), 4.11 (t, J=6.4 Hz, 2H), 3.52-3.40 (m, 1H), 3.33 (dd, J=13.2, 10.3 Hz, 1H), 3.18-3.05 (m, 1H), 2.41-2.29 (m, 1H), 1.50 (brs, 18H), 1.43-1.19 (14H), 0.88 (t, J=6.7 Hz, 3H).

tert-butyl (E)-(((tert-butoxycarbonyl)amino)(3-(3-(3-(trifluoromethyl)-4-((4-(trifluoromethyl)benzyl)oxy)phenyl)-1,2,4-oxadiazol-5-yl)azetidin-1-yl)methylene)carbamate (22g)

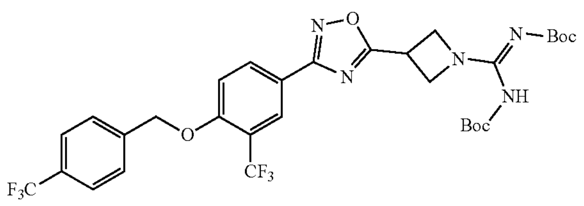 [SMILES: CC(C)(C)OC(=O)/N=C(\NC(=O)OC(C)(C)C)N1CC(c2nc(-c3ccc(OCc4ccc(C(F)(F)F)cc4)c(C(F)(F)F)c3)no2)C1]

Synthesized according to General Procedure 1E. Yellow oil, 35 mg (57%) yield. $^1$H NMR (400 MHz, $CDCl_3$) δ 8.35 (d, J=2.0 Hz, 1H), 8.21 (d, J=8.5 Hz, 1H), 7.67 (d, J=8.1 Hz, 2H), 7.57 (d, J=8.0 Hz, 2H), 7.12 (d, J=8.7 Hz, 1H), 5.31 (s, 2H), 4.75-4.67 (m, 2H), 4.64-4.58 (m, 2H), 4.18-4.08 (m, 1H), 1.49 (brs, 18H).

tert-butyl (R)-(((tert-butoxycarbonyl)amino)(3-(3-(3-(trifluoromethyl)-4-((4-(trifluoromethyl)benzyl)oxy)phenyl)-1,2,4-oxadiazol-5-yl)piperidin-1-yl)methylene)carbamate (22h)

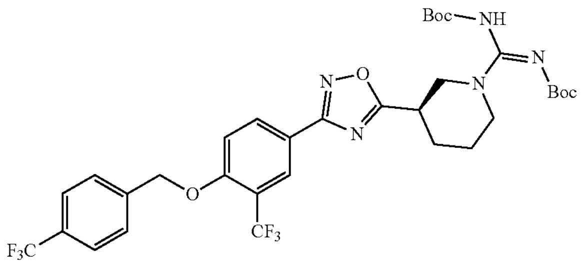 [SMILES: CC(C)(C)OC(=O)/N=C(/NC(=O)OC(C)(C)C)N1CCC[C@@H](c2nc(-c3ccc(OCc4ccc(C(F)(F)F)cc4)c(C(F)(F)F)c3)no2)C1]

Synthesized according to General Procedure 1E. Yellow oil, 35 mg (57%) yield. $^1$H NMR (400 MHz, $CDCl_3$) δ 10.16 (brs, 1H), 8.33 (d, J=2.1 Hz, 1H0, 8.19 (dd, J=8.7, 2.1 Hz, 1H), 7.66 (d, J=8.2, 2H), 7.57 (d, J=8.1 Hz, 2H), 7.10 (d, J=8.7 Hz, 1H), 5.30 (s, 2H), 4.54-4.03 (m, 2H), 3.54-3.39 (m, 1H), 3.39-3.25 (m, 1H), 3.18-3.04 (m, 1H), 2.40 (m, 1H), 1.97-1.71 (m, 3H), 1.50 (brs, 18H).

tert-butyl (E)-(((tert-butoxycarbonyl)amino)(3-(3-(4-(3-phenylpropoxy)-3-(trifluoromethyl)phenyl)-1,2,4-oxadiazol-5-yl)azetidin-1-yl)methylene)carbamate (22i)

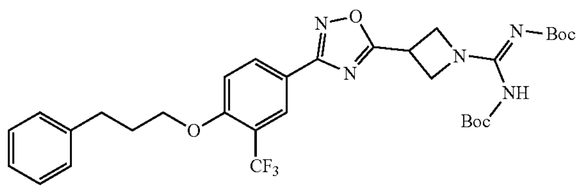 [SMILES: CC(C)(C)OC(=O)/N=C(\NC(=O)OC(C)(C)C)N1CC(c2nc(-c3ccc(OCCCc4ccccc4)c(C(F)(F)F)c3)no2)C1]

Synthesized according to General Procedure 1E. Yellow oil, 46 mg (62%) yield. $^1$H NMR (400 MHz, $CDCl_3$) δ 8.32 (s, 1H), 8.18 (dd, 8.7, 2.1 Hz, 1H), 7.32-7.24 (m, 3H), 7.21 (d, J=7.2 Hz, 2H), 7.02 (d, J=8.7 Hz, 1H), 4.84-4.55 (m, 4H), 4.20-4.05 (m, 3H), 2.86 (t, J=7.4 Hz, 2H), 8.18 (dd, J=8.7, 2.1 Hz, 2H), 1.50 (brs, 18H).

tert-butyl (R,Z)-(((tert-butoxycarbonyl)amino)(3-(3-(4-(3-phenylpropoxy)-3-(trifluoromethyl)phenyl)-1,2,4-oxadiazol-5-yl)piperidin-1-yl)methylene)carbamate (22j)

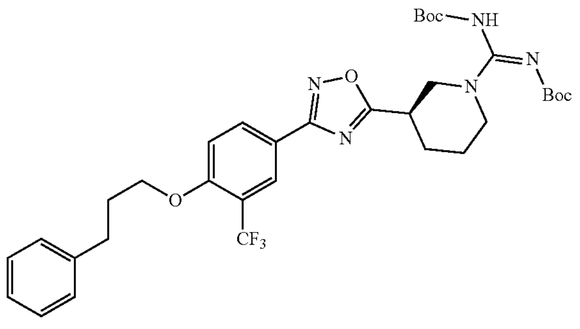 [SMILES: CC(C)(C)OC(=O)/N=C(/NC(=O)OC(C)(C)C)N1CCC[C@@H](c2nc(-c3ccc(OCCCc4ccccc4)c(C(F)(F)F)c3)no2)C1]

Synthesized according to General Procedure 1E. Yellow oil, 47 mg (65%) yield. $^1H$ NMR (400 MHz, $CDCl_3$) δ 10.12 (brs, 1H), 8.30 (s, 1H), 8.16 (dd, J=8.7, 2.2 Hz, 1H), 7.33-7.24 (m, 2H), 7.33-7.24 (m, 3H), 7.23-7.17 (m, 2H), 7.01 (d, J=8.7 Hz, 1H), 4.46-4.12 (m, 2H), 4.09 (t, J=6.0 Hz, 2H), 3.51-3.41 (m, 1H), 3.38-3.29 (m, 1H), 3.17-3.07 (m, 1H), 2.86 (t, J=7.5 Hz, 2H), 2.39-2.30 (m, 1H), 2.22-2.12 (m, 2H), 1.98 (m, 3H), 1.50 (brs, 18H).

3-(3-(4-(octyloxy)-3-(trifluoromethyl)phenyl)-1,2,4-oxadiazol-5-yl)azetidine-1-carboximidamide hydrochloride (23a)

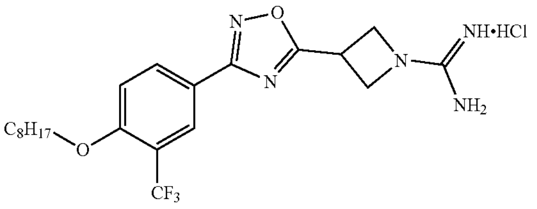

Synthesized according to General Procedure 1D. White solid, 0.0650 g, 69%. $^1H$ NMR (600 MHz, Methanol-$d_4$) δ 8.28-8.26 (m, 2H), 7.34 (d, J=8.6 Hz, 1H), 4.65 (t, J=8.9 Hz, 2H), 4.49 (dd, J=8.7, 5.8 Hz, 2H), 4.44-4.39 (m, 1H), 4.19 (t, J=6.2 Hz, 2H), 1.84 (tt, J=14.4, 6.3 Hz, 2H), 1.53 (p, J=7.3 Hz, 2H), 1.42-1.29 (m, 8H), 0.91 (t, J=6.9 Hz, 3H); $^{13}C$ NMR (151 MHz, Methanol-$d_4$) δ 180.39, 168.73, 160.82, 158.33, 133.87, 127.11 (q, J=5.3 Hz), 124.72 (q, J=271.7 Hz), 120.25 (J=31.3 Hz), 119.60, 70.30, 55.79, 32.90, 30.33, 30.25, 30.03, 27.17, 26.91, 23.69, 14.41; $^{19}F$ NMR (376 MHz, Methanol-$d_4$) δ −64.22; HRMS (ESI): Calcd for $C_{21}H_{29}F_3N_5O_2[M+H]^+$: 440.2268, Found: 440.2264.

3-(3-(4-(nonyloxy)-3-(trifluoromethyl)phenyl)-1,2,4-oxadiazol-5-yl)azetidine-1-carboximidamide hydrochloride (23b)

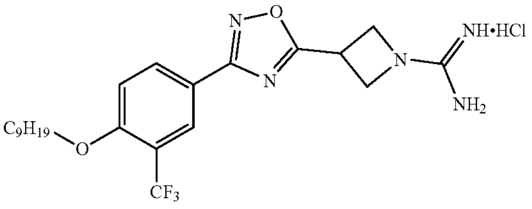

Synthesized according to General Procedure 1D. White solid, 21 mg, 69%. $^1H$ NMR (400 MHz, Methanol-$d_4$) δ 8.34-8.26 (m, 2H), 7.77-7.62 (m, 4H), 7.44 (d, J=8.5 Hz, 1H), 5.42 (s, 2H), 4.66 (t, J=8.9 Hz, 2H), 4.49 (dd, J=8.5, 5.8 Hz, 2H), 4.45-4.37 (m, 1H); $^{13}C$ NMR (101 MHz, Methanol-$d_4$) δ 180.50, 168.57, 159.81, 158.30, 141.97, 133.97, 131.22 (q, J=32.3 Hz), 128.52, 127.24 (q, J=5.4 Hz), 126.53 (q, J=3.8 Hz), 125.61 (q, J=271.2 Hz), 124.73 (q, J=271.8 Hz), 120.56 (q, J=31.3 Hz), 120.48, 115.42, 70.83, 55.80, 49.00, 27.16; $^{19}F$ NMR (376 MHz, Methanol-$d_4$) δ −67.11, −67.14; HRMS (ESI): Calcd for $C_{21}H_{18}F_6N_5O_2$ $[M+H]^+$: 486.1359, Found: 486.1366.

(R)-3-(3-(4-(heptyloxy)-3-(trifluoromethyl)phenyl)-1,2,4-oxadiazol-5-yl)piperidine-1-carboximidamide hydrochloride (23c)

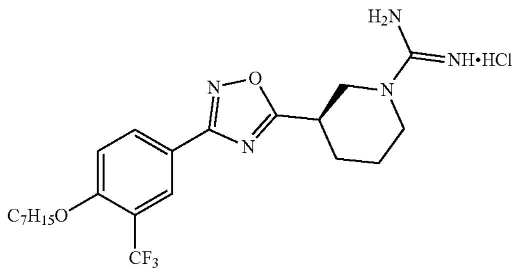

Synthesized according to General Procedure 1D. White solid, 32 mg (82%). $^1H$ NMR (400 MHz, Methanol-$d_4$) δ 8.28-8.20 (m, 2H), 7.32 (d, J=9.4 Hz, 1H), 4.18 (t, J=6.2 Hz, 2H), 4.08 (dd, J=13.9, 3.6 Hz, 1H), 3.82 (dd, J=13.9, 8.2 Hz, 1H), 3.75-3.66 (m, 1H), 3.51-3.40 (m, 2H), 2.40-2.29 (m, 1H), 2.16-2.04 (m, 1H), 1.95-1.71 (m, 4H), 1.52 (p, J=7.9 Hz, 2H), 1.45-1.26 (m, 6H), 0.91 (t, J=6.7 Hz, 3H); HRMS (ESI): Calcd for $C_{22}H_{31}F_3N_5O_2[M+H]^+$: 454.2424, Found: 454.2417.

(R)-3-(3-(4-(octyloxy)-3-(trifluoromethyl)phenyl)-1,2,4-oxadiazol-5-yl)piperidine-1-carboximidamide hydrochloride (23d)

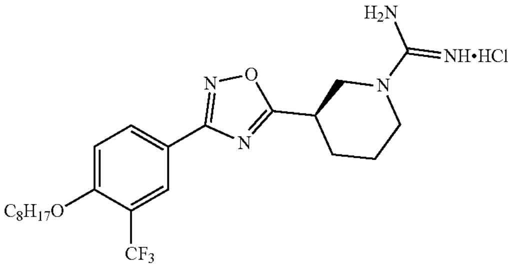

Synthesized according to General Procedure 1D. White solid, 46 mg (92%). $^{1}H$ NMR (400 MHz, Methanol-$d_4$) δ 8.27-8.21 (m, 2H), 7.32 (d, J=8.6 Hz, 1H), 4.17 (t, J=4.8 Hz, 2H), 4.08 (d, J=13.8 Hz, 1H), 3.81 (dd, J=13.9, 8.2 Hz, 1H), 3.75-3.66 (m, 1H), 3.50-3.40 (m, 2H), 2.39-2.28 (m, 1H), 2.17-2.01 (m, 1H), 1.96-1.70 (m, 4H), 1.52 (p, J=7.2 Hz, 2H), 1.43-1.26 (m, 8H), 0.90 (t, J=5.7 Hz, 3H); $^{13}C$ NMR (101 MHz, Methanol-$d_4$) δ 180.97, 168.32, 160.72, 158.15, 133.82, 127.04 (q, J=5.4 Hz), 124.75 (q, J=271.9 Hz), 120.19 (q, J=31.5 Hz), 119.68, 70.27, 49.00, 48.93, 47.39, 35.27, 32.91, 30.35, 30.27, 30.03, 28.57, 26.92, 24.22, 23.71, 14.46; $^{19}F$ NMR (376 MHz, Methanol-$d_4$) δ −64.14; HRMS (ESI): Calcd for $C_{23}H_{33}F_3N_3O_2[M+H]^+$: 468.2581, Found: 468.2582.

(R)-3-(3-(4-(nonyloxy)-3-(trifluoromethyl)phenyl)-1,2,4-oxadiazol-5-yl)piperidine-1-carboximidamide hydrochloride (23e)

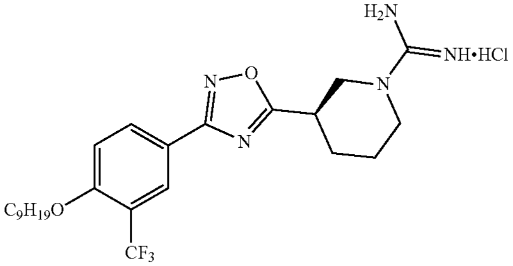

Synthesized according to General Procedure 1D. White solid, 34 mg (89%). $^{1}H$ NMR (400 MHz, Methanol-$d_4$) δ 8.28-8.20 (m, 2H), 7.32 (d, J=9.2 Hz, 1H), 4.17 (t, J=6.2 Hz, 3H), 4.08 (dd, J=13.9, 3.8 Hz, 2H), 3.81 (dd, J=13.9, 8.2 Hz, 1H), 3.75-3.66 (m, 1H), 3.50-3.40 (m, 2H), 2.40-2.27 (m, 1H), 2.16-2.04 (m, 2H), 1.95-1.69 (m, 4H), 1.52 (p, J=6.8 Hz, 2H), 1.42-1.25 (m, 10H), 0.89 (t, J=6.7 Hz, 3H$^{13}C$ NMR (101 MHz, Methanol-$d_4$) δ 180.96, 168.31, 160.70, 158.15, 133.82, 127.02 (q, J=5.4 Hz), 124.74 (q, J=271.8 Hz), 120.19 (q, J=31.3 Hz), 119.68, 114.78, 70.26, 49.64, 49.43, 49.21, 49.00, 48.92, 48.79, 48.58, 48.36, 47.38, 35.27, 33.02, 30.62, 30.31, 30.29, 30.03, 28.57, 26.90, 24.21, 23.73, 14.44; $^{19}F$ NMR (376 MHz, Methanol-$d_4$) δ −64.18; HRMS (ESI): Calcd for $C_{21}H_{29}F_3N_5O_2[M+H]^+$: 482.2737, Found: 482.2784.

(R)-3-(3-(4-(decyloxy)-3-(trifluoromethyl)phenyl)-1,2,4-oxadiazol-5-yl)piperidine-1-carboximidamide hydrochloride (23f)

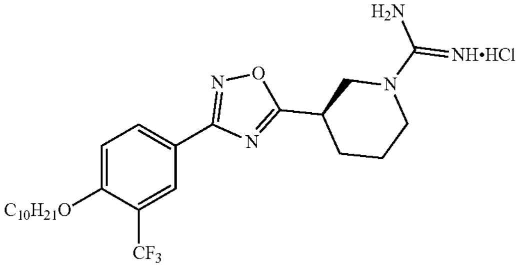

Synthesized according to General Procedure 1D. White solid, 30 mg (82%). $^{1}H$ NMR (600 MHz, Methanol-$d_4$) δ 8.27-8.22 (m, 2H), 7.32 (d, J=8.9 Hz, 1H), 4.18 (t, J=6.2 Hz, 2H), 4.08 (dd, J=13.9, 3.7 Hz, 1H), 3.82 (dd, J=13.9, 8.2 Hz, 1H), 3.73-3.67 (m, 1H), 3.50-3.41 (m, 2H), 2.39-2.30 (m, 1H), 2.17-2.05 (m, 1H), 1.95-1.86 (m, 1H), 1.83 (p, J=6.4 Hz, 2H), 1.80-1.73 (m, 1H), 1.52 (p, J=7.3 Hz, 2H), 1.42-1.23 (m, 12H), 0.89 (t, J=7.0 Hz, 3H); HRMS (ESI): Calcd for $C_{25}H_{37}F_3N_5O_2[M+H]^+$: 496.2894, Found: 496.2889.

3-(3-(3-(trifluoromethyl)-4-((4-(trifluoromethyl)benzyl)oxy)phenyl)-1,2,4-oxadiazol-5-yl)azetidine-1-carboximidamide hydrochloride (23g)

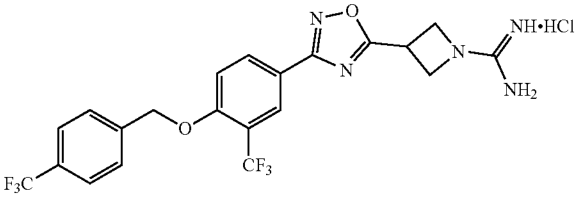

Synthesized according to General Procedure 1D. White solid, 21 mg (77%). $^{1}H$ NMR (400 MHz, Methanol-$d_4$) δ 8.34-8.26 (m, 2H), 7.77-7.62 (m, 4H), 7.44 (d, J=8.5 Hz, 1H), 5.42 (s, 2H), 4.66 (t, J=8.9 Hz, 2H), 4.49 (dd, J=8.5, 5.8 Hz, 2H), 4.45-4.37 (m, 1H); $^{13}C$ NMR (101 MHz, Methanol-$d_4$) δ 180.50, 168.57, 159.81, 158.30, 141.97, 133.97, 131.22 (q, J=32.3 Hz), 128.52, 127.24 (q, J=5.4 Hz), 126.53 (q, J=3.8 Hz), 125.61 (q, J=271.2 Hz), 124.73 (q, J=271.8 Hz), 120.56 (q, J=31.3 Hz), 120.48, 115.42, 70.83, 55.80, 49.00, 27.16; $^{19}F$ NMR (376 MHz, Methanol-$d_4$) δ −67.11, −67.14; HRMS (ESI): Calcd for $C_{21}H_{18}F_6N_5O_2$ [M+H]$^+$: 486.1359, Found: 486.1366.

(R)-3-(3-(3-(trifluoromethyl)-4-((4-(trifluoromethyl)benzyl)oxy)phenyl)-1,2,4-oxadiazol-5-yl)piperidine-1-carboximidamide hydrochloride (23h)

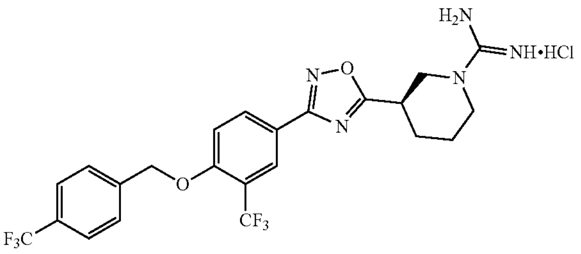

Synthesized according to General Procedure 1D. White solid, 24 mg (88%). $^{1}$H NMR (400 MHz, Methanol-$d_4$) δ 8.32-8.23 (m, 2H), 7.70 (q, J=8.6 Hz, 4H), 7.43 (d, J=8.5 Hz, 1H), 5.42 (s, 2H), 4.07 (dd, J=13.9, 3.6 Hz, 1H), 3.82 (dd, J=13.9, 8.1 Hz, 1H), 3.75-3.66 (m, 1H), 3.51-3.40 (m, 2H), 2.39-2.29 (m, 1H), 2.17-2.04 (m, 1H), 1.94-1.85 (m, 1H), 1.83-1.71 (m, 1H); $^{13}$C NMR (101 MHz, Methanol-$d_4$) δ 180.36, 168.26, 159.76, 141.95, 133.95, 131.20 (q, J=32.3 Hz), 127.25 (q, J=5.4 Hz), 126.53 (q, J=3.8 Hz), 125.60 (q, J=271.2 Hz), 124.73 (q, J=271.8 Hz), 120.51 (q, J=31.6 Hz), 120.47, 115.38, 70.80, 49.00, 46.63, 45.27, 33.80, 27.40, 22.71; $^{19}$F NMR (376 MHz, Methanol-$d_4$) δ −64.04; HRMS (ESI): Calcd for $C_{23}H_{22}F_6N_5O_2[M+H]^+$: 514.1672, Found: 514.1645.

3-(3-(4-(3-phenylpropoxy)-3-(trifluoromethyl)phenyl)-1,2,4-oxadiazol-5-yl)azetidine-1-carboximidamide hydrochloride (23i)

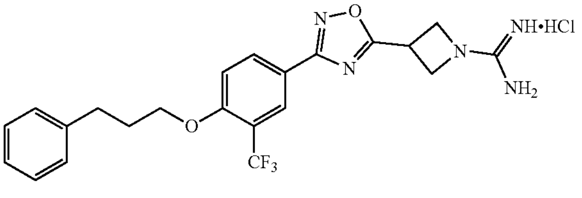

Synthesized according to General Procedure 1D. White solid, 20 mg (76%). $^{1}$H NMR (400 MHz, Methanol-$d_4$) δ 8.32-8.21 (m, 2H), 7.32-7.23 (m, 3H), 7.23-7.12 (m, 3H), 4.65 (t, J=8.9 Hz, 2H), 4.49 (dd, J=8.5, 5.8 Hz, 2H), 4.46-4.36 (m, 1H), 4.14 (t, J=6.0 Hz, 2H), 2.84 (t, J=7.5 Hz, 2H), 2.13 (p, J=13.2, 6.1 Hz, 2H); $^{13}$C NMR (151 MHz, Methanol-$d_4$) δ 180.39, 168.68, 160.63, 158.31, 124.82 (q, J=271.6 Hz), 133.92, 129.54, 129.47, 127.14 (q, J=5.5 Hz), 127.08, 127.03, 124.82, 120.23 (q, J=31.7 Hz), 119.73, 114.76, 68.99, 55.80, 49.00, 32.72, 31.85, 27.16; $^{19}$F NMR (376 MHz, Methanol-$d_4$) δ −64.04, −67.14; HRMS (ESI): Calcd for $C_{22}H_{23}F_3N_5O_2[M+H]^+$: 446.1798, Found: 446.1797.

(R)-3-(3-(4-(3-phenylpropoxy)-3-(trifluoromethyl)phenyl)-1,2,4-oxadiazol-5-yl)piperidine-1-carboximidamide hydrochloride (23j)

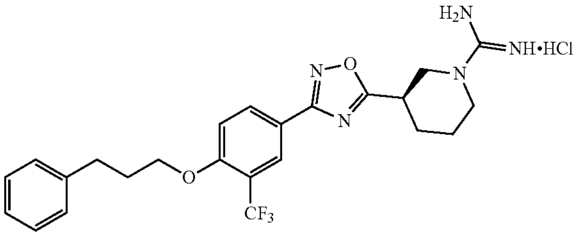

Synthesized according to General Procedure 1D. White solid, 29 mg (85%). $^{1}$H NMR (400 MHz, Methanol-$d_4$) δ 8.30-8.21 (m, 2H), 7.31-7.24 (m, 3H), 7.23-7.12 (m, 3H), 4.15 (t, J=5.9 Hz, 2H), 4.07 (dd, J=13.9, 3.8 Hz, 1H), 3.82 (dd, J=13.9, 8.2 Hz, 1H), 3.74-3.66 (m, 1H), 3.51-3.40 (m, 2H), 2.85 (t, J=7.5 Hz, 2H), 2.40-2.29 (m, 1H), 2.19-2.04 (m, 3H), 1.94-1.85 (m, 1H), 1.83-1.73 (m, 1H; $^{13}$C NMR (101 MHz, Methanol-$d_4$) δ 181.00, 168.32, 160.60, 160.59, 158.15, 142.52, 133.85, 129.56, 129.49, 127.10 (q, J=5.3 Hz), 127.05, 124.84 (q, J=271.73 Hz), 120.19 (q, J=31.5 Hz), 119.84, 114.75, 68.94, 49.64, 49.43, 49.21, 49.00, 48.93, 48.79, 48.57, 48.36, 47.39, 35.27, 32.72, 31.88, 28.55, 24.20; $^{19}$F NMR (376 MHz, Methanol-$d_4$) δ −64.07; HRMS (ESI): Calcd for $C_{24}H_{27}F_3N_5O_2[M+H]^+$: 474.2111, Found: 474.2125.

Scheme 4-Synthetic Route to 30a-g

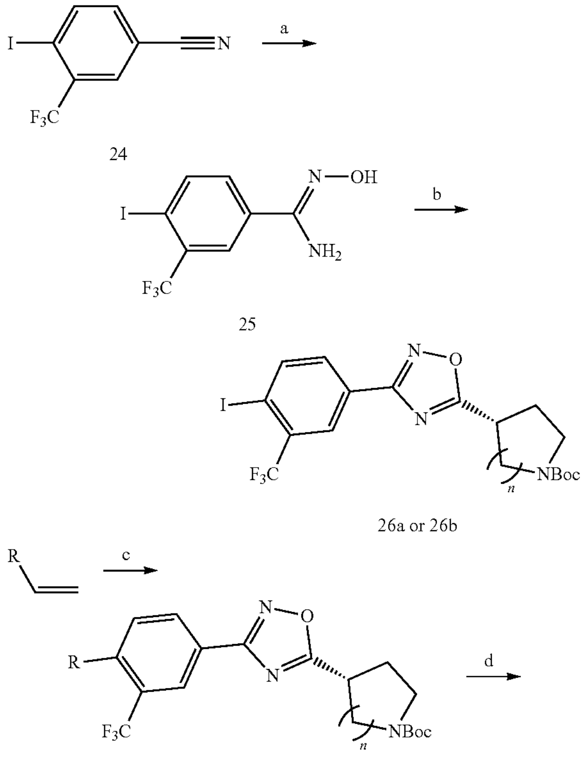

24

25

26a or 26b 27a-g

-continued

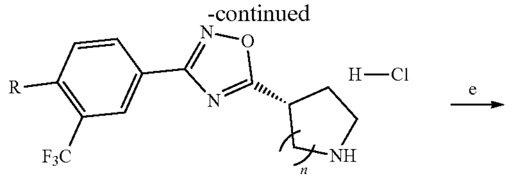

28a-g

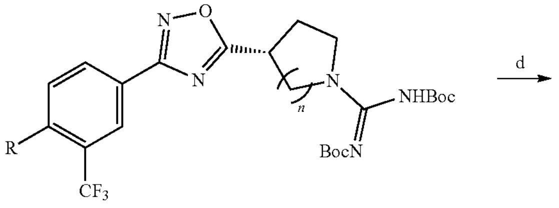

29a-g

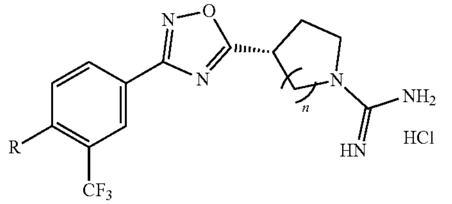

30a-g a. $NH_2OH$•HCl (2 equiv), TEA (3 equiv), EtOH, reflux; b. N-Boc-β-amino acid (1.1 equiv), HCTU (1.1 equiv), DIEA (1.8 equiv), DMF, 100° C.; c. Alkene (1.1 equiv), 9-BBN (1.1 equiv), $PdCl_2$(dppf) (0.01 equiv), 3M $KOH_{(aq)}$ (2 equiv), THF, 70° C.; d. $HCl_{(g)}$, MeOH, rt; e. N,N'-Di-Boc-1H-pyrazole-1-carboxiamidine (1 equiv), DIEA (15 equiv), MeCN, 50° C. μW.

General Procedure AA: Amidoxime Synthesis

To a round bottom flask containing ethanol was added 4-iodobenzonitrile (1 equiv), hydroxylamine hydrochloride (2 equiv), and triethylamine (3 equiv) under ambient air. The reaction mixture was then heated to reflux until complete as monitored by TLC (1-4 hours). The resulting solution was allowed to cool to room temperature, followed by concentration in vacuo, to afford the crude mixture as a solid. Purification by column chromatography (0-30% ethyl acetate in hexanes) afforded pure 25.

General Procedure BB: 1,2,4-Oxadiazole Synthesis

Amidoxime 25 (1 equiv), N-Boc protected β-amino acid (1.1 equiv), and DIEA (1.8 equiv) were added to a round bottom flask containing DMF at room temperature. HCTU (1.1 equiv) was then added and the resulting mixture was heated to 100° C. until completion as monitored by TLC (6-16 hours). Upon cooling to room temperature, the resulting mixture was diluted in ethyl acetate and washed with a saturated lithium bromide solution. The resulting aqueous layer was then extracted with ethyl acetate. The organic layers were then combined and washed with a brine solution, followed by drying over anhydrous sodium sulfate. Concentration in vacuo afforded the crude product, which was then purified by column chromatography (0-20% ethyl acetate in hexanes) to afford products 26a-g.

General Procedure CC: Suzuki-Miyaura Cross Coupling

To a round bottom flask a containing terminal alkene (1.1 equiv) in THF was added 9BBN (1.5 equiv) and then heated to reflux until consumption of alkene as monitored by TLC (30-60 minutes). Aryl iodide (26a or 26b) (1 equiv) and Pd(dppf)$Cl_2$ (0.05 equiv) were then added to the mixture, followed by dropwise addition of a 3M $KOH_{(aq)}$ solution (3 equiv). The resulting mixture was then heated to reflux until consumption of aryl iodide (26a or 26b) as monitored by TLC (2-6 hours). Upon cooling to room temperature, the reaction mixture was filtered over a pad of celite, diluted in ethyl acetate, and washed with a brine solution. The organic layer was then dried over sodium sulfate and concentrated in vacuo to afford the crude product as a yellow oil, which was then purified by column chromatography (0-30% ethyl acetate in hexanes) to afford products 27a-g General Procedure DD: HCl Boc Deprotection Boc protected starting material (27a-g or diBoc-guanidino compounds 29a-g) (1 equiv) was added to a round bottom flask and dissolved in methanol. $HCl_{(g)}$ was then bubbled into the solution for 1 minute. The resulting solution was allowed to stir at room temperature until consumption of Boc protected starting material as monitored by TLC (30-60 minutes). Concentration in vacuo afforded a white to off-white solid, which was then washed with diethyl ether to afford the pure secondary amine (28a-g) or guanidine compounds (30a-g) as HCl salts.

General Procedure EE: Guanylation

HCl salt (28a-g) (1 equiv), DIEA (15 equiv), and (Z)-tert-butyl (((tert-butoxycarbonyl)imino)(1H-pyrazol-1-yl)methyl)carbamate (1 equiv) were added to a microwave vial containing MeCN at room temperature. The resulting solution was then placed in a CEM microwave synthesized and heated to 50° C. for 3 hours. After cooling down to room temperature, the solution was concentrated in vacuo to afford the crude mixture as a yellow oil, which was then purified by column chromatography using the appropriate ethyl acetate and hexanes solvent system.

N'-hydroxy-4-iodo-3-(trifluoromethyl)benzimidamide (25)

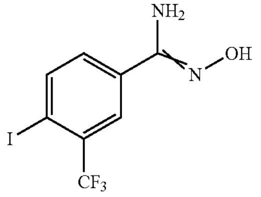 [SMILES: NC(=NO)c1ccc(I)c(C(F)(F)F)c1]

Synthesized according to General Procedure AA. White solid (90%, 105 mg) $^1H$ NMR (400 MHz, $CDCl_3$) δ 8.11 (d, J=8.38, 1H), 7.98 (s, 1H), 7.54 (d, J=8.35, 1H), 4.89 (brs, 2H).

tert-butyl 3-(3-(4-iodo-3-(trifluoromethyl)phenyl)-1,2,4-oxadiazol-5-yl)azetidine-1-carboxylate (26a)

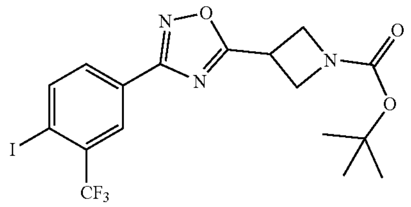 [SMILES: CC(C)(C)OC(=O)N1CC(c2nc(-c3ccc(I)c(C(F)(F)F)c3)no2)C1]

Synthesized according to General Procedure BB. Purified by silica chromatography (10% EtOAc in hexanes). Yellow oil (71%, 102 mg). $^1H$ NMR (400 MHz, $CDCl_3$) δ 8.36 (s, 1H), 8.17 (d, J=8.24, 1H), 7.90 (d, J=8.24, 1H), 4.44-4.28 (m, 4H), 4.12-4.03 (m, 1H), 1.47 (s, 9H).

tert-butyl (R)-3-(3-(4-iodo-3-(trifluoromethyl)phenyl)-1,2,4-oxadiazol-5-yl)piperidine-1-carboxylate (26b)

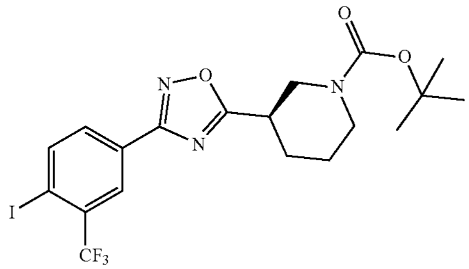 [SMILES: CC(C)(C)OC(=O)N1CCC[C@@H](c2nc(-c3ccc(I)c(C(F)(F)F)c3)no2)C1]

Synthesized according to General Procedure BB. Purified by silica chromatography (20% EtOAc in hexanes). Yellow oil (64%, 492 mg). $^1$H NMR (400 MHz, $CDCl_3$) δ 8.31 (s, 1H), 8.26-8.22 (d, J=8.15, 1H), (d, J=8.16, 1H), 7.30 (d, J=9.20, 1H), 4.46-4.04 (m, 1H), 3.96-3.82 (m, 1H), 3.43-2.91 (m, 3H), 2.26-2.20 (m, 1H), 1.94-1.74 (m, 2H), 1.64-1.53 (m, 1H), 1.43 (s, 9H).

tert-butyl 3-(3-(4-nonyl-3-(trifluoromethyl)phenyl)-1,2,4-oxadiazol-5-yl)azetidine-1-carboxylate (27a)

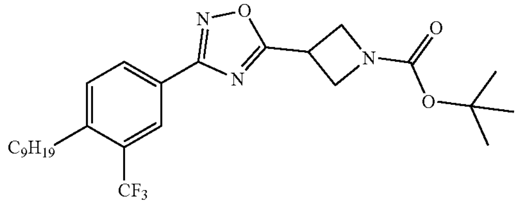

Synthesized according to General Procedure CC. Yellow oil, 67 mg (50%). $^1$H NMR (400 MHz, $CDCl_3$) δ 8.34 (s, 1H), 8.16 (dd, J=8.0, 1.8 Hz, 1H), 7.47 (d, J=8.1 Hz, 1H), 4.43-4.30 (m, 4H), 4.07 (tt, J=8.9, 6.0, 1 Hz, 1H), 2.83 (t, J=7.7 Hz, 2H), 1.70-1.59 (m, 2H), 1.48 (brs, 9H), 1.45-1.20 (m, 12H), 0.88 (t, J=6.8 Hz, 3H).

tert-butyl 3-(3-(4-decyl-3-(trifluoromethyl)phenyl)-1,2,4-oxadiazol-5-yl)azetidine-1-carboxylate (27b)

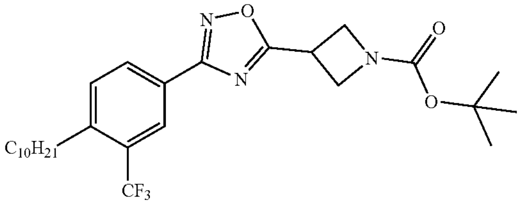

Synthesized according to General Procedure BB. Yellow oil, 37 mg (35%) $^1$H NMR (400 MHz, $CDCl_3$) δ 8.34 (s, 1H), 8.16 (dd, J=8.1, 1.8 Hz, 1H), 7.47 (d, J=8.0 Hz, 1H), 4.44-4.29 (m, 4H), 4.06 (tt, J=8.9, 6.0 Hz, 1H), 2.83 (t, J=8.1 Hz, 2H), 1.72-1.59 (m, 2H), 1.47 (brs, 9H), 1.45-1.20 (m, 14H) 0.88 (t, J=6.5 Hz, 3H).

tert-butyl 3-(3-(3-(trifluoromethyl)-4-undecylphenyl)-1,2,4-oxadiazol-5-yl)azetidine-1-carboxylate (27c)

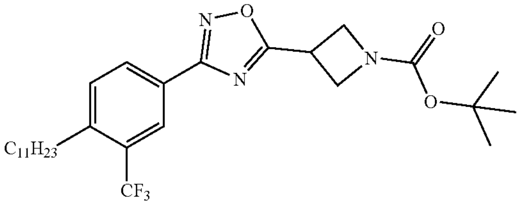

Synthesized according to General Procedure BB. Yellow oil, 35 mg (31%). $^1$H NMR (400 MHz, $CDCl_3$) δ 8.34 (s, 1H), 8.16 (dd, J=8.0, 1.8 Hz, 1H), 7.47 (d, J=8.1 Hz, 1H), 4.46-4.27 (m, 4H), 4.15-3.96 (m, 1H), 2.83 (t, J=7.7 Hz, 2H), 1.73-1.57 (m, 2H), 1.48 (s, 9H), 1.45-1.16 (m, 16H), 0.88 (t, J=6.5 Hz 3H).

tert-butyl (R)-3-(3-(4-nonyl-3-(trifluoromethyl)phenyl)-1,2,4-oxadiazol-5-yl)piperidine-1-carboxylate (27d)

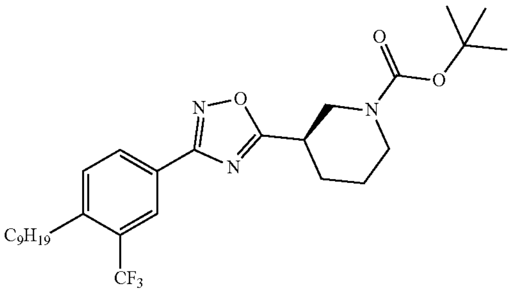

Synthesized according to General Procedure BB. Yellow oil, 67 mg (50%). $^1$H NMR (400 MHz, $CDCl_3$) δ 8.32 (s, 1H), 8.14 (dd, J=8.1, 1.8 Hz, 1H), 7.44 (d, J=8.1 Hz, 1H), 4.59-4.04 (m, 1H), 4.03-3.87 (m, 1H), 3.51-3.28 (m, 1H), 3.22-3.10 (m, 1H), 3.08-2.89 (m, 1H), 2.81 (t, J=7.7 Hz, 2H), 2.31-2.20 (m, 1H), 1.97-1.79 (m, 2H), 1.68-1.56 (m, 3H), 1.46 (brs, 9H), 1.43-1.20 (m, 12), 0.87 (t, J=6.7 Hz, 3H).

tert-butyl (R)-3-(3-(4-nonyl-3-(trifluoromethyl)phenyl)-1,2,4-oxadiazol-5-yl)piperidine-1-carboxylate (27e)

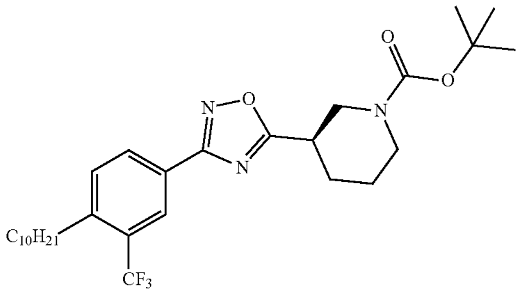

Synthesized according to General Procedure BB. Yellow oil, 33 mg (32%). $^1H$ NMR (400 MHz, $CDCl_3$) δ 8.33 (s, 1H), 8.15 (dd, J=8.0, 1.8 Hz, 1H), 7.45 (d, J=8.1 Hz, 1H), 4.53-4.05 (m, 1H), 4.01-3.92 (1H), 3.49-3.28 (m, 1H), 3.21-3.10 (m, 1H), 3.07-2.92 (m, 1H), 2.82 (t, J=7.7 Hz, 2H), 2.34-2.17 (m, 1H), 2.00-1.51 (m, 5H), 1.47 (brs, 9H), 1.44-1.20 (m, 14H), 0.88 (t, J=6.6 Hz, 3H).

tert-butyl (R)-3-(3-(3-(trifluoromethyl)-4-undecylphenyl)-1,2,4-oxadiazol-5-yl)piperidine-1-carboxylate (27f)

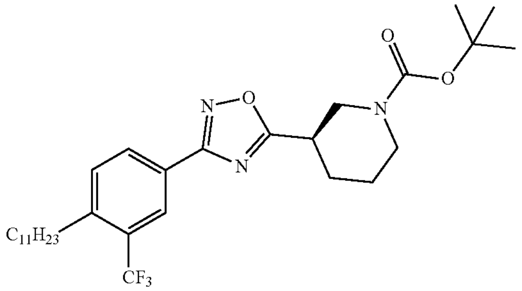

Synthesized according to General Procedure BB. Yellow oil, 37 mg (34%). $^1H$ NMR (400 MHz, $CDCl_3$) δ 8.33 (s, 1H), 8.15 (dd, J=8.1, 1.8 Hz, 1H), 7.45 (d, J=8.1 Hz, 1H), 4.39-4.06 (m, 1H), 4.03-3.87 (m, 1H), 3.58-3.30 (m, 1H), 3.28-3.12 (m, 1H), 3.09-2.92 (m, 1H), 2.82 (t, J=7.7 Hz, 2H), 2.37-2.19 (m, 1H), 1.97-1.77 (m, 2H), 1.71-1.56 (m, 2H), 1.47 (s, 9H), 1.44-1.20 (m, 16H), 0.88 (t, J=6.6 Hz, 3H).

5-(azetidin-3-yl)-3-(4-nonyl-3-(trifluoromethyl)phenyl)-1,2,4-oxadiazole hydrochloride (28a)

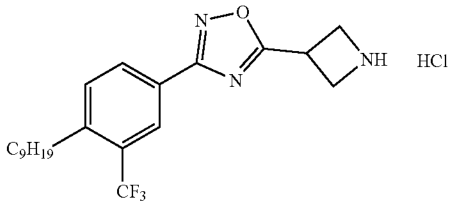

Synthesized according to General Procedure DD. Crude mixture dried in vacuo and carried forward to the next reaction without purification.

5-(azetidin-3-yl)-3-(4-decyl-3-(trifluoromethyl)phenyl)-1,2,4-oxadiazole hydrochloride (28b)

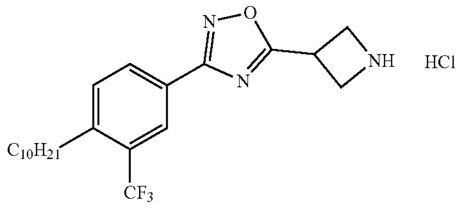

Synthesized according to General Procedure DD. Crude mixture dried in vacuo and carried forward to the next reaction without purification.

5-(azetidin-3-yl)-3-(3-(trifluoromethyl)-4-undecylphenyl)-1,2,4-oxadiazole hydrochloride (28c)

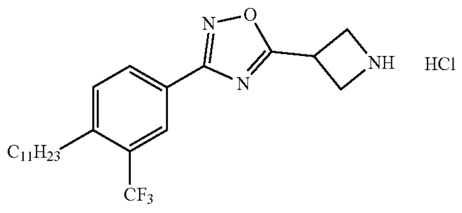

Synthesized according to General Procedure DD. Crude mixture dried in vacuo and carried forward to the next reaction without purification.

(R)-3-(4-nonyl-3-(trifluoromethyl)phenyl)-5-(piperidin-3-yl)-1,2,4-oxadiazole hydrochloride (28d)

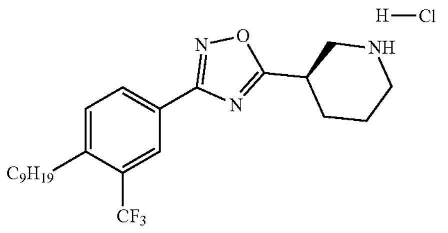

Synthesized according to General Procedure DD. White Solid, 41 mg, 79%. $^1H$ NMR (400 MHz, Methanol-$d_4$) δ 8.27 (d, J=1.3 Hz, 1H), 8.18 (dd, J=8.1, 1.4 Hz, 1H), 7.56 (d, J=8.1 Hz, 1H), 3.52 (dd, J=12.3, 3.4 Hz, 1H), 3.43-3.34 (m, 1H), 3.20-3.11 (m, 2H), 2.91-2.75 (m, 3H), 2.35-2.27 (m, 1H), 2.02-1.85 (m, 2H), 1.83-1.69 (m, 1H), 1.64 (p, J=8.0, 7.5 Hz, 2H), 1.46-1.22 (m, 12H), 0.89 (t, J=6.9 Hz, 3H); HRMS (ESI): Calcd for $C_{23}H_{33}F_3N_3O$ $[M+H]^+$: 424.2570, Found: 424.2558.

(R)-3-(4-decyl-3-(trifluoromethyl)phenyl)-5-(piperidin-3-yl)-1,2,4-oxadiazole hydrochloride (28e)

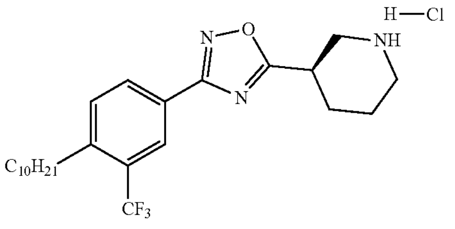

Synthesized according to General Procedure DD. White Solid, 19 mg, 67%. $^1$H NMR (400 MHz, Methanol-$d_4$) δ 8.30 (s, 1H), 8.22 (d, J=8.0 Hz, 1H), 7.60 (d, J=8.1 Hz, 1H), 3.80 (dd, J=12.5, 3.9 Hz, 1H), 3.72-3.62 (m, 1H), 3.50 (dd, J=12.2, 10.4 Hz, 1H), 3.46-3.39 (m, 1H), 3.21-3.07 (m, 1H), 2.84 (t, J=8.0 Hz, 2H), 2.44-2.34 (m, 1H), 2.11-1.92 (m, 3H), 1.65 (p, J=7.5 Hz, 2H), 1.48-1.21 (m, 14H), 0.89 (t, J=6.6 Hz, 3H); HRMS (ESI): Calcd for $C_{24}H_{35}F_3N_3O$ [M+H]$^+$: 438.2727, Found: 438.2731.

(R)-5-(piperidin-3-yl)-3-(3-(trifluoromethyl)-4-undecylphenyl)-1,2,4-oxadiazole hydrochloride (28f)

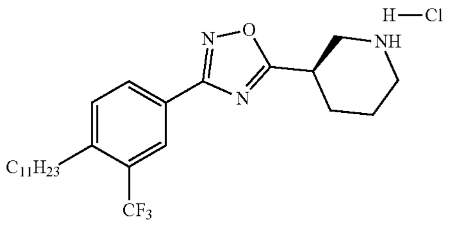

Synthesized according to General Procedure DD. White Solid, 28 mg, 86%. $^1$H NMR (400 MHz, Methanol-$d_4$) δ 8.29 (s, 1H), 8.21 (d, J=7.9 Hz, 1H), 7.59 (d, J=8.0 Hz, 1H), 3.72 (dd, J=12.6, 3.8 Hz, 1H), 3.59 (m, 1H), 3.40 (dd, J=12.6, 10.1 Hz, 1H), 3.38-3.28 (m, 1H), 3.06 (m, 1H), 2.83 (t, J=8.0 Hz, 2H), 2.40-2.29 (m, 1H), 2.09-1.82 (m, 3H), 1.65 (p, J=7.3 Hz, 2H), 1.49-1.19 (m, 16H), 0.89 (t, J=6.6 Hz, 3H); HRMS (ESI): Calcd for $C_{25}H_{37}F_3N_3O$ [M+H]$^+$: 452.2883, Found: 425.2895.

(S)-3-(4-decyl-3-(trifluoromethyl)phenyl)-5-(pyrrolidin-3-ylmethyl)-1,2,4-oxadiazole hydrochloride (28g)

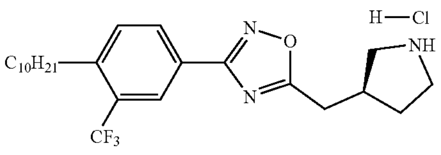

Synthesized according to General Procedure DD. White Solid, 103 mg, 961H NMR (400 MHz, Methanol-$d_4$) δ 8.28 (s, 1H), 8.20 (d, J=8.1 Hz, 1H), 7.60 (d, J=8.1 Hz, 1H), 3.67 (dd, J=11.7, 7.7 Hz, 1H), 3.48 (m, 1H), 3.40-3.30 (m, 1H), 3.25 (dd, J=7.3, 3.4 Hz, 2H), 3.14 (dd, J=11.7, 9.0 Hz, 1H), 2.97 (hept, J=7.5 Hz, 1H), 2.88-2.79 (m, 2H), 2.45-2.31 (m, 1H), 1.95-1.80 (m, 1H), 1.65 (p, J=7.6 Hz, 2H), 1.47-1.23 (m, 14H), 0.89 (t, J=6.8 Hz, 3H);

tert-butyl (((tert-butoxycarbonyl)amino)(3-(3-(4-nonyl-3-(trifluoromethyl)phenyl)-1,2,4-oxadiazol-5-yl)azetidin-1-yl)methylene)carbamate (29a)

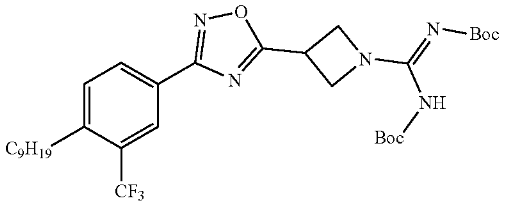

Synthesized according to General Procedure EE. Yellow oil, 29 mg (54%) yield. $^1$H NMR (400 MHz, $CDCl_3$) δ 11.03 (s, 1H), 8.33 (s, 1H), 8.15 (d, J=8.0 Hz, 1H), 7.46 (d, J=8.1 Hz, 1H), 4.88-4.56 (m, 4H), 4.19 (m, 4.09 (m, 1H), 2.82 (t, J=7.77 Hz, 2H), 1.71-1.20 (m, 32H), 0.88 (t, J=6.8 Hz, 3H).

tert-butyl (((tert-butoxycarbonyl)amino)(3-(3-(4-decyl-3-(trifluoromethyl)phenyl)-1,2,4-oxadiazol-5-yl)azetidin-1-yl)methylene)carbamate (29b)

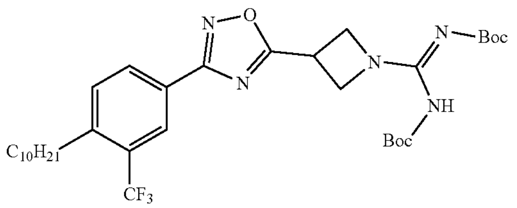

Synthesized according to General Procedure EE. Yellow oil, 19 mg (48%) yield. $^1$H NMR (400 MHz, $CDCl_3$) δ 8.32 (s, 1H), 8.15 (dd, J=8.0, 1.8 Hz, 1H0, 7.46 (d, J=8.0 Hz, 1H), 4.82-4.57 (m, 4H), 4.15 (brs, 1H), 2.82 (t, J=8.0 Hz, 2H), 1.70-1.16 (m, 34H), 0.87 (t, J=6.6 Hz, 3H).

tert-butyl (E)-(((tert-butoxycarbonyl)amino)(3-(3-(3-(trifluoromethyl)-4-undecylphenyl)-1,2,4-oxadiazol-5-yl)azetidin-1-yl)methylene)carbamate (29c)

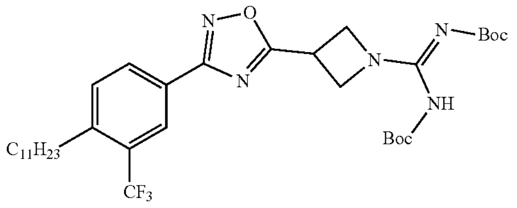

Synthesized according to General Procedure EE. Yellow oil, 29 mg (57%) yield. $^1$H NMR (400 MHz, $CDCl_3$) δ 11.01 (s, 1H), 8.32 (s, 1H), 8.15 (dd, J=8.1, 1.8 Hz, 1H), 7.46 (d, J=8.1 Hz, 1H), 4.77-4.66 (m, 2H), 4.62 (dd, J=10.1, 6.3 Hz, 2H), 4.14 (tt, J=9.0, 6.4 Hz, 1H), 2.82 (t, J=7.7 Hz, 2H), 1.69-1.19 (m, 36H), 0.87 (t, J=6.8 Hz, 3H).

tert-butyl (R,Z)-(((tert-butoxycarbonyl)amino)(3-(3-(4-nonyl-3-(trifluoromethyl)phenyl)-1,2,4-oxadiazol-5-yl)piperidin-1-yl)methylene)carbamate (29d)

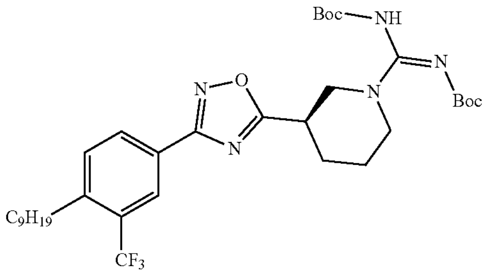

Synthesized according to General Procedure EE. Yellow oil, 37 mg (65%) yield. $^{1}$H NMR (400 MHz, $CDCl_3$) δ 10.17 (brs, 1H), 8.30 (d, J=1.7 Hz, 1H), 8.13 (dd, J=8.0 Hz, 1.8 Hz, 1H), 7.44 (d, J=8.1 Hz, 1H), 4.49-4.02 (m, 2H), 3.54-3.40 (m, 1H), 3.33 (t, J=11.7 Hz, 1H), 3.16-3.04 (m, 1H), 2.81 (t, J=8.0 Hz, 2H), 2.41-2.29 (m, 1H), 1.98-1.71 (m, 3H), 1.70-1.20 (m, 32H), 0.88 (t, J=6.5 Hz, 3H).

tert-butyl (R)-(((tert-butoxycarbonyl)amino)(3-(3-(4-decyl-3-(trifluoromethyl)phenyl)-1,2,4-oxadiazol-5-yl)piperidin-1-yl)methylene)carbamate (29e)

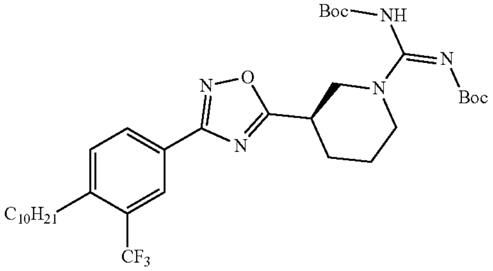

Synthesized according to General Procedure EE. Yellow oil, 14 mg (55%) yield. $^{1}$H NMR (400 MHz, $CDCl_3$) δ 10.1 (brs, 1H), 8.30 (s, 1H), 8.13 (dd, J=8.1, 1.8 Hz, 1H), 7.44 (d, J=8.1 Hz, 1H), 4.57-4.04 (m, 2H), 3.54-3.40 (m, 1H), 3.38-3.27 (m, 1H), 3.15-3.05 (m, 1H0, 2.81 (t, J=7.7 Hz, 2H), 2.39-2.27 (m, 1H), 1.99-1.71 (m, 3H), 1.69-1.17 (m, 34H), 0.87 (t, J=6.6 Hz, 3H).

tert-butyl (R,Z)-(((tert-butoxycarbonyl)amino)(3-(3-(3-(trifluoromethyl)-4-undecylphenyl)-1,2,4-oxadiazol-5-yl)piperidin-1-yl)methylene)carbamate (29f)

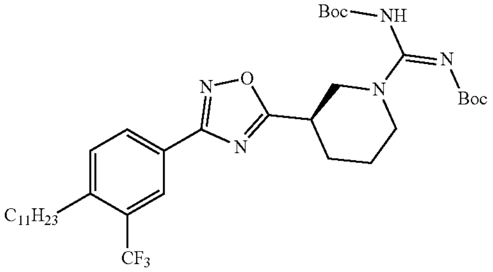

Synthesized according to General Procedure EE. Yellow oil, 19 mg (59%) yield. $^{1}$H NMR (400 MHz, $CDCl_3$) δ 10.15 (brs, 1H), 8.30 (s, 1H), 8.13 (dd, J=8.1 Hz, 1H), 7.44 (d, J=8.0 Hz, 1H), 4.52-4.02 (m, 2H), 3.54-3.40 (m, 1H), 3.33 (dd, J=13.2, 10.3 Hz, 1H), (ddd, J=13.8, 10.8, 3.5 Hz, 1H), 2.81 (t, J=8.1 Hz, 2H), 2.40-2.29 (m, 1H), 2.01-1.72 (m, 3H), 1.69-1.17 (m, 36H), 0.87 (t, J=6.7 Hz, 3H).

tert-butyl (S,Z)-(((tert-butoxycarbonyl)imino)(3-((3-(4-decyl-3-(trifluoromethyl)phenyl)-1,2,4-oxadiazol-5-yl)methyl)pyrrolidin-1-yl)methyl)carbamate (29g)

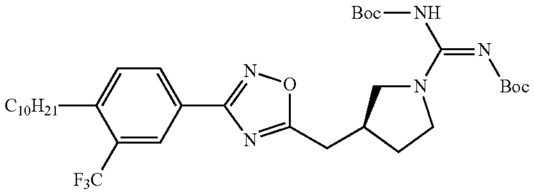

Synthesized according to General Procedure EE. Yellow oil, 34 mg (61%) yield. $^{1}$H NMR (400 MHz, $CDCl_3$) δ 10.38 (s, 1H), 8.30 (s, 1H), 8.13 (dd, J=8.1, 1.8 Hz, 1H), 7.45 (d, J=8.1 Hz, 1H), 3.91-3.62 (m, 3H), 3.47 (dd, 12.1, 8.0 Hz, 1H), 3.11-2.99 (m, 1H), 2.81 (t, J=8.2 Hz, 2H), 2.25-2.15 (m, 1H), 1.82-1.70 (m, 1H), 1.69-1.58 (m, 2H), 1.54-1.17 (m, 32H), 0.87 (t, J=6.8 Hz, 3H). 7.03 (d, J=8.88, 1H), 4.41-4.30 (m, 4H), 4.11-4.02 (m, 3H), 2.86 (t, J=7.33, 2H), 2.17 (p, J=7.04, 2H), 1.47 (s, 9H).

3-(3-(4-nonyl-3-(trifluoromethyl)phenyl)-1,2,4-oxadiazol-5-yl)azetidine-1-carboximidamide hydrochloride (30a)

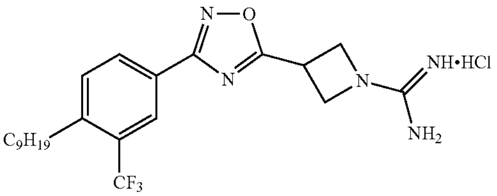

Synthesized according to General Procedure DD. White solid, 92 mg (90%/). $^{1}$H NMR (400 MHz, Methanol-$d_4$) δ 8.33 (d, J=1.8 Hz, 1H), 8.24 (dd, J=8.0, 1.8 Hz, 1H), 7.62 (d, J=8.1 Hz, 1H), 4.66 (t, J=8.8 Hz, 2H), 4.49 (dd, J=8.4, 5.8 Hz, 2H), 4.47-4.37 (m, 1H), 2.85 (t, J=7.9 Hz, 5H), 1.67 (p, J=15.7, 7.5 Hz, 2H), 1.48-1.24 (m, 12H), 0.90 (t, J=6.9 Hz, 3H); HRMS (ESI): Calcd for $C_{21}H_{31}F_3N_5O$ $[M+H]^+$: 438.2475, Found: 438.2490.

3-(3-(4-decyl-3-(trifluoromethyl)phenyl)-1,2,4-oxadiazol-5-yl)azetidine-1-carboximidamide hydrochloride (30b)

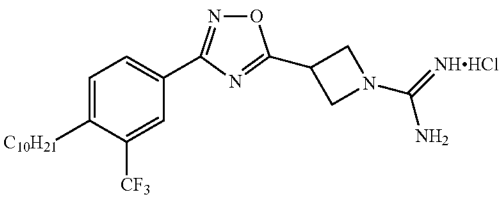

Synthesized according to General Procedure DD. White solid, 88 mg (61%). $^{1}$H NMR (400 MHz, Methanol-$d_4$) δ 8.32 (s, 1H), 8.24 (dd, J=8.1, 1.8 Hz, 1H), 7.62 (d, J=8.1 Hz, 1H), 4.66 (t, J=8.7 Hz, 2H), 4.49 (dd, J=8.4, 5.8 Hz, 2H), 4.47-4.38 (m, 1H), 2.85 (t, J=8.0 Hz, 2H), 1.67 (p, J=7.5 Hz, 2H), 1.51-1.20 (m, 14H), 0.90 (t, J=6.9 Hz, 3H); $^{13}$C NMR (126 MHz, Methanol-$d_4$) δ 180.62, 168.83, 158.34, 146.71, 133.45, 131.64, 130.12 (q, J=30.2 Hz), 125.97, 125.78 (q, J=5.8 Hz), 125.70 (q, J=273.0 Hz), 55.80, 49.51, 49.34, 49.17, 49.00, 48.83, 48.66, 48.49, 33.73, 33.03, 32.75, 30.72, 30.65, 30.60, 30.43, 30.40, 27.22, 23.70, 14.40; $^{19}$F NMR (376 MHz, Methanol-$d_4$) δ −61.32; HRMS (ESI): Calcd for $C_{21}H_{29}F_3N_5O_2$[M+H]$^+$: 452.2632, Found: 452.2630.

3-(3-(3-(trifluoromethyl)-4-undecylphenyl)-1,2,4-oxadiazol-5-yl)azetidine-1-carboximidamide hydrochloride (30c)

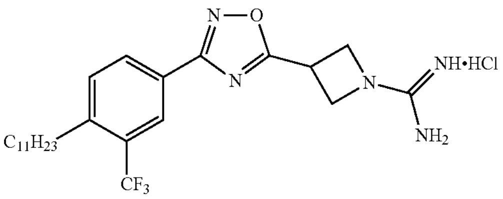

Synthesized according to General Procedure DD. White solid, 65 mg (69%). $^{1}$H NMR (400 MHz, Methanol-$d_4$) δ 8.32 (s, 1H), 8.24 (d, J=8.1 Hz, 1H), 7.62 (d, J=8.1 Hz, 1H), 4.66 (t, J=8.8 Hz, 2H), 4.49 (dd, J=8.6, 5.7 Hz, 2H), 4.47-4.39 (m, 1H), 2.85 (t, J=8.1 Hz, 2H), 1.67 (p, J=8.0, 7.6 Hz, 2H), 1.49-1.21 (m, 16H), 0.90 (d, J=6.8 Hz, 3H); $^{13}$C NMR (101 MHz, Methanol-$d_4$) δ 180.67, 168.79, 158.30, 146.70, 133.47, 131.65, 130.07 (q, J=30.2 Hz), 125.97, 125.74 (q, J=5.8 Hz), 125.70 (q, J=273.3 Hz), 55.79, 49.64, 49.43, 49.21, 49.00, 48.79, 48.57, 48.36, 33.75, 33.08, 32.83, 30.76, 30.73, 30.63, 30.47, 27.17, 23.75, 14.45; $^{19}$F NMR (376 MHz, Methanol-$d_4$) δ −61.32; HRMS (ESI): Calcd for $C_{24}H_{35}F_3N_5O$ [M+H]$^+$: 466.2788, Found: 466.2796.

(R)-3-(3-(4-nonyl-3-(trifluoromethyl)phenyl)-1,2,4-oxadiazol-5-yl)piperidine-1-carboximidamide hydrochloride (30d)

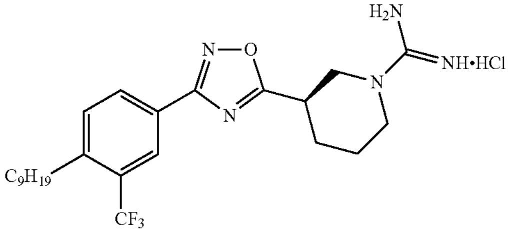

Synthesized according to General Procedure DD. White solid, 24 mg (85%). $^{1}$H NMR (400 MHz, Methanol-$d_4$) δ 8.30 (s, 1H), 8.22 (d, J=8.1 Hz, 1H), 7.61 (d, J=8.1 Hz, 1H), 4.09 (dd, J=13.9, 3.7 Hz, 1H), 3.82 (dd, J=13.9, 8.2 Hz, 1H), 3.77-3.66 (m, 1H), 3.53-3.40 (m, 2H), 2.84 (t, J=8.0 Hz, 2H), 2.40-2.29 (m, 1H), 2.18-2.04 (m, 1H), 1.96-1.83 (m, 1H), 1.86-1.72 (m, 1H), 1.66 (p, J=7.9, 7.5 Hz, 2H), 1.49-1.23 (m, 12H), 0.90 (d, J=6.8 Hz, 3H); HRMS (ESI): Calcd for $C_{24}H_{35}F_3N_5O$ [M+H]$^+$: 466.2788, Found: 466.2791.

(R)-3-(3-(4-decyl-3-(trifluoromethyl)phenyl)-1,2,4-oxadiazol-5-yl)piperidine-1-carboximidamide hydrochloride (30e)

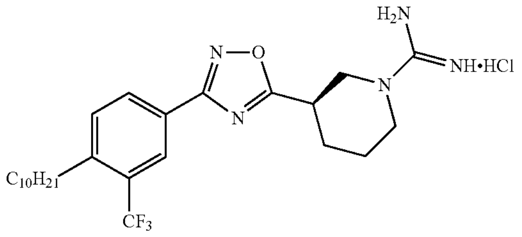

Synthesized according to General Procedure DD. White solid, 9 mg (83%). $^{1}$H NMR (400 MHz, Methanol-$d_4$) δ 8.31 (d, J=1.8 Hz, 1H), 8.22 (dd, J=8.1, 1.8 Hz, 1H), 7.62 (d, J=8.1 Hz, 1H), 4.08 (dd, J=13.9, 3.8 Hz, 1H), 3.83 (dd, J=13.9, 8.2 Hz, 1H), 3.74-3.66 (m, 1H), 3.51-3.41 (m, 2H), 2.85 (t, J=8.1 Hz, 2H), 2.41-2.30 (m, 1H), 2.16-2.06 (m, 1H), 1.95-1.86 (m, 1H), 1.84-1.73 (m, 1H), 1.66 (p, J=7.5 Hz, 2H), 1.47-1.25 (m, 14H), 0.90 (t, J=6.9 Hz, 3H); HRMS (ESI): Calcd for $C_{25}H_{37}F_3N_5O$ [M+H]$^+$: 480.2945, Found: 480.2946.

(R)-3-(3-(3-(trifluoromethyl)-4-undecylphenyl)-1,2,4-oxadiazol-5-yl)piperidine-1-carboximidamide hydrochloride (30f)

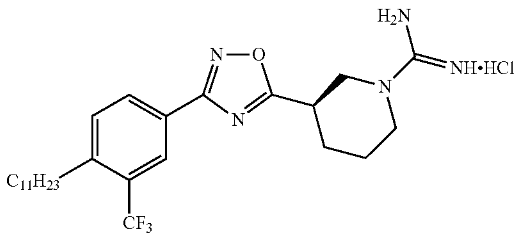

Synthesized according to General Procedure DD. White solid, 14 mg (92%). $^1$H NMR (400 MHz, Methanol-$d_4$) δ 8.30 (s, 1H), 8.22 (d, J=8.0 Hz, 1H), 7.62 (d, J=8.1 Hz, 1H), 4.08 (dd, J=13.9, 3.8 Hz, 1H), 3.83 (dd, J=13.9, 8.2 Hz, 1H), 3.70 (dt, J=13.8, 4.5 Hz, 1H), 3.54-3.39 (m, 2H), 2.85 (t, J=8.0 Hz, 2H), 2.41-2.30 (m, 1H), 2.18-2.05 (m, 1H), 1.96-1.85 (m, 1H), 1.84-1.73 (m, 1H), 1.66 (p, J=7.5 Hz, 2H), 1.49-1.24 (m, 16H), 0.90 (t, J=6.7 Hz, 3H); HRMS (ESI): Calcd for $C_{26}H_{39}F_3N_3O$ $[M+H]^+$: 494.3101, Found: 494.3122.

(S)-3-((3-(4-decyl-3-(trifluoromethyl)phenyl)-1,2,4-oxadiazol-5-yl)methyl)pyrrolidine-1-carboximidamide hydrochloride (30g)

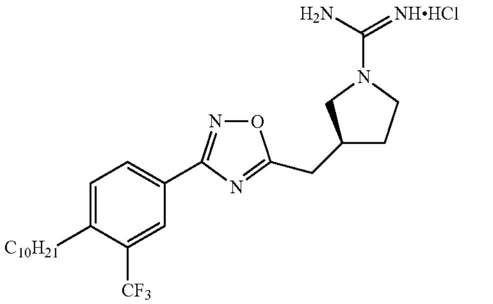

Synthesized according to General Procedure DD. White solid, 22 mg (85%). $^1$H NMR (400 MHz, Methanol-$d_4$) δ 8.30 (s, 1H), 8.22 (d, J=8.0 Hz, 1H), 7.61 (d, J=8.1 Hz, 1H), 3.78 (dd, J=10.2, 7.3 Hz, 1H), 3.64-3.56 (m, 1H), 3.49 (dd, J=16.7, 9.5 Hz, 1H), 3.29-3.14 (m, 3H), 2.98 (hept, J=7.5 Hz, 1H), 2.85 (t, J=8.1 Hz, 2H), 2.42-2.30 (m, 1H), 2.01-1.88 (m, 1H), 1.65 (p, J=7.8 Hz, 2H), 1.49-1.23 (m, 14H), 0.90 (t, J=6.9 Hz, 3H); HRMS (ESI): Calcd for $C_{25}H_{37}F_3N_3O$ $[M+H]^+$: 480.2945, Found: 480.2946.

Scheme 5 - Synthetic Route to 40a-n

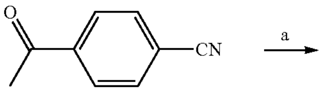

31

-continued

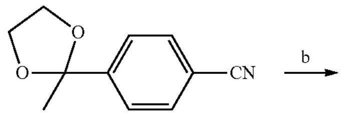

32

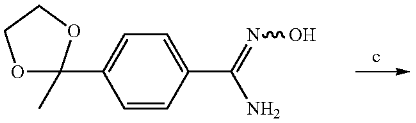

33

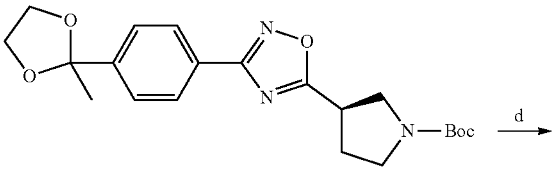

34

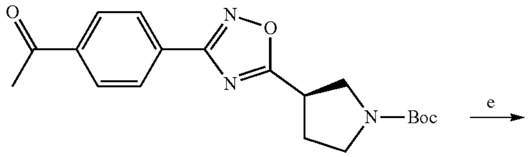

35

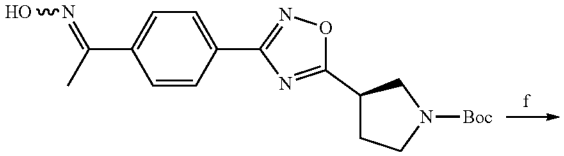

36

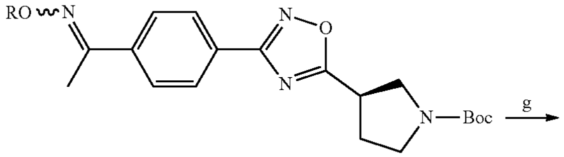

37a-n

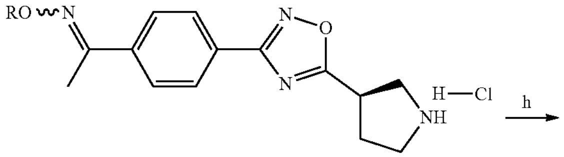

38a-n

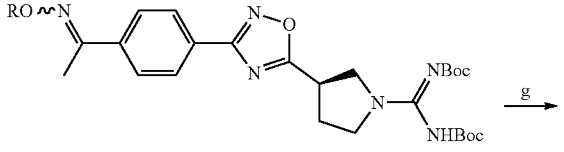

39a-n

-continued

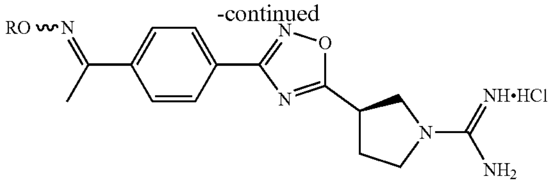

40a-n a. Ethylene glycol (10 equiv), $NH_4Cl$ (0.5 equiv) toluene, reflux, Dean-Stark;
b. $NH_2OH$•HCl (2 equiv), TEA (3 equiv), EtOH, reflux;
c. N-Boc-β-amino acid (1.1 equiv), HCTU (1.1 equiv), DIEA (1.8 equiv), DMF, 100° C.;
d. Acetone:$H_2O$:AcOH (1:1:1), 70° C.;
e. $NH_2OH$•HCl (2 equiv), $NaCO_3$ (3 equiv), EtOH, reflux;
f. NaH (1.5 equiv), R-Br (1.5 equiv), THF reflux;
g. $HCl_{(g)}$, MeOH, rt;
h. N,N'-Di-Boc-1H-pyrazole-1-caboxamidine (1 equiv), DIEA (15 equiv), MeCN, 50° C. μW.

General Procedure 1.1 Ketone Protection

Ketone 31 (1 equiv), ethylene glycol (10 equiv), ammonium chloride (0.5 equiv) were added to a round bottom flask containing toluene with Dean-Stark apparatus attached. The mixture was heated to reflux overnight (16-20 hours). Upon cooling to room temperature, excess potassium carbonate was added to quench acid, followed by filtration, concentration in vacuo, and column chromatography (hexanes and ethyl acetate) to afford the pure acetal product 32.

General Procedure 1.2: Amidoxime Synthesis

To a round bottom flask containing ethanol was added 32 (1 equiv), hydroxylamine hydrochloride (2 equiv), and trimethylamine (3 equiv) under ambient air. The reaction mixture was then heated to reflux until complete as monitored by TLC (1-4 hours). The resulting solution was allowed to cool to room temperature, followed by concentration in vacuo, to afford the crude mixture as a solid. Purification by column chromatography (0-20% ethyl acetate in dichloromethane) afforded the pure amidoxime product 33.

General Procedure 1.3: 1,2,4-Oxadiazole Synthesis

Amidoxime 33 (1 equiv), N-Boc protected β-amino acid (1.1 equiv), and DIEA (1.8 equiv) were added to a round bottom flask containing DMF at room temperature. HCTU (1.1 equiv) was then added and the resulting mixture was heated to 100° C. until completion as monitored by TLC (6-16 hours). Upon cooling to room temperature, the resulting mixture was diluted in ethyl acetate and washed with a saturated lithium bromide solution. The resulting aqueous layer was then extracted with ethyl acetate. The organic layers were then combined and washed with a brine solution, followed by drying over anhydrous sodium sulfate. Concentration in vacuo afforded the crude product, which was then purified by column chromatography (0-30% ethyl acetate in hexanes) to afford the pure 1,2,4-oxadiazole product 34.

General Procedure 1.4: Dioxolane Deprotection

To a round bottom flask was added acetal compound 34, followed by a 1:1:1 solution of AcOH:$H_2O$:acetone, and the mixture was heated to 70° C. until consumption of starting material as monitored by TLC (approximately 3 hours). Upon cooling to room temperature, the solution was washed with saturated sodium bicarbonate and brine solutions and extracted with ethyl acetate. The organic layer was then dried over anhydrous sodium sulfate, followed by concentration in vacuo and purification by column chromatography (30% ethyl acetate in hexanes) to afford ketone 35.

General Procedure 1.5: HCl Boc Deprotection

Boc protected secondary amine 37a-n or diBoc-protected guanidine compound 39a-n (1 equiv) was added to a round bottom flask and dissolved in methanol. HCl) was then bubbled into the solution for 1 minute. The resulting solution was allowed to stir at room temperature until consumption of Boc protected starting material as monitored by TLC (30-60 minutes). Concentration in vacuo afforded a white to off-white solid, which was then washed with diethyl ether to afford the secondary amine (38a-n) or guanidine compounds (40a-n) as pure HCl salts.

General Procedure 1.6 Oxime Synthesis

Ketone 35 (1 equiv), hydroxylamine hydrochloride (2 equiv), and sodium acetate (5 equiv) were added to a microwave vial containing methanol. The mixture was then placed in a CEM microwave synthesizer and heated to 100° C. for 30 minutes. Upon cooling to room temperature, the mixture was filtered, followed by concentration in vacuo and purification by column chromatography to afford the oxime product 36.

General Procedure 1.7 Nucleophilic Substitution

Oxime 36 (1 equiv) was added to a round bottom flask containing THF. To this solution was added NaH (1.5 equiv) and stirred for 30 minutes at room temperature. Alkyl bromide (1.5 equiv) was then added to the solution and the mixture was heated to reflux (approximately 16 hours). Upon cooling to room temperature, excess NaH was quenched with water, followed by ethyl acetate. The organic layer was then dried over anhydrous sodium sulfate and concentrated in vacuo to afford the crude mixture as an oil which was then purified by column chromatography (20% ethyl acetate in hexanes) to afford the products 37a-n.

General Procedure 1.8: Guanylation

HCl salt 38a-n (1 equiv), DIEA (15 equiv), and (Z)-tert-butyl (((tert-butoxycarbonyl)imino)(1H-pyrazol-1-yl)methyl)carbamate (1 equiv) were added to a microwave vial containing MeCN at room temperature. The resulting solution was then placed in a CEM microwave synthesizer and heated to 50° C. for 3 hours. After cooling down to room temperature, the solution was concentrated in vacuo to afford the crude mixture as a yellow oil, which was then purified by column chromatography (0-30% ethyl acetate in hexanes) to afford diBoc protected guanidine product (39a-n).

4-(2-methyl-1,3-dioxolan-2-yl)benzonitrile (32)

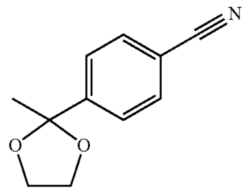

Synthesized according to General Procedure 1.1. Purified by silica chromatography (10% EtOAc in hexanes). White solid (94%, 2439 mg). $^1$H NMR (400 MHz, $CDCl_3$) δ 7.64-7.57 (m, 4H), 4.08-3.99 (m, 2H), 3.78-3.67 (m, 2H), 1.61 (s, 9H).

N'-hydroxy-4-(2-methyl-1,3-dioxolan-2-yl)benzimidamide (33)

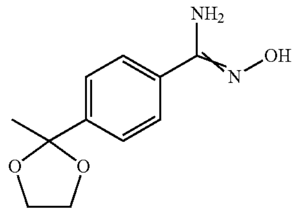 [SMILES: CC1(c2ccc(C(N)=NO)cc2)OCCO1]

Synthesized according to General Procedure 1.2. Purified by silica chromatography (40% EtOAc in hexanes). Yellow oil (91%, 2640 mg). $^{1}$H NMR (400 MHz, Methanol-$d_4$) δ 7.62 (d, J=8.31, 2H), 7.47 (d, J=8.51, 2H), 4.05-3.97 (m, 2H), 3.76-3.67 (m, 2H), 1.58 (s, 9H).

tert-butyl (R)-3-(3-(4-(2-methyl-1,3-dioxolan-2-yl)phenyl)-1,2,4-oxadiazol-5-yl)pyrrolidine-1-carboxylate (34)

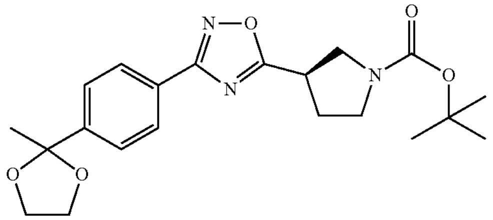 [SMILES: CC(C)(C)OC(=O)N1CC[C@@H](c2nc(-c3ccc(C4(C)OCCO4)cc3)no2)C1]

Synthesized according to General Procedure 1.3. Purified by silica chromatography (30% EtOAc in hexanes). Colorless oil (96%, 4420 mg). $^{1}$H NMR (400 MHz, $CDCl_3$) δ 8.02 (d, J=8.56, 2H), 7.57 (d, J=8.53, 2H), 4.05-4.01 (m, 2H), 3.89-3.48 (m, 7H), 2.43-2.29 (m, 2H), 1.64 (s, 3H), 1.45 (s, 1H).

tert-butyl (R)-3-(3-(4-acetylphenyl)-1,2,4-oxadiazol-5-yl)pyrrolidine-1-carboxylate (35)

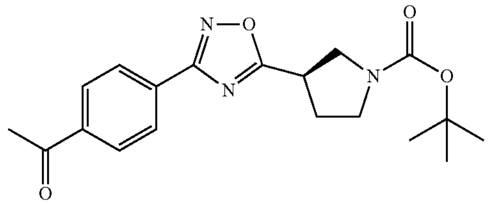 [SMILES: CC(=O)c1ccc(-c2noc([C@@H]3CCN(C(=O)OC(C)(C)C)C3)n2)cc1]

Synthesized according to General Procedure 1.4. Purified by silica chromatography (30% EtOAc in hexanes). White solid (73%, 2900 mg). $^{1}$H NMR (400 MHz, $CDCl_3$) δ 8.17 (d, J=8.51, 2H), 8.04 (d, J=8.51, 2H), 3.92-3.47 (m, 5H), 2.64 (s, 3H), 2.47-2.32 (m, m 2H), 1.47 (s, 9H).

tert-butyl (R)-3-(3-(4-(1-(hydroxyimino)ethyl)phenyl)-1,2,4-oxadiazol-5-yl)pyrrolidine-1-carboxylate (36)

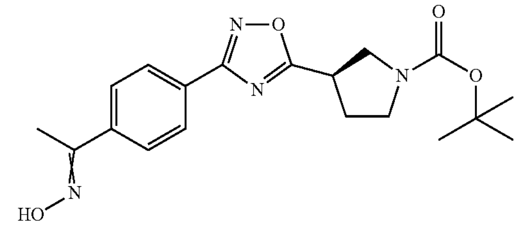 [SMILES: CC(=NO)c1ccc(-c2noc([C@@H]3CCN(C(=O)OC(C)(C)C)C3)n2)cc1]

Synthesized according to General Procedure 1.6. Purified by silica chromatography (30% EtOAc in hexanes). White solid (63%, 670 mg). $^{1}$H NMR (400 MHz, $CDCl_3$) δ 9.48 (brs, 1H), 8.06 (d, J=7.73, 2H), 7.73, (d, J=7.16, 2H), 3.96-3.44 (m, 5H), 2.46-2.27 (m, 5H), 1.47 (s, 9H).

tert-butyl (R)-3-(3-(4-(1-((4-phenylbutoxy)imino)ethyl)phenyl)-1,2,4-oxadiazol-5-yl)pyrrolidine-1-carboxylate (37a)

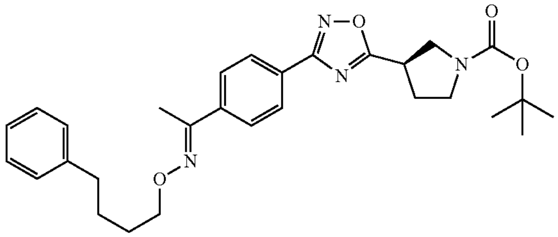 [SMILES: C/C(=N\OCCCCc1ccccc1)c1ccc(-c2noc([C@@H]3CCN(C(=O)OC(C)(C)C)C3)n2)cc1]

Synthesized according to General Procedure 1.7. Clear oil, 187 mg, 92%. $^{1}$H NMR (400 MHz, Chloroform-d) δ 8.07 (d, J=8.5 Hz, 2H), 7.77 (d, J=8.5 Hz, 2H), 7.31-7.25 (m, 2H), 7.23-7.14 (m, 3H), 4.25 (t, J=5.9 Hz, 2H), 3.96-3.43 (m, 5H), 2.68 (t, J=7.0 Hz, 2H), 2.43-2.32 (m, 2H), 2.25 (s, 3H), 1.84-1.73 (m, 4H), 1.49 (s, 9H); HRMS (ESI): Calcd for $C_{29}H_{37}N_4O_4$ $[M+H]^+$: 505.2809, Found: 505.2796.

tert-butyl (R)-3-(3-(4-(1-(((3,5-bis(trifluoromethyl)benzyl)oxy)imino)ethyl)phenyl)-1,2,4-tert-butyl (R,E)-3-(3-(4-(1-(((4-(trifluoromethyl)benzyl)oxy)imino)ethyl)phenyl)-1,2,4-oxadiazol-5-yl)pyrrolidine-1-carboxylate oxadiazol-5-yl)pyrrolidine-1-carboxylate (37b)

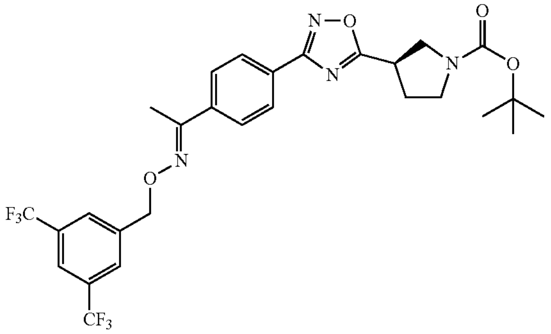 [SMILES: C/C(=N\OCc1cc(C(F)(F)F)cc(C(F)(F)F)c1)c1ccc(-c2noc([C@@H]3CCN(C(=O)OC(C)(C)C)C3)n2)cc1]

Synthesized according to General Procedure 1.7. Purified by silica chromatography (10% EtOAc in hexanes). Yellow oil (72%, 103 mg). $^1$H NMR (400 MHz, $CDCl_3$) δ 8.06 (d, J=8.44, 2H), 7.75 (d, J=8.35, 2H), 7.62 (d, J=8.27, 2H), 7.52 (d, J=8.04, 2H), 3.91-3.46 (m, 5H), 2.44-2.33 (m, 2H), 2.31 (s, 3H), 1.48 (s, 9H)

tert-butyl (R,E)-3-(3-(4-(1-(((4-(trifluoromethyl) benzyl)oxy)imino)ethyl)phenyl)-1,2,4-oxadiazol-5-yl)pyrrolidine-1-carboxylate (37c)

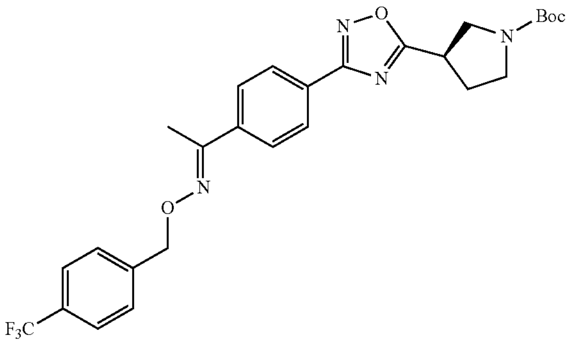 [SMILES: C/C(=N\OCc1ccc(C(F)(F)F)cc1)c1ccc(-c2noc([C@@H]3CCN(C(=O)OC(C)(C)C)C3)n2)cc1]

Synthesized according to General Procedure 1.7. White Solid, 314 mg, 98%. $^1$H NMR (400 MHz, Chloroform-d) δ 8.05 (d, J=7.9 Hz, 2H), 7.86 (s, 2H), 7.82 (s, 1H), 7.72 (d, J=7.8 Hz, 2H), 5.33 (s, 2H), 3.94-3.42 (m, 5H), 2.48-2.25 (m, 5H), 1.47 (s, 9H).

tert-butyl (S,E)-3-(3-(4-(1-(([1,1'-biphenyl]-4-yl-methoxy)imino)ethyl)phenyl)-1,2,4-oxadiazol-5-yl) pyrrolidine-1-carboxylate (37d)

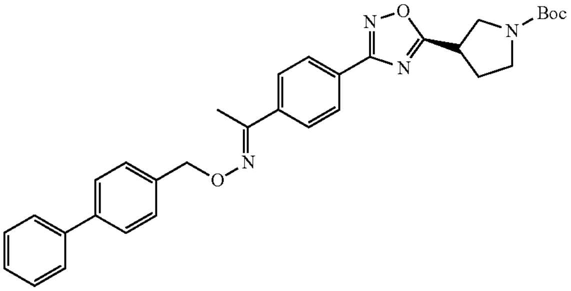

Synthesized according to General Procedure 1.7. Purified by silica chromatography (10% EtOAc in hexanes). Yellow oil (69%, 69 mg). $^1$H NMR (400 MHz, $CDCl_3$) δ 8.08 (d, J=8.46, 2H), 7.76 (d, J=8.51, 2H), 7.67 (s, 1H), 7.62 (d, J=7.62, 2H), 7.56 (d, J=7.23, 1H), 7.48-7.42 (m, 4H), 7.36 (t, J=7.30, 1H), 5.39 (s, 2H), 3.99-3.47 (m, 5H), 2.45-2.35 (m, 2H), 2.32 (s, 3H), 1.50 (s, 9H).

(R)-1-(4-(5-(pyrrolidin-3-yl)-1,2,4-oxadiazol-3-yl) phenyl)ethan-1-one O-(4-phenylbutyl) oxime hydrochloride (38a)

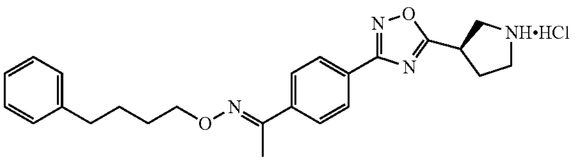

Synthesized according to General Procedure 1.5. White Solid, 130 mg, 79%. $^1$H NMR (400 MHz, Methanol-$d_4$) δ 8.05 (d, J=8.6 Hz, 2H), 7.78 (d, J=8.6 Hz, 2H), 7.27-7.19 (m, 2H), 7.19-7.10 (m, 3H), 4.24-4.16 (m, 2H), 4.04 (m, 1H), 3.83-3.66 (m, 2H), 3.55-3.39 (m, 2H), 2.68-2.62 (m, 2H), 2.62-2.54 (m, 1H), 2.47-2.36 (m, 1H), 2.22 (s, 3H), 1.77-1.70 (m, 4H); HRMS (ESI): Calcd for $C_{24}H_{29}N_4O_2$ $[M+H]^+$: 405.2285, Found: 405.2286.

(R)-1-(4-(5-(pyrrolidin-3-yl)-1,2,4-oxadiazol-3-yl) phenyl)ethan-1-one O-(3,5-bis(trifluoromethyl)benzyl) oxime hydrochloride (38b)

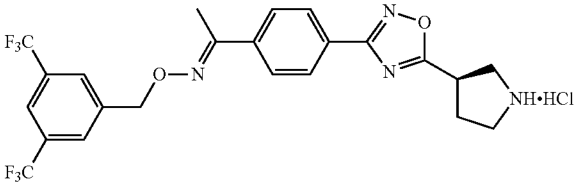

Synthesized according to General Procedure 1.5. White Solid, 220 mg, 78%. $^1$H NMR (400 MHz, Methanol-$d_4$) δ 8.07 (d, J=8.5 Hz, 2H), 8.01 (s, 2H), 7.91 (s, 1H), 7.81 (d, J=8.5 Hz, 2H), 5.40 (s, 2H), 4.11 (m, 1H), 3.89-3.74 (m, 2H), 3.61-3.45 (m, 2H), 2.70-2.56 (m, 1H), 2.46 (m, 1H), 2.34 (s, 3H); HRMS (ESI): Calcd for $C_{23}H_{21}F_6N_4O_2$$[M+H]^+$: 499.1563, Found: 499.1570.

(R)-1-(4-(5-(pyrrolidin-3-yl)-1,2,4-oxadiazol-3-yl) phenyl)ethan-1-one O-(4-(trifluoromethyl)benzyl) oxime hydrochloride (38c)

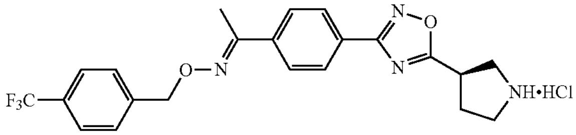

Synthesized according to General Procedure 1.5. Crude mixture dried in vacuo and carried forward to the next reaction without purification.

(R)-1-(4-(5-(pyrrolidin-3-yl)-1,2,4-oxadiazol-3-yl)phenyl)ethan-1-one O-([1,1'-biphenyl]-4-ylmethyl) oxime hydrochloride (38d)

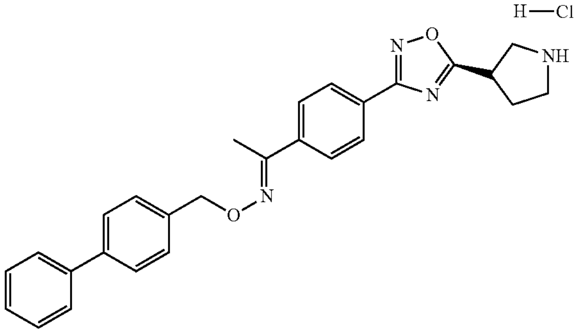

Synthesized according to General Procedure 1.5. Crude mixture dried in vacuo and carried forward to the next reaction without purification.

(R)-1-(4-(5-(pyrrolidin-3-yl)-1,2,4-oxadiazol-3-yl)phenyl)ethan-1-one O-([1,1'-biphenyl]-3-ylmethyl) oxime hydrochloride (38e)

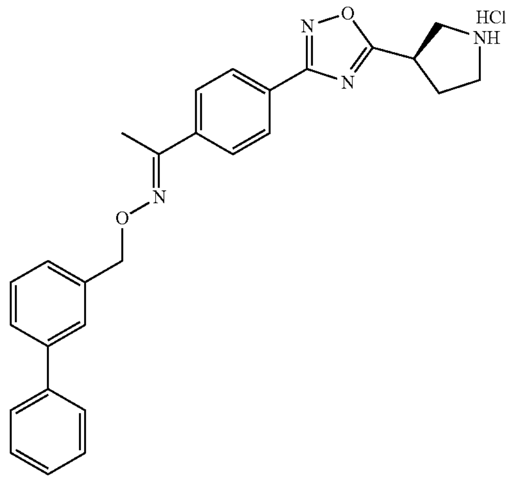 [SMILES: C/C(=N\OCc1cccc(-c2ccccc2)c1)c1ccc(-c2noc([C@@H]3CCNC3)n2)cc1 ; Cl]

Synthesized according to General Procedure 1.5. Crude mixture dried in vacuo and carried forward to the next reaction without purification.

1-(4-(5-(pyrrolidin-3-yl)-1,2,4-oxadiazol-3-yl)phenyl)ethan-1-one O-(1-phenylethyl) oxime hydrochloride (38f)

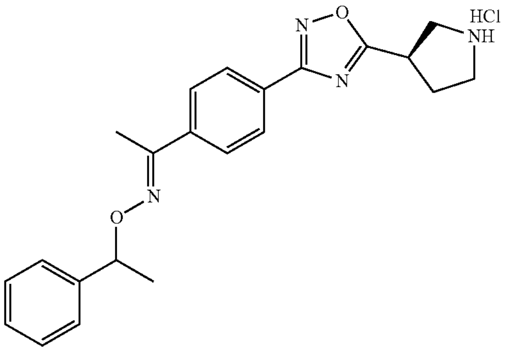 [SMILES: C/C(=N\OC(C)c1ccccc1)c1ccc(-c2noc([C@@H]3CCNC3)n2)cc1 ; Cl]

Synthesized according to General Procedure 1.5. Crude mixture dried in vacuo and carried forward to the next reaction without purification.

(R)-1-(4-(5-(pyrrolidin-3-yl)-1,2,4-oxadiazol-3-yl)phenyl)ethan-1-one O-benzyl oxime hydrochloride (38g)

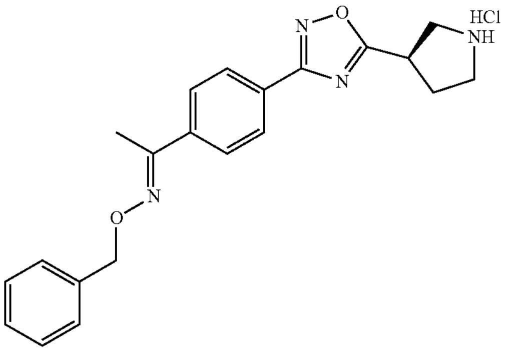 [SMILES: C/C(=N\OCc1ccccc1)c1ccc(-c2noc([C@@H]3CCNC3)n2)cc1 ; Cl]

Synthesized according to General Procedure 1.5. White solid (86%, 91 mg). $^1$H NMR (400 MHz, Methanol-$d_4$) δ 8.05 (d, J=8.59, 2H), 7.80 (d, J=8.68, 2H), 7.44-7.26 (m, 5H), 5.24 (s, 2H), 4.12 (p, J=7.12, 1H), 3.89-3.76 (m, 2H), 3.60-3.49 (m, 2H), 2.69-2.59 (m, 1H), 2.51-2.42 (m, 1H), 2.28 (s, 3H). HRMS: (ESI) $[M+H]^+$ calc. for $C_{21}H_{23}N_4O_2$, 363.1816, Found: 363.1815.

(R)-1-(4-(5-(pyrrolidin-3-yl)-1,2,4-oxadiazol-3-yl) phenyl)ethan-1-one O-((5,5,8,8-tetramethyl-5,6,7,8-tetrahydronaphthalen-2-yl)methyl) oxime hydrochloride (38h)

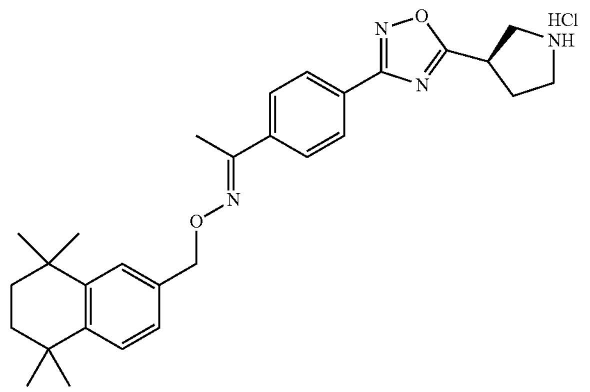 [SMILES: C/C(=N\OCc1ccc2c(c1)C(C)(C)CCC2(C)C)c1ccc(-c2noc([C@@H]3CCNC3)n2)cc1 ; Cl]

Synthesized according to General Procedure 1.5. White Solid, 53 mg, 68%. $^1$H NMR (400 MHz, Methanol-$d_4$) δ 8.06 (d, J=8.4 Hz, 2H), 7.83 (d, J=8.4 Hz, 2H), 7.36 (d, J=1.5 Hz, 1H), 7.31 (d, J=8.1 Hz, 1H), 7.16 (dd, J=8.1, 1.7 Hz, 1H), 5.25-5.13 (s, 2H), 4.08 (p, J=6.9 Hz, 1H), 3.98 (dd, J=10.4, 7.3 Hz, 1H), 3.90 (dd, J=10.4, 6.3 Hz, 1H), 3.74-3.60 (m, 2H), 2.69-2.57 (m, 1H), 2.55-2.44 (m, 1H), 2.28 (s, 3H), 1.71 (s, 4H), 1.31-1.26 (m, 12H); HRMS: (ESI) $[M+H]^+$ calc. for $C_{29}H_{37}N_4O_2$, 473.2911, observed, 473.2906.

(R)-3-(3-(4-(1-((heptyloxy)imino)ethyl)phenyl)-1,2,4-oxadiazol-5-yl)pyrrolidine-1-carboximidamide hydrochloride (38i)

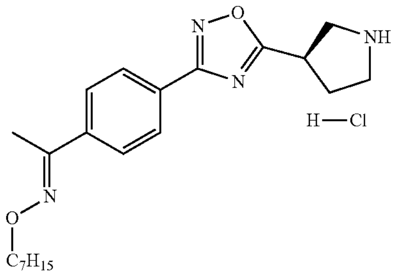

Synthesized according to General Procedure 1.5. White Solid, 82 mg, 76%. $^1$H NMR (400 MHz, Methanol-$d_4$) δ 8.05 (d, J=8.7 Hz, 2H), 7.80 (d, J=8.7 Hz, 2H), 4.18 (t, J=8.7 Hz, 2H), 4.16-4.08 (m, 1H), 3.90-3.76 (m, 2H), 3.59-3.51 (m, 2H), 2.69-2.59 (m, 1H), 2.50-2.40 (m, 1H), 2.23 (s, 3H), 1.72 (p, J=6.6 Hz, 2H), 1.46-1.24 (m, 8H), 0.89 (t, J=6.7 Hz, 3H). HRMS: (ESI) $[M+H]^+$ calc. for $C_{21}H_{31}N_4O_2$, 361.2442, Found: 371.2444.

(R)-1-(4-(5-(pyrrolidin-3-yl)-1,2,4-oxadiazol-3-yl) phenyl)ethan-1-one O-heptyl oxime hydrochloride (38j)

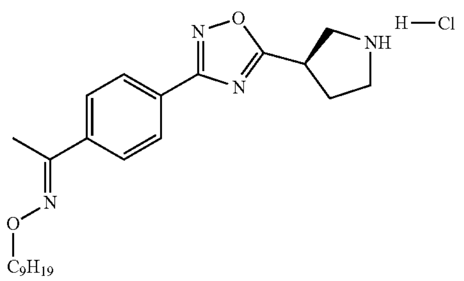

Synthesized according to General Procedure 1.5. White Solid, 58 mg, 75%. $^1$H NMR (400 MHz, Methanol-$d_4$) δ 8.05 (d, J=8.8 Hz, 2H), 7.80 (d, J=8.8 Hz, 2H), 4.18 (t, J=6.6 Hz, 2H), 4.16-4.07 (m, 1H), 3.90-3.76 (m, 2H), 3.58-3.51 (m, 2H), 2.69-2.59 (m, 1H), 2.50-2.40 (m, 1H), 2.23 (s, 3H), 1.76-1.67 (m, 2H), 1.45-1.22 (m, 12H), 0.88 (t, J=6.6 Hz, 3H). HRMS: (ESI) $[M+H]^+$ calc. for $C_{23}H_{35}N_4O_2$, 399.2755, Found: 399.2756.

(R,E)-1-(4-(5-(pyrrolidin-3-yl)-1,2,4-oxadiazol-3-yl) phenyl)ethan-1-one O-(4-(tert-butyl)benzyl) oxime hydrochlorid (38k)

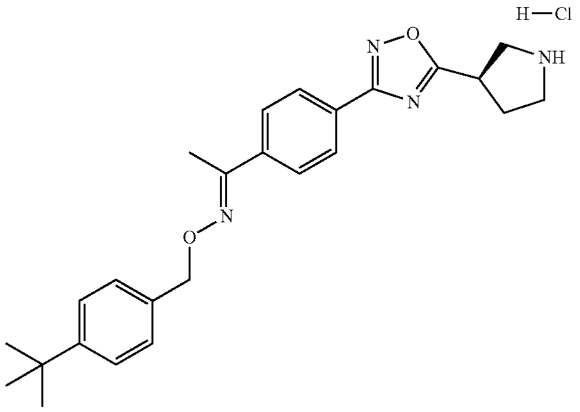

Synthesized according to General Procedure 1.5. White Solid, 40 mg, 79%. $^1$H NMR (400 MHz, Methanol-$d_4$) δ 8.05 (d, J=8.7 Hz, 2H), 7.79 (d, J=8.7 Hz, 2H), 7.39 (d, J=8.6 Hz, 2H), 7.33 (d, J=8.6 Hz, 2H), 5.19 (s, 2H), 4.16-4.06 (m, 1H), 3.88-3.75 (m, 2H), 3.59-3.46 (m, 2H), 2.68-2.58 (m, 1H), 2.50-2.41 (m, 1H), 2.25 (s, 3H). HRMS: (ESI) $[M+H]^+$ calc. for $C_{25}H_{31}N_4O_2$, 419.2442, observed, 419.2442.

(R)-1-(4-(5-(pyrrolidin-3-yl)-1,2,4-oxadiazol-3-yl) phenyl)ethan-1-one O-pentyl oxime hydrochloride (38l)

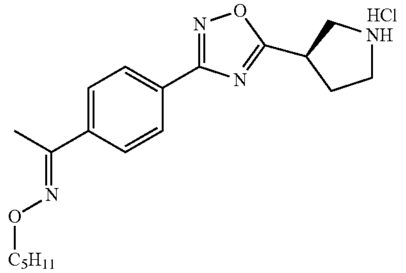

Synthesized according to General Procedure 1.5. White solid (80%, 162 mg). $^{1}$H NMR (400 MHz, Methanol-$d_4$) δ 8.06 (d, J=8.53, 2H), 7.81 (d, J=8.54, 2H), 4.19 (t, J=6.78, 2H), 4.12 (p, J=7.31, 1H), 3.89-3.79 (m, 2H), 3.60-3.49 (m, 2H), 2.69-2.59 (m, 1H), 2.51-2.42 (m, 1H), 2.24 (s, 3H), 1.77-1.69 (p, J=6.80, 2H), 1.49-1.35 (m, 4H), 0.88 (t, J=6.88, 3H). HRMS: (ESI) $[M+H]^+$ calc. for $C_{19}H_{27}N_4O_2$, 343.2129, observed, 343.2136.

(R)-1-(4-(5-(pyrrolidin-3-yl)-1,2,4-oxadiazol-3-yl) phenyl)ethan-1-one O-(4-fluorobenzyl) oxime hydrochloride (38m)

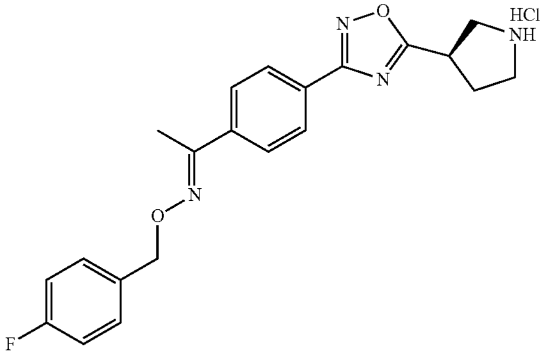 [SMILES: C/C(=N\OCc1ccc(F)cc1)c1ccc(-c2noc([C@@H]3CCNC3)n2)cc1 ; Cl]

Synthesized according to General Procedure 1.5. Crude mixture dried in vacuo and carried forward to the next reaction without purification.

(R)-1-(4-(5-(pyrrolidin-3-yl)-1,2,4-oxadiazol-3-yl) phenyl)ethan-1-one O-(4-bromobenzyl) oxime hydrochloride (38n)

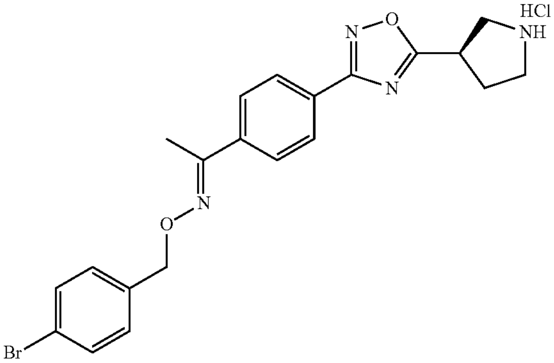 [SMILES: Cl ; C/C(=N\OCc1ccc(Br)cc1)c1ccc(-c2noc([C@@H]3CCNC3)n2)cc1]

Synthesized according to General Procedure 1.5. White solid (91%, 120 mg). $^{1}$H NMR (400 MHz, Methanol-$d_4$) δ 8.06 (d, J=8.86, 2H), 7.80 (d, J=8.31, 2H), 7.50 (d, J=8.31, 2H), 7.33 (d, J=8.31, 2H), 5.20 (s, 2H), 4.08-4.01 (m, 1H), 3.80-3.68 (m, 2H), 3.52-3.41 (m, 2H), 2.68-2.58 (m, 1H), 2.48-2.38 (m, 1H), 2.28 (s, 3H). HRMS: (ESI) $[M+H]^+$ calc. for $C_{21}H_{22}BrN_4O_2$, 441.0921, observed, 441.0921.

tert-butyl (R)-(((tert-butoxycarbonyl)imino)(3-(3-(4-(1-((4-phenylbutoxy)imino)ethyl)phenyl)-1,2,4-oxadiazol-5-yl)pyrrolidin-1-yl)methyl)carbamate (39a)

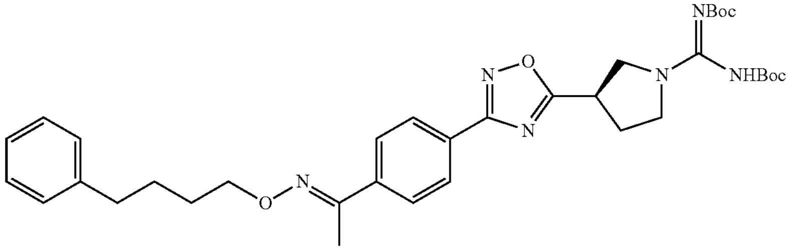

Synthesized according to General Procedure 1.8. White Solid, 64 mg, 55%. $^1$H NMR (400 MHz, Chloroform-d) δ 10.45 (s, 1H), 8.05 (d, J=8.4 Hz, 2H), 7.75 (d, J=8.4 Hz, 2H), 7.32-7.23 (m, 2H), 7.18 (m, 3H), 4.24 (t, J=5.9 Hz, 2H), 4.16-3.99 (m, 2H), 3.78 (m, 3H), 2.68 (t, J=7.1 Hz, 2H), 2.51-2.36 (m, 2H), 2.25 (s, 3H), 1.81-1.72 (m, 4H), 1.50 (s, 18H); HRMS (ESI): Calcd for $C_{33}H_{47}F_6N_6O_6[M+H]^+$: 647.3552, Found: 647.3557.

tert-butyl (R)-((3-(3-(4-(1-(((3,5-bis(trifluoromethyl)benzyl)oxy)imino)ethyl)phenyl)-1,2,4-oxadiazol-5-yl)pyrrolidin-1-yl)((tert-butoxycarbonyl)imino)methyl)carbamate (39b)

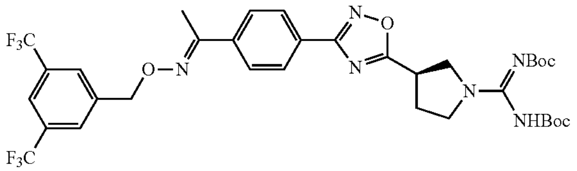

Synthesized according to General Procedure 1.8. White Solid, 70 mg, 50%. $^1$H NMR (400 MHz, Chloroform-d) δ 10.44 (s, 1H), 8.06 (d, J=8.5 Hz, 2H), 7.87 (s, 2H), 7.83 (s, 1H), 7.73 (d, J=8.5 Hz, 2H), 5.34 (s, 2H), 4.06 (s, 2H), 3.87-3.69 (m, 3H), 2.50-2.39 (m, 2H), 2.32 (s, 3H), 1.50 (m, 18H); HRMS (ESI): Calcd for $C_{34}H_{39}F_6N_6O_6[M+H]^+$: 741.2830, Found: 741.2843.

tert-butyl (((tert-butoxycarbonyl)imino)((R)-3-(3-(4-((E)-1-(((4-(trifluoromethyl)benzyl)oxy)imino)ethyl)phenyl)-1,2,4-oxadiazol-5-yl)pyrrolidin-1-yl)methyl)carbamate (39c)

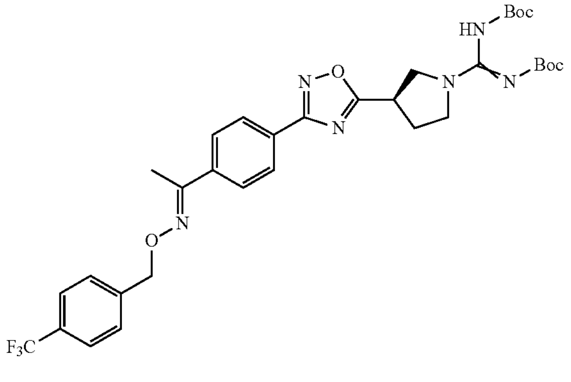 [SMILES: C/C(=N\OCc1ccc(C(F)(F)F)cc1)c1ccc(-c2noc([C@@H]3CCN(C(=NC(=O)OC(C)(C)C)NC(=O)OC(C)(C)C)C3)n2)cc1]

Synthesized according to General Procedure 1.8. Purified by silica chromatography (25% EtOAc in hexanes). Yellow oil (45%, 61 mg). $^1$H NMR (400 MHz, $CDCl_3$) δ 10.44 (brs, 1H), 8.04 (d, J=8.19, 2H), 7.74 (d, J=7.89, 2H), 7.62 (d, J=7.61, 2H), 7.51 (d, J=7.76, 2H), 5.30 (s, 2H), 4.13-4.00 (m, 2H), 3.84-3.70 (m, 3H), 2.48-2.38 (m, 2H), 2.30 (s, 3H), 1.48 (s, 18H).

tert-butyl (((R)-3-(3-(4-(−1-(([1,1'-biphenyl]-4-ylmethoxy)imino)ethyl)phenyl)-1,2,4-oxadiazol-5-yl)pyrrolidin-1-yl)((tert-butoxycarbonyl)imino)methyl)carbamate (39d)

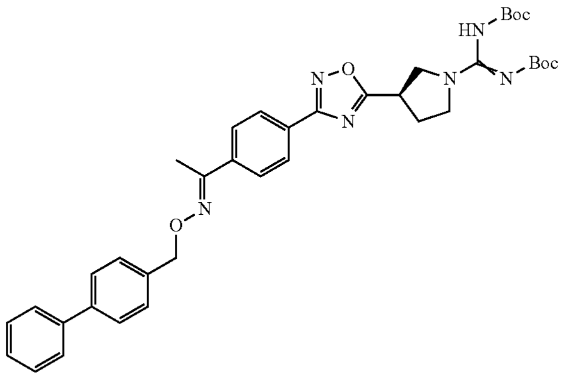 [SMILES: C/C(=N\OCc1ccc(-c2ccccc2)cc1)c1ccc(-c2noc([C@@H]3CCN(C(=NC(=O)OC(C)(C)C)NC(=O)OC(C)(C)C)C3)n2)cc1]

Synthesized according to General Procedure 1.8. White Solid, 71 mg, 56%. $^1$H NMR (400 MHz, Chloroform-d) δ 10.46 (s, 1H), 8.06 (d, J=8.5 Hz, 2H), 7.79 (d, J=8.6 Hz, 2H), 7.63-7.58 (m, 4H), 7.51 (d, J=8.2 Hz, 2H), 7.47-7.41 (m, 2H), 7.36-7.31 (m, 1H), 5.31 (s, 2H), 4.18-4.00 (m, 2H), 3.87-3.78 (m, 2H), 3.75 (t, J=7.3 Hz, 1H), 2.45 (m, 2H), 2.31 (s, 3H), 1.50 (s, 18H); HRMS (ESI): Calcd for $C_{38}H_{45}N_6O_6$ $[M+H]^+$: 681.3395, Found: 681.3399.

(R)-3-(3-(4-(1-((4-phenylbutoxy)imino)ethyl)phenyl)-1,2,4-oxadiazol-5-yl)pyrrolidine-1-carboximidamide hydrochloride (40a)

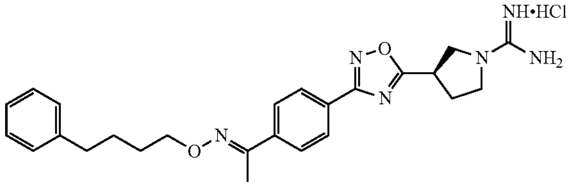

Synthesized according to General Procedure 1.5. White Solid, 36 mg, 76%. $^1$H NMR (400 MHz, Methanol-$d_4$) δ 8.03 (d, J=8.4 Hz, 2H), 7.79 (d, J=8.4 Hz, 2H), 7.28-7.20 (m, 2H), 7.20-7.09 (m, 3H), 4.25-4.17 (m, 2H), 4.05 (m, 1H), 3.98 (dd, J=10.3, 7.4 Hz, 1H), 3.89 (dd, J=10.3, 6.2 Hz, 1H), 3.74-3.58 (m, 2H), 2.69-2.56 (m, 3H), 2.53-2.42 (m, 1H), 2.23 (s, 3H), 1.77-1.70 (m, 4H); HRMS (ESI): Calcd for $C_{25}H_{31}N_6O_2$ $[M+H]^+$: 447.2503, Found: 447.2507.

(R)-3-(3-(4-(1-(((3,5-bis(trifluoromethyl)benzyl)oxy)imino)ethyl)phenyl)-1,2,4-oxadiazol-5-yl)pyrrolidine-1-carboximidamide hydrochloride (40b)

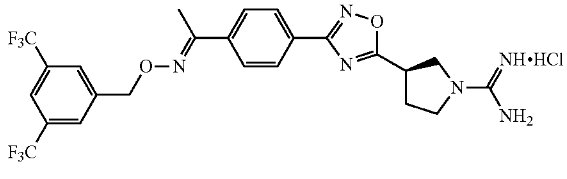

Synthesized according to General Procedure 1.5. White Solid, 44 mg, 81%. $^{1}$H NMR (400 MHz, Methanol-$d_4$) δ 8.02 (d, J=8.5 Hz, 2H), 7.99 (s, 2H), 7.89 (s, 1H), 7.78 (d, J=8.5 Hz, 2H), 5.38 (s, 2H), 4.08 (p, J=6.8 Hz, 1H), 4.00 (dd, J=10.3, 7.4 Hz, 1H), 3.90 (dd, J=10.3, 6.1 Hz, 1H), 3.75-3.59 (m, 2H), 2.63 (p, J=6.8 Hz, 1H), 2.48 (p, J=6.7 Hz, 1H), 2.31 (s, 3H); HRMS (ESI): Calcd for $C_{24}H_{23}F_6N_6O_2$[M+H]$^+$: 541.1781, Found: 541.1787.

(R)-3-(3-(4-(1-(((4-(trifluoromethyl)benzyl)oxy)imino)ethyl)phenyl)-1,2,4-oxadiazol-5-yl)pyrrolidine-1-carboximidamide hydrochloride (40c)

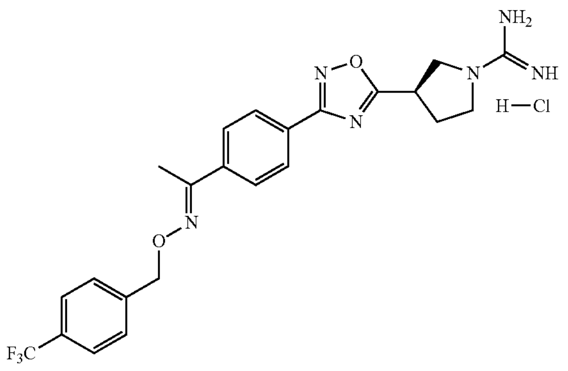

Synthesized according to General Procedure 1.5. White Solid, 24 mg, 79%. $^{1}$H NMR (400 MHz, Methanol-$d_4$) δ 8.03 (d, J=8.4 Hz, 2H), 7.79 (d, J=8.4 Hz, 2H), 7.65 (d, J=8.2 Hz, 2H), 7.58 (d, J=8.1 Hz, 2H), 5.32 (s, 2H), 4.07 (p, J=6.8 Hz, 1H), 4.02-3.95 (m, 1H), 3.90 (dd, J=10.3, 6.2 Hz, 1H), 3.73-3.59 (m, 2H), 2.70-2.56 (m, 1H), 2.54-2.42 (m, 1H), 2.31 (s, 3H); HRMS (ESI): Calcd for $C_{23}H_{24}F_3N_6O_2$[M+H]$^+$: 473.1907, Found: 473.1909.

(R)-3-(3-(4-(1-(([1,1'-biphenyl]-4-ylmethoxy)imino)ethyl)phenyl)-1,2,4-oxadiazol-5-yl)pyrrolidine-1-carboximidamide hydrochloride (40d)

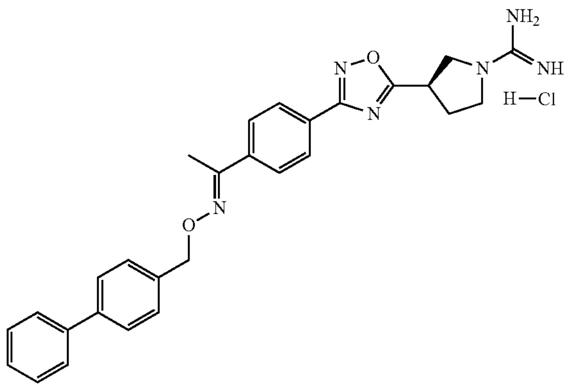

Synthesized according to General Procedure 1.5. White Solid, 28 mg, 51%. $^{1}$H NMR (400 MHz, Methanol-$d_4$) δ 8.05 (d, J=8.7 Hz, 2H), 7.81 (d, J=8.7 Hz, 2H), 7.67-7.58 (m, 4H), 7.50 (d, J=8.3 Hz, 2H), 7.43 (t, J=7.5 Hz, 2H), 7.37-7.28 (m, 1H), 5.29 (s, 2H), 4.14-3.86 (m, 3H), 3.74-3.57 (m, 2H), 2.69-2.45 (m, 2H), 2.31 (s, 3H); HRMS (ESI): Calcd for $C_{28}H_{29}N_6O_2$ [M+H]$^+$: 481.2347, Found: 481.2351.

(R)-3-(3-(4-(1-(([1,1'-biphenyl]-3-ylmethoxy)imino)ethyl)phenyl)-1,2,4-oxadiazol-5-yl)pyrrolidine-1-carboximidamide hydrochloride (40e)

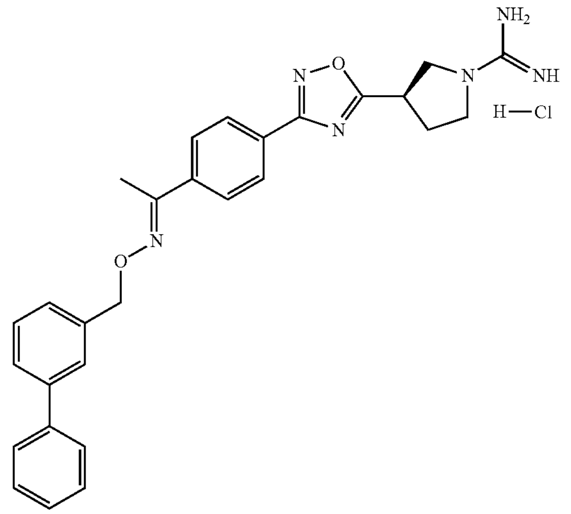

Synthesized according to General Procedure 1.5. White Solid (62%, 29 mg). $^{1}$H NMR (400 MHz, Methanol-$d_4$) δ 8.05 (d, J=8.7 Hz, 2H), 7.81 (d, J=8.7 Hz, 2H), 7.67-7.58 (m, 4H), 7.50 (d, J=8.3 Hz, 2H), 7.43 (t, J=7.5 Hz, 2H), 7.37-7.28 (m, 1H), 5.29 (s, 2H), 4.14-3.86 (m, 3H), 3.74-3.57 (m, 2H), 2.69-2.45 (m, 2H), 2.31 (s, 3H); HRMS (ESI): Calcd for $C_{28}H_{29}N_6O_2$ [M+H]$^+$: 481.2347, Found: 481.2353.

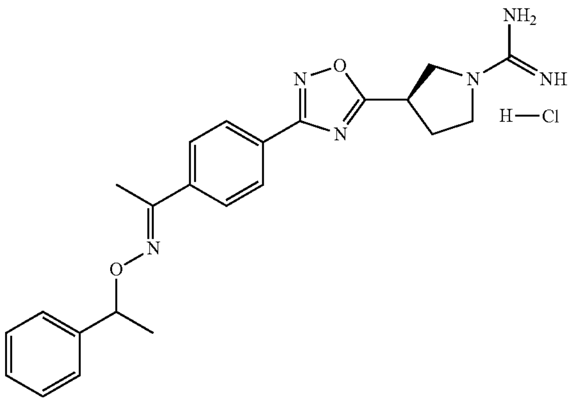

(R)-1-(4-(5-(pyrrolidin-3-yl)-1,2,4-oxadiazol-3-yl)phenyl)ethan-1-one O-benzyl oxime hydrochloride (40f)

Synthesized according to General Procedure 1.5. White Solid (100%, 104 mg). $^{1}$H NMR (400 MHz, Methanol-$d_4$) δ 8.01 (d, J=8.5 Hz, 2H), 7.75 (d, J=8.5 Hz, 2H), 7.40-7.31 (m, 4H), 7.28-7.21 (m, 1H), 5.37 (q, J=6.6 Hz, 1H), 4.06 (p, J=6.8 Hz, 1H), 3.97 (dd, J=10.3, 7.4 Hz, 1H), 3.89 (dd, J=10.3, 6.2 Hz, 1H), 3.73-3.57 (m, 1H), 2.67-2.56 (m, 1H), 2.53-2.42 (m, 1H), 2.31 (s, 3H), 1.60 (d, J=6.6 Hz, 3H); HRMS (ESI): Calcd for $C_{23}H_{27}N_6O_2$ $[M+H]^+$: 419.2190, Found: 419.2192.

(R)-3-(3-(4-(1-((benzyloxy)imino)ethyl)phenyl)-1,2,4-oxadiazol-5-yl)pyrrolidine-1-carboximidamide hydrochloride (40g)

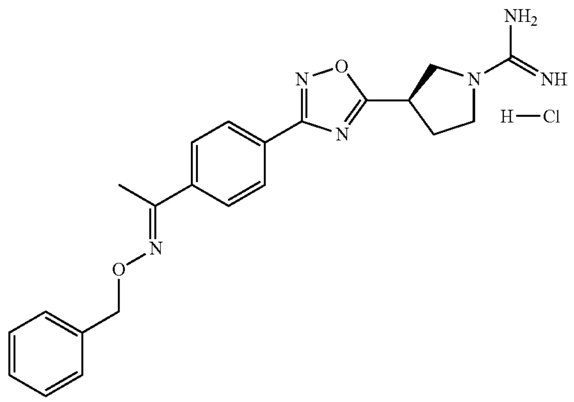

Synthesized according to General Procedure 1.5. White Solid (55%, 16 mg). $^1$H NMR (400 MHz, Methanol-$d_4$) δ 8.05 (d, J=8.5 Hz, 2H), 7.81 (d, J=8.5 Hz, 2H), 7.43-7.39 (m, 2H), 7.38-7.33 (m, 2H), 7.32-7.27 (m, 2H), 5.24 (s, 2H), 4.07 (p, J=6.9 Hz, 1H), 3.98 (dd, J=10.3, 7.4 Hz, 1H), 3.90 (dd, J=10.3, 6.2 Hz, 1H), 3.74-3.58 (m, 2H), 2.63 (m, 1H), 2.55-2.42 (m, 1H), 2.28 (s, 3H); HRMS (ESI): Calcd for $C_{22}H_{25}N_6O_2$ $[M+H]^+$: 405.2034, Found: 405.2040.

(R)-3-(3-(4-(1-(((5,5,8,8-tetramethyl-5,6,7,8-tetrahydronaphthalen-2-yl)methoxy)imino)ethyl)phenyl)-1,2,4-oxadiazol-5-yl)pyrrolidine-1-carboximidamide hydrochloride (40h)

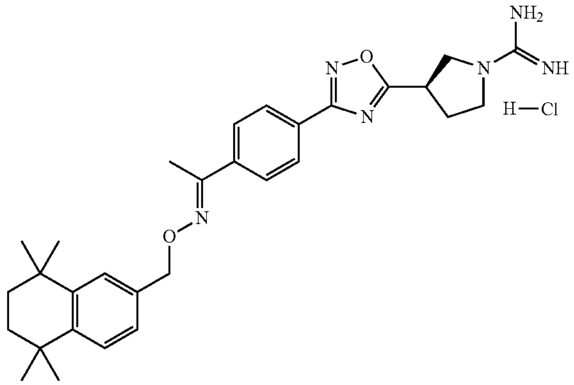

Synthesized according to General Procedure 1.5. White Solid (34%, 82 mg). $^1$H NMR (400 MHz, Methanol-$d_4$) δ 8.06 (d, J=8.4 Hz, 2H), 7.83 (d, J=8.4 Hz, 2H), 7.36 (d, J=1.9 Hz, 1H), 7.31 (d, J=8.1 Hz, 1H), 7.16 (dd, J=8.1, 1.9 Hz, 1H), 5.17 (s, 2H), 4.08 (p, J=6.8 Hz, 1H), 3.98 (dd, J=10.4, 7.3 Hz, 1H), 3.90 (dd, J=10.3, 6.2 Hz, 1H), 3.75-3.59 (m, 2H), 2.62 (m, 1H), 2.57-2.41 (m, 1H), 2.28 (s, 3H), 1.71 (s, 4H), 1.28 (d, J=4.1 Hz, 12H); HRMS (ESI): Calcd for $C_{30}H_{39}N_6O_2[M+H]^+$: 515.3129, Found: 515.3130.

(R)-3-(3-(4-(1-((heptyloxy)imino)ethyl)phenyl)-1,2,4-oxadiazol-5-yl)pyrrolidine-1-carboximidamide hydrochloride (40i)

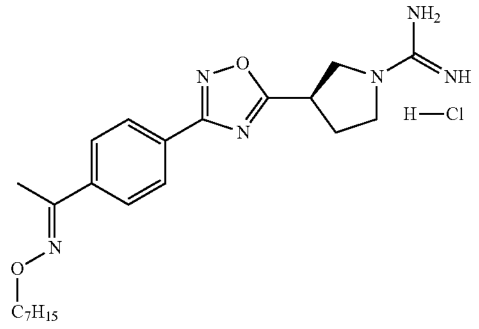

Synthesized according to General Procedure 1.5. White Solid (68%, 20 mg). $^1$H NMR (400 MHz, Methanol-$d_4$) δ 8.06 (d, J=8.4 Hz, 2H), 7.83 (d, J=8.4 Hz, 2H), 4.20 (t, J=6.6 Hz, 2H), 4.07 (m, 1H), 3.98 (dd, J=10.4, 7.3 Hz, 1H), 3.91 (dd, J=10.4, 6.2 Hz, 1H), 3.75-3.58 (m, 2H), 2.70-2.58 (m, 1H), 2.55-2.44 (m, 1H), 2.25 (s, 3H), 1.74 (p, J=6.8 Hz, 2H), 1.50-1.21 (m, 8H), 0.91 (t, J=6.9 Hz, 3H); HRMS (ESI): Calcd for $C_{22}H_{33}N_6O_2$ $[M+H]^+$: 413.2660, Found: 413.2669.

(R)-3-(3-(4-(1-((nonyloxy)imino)ethyl)phenyl)-1,2,4-oxadiazol-5-yl)pyrrolidine-1-carboximidamide hydrochloride (40j)

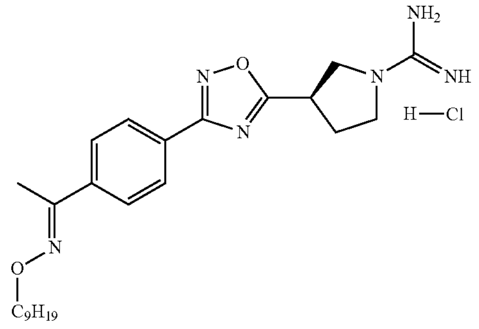

Synthesized according to General Procedure 1.5. White Solid (69%, 19 mg). $^1$H NMR (400 MHz, Methanol-$d_4$) δ 8.06 (d, J=8.6 Hz, 2H), 7.82 (d, J=8.6 Hz, 2H), 4.20 (t, J=6.6 Hz, 2H), 4.14-4.00 (m, 1H), 3.99 (dd, J=10.3, 7.3 Hz, 1H), 3.91 (dd, J=10.3, 6.2 Hz, 1H), 3.75-3.59 (m, 2H), 2.69-2.57 (m, 1H), 2.55-2.44 (m, 1H), 2.25 (s, 3H), 1.77-1.67 (m, 2H), 1.48-1.18 (m, 12H), 0.93-0.83 (m, 3H).

(R)-3-(3-(4-(1-(((4-(tert-butyl)benzyl)oxy)imino)ethyl)phenyl)-1,2,4-oxadiazol-5-yl)pyrrolidine-1-carboximidamide hydrochloride (40k)

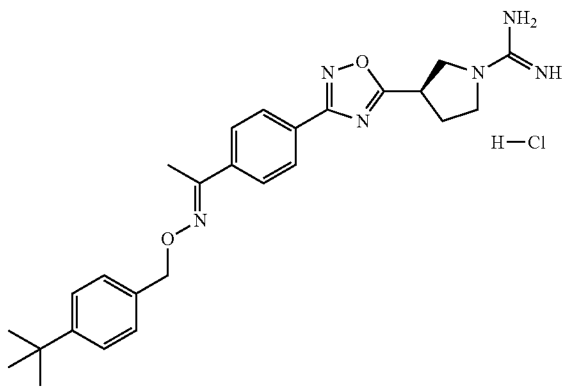

Synthesized according to General Procedure 1.5. White Solid (57%, 13 mg). $^1$H NMR (400 MHz, Methanol-$d_4$) δ 8.04 (d, J=6.3 Hz, 2H), 7.85-7.71 (m, 2H), 7.40 (d, J=6.8 Hz, 2H), 7.33 (d, J=7.8 Hz, 21H), 5.20 (s, 2H), 4.07 (p, J=6.2 Hz, 1H), 3.98 (dd, J=10.4, 7.3 Hz, 1H), 3.90 (dd, J=10.3, 6.2 Hz, 1H), 3.74-3.60 (m, 2H), 2.70-2.56 (m, 1H), 2.55-2.44 (m, 1H), 2.26 (s, 3H), 1.32 (s, 9H); HRMS (ESI): Calcd for $C_{26}H_{33}N_6O_2$ [M+H]$^+$: 461.2660, Found: 461.2660.

(R)-3-(3-(4-(1-((pentyloxy)imino)ethyl)phenyl)-1,2,4-oxadiazol-5-yl)pyrrolidine-1-carboximidamide hydrochloride (40l)

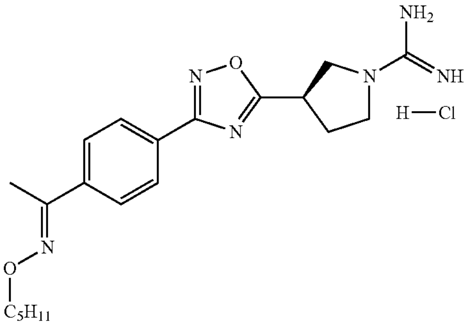

Synthesized according to General Procedure 1.5. White Solid (72%, 21 mg). $^1$H NMR (400 MHz, Methanol-$d_4$) δ 8.04 (d, J=8.5 Hz, 2H), 7.81 (d, J=8.5 Hz, 2H), 4.19 (t, J=6.6 Hz, 2H), 4.07 (p, J=6.9 Hz, 1H), 3.98 (dd, J=10.4, 7.3 Hz, 1H), 3.90 (dd, J=10.3, 6.2 Hz, 1H), 3.75-3.59 (m, 2H), 2.63 (m, 1H), 2.55-2.42 (m, 1H), 2.27-2.21 (s, 3H), 1.73 (p, J=6.9 Hz, 2H), 1.40 (m, 4H), 0.93 (t, J=7.0 Hz, 3H); HRMS (ESI): Calcd for $C_{20}H_{29}N_6O_2$ [M+H]: 385.2347, Found: 385.2353.

(R)-3-(3-(4-(1-(((4-fluorobenzyl)oxy)imino)ethyl)phenyl)-1,2,4-oxadiazol-5-yl)pyrrolidine-1-carboximidamide hydrochloride (40m)

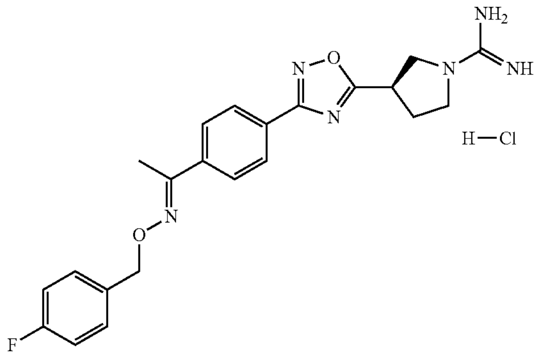

Synthesized according to General Procedure 1.5. White Solid (74%, 28 mg). $^1$H NMR (400 MHz, Methanol-$d_4$) δ 8.04 (d, J=8.5 Hz, 2H), 7.80 (d, J=8.5 Hz, 2H), 7.43 (dd, 2H), 7.13-7.01 (m, 2H), 5.20 (s, 2H), 4.07 (p, J=6.8 Hz, 1H), 3.98 (dd, J=10.3, 7.3 Hz, 1H), 3.90 (dd, J=10.3, 6.2 Hz, 1H), 3.74-3.59 (m, 2H), 2.69-2.56 (m, 1H), 2.55-2.40 (m, 1H), 2.26 (s, 3H); HRMS (ESI): Calcd for $C_{22}H_{24}FN_6O_2$[M+H]$^+$: 423.1939, Found: 423.1943.

(R)-3-(3-(4-(1-(((4-bromobenzyl)oxy)imino)ethyl)phenyl)-1,2,4-oxadiazol-5-yl)pyrrolidine-1-carboximidamide hydrochloride (40n)

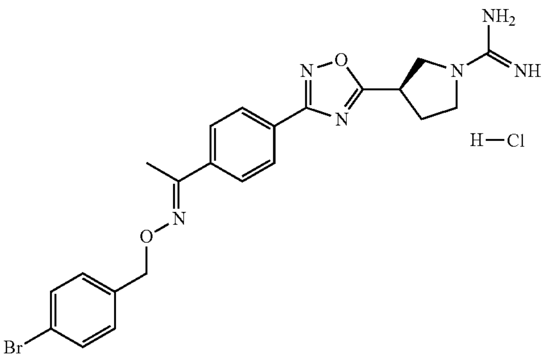

Synthesized according to General Procedure 1.5. White Solid (69%, 31 mg). $^1$H NMR (400 MHz, Methanol-$d_4$) δ 8.05 (d, J=8.7 Hz, 2H), 7.80 (d, J=8.7 Hz, 2H), 7.51 (d, J=8.4 Hz, 2H), 7.34 (d, J=8.4 Hz, 2H), 5.20 (s, 2H), 4.07 (p, J=6.9 Hz, 1H), 3.98 (dd, J=10.4, 7.3 Hz, 1H), 3.90 (dd, J=10.4, 6.2 Hz, 1H), 3.75-3.60 (m, 2H), 2.68-2.57 (m, 1H), 2.54-2.44 (m, 1H), 2.29 (s, 3H); HRMS (ESI): Calcd for $C_{22}H_{24}BrN_6O_2$ [M+H]: 483.1139, Found: 483.1143.

Scheme 6-Synthesis of amide derivatives

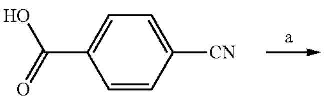

41

-continued

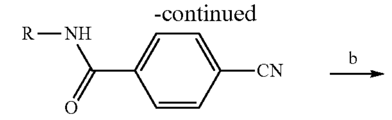

35o-p

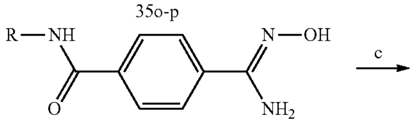

36o-p

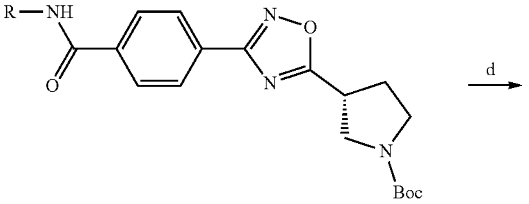

37o-p

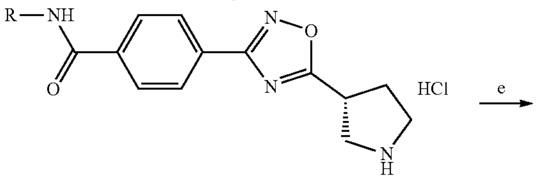

38o-p

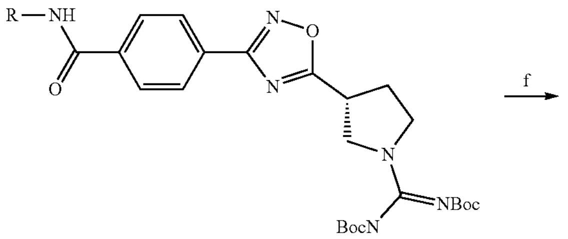

39o-p

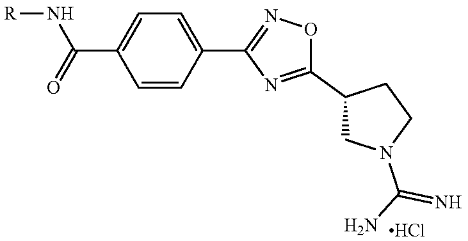

40p a. primary amine (1.1 equiv), HCTU (1.1 equiv), DIEA (1.8 equiv), DMF, r.t. b. $NH_2OH$•HCl (2 equiv), TEA (3 equiv), EtOH, reflux, c. N-boc-amino acid (1.1 equiv), HCTU (1.1 equiv), DIEA (1.8 equiv), DMF, 100° C. d. HCl, dioxane, rt. e. N,N'-Di-Boc-1H-pyrazole-1-carboxamidine (1 equiv), DIEA (15 equiv), MeCN, 50° C. μw. f. HCl, dioxane, r.t.

General Procedure 11: HCTU Coupling

To a 6-dram vial containing 4-cyanobenzoic acid (1.0 equiv) was added DMF (0.2 M), DIEA (1.8 equiv), and HCTU (1.1 equiv). The resulting mixture was allowed to stir at rt for 5 minutes, followed by addition of linear amine derivative (1 equiv). The resulting mixture was allowed to stir at rt until consumption of intermediate as monitored by TLC (1-4 hours). The resulting reaction mixture was diluted in ethyl acetate and washed with a saturated lithium bromide solution. The organic layer was then dried over anhydrous sodium sulfate and concentrated in vacuo to afford an oil which was then subjected to flash chromatography with an appropriate ethyl acetate in dichloromethane solvent system to afford the pure product.

N-butyl-4-cyanobenzamide (35o)

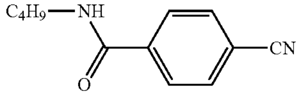

Synthesized according to General Procedure 11. Purified by silica chromatography (50% ethyl acetate in hexanes). Clear oil (97%, 799 mg). $^1$H NMR (400 MHz, Chloroform-d) δ 7.92 (d, J=8.4 Hz, 2H), 7.70 (d, J=8.4 Hz, 2H), 7.17 (t, J=5.7 Hz, 1H), 3.43 (q, J=6.9, 2H), 1.59 (q, J=7.9 Hz, 2H), 1.38 (h, J=7.3 Hz, 2H), 0.93 (t, J=7.4 Hz, 3H). $^{13}$C NMR (101 MHz, Chloroform-d) δ 165.96, 138.75, 132.22, 127.77, 118.05, 114.58, 40.08, 31.42, 20.09, 13.69.

4-cyano-N-octylbenzamide (35p)

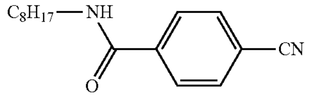

Synthesized according to General Procedure 11. Purified by silica chromatography (50% ethyl acetate in hexanes). Clear oil (94%, 822 mg). $^1$H NMR (400 MHz, Chloroform-d) δ 7.85 (d, J=8.3 Hz, 2H), 7.72 (d, J=8.3 Hz, 2H), 6.29 (t, J=5.9 Hz, 1H), 3.44 (q, J=7.3 Hz, 2H), 1.61 (p, J=7.4 Hz, 2H), 1.40-1.22 (m, 10H), 0.86 (t, J=6.8 Hz, 3H). $^{13}$C NMR (101 MHz, Chloroform-d) δ 165.82, 138.88, 132.53, 127.72, 118.17, 115.01, 40.52, 31.89, 29.65, 29.37, 29.31, 27.10, 22.76, 14.22. HRMS: (ESI) $[M+H]^+$ calc. for $C_{16}H_{23}N_2O$, 259.1805, observed, 259.1804.

N-butyl-4-(N'-hydroxycarbamimidoyl)benzamide (36o)

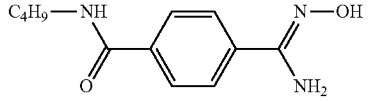

Synthesized according to General Procedure 1.2. Purified by silica chromatography (90% ethyl acetate in hexanes). White solid (61%, 554 mg). $^1$H NMR (400 MHz, Methanol-$d_4$) δ 7.84 (d, J=8.5 Hz, 2H), 7.74 (d, J=8.5 Hz, 2H), 3.39 (t, J=7.2 Hz, 2H), 1.62 (p, J=7.3 Hz, 2H), 1.43 (h, J=7.3 Hz, 2H), 0.99 (t, J=7.4 Hz, 3H). $^{13}$C NMR (101 MHz, Methanol-$d_4$) δ 169.50, 154.45, 137.13, 136.79, 128.30, 127.25, 40.79, 32.61, 21.19, 14.14.

4-(N'-hydroxycarbamimidoyl)-N-octylbenzamide (36p)

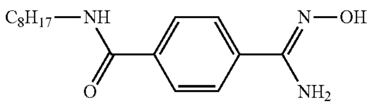

Synthesized according to General Procedure 1.2. Purified by silica chromatography (90% ethyl acetate in hexanes). White solid (52%, 555 mg). $^{1}$H NMR (400 MHz, Methanol-$d_4$) δ 7.87 (d, J=8.3 Hz, 2H), 7.77 (d, J=8.5 Hz, 2H), 3.41 (t, J=7.2 Hz, 2H), 1.66 (p, J=7.1 Hz, 2H), 1.47-1.30 (m, 10H), 0.93 (t, J=6.8 Hz, 3H). $^{13}$C NMR (101 MHz, Methanol-$d_4$) δ 169.52, 162.59, 137.16, 136.83, 128.30, 127.26, 41.09, 32.99, 30.48, 30.43, 30.37, 28.11, 23.70, 14.41.

tert-butyl (R)-3-(3-(4-(butylcarbamoyl)phenyl)-1,2,4-oxadiazol-5-yl)pyrrolidine-1-carboxylate (37o)

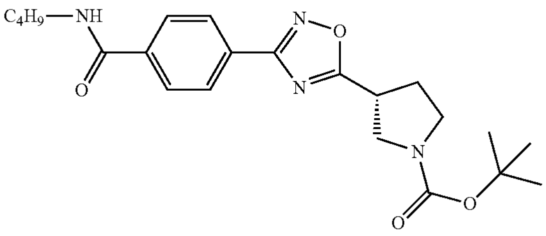

Synthesized according to General Procedure 1.3. Purified by silica chromatography (60% ethyl acetate in hexanes). Yellow solid (67%, 329 mg). $^{1}$H NMR (400 MHz, Chloroform-d) δ 8.08 (d, J=8.1 Hz, 2H), 7.85 (d, J=8.2 Hz, 2H), 6.54 (t, J=5.7 Hz, 1H), 3.88-3.54 (m, 4H), 3.52-3.40 (m, 3H), 2.43-4.28 (m, 2H), 1.59 (p, J=8.0, 2H), 1.45 (s, 9H), 1.38 (h, J=7.4 Hz, 2H), 0.93 (t, J=7.3 Hz, 3H). $^{13}$C NMR (101 MHz, Chloroform-d) δ 179.87, 167.78, 166.82, 154.27, 137.37, 129.25, 127.63, 127.55, 79.90, 49.44, 49.23, 45.34, 45.11, 40.04, 36.65, 35.86, 31.76, 30.44, 29.67, 28.55, 20.25, 13.87.

tert-butyl (R)-3-(3-(4-(octylcarbamoyl)phenyl)-1,2,4-oxadiazol-5-yl)pyrrolidine-1-carboxylate (37p)

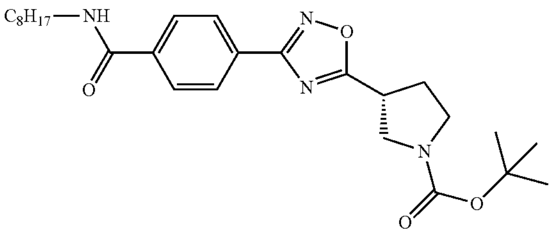

Synthesized according to General Procedure 1.3. Purified by silica chromatography (60% ethyl acetate in hexanes). White solid (69%, 329 mg). $^{1}$H NMR (400 MHz, Chloroform-d) δ 8.00 (d, J=8.0 Hz, 2H), 7.83 (d, J=8.0 Hz, 2H), 7.03 (t, J=5.7 Hz, 1H), 3.85-3.75 (m, 1H), 3.71-3.50 (m, 3H), 3.47-3.31 (m, 3H), 2.38-2.22 (m, 2H), 1.54 (p, J=7.4 Hz, 2H), 1.40 (s, 9H), 1.33-1.08 (m, 10H), 0.79 (t, J=6.7 Hz, 3H). $^{13}$C NMR (101 MHz, Chloroform-d) δ 179.72, 167.64, 166.79, 154.16, 137.30, 129.02, 127.55, 127.39, 79.76, 49.03, 45.03, 40.27, 36.05, 31.74, 30.27, 29.56, 29.26, 29.16, 28.42, 27.01, 22.57, 14.04.

(R)—N-butyl-4-(5-(pyrrolidin-3-yl)-1,2,4-oxadiazol-3-yl)benzamide hydrochloride (38o)

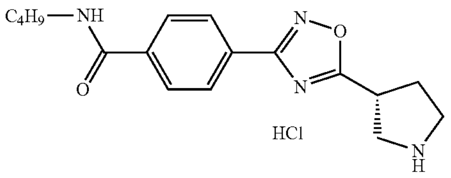

Synthesized according to General Procedure 1.5. White solid (36%, 102 mg). $^{1}$H NMR (400 MHz, Methanol-$d_4$) δ 8.11 (d, J=8.4 Hz, 2H), 7.93 (d, J=8.4 Hz, 2H), 3.91 (p, J=8.2, 1H), 3.65-3.58 (m, 1H), 3.53-3.47 (m, 1H), 3.39 (t, J=7.2 Hz, 2H), 3.36-3.26 (m, 2H) 2.49 (h, J=7.9 Hz, 1H), 2.34 (h, J=7.8 Hz, 1H), 1.60 (q, J=7.9 Hz, 2H), 1.41 (h, J=7.3 Hz, 2H), 0.96 (t, J=7.3 Hz, 3H). $^{13}$C NMR (101 MHz, Methanol-$d_4$) δ 182.13, 169.06, 168.85, 138.45, 130.56, 128.90, 128.40, 50.86, 47.13, 40.83, 37.41, 32.57, 31.43, 21.19, 14.15. HRMS: (ESI) [M+H]+ calc. for $C_{17}H_{23}N_4O_2$, 315.1816, observed, 315.18225.

(R)—N-octyl-4-(5-(pyrrolidin-3-yl)-1,2,4-oxadiazol-3-yl)benzamide hydrochloride (38p)

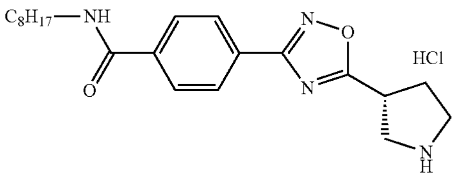

Synthesized according to General Procedure 1.5. White solid (76%, 216 mg). $^{1}$H NMR (400 MHz, Methanol-$d_4$) δ 8.60 (t, J=5.7 Hz, 1H), 8.16 (d, J=8.4 Hz, 2H), 7.95 (d, J=8.4 Hz, 2H), 4.12 (p, J=7.1 Hz, 1H), 3.89-3.74 (m, 2H), 3.61-3.46 (m, 2H), 3.42-3.35 (m, 2H), 2.69-2.58 (m, 1H), 2.51-2.42 (m, 1H), 1.63 (p, J=7.1 Hz, 2H), 1.44-1.26 (m, 10H), 0.88 (t, J=6.8 3H). $^{13}$C NMR (101 MHz, Methanol-$d_4$) δ 179.13, 167.68, 167.60, 137.24, 128.99, 127.54, 127.06, 48.05, 45.19, 39.86, 39.73, 35.25, 31.57, 29.03, 29.01, 28.95, 26.69, 22.28, 13.00. HRMS: (ESI) $[M+H]^+$ calc. for $C_{21}H_{31}N_4O_2$, 371.2442, observed, 371.2435.

tert-butyl (R)-(((tert-butoxycarbonyl)imino)(3-(3-(4-(octylcarbamoyl)phenyl)-1,2,4-oxadiazol-5-yl)pyrrolidin-1-yl)methyl)carbamate (39p)

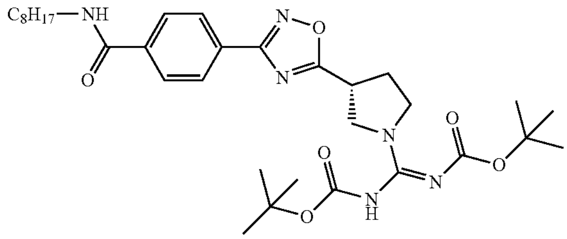

Synthesized according to General Procedure 1.8. Purified by silica chromatography (30% ethyl acetate in hexanes). White solid (78%, 253 mg). $^{1}H$ NMR (400 MHz, Chloroform-d) δ 10.37 (s, 1H), 8.04 (d, J=8.4 Hz, 2H), 7.84 (d, J=8.4 Hz, 2H), 6.66 (t, J=5.7 Hz, 1H), 4.12-3.94 (m, 2H), 3.73 (m, 3H), 3.41 (q, J=6.6 Hz, 2H), 2.48-2.31 (m, 2H), 1.58 (p, J=7.5 Hz, 2H), 1.45 (s, 18H), 1.36-1.19 (m, 10H), 0.82 (t, J=6.9 Hz, 3H). $^{13}C$ NMR (101 MHz, Chloroform-d) δ 179.07, 167.75, 166.78, 154.20, 137.32, 129.08, 127.59, 127.54, 51.90, 47.98, 40.32, 35.38, 31.81, 29.63, 29.31, 29.22, 28.17, 28.05, 27.06, 22.65, 14.11.

(R)-4-(5-(1-carbamimidoylpyrrolidin-3-yl)-1,2,4-oxadiazol-3-yl)-N-octylbenzamide hydrochloride (40p)

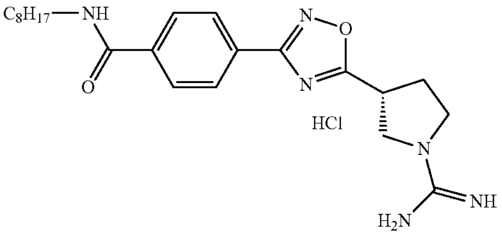

Synthesized according to General Procedure 1.5. White solid (58%, 29 mg). $^{1}H$ NMR (400 MHz, Methanol-$d_4$) δ 8.12 (d, J=8.1 Hz, 2H), 7.95 (d, J=8.1 Hz, 2H), 4.14-3.88 (m, 3H), 3.74-3.60 (m, 2H), 3.39 (t, J=7.2 Hz, 2H), 2.69-2.60 (m, 1H), 2.55-2.45 (m, 1H), 1.63 (p, J=7.1 Hz, 2H), 1.46-1.17 (m, 11H), 0.89 (t, J=6.6 Hz, 3H). $^{13}C$ NMR (101 MHz, Methanol-$d_4$) δ 180.85, 169.04, 168.96, 156.37, 138.52, 130.46, 128.94, 128.41, 51.31, 47.68, 41.15, 37.30, 32.97, 30.51, 30.44, 30.41, 30.36, 28.10, 23.69, 14.43. HRMS: (ESI) $[M+H]^+$ calc. for $C_{22}H_{33}N_6O_2$, 413.2660, observed, 413.2656.

S1P Transporter Assay

Transporter assays are vectorial and, therefore, require measurement of the transported analyte in different compartments. The assay of S1P transporters is problematic because S1P is exported, but not imported, by SPNS2, which obviates measuring uptake of mass- or radio-labeled S1P into transporter-expressing cells.

To assay for SPNS2 inhibitor hits, we took advantage of the growth inhibitory effects of excessive levels of phosphorylated Long Chain Base (phospho-LCB) levels on the budding yeast, *S. cerevisiae* (Kharel Y, et al. *Saccharomyces cerevisiae* as a platform for assessing sphingolipid lipid kinase inhibitors. *PLoS One* 13, e0192179 (2018) PMC5908134). Yeast lack the desaturase that converts dihydroceramide to ceramide and, therefore, have neither sphingosine nor S1P. Rather, yeast have the reduced form, dihydrosphingosine, and the 4-hydroxyl analog, phytosphingosine and their respective phosphates. Like all eukaryotes, the yeast synthesizes (via LCB kinases (SphKs)) and degrades (via phospho-LCB lyase and phosphatase) phospho-LCBs, (dhS1P, phytoS1P). Yeast lack phospho-LCB transporters such as SPNS2, which are found only in vertebrates. To assess inhibition of SPNS2 in vitro, we used a strain of *S. cerevisiae* wherein expression of a mammalian SphK and human SPNS2 were forced. SPNS2 inhibitors decrease the growth of this strain. Table 2 below presents in vitro inhibition data against SPNS2 for exemplary compounds, presented here as their pharmaceutical salts, of the disclosure (A≤2 μM, B>2 μM).

TABLE 2

| Compound | Structure | $IC_{50}$ |
|---|---|---|
| 5a | 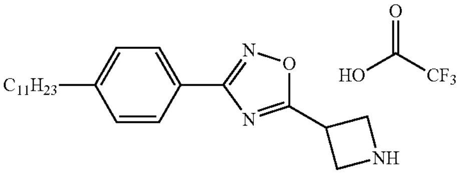 | B |
| 5e | 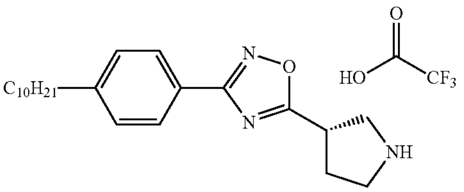 | B |

TABLE 2-continued
| Compound | Structure | $IC_{50}$ |
| --- | --- | --- |
| 5f | 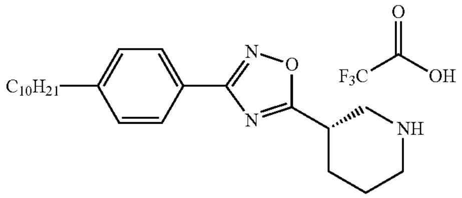 | B |
| 5g | 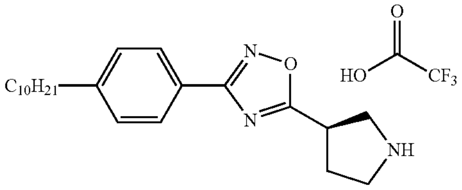 | B |
| 5h | 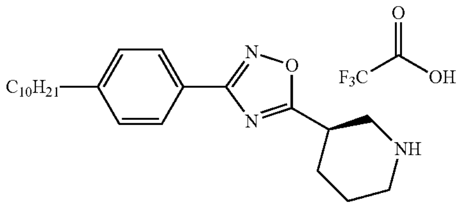 | B |
| 5j | 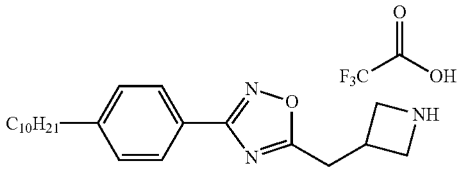 | A |
| 5l | 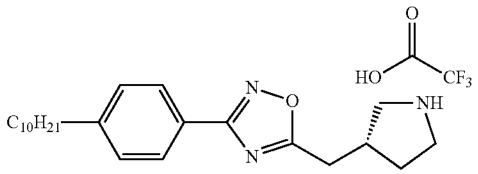 | A |
| 5p | 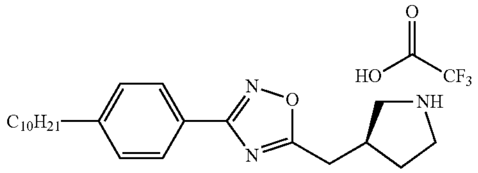 | A |
| 5q | 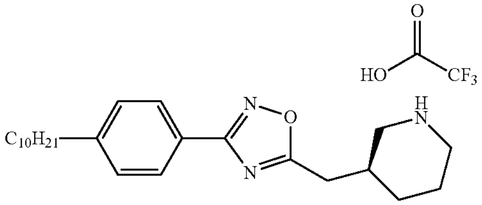 | A |
| 5aa | 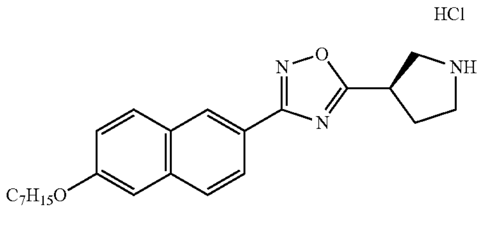 | A |

TABLE 2-continued
| Compound | Structure | $IC_{50}$ |
|---|---|---|
| 7a | 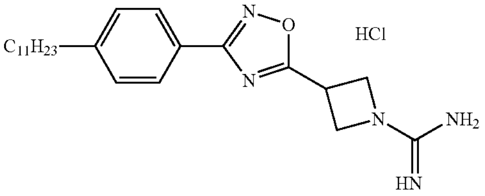 | B |
| 7b | 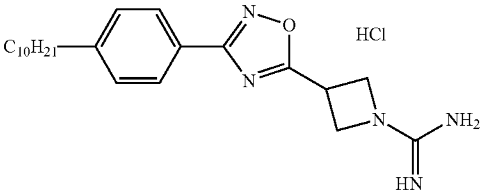 | A |
| 7c | 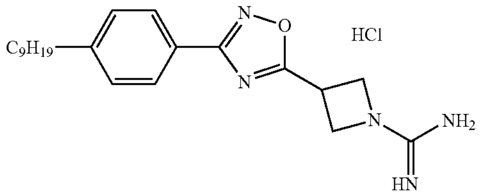 | A |
| 7d | 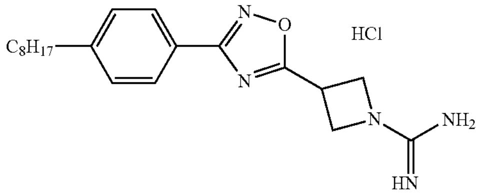 | B |
| 7e | 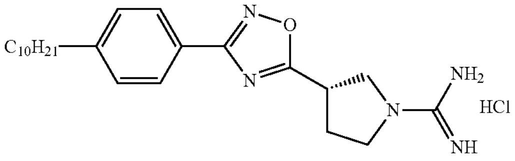 | B |
| 7f | 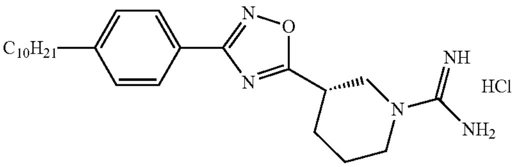 | A |
| 7g | 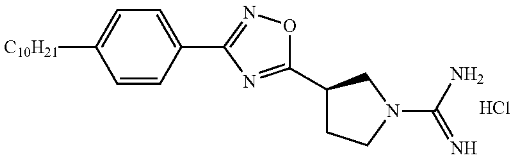 | B |
| 7h | 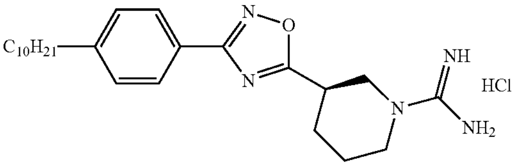 | B |

TABLE 2-continued
| Compound | Structure | $IC_{50}$ |
| --- | --- | --- |
| 7i | 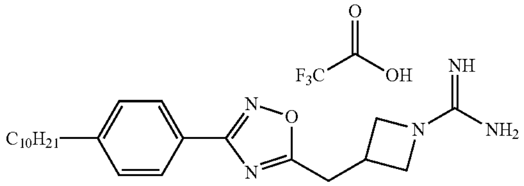 | A |
| 7j | 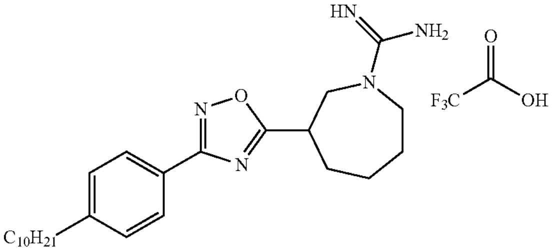 | A |
| 7k | 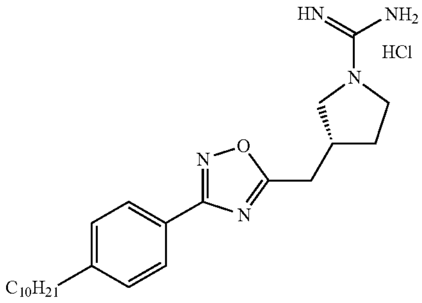 | A |
| 7kk | 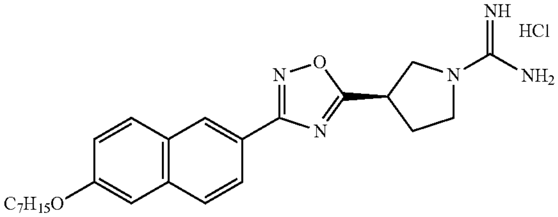 | A |
| 7p | 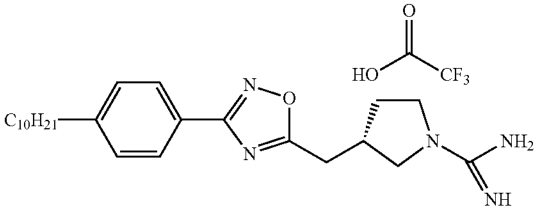 | A |
| 7q | 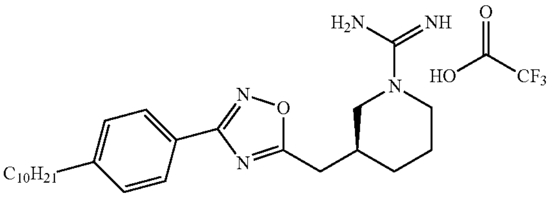 | A |
| 7t | 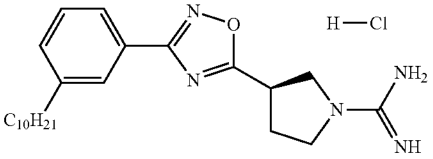 | B |

TABLE 2-continued
| Compound | Structure | $IC_{50}$ |
|---|---|---|
| 7xa | 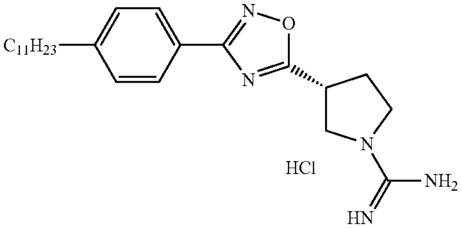 | A |
| 7xb | 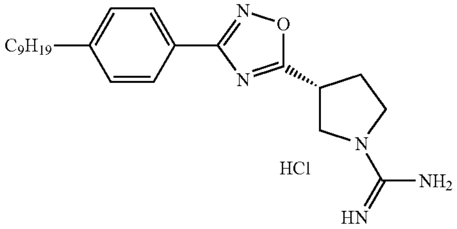 | A |
| 7ya | 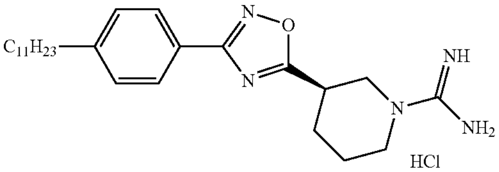 | A |
| 7yb | 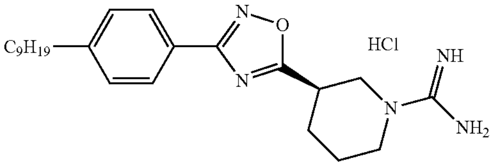 | A |
| 13a | 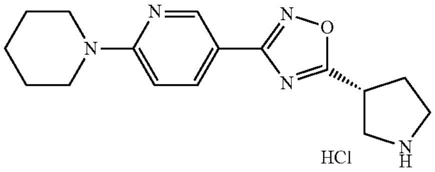 [SMILES: c1cc(N2CCCCC2)ncc1-c1noc([C@@H]2CCNC2)n1 ; Cl] | B |
| 13b | 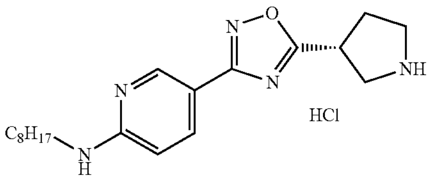 | B |
| 13c | 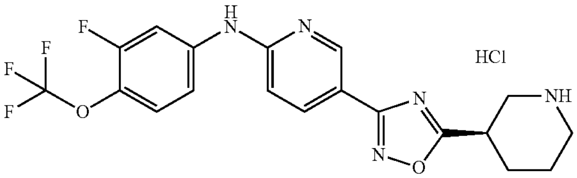 [SMILES: Fc1cc(Nc2ccc(-c3noc([C@@H]4CCCNC4)n3)cn2)ccc1OC(F)(F)F ; Cl] | B |
| 13d | 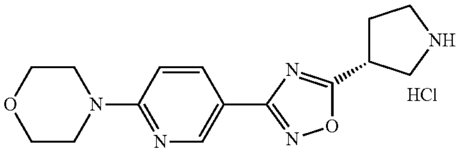 | B |

TABLE 2-continued
| Compound | Structure | $IC_{50}$ |
|---|---|---|
| 13e | 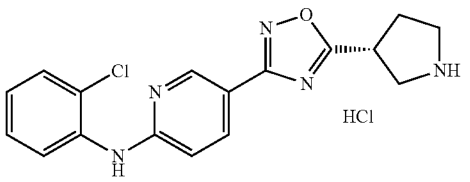 [SMILES: Clc1ccccc1Nc1ccc(-c2noc([C@@H]3CCNC3)n2)cn1 ; Cl] | B |
| 13f | 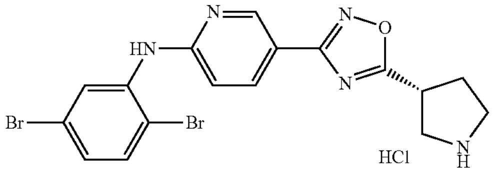 [SMILES: Brc1ccc(Br)c(Nc2ccc(-c3noc([C@@H]4CCNC4)n3)cn2)c1 ; Cl] | B |
| 13g | 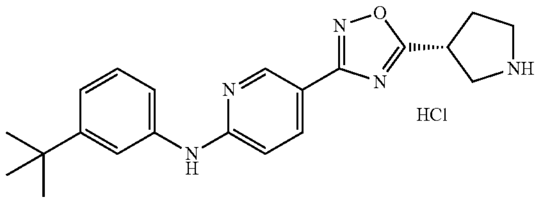 [SMILES: CC(C)(C)c1cccc(Nc2ccc(-c3noc([C@@H]4CCNC4)n3)cn2)c1 ; Cl] | B |
| 13h | 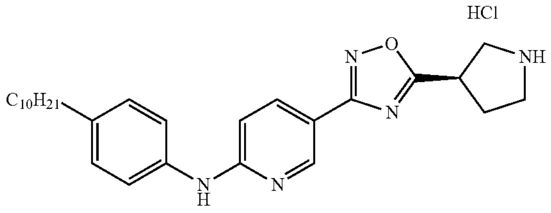 | B |
| 13i | 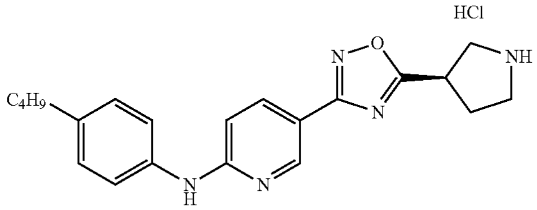 | B |
| 13j | 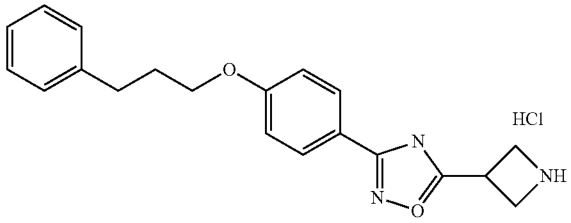 | B |
| 15a | 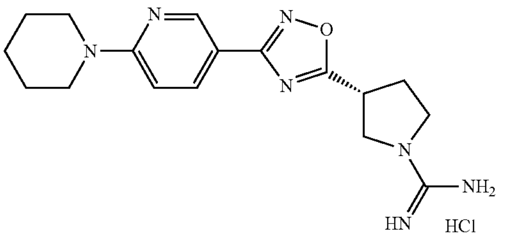 [SMILES: N=C(N)N1CC[C@@H](c2nc(-c3ccc(N4CCCCC4)nc3)no2)C1 ; Cl] | B |

TABLE 2-continued
| Compound | Structure | $IC_{50}$ |
| --- | --- | --- |
| 15b | 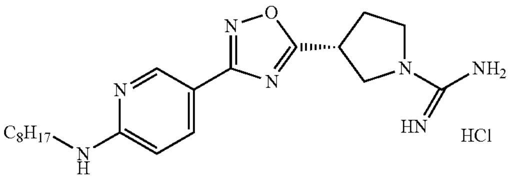 | B |
| 15c | 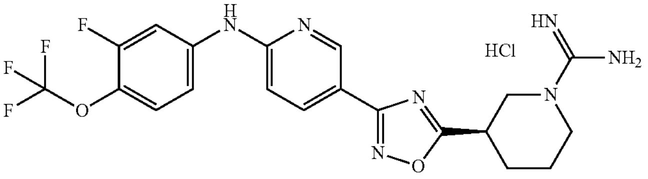 [SMILES: N=C(N)N1CCC[C@@H](c2nc(-c3ccc(Nc4ccc(OC(F)(F)F)c(F)c4)nc3)no2)C1 ; Cl] | B |
| 15d | 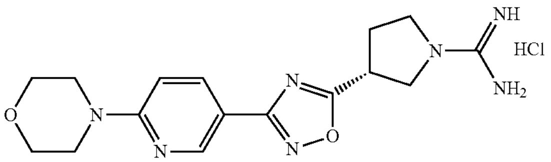 [SMILES: N=C(N)N1CC[C@@H](c2nc(-c3ccc(N4CCOCC4)nc3)no2)C1 ; Cl] | B |
| 15e | 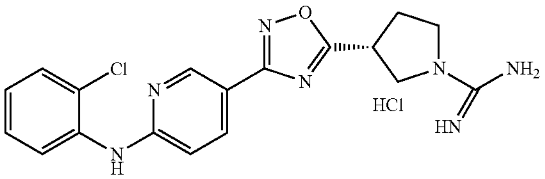 [SMILES: N=C(N)N1CC[C@@H](c2nc(-c3ccc(Nc4ccccc4Cl)nc3)no2)C1 ; Cl] | B |
| 15f | 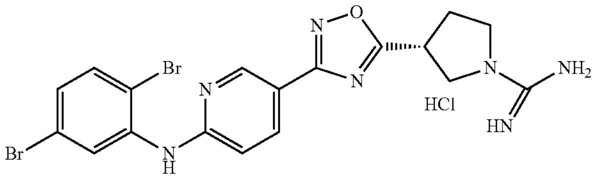 [SMILES: N=C(N)N1CC[C@@H](c2nc(-c3ccc(Nc4cc(Br)ccc4Br)nc3)no2)C1 ; Cl] | B |
| 15g | 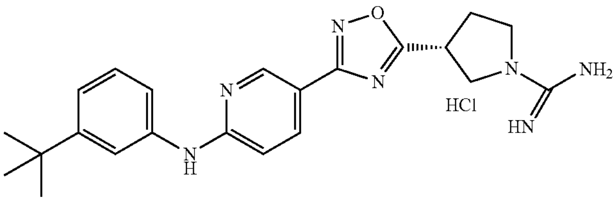 [SMILES: CC(C)(C)c1cccc(Nc2ccc(-c3noc([C@@H]4CCN(C(=N)N)C4)n3)cn2)c1 ; Cl] | B |
| 15h | 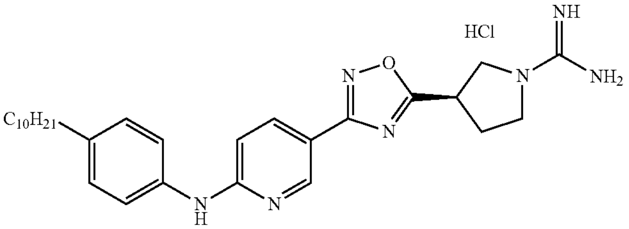 | A |

TABLE 2-continued
| Compound | Structure | $IC_{50}$ |
| --- | --- | --- |
| 15i | 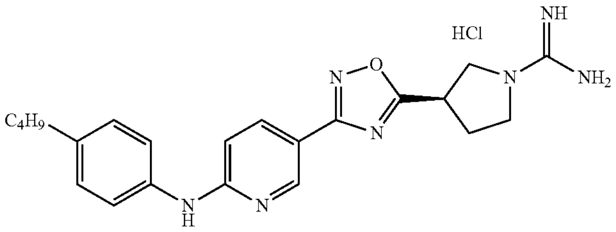 | B |
| 15j | 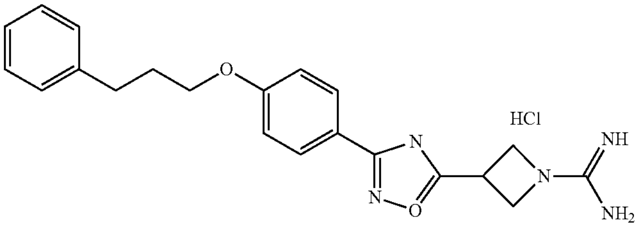 | B |
| 21c | 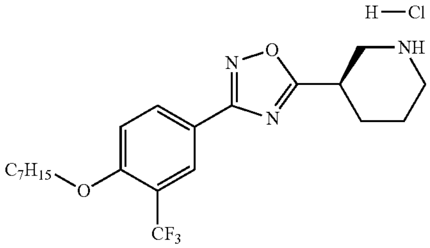 | B |
| 21d | 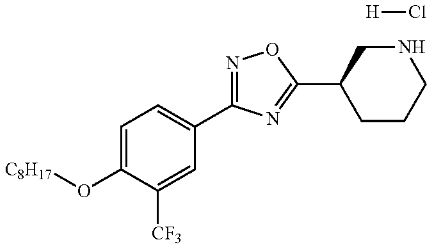 | B |
| 12e | 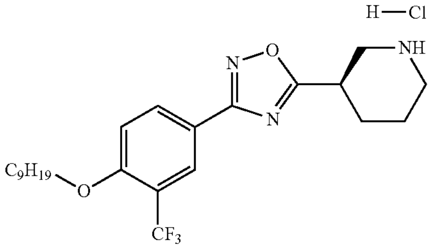 | A |
| 21f | 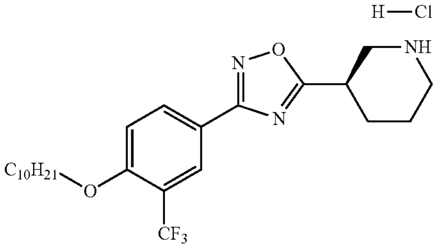 | B |

TABLE 2-continued
| Compound | Structure | $IC_{50}$ |
| --- | --- | --- |
| 21g | 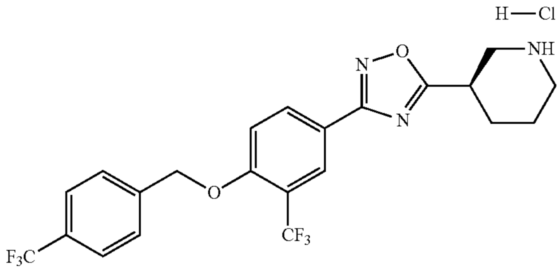 | B |
| 21j | 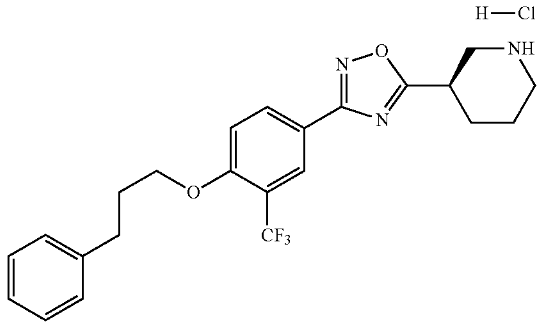 | B |
| 28d | 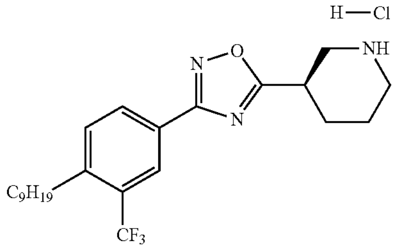 | B |
| 28e | 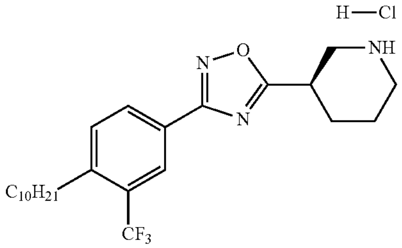 | B |
| 28f | 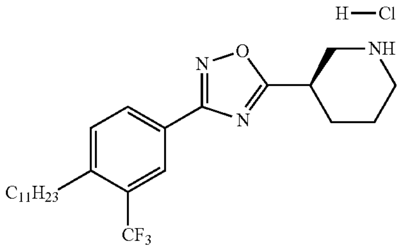 | B |
| 28g | 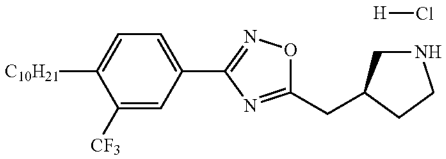 | B |

TABLE 2-continued
| Compound | Structure | IC50 |
| --- | --- | --- |
| 23a | 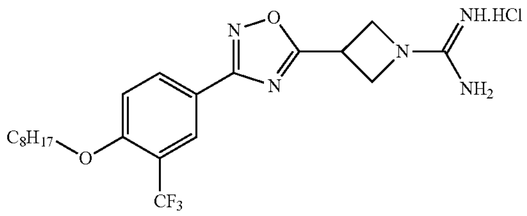 | A |
| 23b | 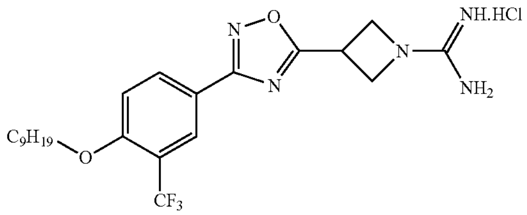 | A |
| 23c | 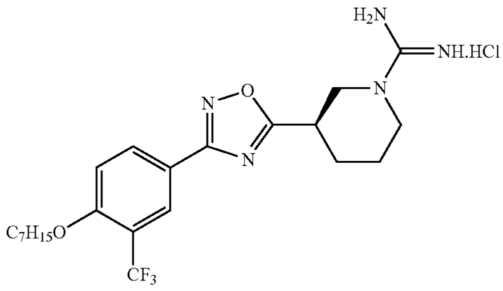 | A |
| 23d | 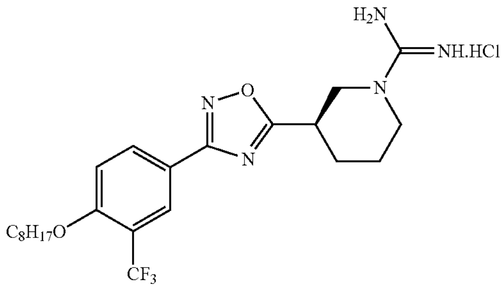 | B |
| 23e | 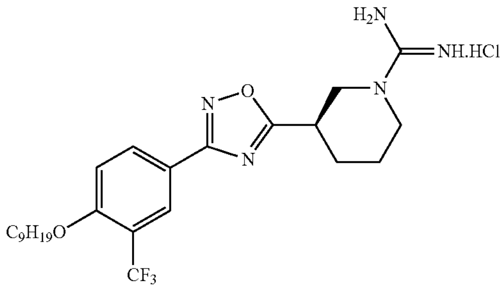 | A |

TABLE 2-continued
| Compound | Structure | $IC_{50}$ |
|---|---|---|
| 23f | 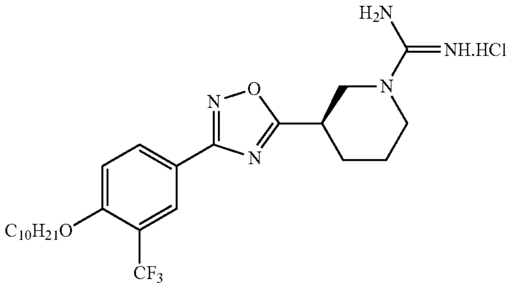 | A |
| 23g | 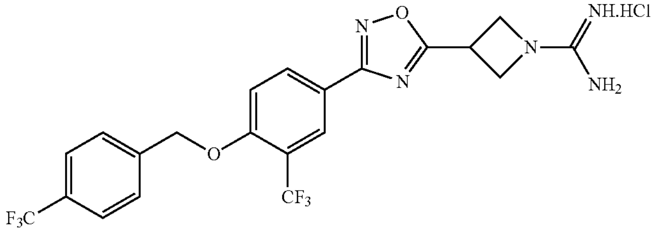 | B |
| 23h | 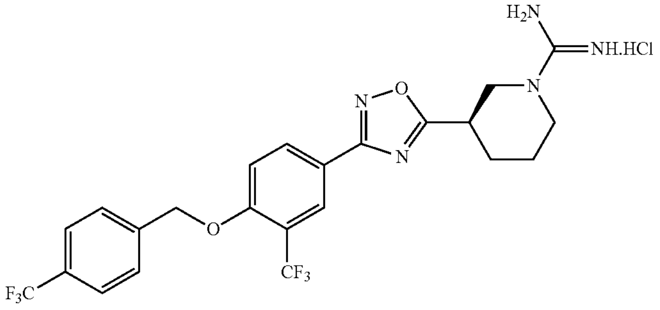 | B |
| 23i | 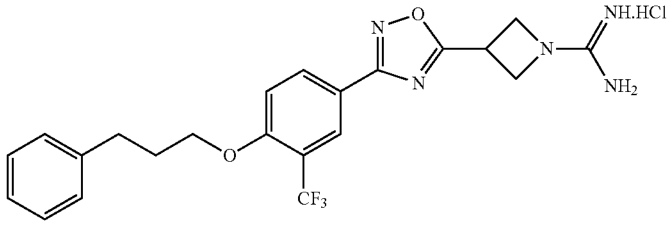 | B |
| 23j | 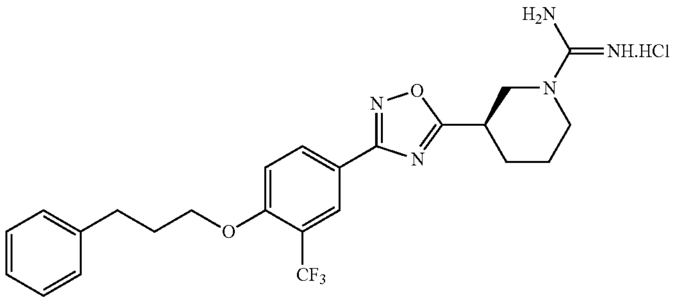 | B |
| 30a | 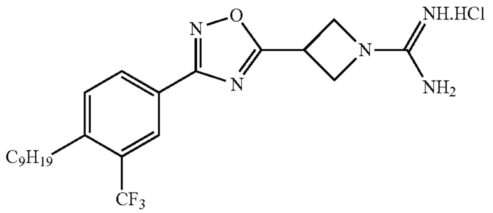 | A |

TABLE 2-continued
| Compound | Structure | $IC_{50}$ |
| --- | --- | --- |
| 30b | 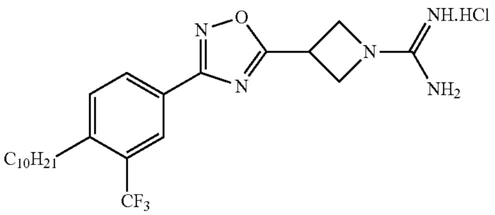 | A |
| 30c | 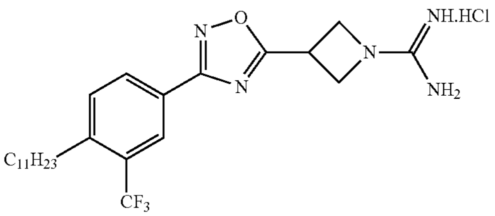 | B |
| 30d | 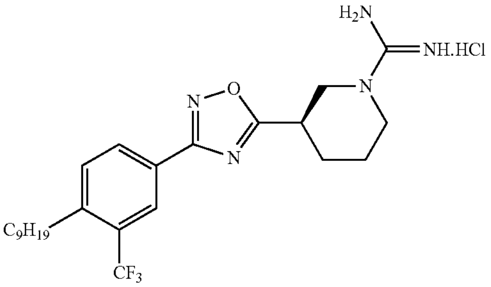 | A |
| 30e | 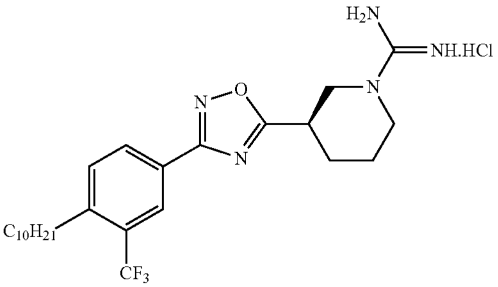 | A |
| 30f | 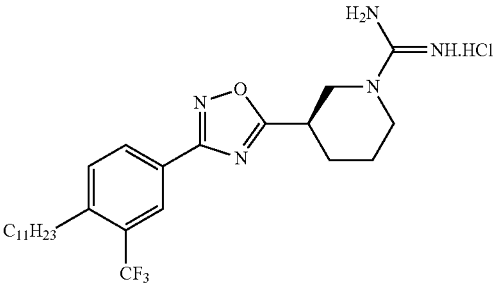 | B |

TABLE 2-continued
| Compound | Structure | $IC_{50}$ |
| --- | --- | --- |
| 30g | 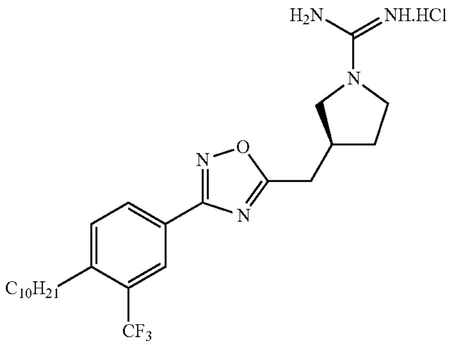 | B |
| 38a | 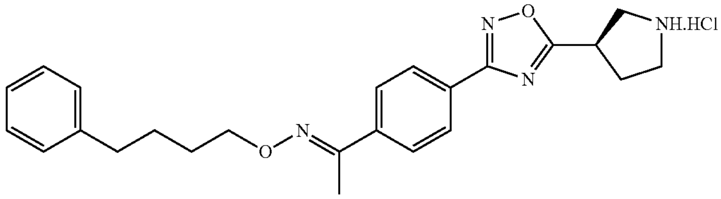 | A |
| 38b | 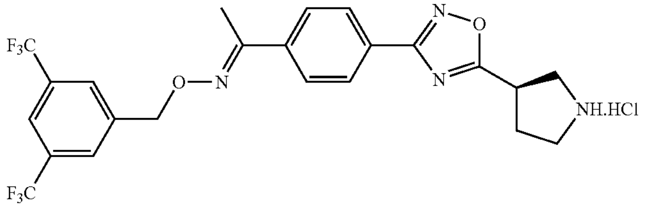 | A |
| 38c | 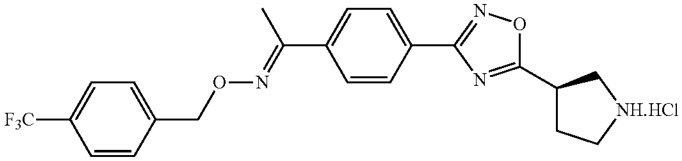 | B |
| 38d | 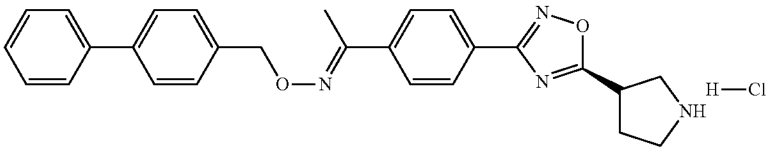 | B |
| 38g | 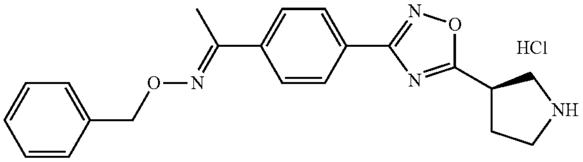 [SMILES: C/C(=N\OCc1ccccc1)c1ccc(-c2noc([C@@H]3CCNC3)n2)cc1 ; Cl] | B |
| 38h | 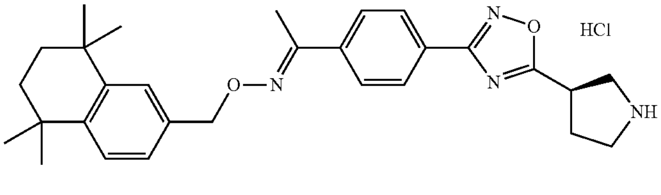 [SMILES: C/C(=N\OCc1ccc2c(c1)C(C)(C)CCC2(C)C)c1ccc(-c2noc([C@@H]3CCNC3)n2)cc1 ; Cl] | B |

TABLE 2-continued
| Compound | Structure | $IC_{50}$ |
|---|---|---|
| 38i | 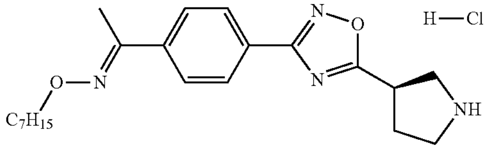 | B |
| 38j | 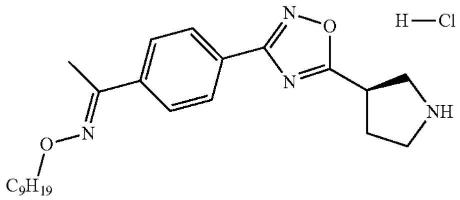 | B |
| 38k | 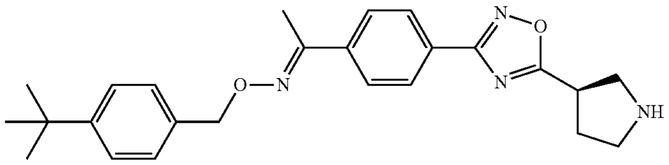 | A |
| 38l | 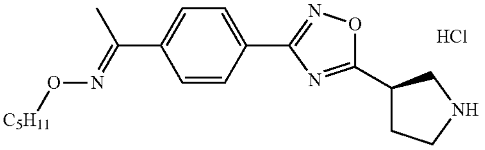 | B |
| 38n | 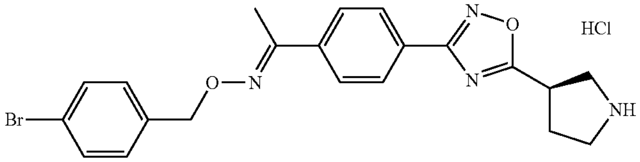 [SMILES: C/C(=N\OCc1ccc(Br)cc1)c1ccc(-c2noc([C@@H]3CCNC3)n2)cc1 ; Cl] | A |
| 38o | 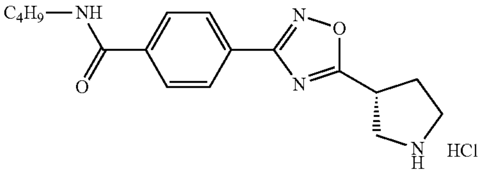 | B |
| 38p | 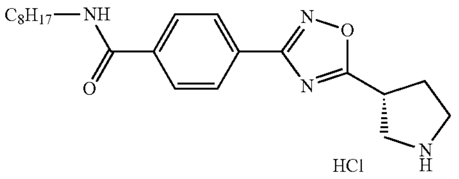 | B |
| 40a | 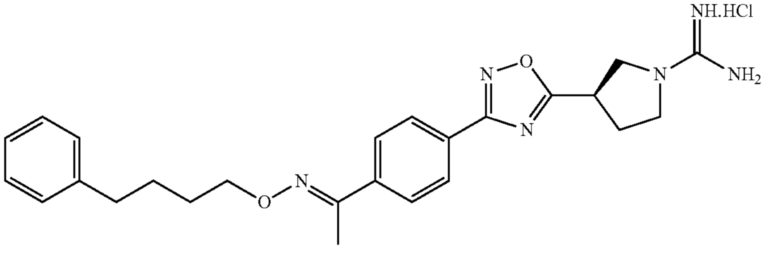 | A |

TABLE 2-continued
| Compound | Structure | $IC_{50}$ |
|---|---|---|
| 40b | 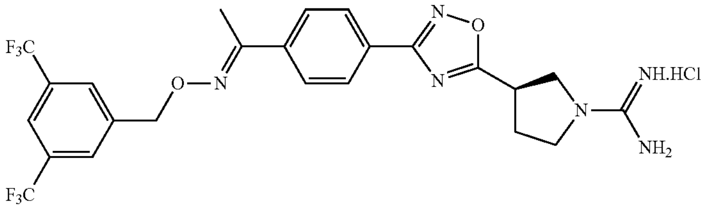 | A |
| 40c | 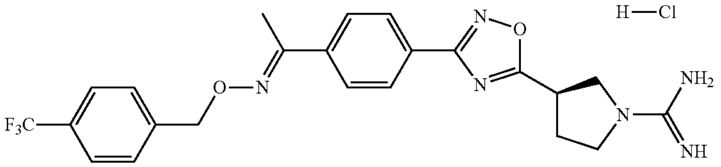 [SMILES: Cl ; C/C(=N\OCc1ccc(C(F)(F)F)cc1)c1ccc(-c2noc([C@@H]3CCN(C(=N)N)C3)n2)cc1] | B |
| 40d | 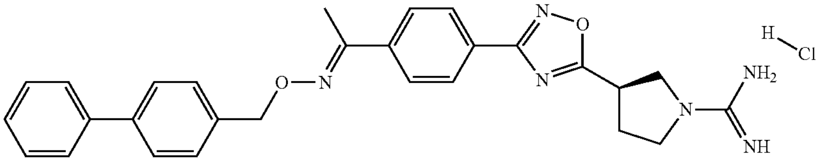 | A |
| 40e | 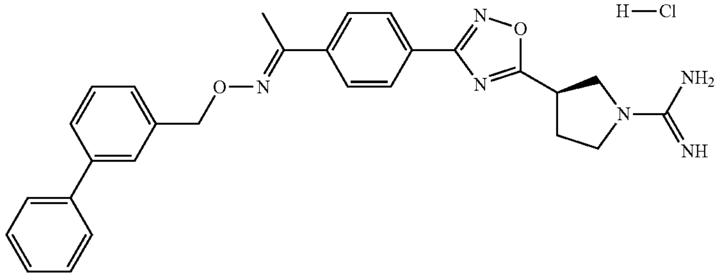 [SMILES: Cl ; C/C(=N\OCc1cccc(-c2ccccc2)c1)c1ccc(-c2noc([C@@H]3CCN(C(=N)N)C3)n2)cc1] | A |
| 40f | 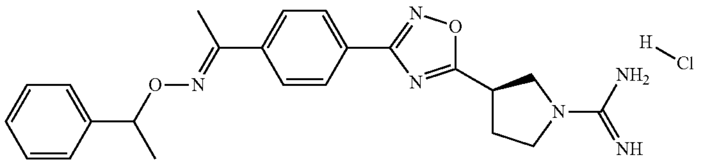 | B |
| 40g | 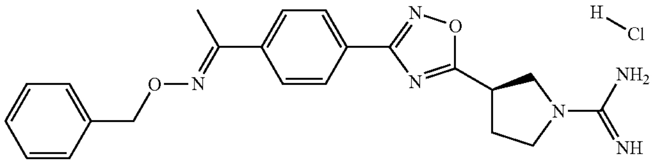 | B |
| 40h | 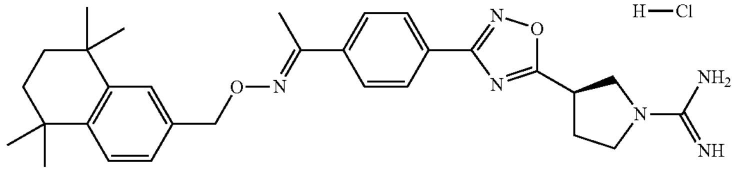 [SMILES: C/C(=N\OCc1ccc2c(c1)C(C)(C)CCC2(C)C)c1ccc(-c2noc([C@@H]3CCN(C(=N)N)C3)n2)cc1 ; Cl] | A |
| 40i | 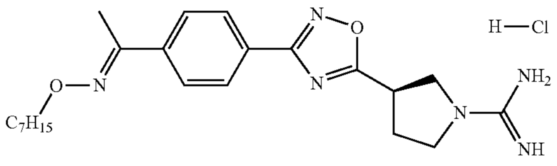 | A |

TABLE 2-continued
| Compound | Structure | $IC_{50}$ |
|---|---|---|
| 40j | 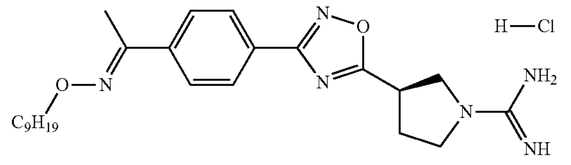 | B |
| 40k | 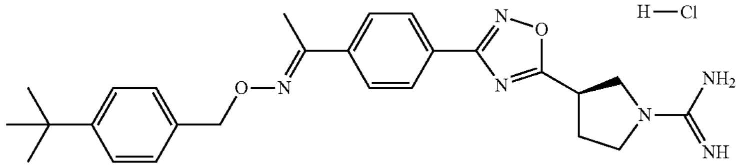 | A |
| 40l | 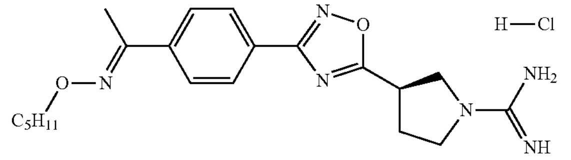 | B |
| 40m | 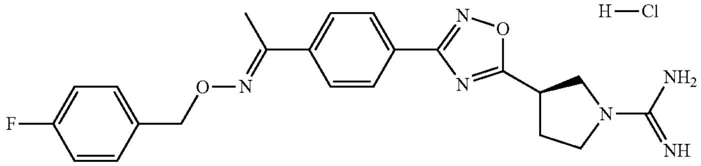 [SMILES: Cl ; C/C(=N\OCc1ccc(F)cc1)c1ccc(-c2noc([C@@H]3CCN(C(=N)N)C3)n2)cc1] | B |
| 40n | 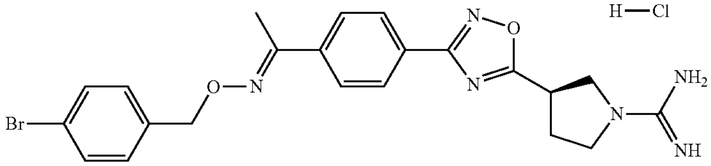 [SMILES: Cl ; C/C(=N\OCc1ccc(Br)cc1)c1ccc(-c2noc([C@@H]3CCN(C(=N)N)C3)n2)cc1] | B |
| 40p | 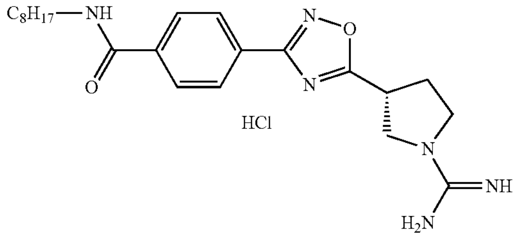 | B |
We claim:
1. A compound or pharmaceutically acceptable salt thereof, wherein the compound is selected from the following table:
| Compound | Structure |
|---|---|
| 5a | 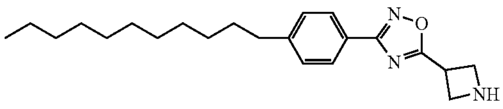 [SMILES: CCCCCCCCCCCc1ccc(-c2noc(C3CNC3)n2)cc1] |
| 5e | 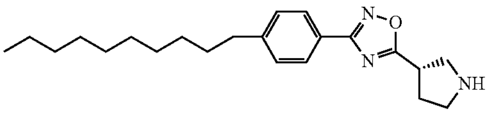 [SMILES: CCCCCCCCCCc1ccc(-c2noc([C@H]3CCNC3)n2)cc1] |
-continued
| Compound | Structure |
|---|---|
| 5f | 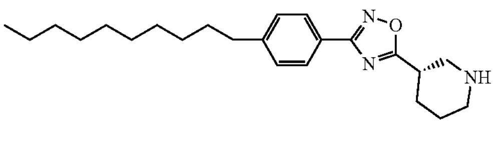 [SMILES: CCCCCCCCCCc1ccc(-c2noc([C@H]3CCCNC3)n2)cc1] |
| 5g | 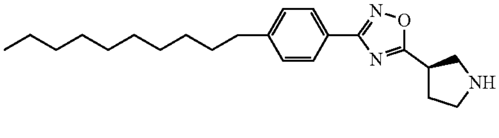 [SMILES: CCCCCCCCCCc1ccc(-c2noc([C@@H]3CCNC3)n2)cc1] |

-continued
| Compound | Structure |
|---|---|
| 5h | 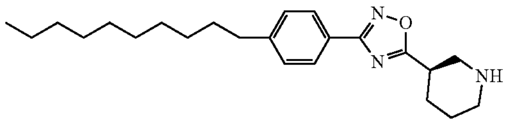 [SMILES: CCCCCCCCCCc1ccc(-c2noc([C@@H]3CCCNC3)n2)cc1] |
| 5j | 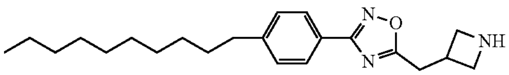 [SMILES: CCCCCCCCCCc1ccc(-c2noc(CC3CNC3)n2)cc1] |
| 51 | 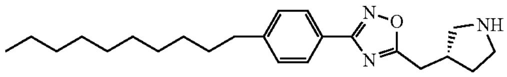 |
| 5p | 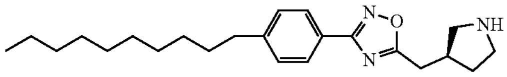 |
| 5q | 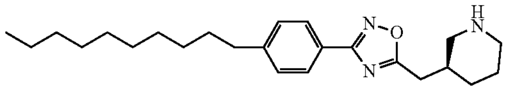 [SMILES: CCCCCCCCCCc1ccc(-c2noc(C[C@@H]3CCCNC3)n2)cc1] |
| 5aa | 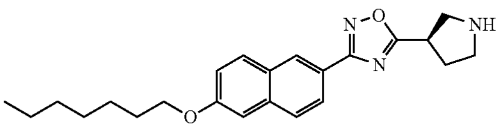 [SMILES: CCCCCCCOc1ccc2cc(-c3noc([C@@H]4CCNC4)n3)ccc2c1] |
| 13b | 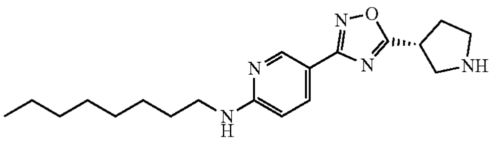 [SMILES: CCCCCCCCNc1ccc(-c2noc([C@@H]3CCNC3)n2)cn1] |
| 13c | 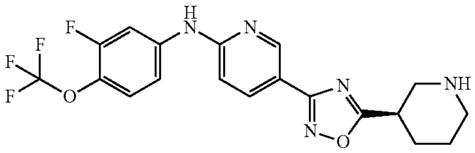 [SMILES: Fc1cc(Nc2ccc(-c3noc([C@@H]4CCCNC4)n3)cn2)ccc1OC(F)(F)F] |
| 13d | 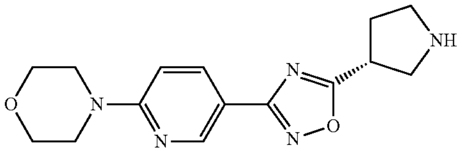 [SMILES: c1cc(N2CCOCC2)ncc1-c1noc([C@@H]2CCNC2)n1] |
| 13e | 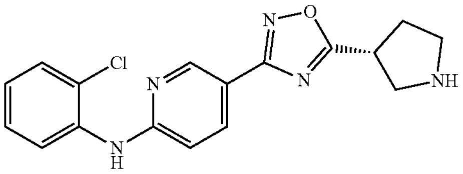 [SMILES: Clc1ccccc1Nc1ccc(-c2noc([C@@H]3CCNC3)n2)cn1] |
| 13f | 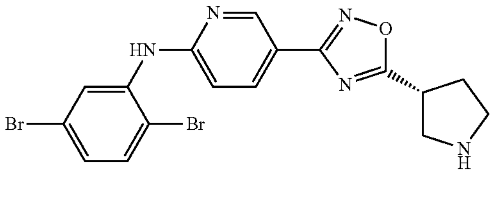 [SMILES: Brc1ccc(Br)c(Nc2ccc(-c3noc([C@@H]4CCNC4)n3)cn2)c1] |
-continued
| Compound | Structure |
|---|---|
| 13g | 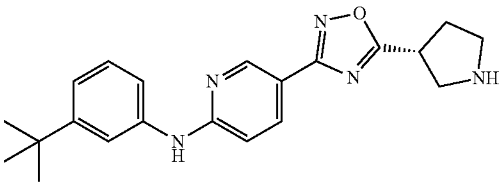 [SMILES: CC(C)(C)c1cccc(Nc2ccc(-c3noc([C@@H]4CCNC4)n3)cn2)c1] |
| 13h | 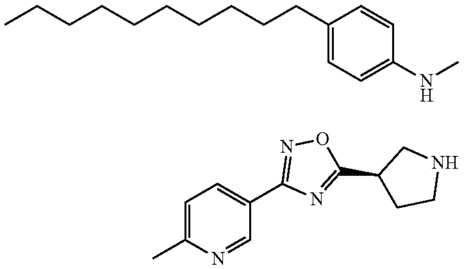 |
| 13i | 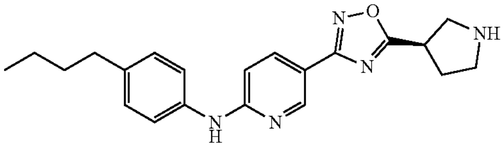 [SMILES: CCCCc1ccc(Nc2ccc(-c3noc([C@@H]4CCNC4)n3)cn2)cc1] |
| 13j | 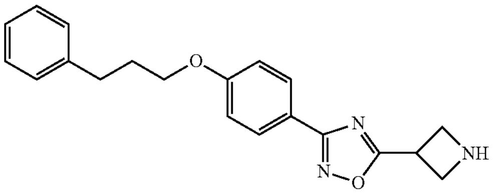 [SMILES: c1ccc(CCCOc2ccc(-c3noc(C4CNC4)n3)cc2)cc1] |
| 21c | 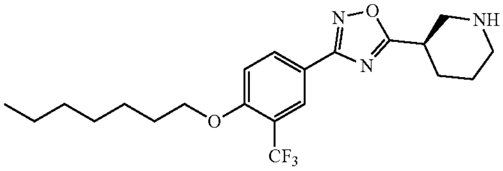 [SMILES: CCCCCCCOc1ccc(-c2noc([C@@H]3CCCNC3)n2)cc1C(F)(F)F] |
| 21d | 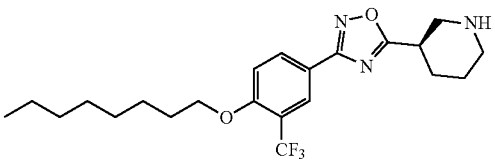 [SMILES: CCCCCCCCOc1ccc(-c2noc([C@@H]3CCCNC3)n2)cc1C(F)(F)F] |
| 21e | 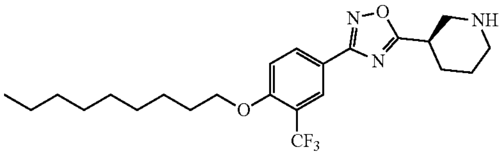 [SMILES: CCCCCCCCCOc1ccc(-c2noc([C@@H]3CCCNC3)n2)cc1C(F)(F)F] |
| 21f | 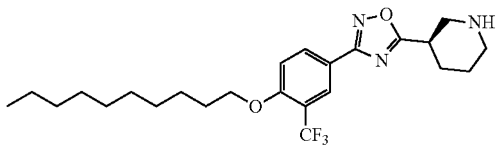 [SMILES: CCCCCCCCCCOc1ccc(-c2noc([C@@H]3CCCNC3)n2)cc1C(F)(F)F] |

-continued
| Compound | Structure |
| --- | --- |
| 21g | 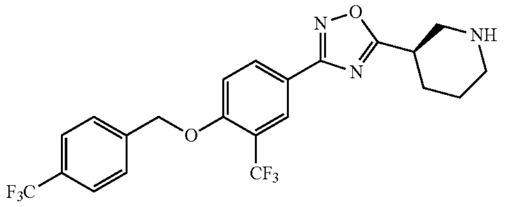 [SMILES: FC(F)(F)c1ccc(COc2ccc(-c3noc([C@@H]4CCCNC4)n3)cc2C(F)(F)F)cc1] |
| 21j | 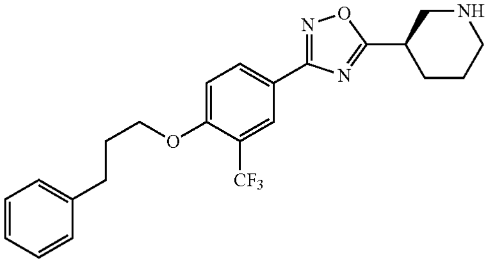 [SMILES: FC(F)(F)c1cc(-c2noc([C@@H]3CCCNC3)n2)ccc1OCCCc1ccccc1] |
| 28d | 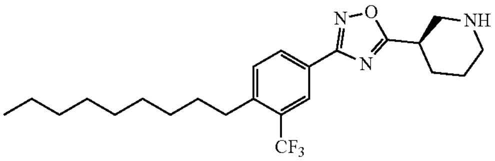 [SMILES: CCCCCCCCCc1ccc(-c2noc([C@@H]3CCCNC3)n2)cc1C(F)(F)F] |
| 28e | 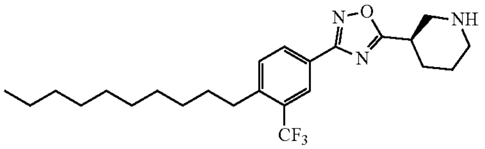 [SMILES: CCCCCCCCCCc1ccc(-c2noc([C@@H]3CCCNC3)n2)cc1C(F)(F)F] |
| 28f | 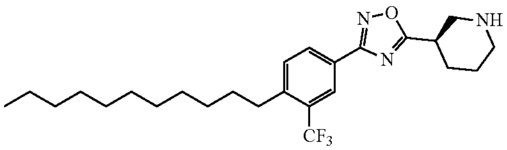 [SMILES: CCCCCCCCCCCc1ccc(-c2noc([C@@H]3CCCNC3)n2)cc1C(F)(F)F] |
| 28g | 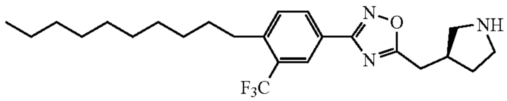 |
| 38a | 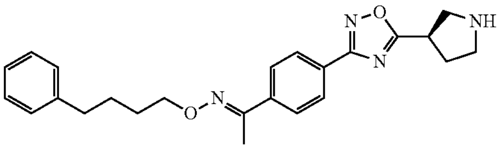 [SMILES: C/C(=N\OCCCCc1ccccc1)c1ccc(-c2noc([C@@H]3CCNC3)n2)cc1] |
| 38b | 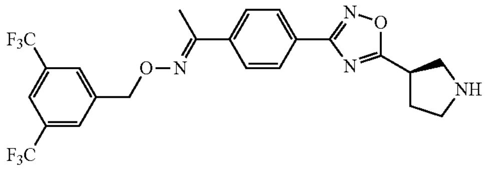 [SMILES: C/C(=N\OCc1cc(C(F)(F)F)cc(C(F)(F)F)c1)c1ccc(-c2noc([C@@H]3CCNC3)n2)cc1] |
| 38c | 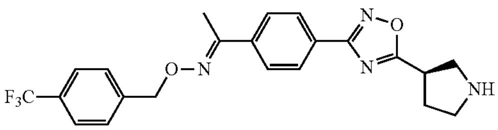 [SMILES: C/C(=N\OCc1ccc(C(F)(F)F)cc1)c1ccc(-c2noc([C@@H]3CCNC3)n2)cc1] |
-continued
| Compound | Structure |
| --- | --- |
| 38d | 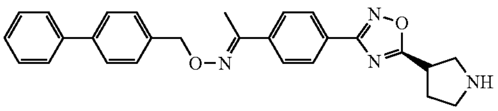 |
| 38g | 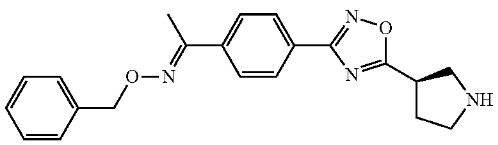 [SMILES: C/C(=N\OCc1ccccc1)c1ccc(-c2noc([C@@H]3CCNC3)n2)cc1] |
| 38h | 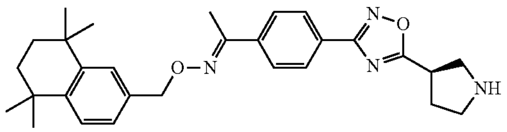 [SMILES: C/C(=N\OCc1ccc2c(c1)C(C)(C)CCC2(C)C)c1ccc(-c2noc([C@@H]3CCNC3)n2)cc1] |
| 38i | 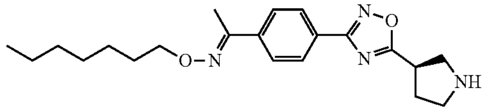 [SMILES: CCCCCCCO/N=C(\C)c1ccc(-c2noc([C@@H]3CCNC3)n2)cc1] |
| 38j | 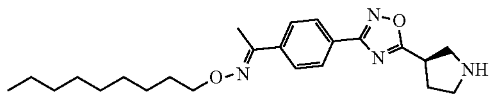 [SMILES: CCCCCCCCCO/N=C(\C)c1ccc(-c2noc([C@@H]3CCNC3)n2)cc1] |
| 38k | 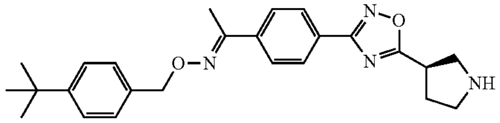 [SMILES: C/C(=N\OCc1ccc(C(C)(C)C)cc1)c1ccc(-c2noc([C@@H]3CCNC3)n2)cc1] |
| 38l | 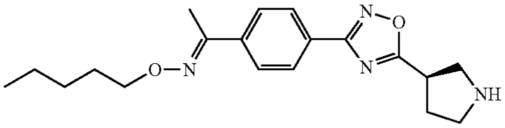 [SMILES: CCCCCO/N=C(\C)c1ccc(-c2noc([C@@H]3CCNC3)n2)cc1] |
| 38n | 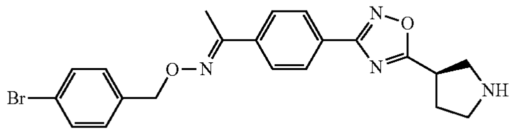 [SMILES: C/C(=N\OCc1ccc(Br)cc1)c1ccc(-c2noc([C@@H]3CCNC3)n2)cc1] |
| 38o | 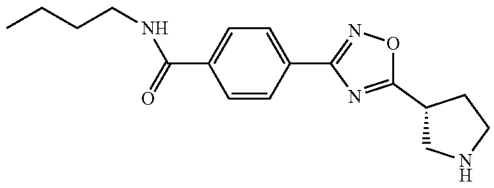 [SMILES: CCCCNC(=O)c1ccc(-c2noc([C@@H]3CCNC3)n2)cc1] |
| 38p | 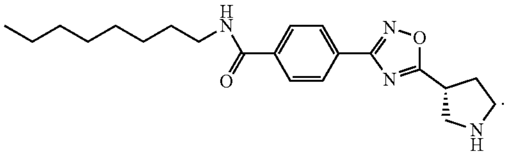 [SMILES: CCCCCCCCNC(=O)c1ccc(-c2noc([C@@H]3CCNC3)n2)cc1 ; "."] |
2. A pharmaceutical composition comprising a therapeutically effective amount of a compound or a pharmaceutically acceptable salt thereof according to claim 1 and a pharmaceutically acceptable carrier.

* * * * *